(12) United States Patent
Funahashi et al.

(10) Patent No.: US 9,945,862 B2
(45) Date of Patent: Apr. 17, 2018

(54) BIOMARKERS FOR PREDICTING AND ASSESSING RESPONSIVENESS OF THYROID AND KIDNEY CANCER SUBJECTS TO LENVATINIB COMPOUNDS

(75) Inventors: Yasuhiro Funahashi, Tsukuba (JP); Tadashi Kadowaki, Tsukuba (JP); Junji Matsui, Tsukuba (JP); Jason S. Simon, Woodcliff Lake, NJ (US); Lucy Xu, Woodcliff Lake, NJ (US)

(73) Assignee: Eisai R&D Management Co., Ltd., Tokyo (JP)

( * ) Notice: Subject to any disclaimer, the term of this patent is extended or adjusted under 35 U.S.C. 154(b) by 895 days.

(21) Appl. No.: 14/122,339

(22) PCT Filed: May 31, 2012

(86) PCT No.: PCT/US2012/040183
§ 371 (c)(1),
(2), (4) Date: Feb. 21, 2014

(87) PCT Pub. No.: WO2012/166899
PCT Pub. Date: Dec. 6, 2012

(65) Prior Publication Data
US 2014/0187577 A1    Jul. 3, 2014

Related U.S. Application Data

(60) Provisional application No. 61/493,294, filed on Jun. 3, 2011.

(51) Int. Cl.
*A61K 31/47* (2006.01)
*G01N 33/574* (2006.01)
*C12Q 1/68* (2018.01)

(52) U.S. Cl.
CPC ....... *G01N 33/57407* (2013.01); *A61K 31/47* (2013.01); *C12Q 1/6886* (2013.01); *G01N 33/57438* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| | | |
|---|---|---|
| 4,526,988 A | 7/1985 | Hertel |
| 4,563,417 A | 1/1986 | Albarella et al. |
| 4,582,789 A | 4/1986 | Sheldon, III et al. |
| 4,742,003 A | 5/1988 | Derynck et al. |
| 4,764,454 A | 8/1988 | Ichijima et al. |
| 5,120,548 A | 6/1992 | McClelland et al. |
| 5,180,818 A | 1/1993 | Cech et al. |
| 5,211,951 A | 5/1993 | Sparer et al. |
| 5,445,934 A | 8/1995 | Fodor et al. |
| 5,464,826 A | 11/1995 | Grindey et al. |
| 5,487,889 A | 1/1996 | Eckert et al. |
| 5,553,037 A | 9/1996 | Tachibana |
| 5,624,937 A | 4/1997 | Reel et al. |
| 5,650,376 A | 7/1997 | Badaye et al. |
| 5,656,454 A | 8/1997 | Lee et al. |
| 5,658,374 A | 8/1997 | Glover |
| 5,733,913 A | 3/1998 | Blankley et al. |
| 5,747,651 A | 5/1998 | Lemischka |
| 5,750,376 A | 5/1998 | Weiss et al. |
| 5,770,599 A | 6/1998 | Gibson |
| 5,792,783 A | 8/1998 | Tang et al. |
| 5,891,996 A | 4/1999 | Mateo de Acosta del Rio et al. |
| 5,948,438 A | 9/1999 | Staniforth et al. |
| 6,027,880 A | 2/2000 | Cronin et al. |
| 6,057,100 A | 5/2000 | Heyneker |
| 6,143,764 A | 11/2000 | Kubo et al. |
| 6,156,501 A | 12/2000 | McGall et al. |
| 6,156,522 A | 12/2000 | Keay et al. |
| 6,217,866 B1 | 4/2001 | Schlessinger et al. |
| 6,242,002 B1 | 6/2001 | Tritthart et al. |
| 6,261,776 B1 | 7/2001 | Pirrung et al. |
| 6,346,398 B1 | 2/2002 | Pavco et al. |
| 6,351,255 B1 | 2/2002 | Ishizuka et al. |
| 6,475,525 B1 | 11/2002 | Komuro et al. |
| 6,476,040 B1 | 11/2002 | Norris et al. |
| 6,524,583 B1 | 2/2003 | Thorpe et al. |
| 6,534,535 B1 | 3/2003 | Zhu et al. |
| 6,544,552 B2 | 4/2003 | Sparks et al. |
| 6,576,424 B2 | 6/2003 | Fodor et al. |
| 6,596,311 B1 | 7/2003 | Dobetti et al. |

(Continued)

FOREIGN PATENT DOCUMENTS

| CA | 2 361 057 | 7/2000 |
|---|---|---|
| CA | 2606719 | 12/2006 |

(Continued)

OTHER PUBLICATIONS

Yamada et al, Clin Cancer Res, 17:2528-2537, Apr. 15, 2011.*
Sherman et al J Clinical Oncol, 29: 5503A, May 20, 2011.*
Granziero et al, Eur. J. Immunol. 1999, 29:1127-1138.*
Byers, T., CA Journal, vol. 49, No. 6, Nov./Dec. 1999.*
Gong et al, Academic Journal of Second Military Medical University, 28:701-703, 2007, English translation).*
"Carboxymethyl Cellulose Sodium." Chemical Land 21. Retrieved Apr. 24, 2012. http://www.chemicalland21.comlindustrialchem/perfonnancepolymer/CARBOXYMETHYL%20CELLULOSE%20SODIUM%20SAL_T.htm, 2 pages.
"Carboxymethylcellulose Sodium." Merck Index: An Encyclopedia of Chemicals, Drugs, & Biologicals: 13th Ed. New Jersey: Merck & Co (2001), p. 308.

(Continued)

*Primary Examiner* — Mark Halvorson
(74) *Attorney, Agent, or Firm* — Fish & Richardson P.C.

(57) ABSTRACT

Biomarkers are provided that are predictive of a subject's responsiveness to a therapy comprising lenvatinib or a pharmaceutically acceptable salt thereof (e.g., lenvatinib mesylate). The biomarkers, compositions, and methods described herein are useful in selecting appropriate treatment modalities for a subject having cancer (e.g., thyroid cancer, kidney cancer), suspected of having cancer, or at risk of developing cancer.

17 Claims, 2 Drawing Sheets

(56) References Cited

U.S. PATENT DOCUMENTS

| | | | |
|---|---|---|---|
| 6,676,941 B2 | 1/2004 | Thorpe et al. |
| 6,762,180 B1 | 7/2004 | Roth et al. |
| 6,797,823 B1 | 9/2004 | Kubo et al. |
| 6,811,779 B2 | 11/2004 | Rockwell et al. |
| 6,812,341 B1 | 11/2004 | Conrad |
| 6,821,987 B2 | 11/2004 | Kubo et al. |
| 7,005,430 B2 | 2/2006 | Ueno et al. |
| 7,101,663 B2 | 9/2006 | Godfrey et al. |
| 7,135,466 B2 | 11/2006 | Sakai et al. |
| 7,169,789 B2 | 1/2007 | Kubo et al. |
| 7,253,286 B2 | 8/2007 | Funahashi et al. |
| 7,435,590 B2 | 10/2008 | Komurasaki |
| 7,485,658 B2 | 2/2009 | Bolger et al. |
| 7,495,104 B2 | 2/2009 | Miwa et al. |
| 7,547,703 B2 | 6/2009 | Roth et al. |
| 7,550,483 B2 | 6/2009 | Sakaguchi et al. |
| 7,612,092 B2 | 11/2009 | Funahashi et al. |
| 7,612,208 B2 | 11/2009 | Matsushima et al. |
| 7,725,303 B2 | 5/2010 | Tramontana |
| 7,759,518 B2 | 7/2010 | Maderna et al. |
| 7,820,664 B2 | 10/2010 | Vernier et al. |
| 7,846,941 B2 | 12/2010 | Zhang et al. |
| 7,855,290 B2 | 12/2010 | Matsushima et al. |
| 7,863,288 B2 | 1/2011 | Ibrahim et al. |
| 7,973,160 B2 | 7/2011 | Funahashi et al. |
| 7,998,948 B2 | 8/2011 | Hiroshi et al. |
| 8,044,240 B2 | 10/2011 | Dimock |
| 8,063,049 B2 | 11/2011 | Koh et al. |
| 8,101,799 B2 | 1/2012 | Maderna et al. |
| 8,143,271 B2 | 3/2012 | Ibrahim et al. |
| 8,252,842 B2 | 8/2012 | Dimock |
| 8,288,538 B2 | 10/2012 | Matsushima et al. |
| 8,372,981 B2 | 2/2013 | Funahashi et al. |
| 8,377,938 B2 | 2/2013 | Matsushima et al. |
| 8,415,469 B2 | 4/2013 | Ibrahim et al. |
| 8,466,316 B2 | 6/2013 | Dimock |
| 8,470,818 B2 | 6/2013 | Ibrahim et al. |
| 8,580,254 B2 | 11/2013 | Adam et al. |
| 8,648,116 B2 | 2/2014 | Vernier et al. |
| 8,759,577 B2 | 6/2014 | Dimock |
| 8,808,742 B2 | 8/2014 | Quart et al. |
| 8,815,241 B2 | 8/2014 | Yamamoto |
| 2002/0010203 A1 | 1/2002 | Lipson et al. |
| 2002/0040127 A1 | 4/2002 | Jiang et al. |
| 2003/0013208 A1 | 1/2003 | Jendoubi |
| 2003/0087907 A1 | 5/2003 | Kubo et al. |
| 2003/0113713 A1 | 6/2003 | Glezer et al. |
| 2003/0215523 A1 | 11/2003 | Ozawa et al. |
| 2004/0002505 A1 | 1/2004 | Ozawa et al. |
| 2004/0009965 A1 | 1/2004 | Collins et al. |
| 2004/0034026 A1 | 2/2004 | Wood et al. |
| 2004/0053908 A1 | 3/2004 | Funahashi et al. |
| 2004/0086915 A1 | 5/2004 | Lin et al. |
| 2004/0132727 A1 | 7/2004 | Sakai et al. |
| 2004/0132772 A1 | 7/2004 | Awad et al. |
| 2004/0152759 A1 | 8/2004 | Abrams et al. |
| 2004/0162333 A1 | 8/2004 | Mezaache et al. |
| 2004/0167134 A1 | 8/2004 | Bruns et al. |
| 2004/0171068 A1 | 9/2004 | Wehland et al. |
| 2004/0191254 A1 | 9/2004 | Fagin |
| 2004/0224972 A1 | 11/2004 | Ozawa et al. |
| 2004/0229876 A1 | 11/2004 | Kubo et al. |
| 2004/0242506 A1 | 12/2004 | Barges Causeret et al. |
| 2004/0253205 A1 | 12/2004 | Yamamoto et al. |
| 2004/0259834 A1 | 12/2004 | Kasprzyk et al. |
| 2005/0014727 A1 | 1/2005 | Muller et al. |
| 2005/0049264 A1 | 3/2005 | Miwa et al. |
| 2005/0119303 A1 | 6/2005 | Wakabayashi et al. |
| 2005/0176802 A1 | 8/2005 | Tang et al. |
| 2005/0187236 A1 | 8/2005 | Tsuruoka et al. |
| 2005/0209452 A1 | 9/2005 | Bornsen et al. |
| 2005/0272688 A1 | 12/2005 | Higgins et al. |
| 2005/0277652 A1 | 12/2005 | Matsushima et al. |
| 2005/0288521 A1 | 12/2005 | Naidu et al. |
| 2006/0004017 A1 | 1/2006 | Stokes et al. |
| 2006/0004029 A1 | 1/2006 | Tsuruoka et al. |
| 2006/0057195 A1 | 3/2006 | Nonomura et al. |
| 2006/0079494 A1 | 4/2006 | Santi et al. |
| 2006/0135486 A1 | 6/2006 | Owa et al. |
| 2006/0160832 A1 | 7/2006 | Funahashi et al. |
| 2006/0178399 A1 | 8/2006 | Nishizawa et al. |
| 2006/0189629 A1 | 8/2006 | Bolger et al. |
| 2006/0292192 A1 | 12/2006 | Hasenzahl et al. |
| 2007/0004773 A1 | 1/2007 | Sakaguchi et al. |
| 2007/0014856 A1 | 1/2007 | Takagi et al. |
| 2007/0027318 A1 | 2/2007 | Kubo et al. |
| 2007/0032521 A1 | 2/2007 | Moussy et al. |
| 2007/0037849 A1 | 2/2007 | Naito et al. |
| 2007/0078159 A1 | 5/2007 | Matsushima |
| 2007/0117842 A1 | 5/2007 | Arimoto et al. |
| 2007/0214604 A1 | 9/2007 | Yi |
| 2007/0298111 A1 | 12/2007 | Ueki |
| 2008/0207617 A1 | 8/2008 | Miwa et al. |
| 2008/0214604 A1 | 9/2008 | Furitsu et al. |
| 2008/0241835 A1 | 10/2008 | Mehraban et al. |
| 2008/0280302 A1* | 11/2008 | Kebebew ............ C12Q 1/6886 435/6.14 |
| 2009/0047278 A1 | 2/2009 | Owa et al. |
| 2009/0047365 A1 | 2/2009 | Owa et al. |
| 2009/0053236 A1 | 2/2009 | Yamamoto |
| 2009/0202541 A1 | 8/2009 | Bruns et al. |
| 2009/0209580 A1 | 8/2009 | Matsui |
| 2009/0247576 A1 | 10/2009 | Kamata |
| 2009/0264464 A1 | 10/2009 | Yamamoto et al. |
| 2009/0304694 A1 | 12/2009 | Oliner et al. |
| 2010/0048503 A1 | 2/2010 | Yamamoto |
| 2010/0048620 A1 | 2/2010 | Yamamoto |
| 2010/0092490 A1 | 4/2010 | Uenaka et al. |
| 2010/0105031 A1 | 4/2010 | Matsui et al. |
| 2010/0239688 A1 | 9/2010 | Yamamoto |
| 2010/0324087 A1 | 12/2010 | Yamamoto |
| 2011/0118470 A1 | 5/2011 | Funahashi et al. |
| 2011/0158983 A1 | 6/2011 | Bascomb et al. |
| 2011/0166174 A1 | 7/2011 | Zhang et al. |
| 2011/0293615 A1 | 12/2011 | Yamamoto |
| 2012/0022076 A1 | 1/2012 | Maderna et al. |
| 2012/0077842 A1 | 3/2012 | Bando |
| 2012/0184452 A1* | 7/2012 | Pastoriza Rodriguez ........... C12Q 1/6886 506/9 |
| 2012/0207753 A1 | 8/2012 | Yu et al. |
| 2012/0219522 A1 | 8/2012 | Xi |
| 2012/0244209 A1 | 9/2012 | Roth et al. |
| 2012/0263677 A1 | 10/2012 | Eagle et al. |
| 2012/0283206 A1 | 11/2012 | Bruns et al. |
| 2013/0123274 A1 | 5/2013 | Nakagawa et al. |
| 2013/0296365 A1 | 11/2013 | Bando |

FOREIGN PATENT DOCUMENTS

| | | |
|---|---|---|
| CH | 656535 | 7/1986 |
| CN | 1293041 | 5/2001 |
| CN | 1473041 | 2/2004 |
| CN | 1478078 | 2/2004 |
| CN | 1634043 | 7/2005 |
| CN | 1772052 | 5/2006 |
| CN | 1890220 | 1/2007 |
| CN | 101001629 | 7/2007 |
| CN | 101029022 | 9/2007 |
| CN | 101316590 | 12/2008 |
| CN | 101454311 | 6/2009 |
| CN | 102470133 | 5/2012 |
| EP | 0 203 126 | 12/1986 |
| EP | 0 297 580 | 1/1989 |
| EP | 0 405 425 | 1/1991 |
| EP | 0 408 496 | 1/1991 |
| EP | 0 427 519 | 5/1991 |
| EP | 0 602 851 | 6/1994 |
| EP | 0 684 637 | 11/1995 |
| EP | 0 684 820 | 12/1995 |
| EP | 0 712 863 | 5/1996 |
| EP | 0 795 556 | 9/1997 |
| EP | 0 837 063 | 4/1998 |
| EP | 0 860 433 | 8/1998 |

(56) References Cited

FOREIGN PATENT DOCUMENTS

| | | |
|---|---|---|
| EP | 0 870 842 | 10/1998 |
| EP | 0 930 305 | 7/1999 |
| EP | 0 930 310 | 7/1999 |
| EP | 1 029 853 | 8/2000 |
| EP | 1 044 969 | 10/2000 |
| EP | 0 543 942 | 1/2001 |
| EP | 1 153 920 | 11/2001 |
| EP | 1 382 604 | 1/2004 |
| EP | 1 411 046 | 4/2004 |
| EP | 1 415 987 | 5/2004 |
| EP | 1 447 045 | 8/2004 |
| EP | 1 447 405 | 8/2004 |
| EP | 1 506 962 | 2/2005 |
| EP | 1 522 540 | 4/2005 |
| EP | 1 535 910 | 6/2005 |
| EP | 1 552 833 | 7/2005 |
| EP | 1 566 379 | 8/2005 |
| EP | 1 604 665 | 12/2005 |
| EP | 1 331 005 | 4/2006 |
| EP | 1 683 785 | 7/2006 |
| EP | 1 698 623 | 9/2006 |
| EP | 1 777 218 | 4/2007 |
| EP | 1 797 877 | 6/2007 |
| EP | 1 797 881 | 6/2007 |
| EP | 1 859 793 | 11/2007 |
| EP | 1 859 797 | 11/2007 |
| EP | 1 889 836 | 2/2008 |
| EP | 1 894 918 | 3/2008 |
| EP | 1 925 676 | 5/2008 |
| EP | 1 925 941 | 5/2008 |
| EP | 1 949 902 | 7/2008 |
| EP | 1 964 837 | 9/2008 |
| EP | 2 062 886 | 5/2009 |
| EP | 2 116 246 | 11/2009 |
| EP | 2 119 707 | 11/2009 |
| EP | 2 133 094 | 12/2009 |
| EP | 2 133 095 | 12/2009 |
| EP | 2 218 712 | 8/2010 |
| EP | 2293071 | 3/2011 |
| EP | 2 711 433 | 3/2014 |
| GB | 2253848 | 9/1992 |
| GB | 2456907 | 8/2009 |
| IL | 148756 | 10/2007 |
| IN | 236500 | 11/2009 |
| JP | 61-148115 | 7/1986 |
| JP | 63-028427 | 6/1988 |
| JP | 1-022874 | 1/1989 |
| JP | 2-291295 | 12/1990 |
| JP | 4-341454 | 11/1992 |
| JP | 6-153952 | 6/1994 |
| JP | 6-287148 | 10/1994 |
| JP | 7-176103 | 7/1995 |
| JP | 8-045927 | 2/1996 |
| JP | 8-048078 | 2/1996 |
| JP | 9-023885 | 1/1997 |
| JP | 9-234074 | 9/1997 |
| JP | 10-114655 | 5/1998 |
| JP | 10-147524 | 6/1998 |
| JP | 3088018 | 6/1998 |
| JP | 10-316576 | 12/1998 |
| JP | 11-501343 | 2/1999 |
| JP | 11-143429 | 5/1999 |
| JP | 11-158149 | 6/1999 |
| JP | 11-322596 | 11/1999 |
| JP | 3040486 | 5/2000 |
| JP | 3420549 | 10/2000 |
| JP | 2000-325080 | 11/2000 |
| JP | 2000-328080 | 11/2000 |
| JP | 2001-047890 | 2/2001 |
| JP | 2001-131071 | 5/2001 |
| JP | 2002-003365 | 1/2002 |
| JP | 2002-505269 | 2/2002 |
| JP | 2002-114710 | 4/2002 |
| JP | 2002-509872 | 4/2002 |
| JP | 2002-536056 | 10/2002 |
| JP | 2002-536414 | 10/2002 |
| JP | 2003-012668 | 1/2003 |
| JP | 2003-026576 | 1/2003 |
| JP | 2003-252737 | 9/2003 |
| JP | 2003-525595 | 9/2003 |
| JP | 2004-513964 | 5/2004 |
| JP | 2004-155773 | 6/2004 |
| JP | 2004-517859 | 6/2004 |
| JP | 2004-531549 | 10/2004 |
| JP | 2005-272474 | 10/2004 |
| JP | 2005-501074 | 1/2005 |
| JP | 2005-504111 | 2/2005 |
| JP | 2005-124034 | 5/2005 |
| JP | 2005-520834 | 7/2005 |
| JP | 3712393 | 11/2005 |
| JP | 2006-508981 | 3/2006 |
| JP | 2006-515884 | 6/2006 |
| JP | 2006-230816 | 9/2006 |
| JP | 2008-546797 | 12/2008 |
| JP | 2009-132660 | 6/2009 |
| JP | 2010-535233 | 11/2010 |
| KR | 10-0589032 | 11/2005 |
| RU | 2328489 | 7/2008 |
| RU | 2362771 | 7/2009 |
| WO | WO 1986/003222 | 6/1986 |
| WO | WO 1992/020642 | 11/1992 |
| WO | WO 1993/11748 | 6/1993 |
| WO | WO 1994/009010 | 4/1994 |
| WO | WO 1995/015758 | 6/1995 |
| WO | WO 1995/017181 | 6/1995 |
| WO | WO 1995/019774 | 7/1995 |
| WO | WO 1996/009294 | 3/1996 |
| WO | WO 1996/026997 | 9/1996 |
| WO | WO 1996/030347 | 10/1996 |
| WO | WO 1996/033980 | 10/1996 |
| WO | WO 1996/039145 | 12/1996 |
| WO | WO 1996/040080 | 12/1996 |
| WO | WO 1996/040142 | 12/1996 |
| WO | WO 1997/003069 | 1/1997 |
| WO | WO 1997/013760 | 4/1997 |
| WO | WO 1997/013771 | 4/1997 |
| WO | WO 1997/017329 | 5/1997 |
| WO | WO 1997/021437 | 6/1997 |
| WO | WO 1997/038984 | 10/1997 |
| WO | WO 1997/048693 | 12/1997 |
| WO | WO 1998/000134 | 1/1998 |
| WO | WO 1998/002434 | 1/1998 |
| WO | WO 1998/002437 | 1/1998 |
| WO | WO 1998/002438 | 1/1998 |
| WO | WO 1998/013350 | 4/1998 |
| WO | WO 1998/014437 | 4/1998 |
| WO | WO 1998/023613 | 6/1998 |
| WO | WO 1998/029137 | 7/1998 |
| WO | WO 1998/032436 | 7/1998 |
| WO | WO 1998/035958 | 8/1998 |
| WO | WO 1998/037079 | 8/1998 |
| WO | WO 1998/050346 | 11/1998 |
| WO | WO 1998/052558 | 11/1998 |
| WO | WO 1999/000357 | 1/1999 |
| WO | WO 1999/032106 | 7/1999 |
| WO | WO 1999/032110 | 7/1999 |
| WO | WO 1999/032111 | 7/1999 |
| WO | WO 1999/032436 | 7/1999 |
| WO | WO 1999/035132 | 7/1999 |
| WO | WO 1999/035146 | 7/1999 |
| WO | WO 1999/043654 | 9/1999 |
| WO | WO 1999/062890 | 12/1999 |
| WO | WO 2000/019985 | 4/2000 |
| WO | WO 2000/031048 | 6/2000 |
| WO | WO 2000/042012 | 7/2000 |
| WO | WO 2000/043366 | 7/2000 |
| WO | WO 2000/043384 | 7/2000 |
| WO | WO 2000/044728 | 8/2000 |
| WO | WO 2000/047212 | 8/2000 |
| WO | WO 2000/050405 | 8/2000 |
| WO | WO 2000/071097 | 11/2000 |
| WO | WO 2001/002369 | 1/2001 |
| WO | WO 2001/023375 | 4/2001 |
| WO | WO 2001/027081 | 4/2001 |

(56) References Cited

FOREIGN PATENT DOCUMENTS

| | | |
|---|---|---|
| WO | WO 2001/032926 | 5/2001 |
| WO | WO 2001/036403 | 5/2001 |
| WO | WO 2001/040217 | 6/2001 |
| WO | WO 2001/045689 | 6/2001 |
| WO | WO 2001/047890 | 7/2001 |
| WO | WO 2001/047931 | 7/2001 |
| WO | WO 2001/060814 | 8/2001 |
| WO | WO 2002/016348 | 2/2002 |
| WO | WO 2002/032872 | 4/2002 |
| WO | WO 2002/036117 | 5/2002 |
| WO | WO 2002/041882 | 5/2002 |
| WO | WO 2002/044156 | 6/2002 |
| WO | WO 2002/072578 | 9/2002 |
| WO | WO 2002/080975 | 10/2002 |
| WO | WO 2002/088110 | 11/2002 |
| WO | WO 2002/092091 | 11/2002 |
| WO | WO 2003/006462 | 1/2003 |
| WO | WO 2003/013529 | 2/2003 |
| WO | WO 2003/024386 | 3/2003 |
| WO | WO 2003/027102 | 3/2003 |
| WO | WO 2003/028711 | 4/2003 |
| WO | WO 2003/033472 | 4/2003 |
| WO | WO 2003/050090 | 6/2003 |
| WO | WO 2003/074045 | 9/2003 |
| WO | WO 2003/079020 | 9/2003 |
| WO | WO 2004/006862 | 1/2004 |
| WO | WO 2004/020434 | 3/2004 |
| WO | WO 2004/032872 | 4/2004 |
| WO | WO 2004/032937 | 4/2004 |
| WO | WO 2004/035052 | 4/2004 |
| WO | WO 2004/039782 | 5/2004 |
| WO | WO 2004/041308 | 5/2004 |
| WO | WO 2004/043472 | 5/2004 |
| WO | WO 2004/045523 | 6/2004 |
| WO | WO 2004/064730 | 8/2004 |
| WO | WO 2004/078144 | 9/2004 |
| WO | WO 2004/080462 | 9/2004 |
| WO | WO 2004/080966 | 9/2004 |
| WO | WO 2004/101526 | 11/2004 |
| WO | WO 2005/004870 | 1/2005 |
| WO | WO 2005/021537 | 3/2005 |
| WO | WO 2005/027972 | 3/2005 |
| WO | WO 2005/030140 | 4/2005 |
| WO | WO 2005/044788 | 5/2005 |
| WO | WO 2005/051366 | 6/2005 |
| WO | WO 2005/056764 | 6/2005 |
| WO | WO 2005/063713 | 7/2005 |
| WO | WO 2005/082854 | 9/2005 |
| WO | WO 2005/092896 | 10/2005 |
| WO | WO 2005/117887 | 12/2005 |
| WO | WO 2006/030826 | 3/2006 |
| WO | WO 2006/030941 | 3/2006 |
| WO | WO 2006/030947 | 3/2006 |
| WO | WO 2006/036941 | 4/2006 |
| WO | WO 2006/038552 | 4/2006 |
| WO | WO 2006/062984 | 6/2006 |
| WO | WO 2006/090930 | 8/2006 |
| WO | WO 2006/090931 | 8/2006 |
| WO | WO 2006/137474 | 12/2006 |
| WO | WO 2007/000347 | 1/2007 |
| WO | WO 2007/014335 | 2/2007 |
| WO | WO 2007/015569 | 2/2007 |
| WO | WO 2007/015578 | 2/2007 |
| WO | WO 2007/023768 | 3/2007 |
| WO | WO 2007/040565 | 4/2007 |
| WO | WO 2007/052849 | 5/2007 |
| WO | WO 2007/052850 | 5/2007 |
| WO | WO 2007/061127 | 5/2007 |
| WO | WO 2007/061130 | 5/2007 |
| WO | WO 2007/136103 | 11/2007 |
| WO | WO 2008/023698 | 2/2008 |
| WO | WO 2008/026748 | 3/2008 |
| WO | WO 2008/088088 | 7/2008 |
| WO | WO 2008/093855 | 8/2008 |
| WO | WO 2008/155387 | 12/2008 |
| WO | 2009/018238 | 2/2009 |
| WO | WO 2009/060945 | 5/2009 |
| WO | WO 2009/077874 | 6/2009 |
| WO | WO 2009/096377 | 8/2009 |
| WO | WO 2009/140549 | 11/2009 |
| WO | WO 2009/150256 | 12/2009 |
| WO | WO 2010/006225 | 1/2010 |
| WO | WO 2010/048304 | 4/2010 |
| WO | WO 2011/017583 | 2/2011 |
| WO | WO 2011/022335 | 2/2011 |
| WO | WO 2011/162343 | 12/2011 |
| WO | WO 2012/154935 | 11/2012 |
| WO | WO 2012/166899 | 12/2012 |

OTHER PUBLICATIONS

"Current Protocols in Molecular Biology", John Wiley & Sons Section 11.4-11.13 (1987), 62, pages.

"Pharmacokinetics (PK) and tolerability of GW786034, a VEGFR tyrosine kinase inhibitor, after daily oral administration to patients with solid tumors.", Proc. Am. Soc. Clin. Oncology, (Abstract 3054), 2004.

"Recent Results and Ongoing Trials with Panitumumab (ABX-EGF), a Fully Human Anti-Epidermal Growth Factor Receptor Antibody, in Metastatic Colorectal Cancer", Clinical Colorectal Cancer. 2005; 5(1):21-3.

"Arzneimittelwirkungen Lehrbuch der Pharmakologie und Toxikologie," Ernst Mutschler ED Mutschler E et al., Arzneimittelwirkungen Lehrbuch der Pharmakologie und Toxikologie, Wissenschaftliche Verlagsgesellschaft, Stuttgart, Jan. 1, 1999, p. 1-p. 5, XP007919509 (English translation).

"Chapter 2.2 Loslichkeit, Losungsgeschwindigkeit, Loslichkeitsverbesserung," Rudolf Voigt ED—Voigt R et al., Pharmazeutische Technologie fuer Studium und Beruf, DT. Apotheker-Verl, Stuttgart; DE, Jan. 1, 2000, p. 40-p. 52, XP008143620 (English translation).

"Clinical Trial: AMG 706 20040273 Thyroid Cancer Study: Stage 4 Cancer Treatments, Chat w/a Cancer Info Expert About Stage 4 Cancer Treatment Options," accessed from www.CancerCenter.com, 4 pages (2005).

Abrams et al., SU11248 Inhibits KIT and Platelet-derived Growth Factor Receptor Beta in Preclinical Models of Human Small Cell Lung CancerMolecular Cancer Therapeutics., 2: 471-478, 2003.

Abuzar et al., "Synthesis of some new 7-chloro-4-substituted quinolines as potential antiparasitic agents," Eur. J. Med. Chem., 21(1):5-8 (1986).

Agarwal et al., "Binding of discoidin domain receptor 2 to collagen I: an atomic force microscopy investigation," Biochemistry, 41(37):11091-11098 (2002).

Altschul et al., "Basic Local Alignment Search Tool", J. Mol. Biol. 215:403-410 (1990).

Amended Claims filed in EP App. Ser. No. 11798224.9, filed Aug. 2, 2013, 35 pages.

Amended Claims filed in KR App. Ser. No. 10-2010-7011023, filed Jul. 17, 2013, 15 pages (with English translation).

Amended Claims filed in RU App. Ser. No. 2013140169, dated Aug. 29, 2013, 17 pages (with English translation).

Amended description filed after receipt of search report for EP Patent App. No. 10809938.3, filed Dec. 8, 2011, 2 pages.

Amended description filed after receipt of search report for EP Patent App. No. 10809938.3, filed Sep. 14, 2010, 2 pages.

Amended Specification filed in AU App. Ser. No. 2012246490, filed Aug. 2, 2013, 15 pages.

Amendment after Allowance filed on Jan. 4, 2011 for CA App. Ser. No. 2426461, 12 pages.

Amendment and Argument filed on Apr. 27, 2012 in response to the JP Office Action for JP2007-542863, 13 pages and English translation.

Amendment and Response for Application No. IL Patent Application No. 195282 dated Jul. 11, 2013, 13 pages (with English translation).

Amendment and Response to Final Office Action under 37 C.F.R. § 1.116 for U.S. Appl. No. 12/092,539, filed Jun. 15, 2011, 9 pages.

(56) References Cited

OTHER PUBLICATIONS

Amendment and Response to Final Office Action under 37 C.F.R. § 1.116 for U.S. Appl. No. 12/864,817, filed Dec. 5, 2011, 10 pages.
Amendment and Response to Non-Final Office Action for U.S. Appl. No. 11/997,543, filed Aug. 19, 2011, 34 pages.
Amendment and Response to Office Action under 37 C.F.R § 1.111 for U.S. Appl. No. 12/439,339, dated Aug. 22, 2013, 14 pages.
Amendment and Response to Office Action under 37 C.F.R. § 1.111 dated Apr. 2, 2013 for U.S. Appl. No. 13/083,338, 9 pages.
Amendment and Response to Office Action under 37 C.F.R. §1.111 for U.S. Appl. No. 11/997,719, filed Dec. 23, 2010, 21 pages.
Amendment and Response to Office Action under 37 C.F.R. §1.111 for U.S. Appl. No. 12/092,539, filed Mar. 11, 2011, 9 pages.
Amendment and Response to Office Action under 37 C.F.R. §1.111 for U.S. Appl. No. 12/439,339, filed Feb. 7, 2012, 11 pages.
Amendment and Response to Office Action under 37 C.F.R. §1.111 for U.S. Appl. No. 12/524,754, filed Feb. 17, 2012, 13 pages.
Amendment and Response to Office Action under 37 C.F.R. §1.111 for U.S. Appl. No. 12/741,682, filed Jul. 30, 2012, 49 pages.
Amendment and Response to Office Action under 37 C.F.R. §1.111 for U.S. Appl. No. 12/864,817, filed Aug. 9, 2011, 12 pages.
Amendment and Response to Office Action under 37 C.F.R. §1.111 for U.S. Appl. No. 13/205,328, filed Apr. 11, 2012, 12 pages.
Amendment and Response to Office Action under 37 C.F.R. §1.116 for U.S. Appl. No. 11/997,543, filed Jan. 9, 2012, 27 pages.
Amendment and Response to Office Action under 37 C.F.R. §1.116 for U.S. Appl. No. 12/439,339, filed Jul. 30, 2012, 9 pages.
Amendment filed in EP App. Ser. No. 12774278.1, filed Aug. 13, 2013, 12 pages.
Amendment filed in JP App. Ser. No. 2008-532141, filed Jul. 5, 2013, 2 pages (with English translation).
Amendment filed in U.S. Appl. No. 13/805,826, dated Sep. 9, 2013, 14 pages.
Amendment filed on Apr. 11, 2006 for Cn App. Ser. No. 01819710.8, 35 pages (with English translation).
Amendment filed on Apr. 17, 2002 for TW App. Ser. No. 90125928, 26 pages (with English translation).
Amendment filed on Apr. 19, 2005 for JP App. Ser. No. 2002-536056, 26 pages (with English translation).
Amendment filed on Aug. 13, 2013 in JP App. Ser. No. P2009-540099, 8 pages (with English translation).
Amendment filed on Aug. 17, 2004 for ZS App. Ser. No. 2003/3567, 39 pages.
Amendment filed on Aug. 29, 2013 in CN App. Ser. No. 201280010898.X, 24 pages (with English translation).
Amendment filed on Aug. 4, 2004 for ZA App. Ser. No. 2003/3567, 95 pages.
Amendment filed on Aug. 6 2013, for JP App. Ser. No. 2009-551518, 6 pages (with English translation).
Amendment filed on Dec. 12, 2011 for JO Patent App. No. 55/2011, 6 pages (with English translation).
Amendment filed on Dec. 15, 2011 for VN App. Ser. No. 1-2011-03484, 5 pages (with English translation).
Amendment filed on Dec. 22, 2011 for ZA App. Ser. No. 2011/08697, 2 pages.
Amendment filed on Feb. 9, 2011 for TW App. Ser. No. 100104281, 2 pages.
Amendment filed on Jan. 11, 2010 for CN App. Ser. No. 200580026468.7, 4 pages (with English translation).
Amendment filed on Jan. 26, 2010 for CN App. Ser. No. 200710007097.9, 9 pages (with English translation).
Amendment filed on Jul. 2, 2009 for CN App. Ser. No. 200710007097.9, 9 pages (with English translation).
Amendment filed on Jun. 22, 2010 for CN App. Ser. No. 200710007097.9, 9 pages (with English translation).
Amendment filed on Mar. 20, 2012 for KR Patent App. No. 10-2012-7003846, 7 pages.
Amendment filed on Mar. 23, 2009 for JP Patent Application No. 2005-124034, 29 pages (with English translation).
Amendment filed on Mar. 6, 2006 for KR App. Ser. No. 10-2003-7005506, 34 pages (with English translation).
Amendment filed on Mar. 7, 2005 for JP App. Ser. No. 2002-536056, 23 pages (with English translation).
Amendment filed on Mar. 8, 2006 for KR App. Ser. No. 10-2005-7020292, 33 pages (with English translation).
Amendment filed on May 10, 2012 for JP Patent Application No. 2011-527665, 5 pages.
Amendment filed on May 21, 2009 for JP App. Ser. No. 2005-124034, 14 pages (with English translation).
Amendment filed on May 28, 2003 for CN App. Ser. No. 01819710.8, 8 pages (with English translation).
Amendment filed on Nov. 19, 2009 for CN App. Ser. No. 200710007097.9, 9 pages (with English translation).
Amendment filed on Nov. 24, 2011 for KR App. Ser. No. 10-2007-7001347, 7 pages (with English translation).
Amendment filed on Oct. 1, 2013 in IN App. Ser. No. 10502/CHENP/2012, 10 pages.
Amendment filed on Oct. 25, 2005 for KR App. Ser. No. 10-2003-7005506, 53 pages (with English translation).
Amendment filed on Oct. 28, 2011 for LB Patent App. No. 9292, 2 pages.
Amendment filed on Oct. 9, 2006 for CN App. Ser. No. 01819710.8, 28 pages (with English translation).
Amendment filed on Sep. 13, 2005 for CN App. Ser. No. 01819710.8, 51 pages (with English translation).
Amendment filed on Sep. 23, 2009 for CN App. Ser. No. 200580026468.7, 11 pages (with English translation).
Amendment filed on Sep. 23, 2013 in AU App. Ser. No. 2011270165, 35 pages.
Amendment for Chinese Patent Application No. 201080030508.6 dated Feb. 7, 2013, 17 pages with English translation.
Amendment for IN App. Ser. No. 7026/CHENP/2013, dated Sep. 5, 2013, 8 pages.
Amendment in Canadian App. Ser. No. 2828946, dated Aug. 30, 2013, 14 pages.
Amendment in Israeli App. Ser. No. 200090, dated Oct. 2, 2013, 10 pages (with English translation).
Amendment in Korean App. Ser. No. 10-2012-7033886, dated Sep. 27, 2013, 34 pages (with English translation).
Amendment in Mexican App. Ser. No. MX/a/2012/014776, dated Oct. 21, 2013, 10 pages (with English translation).
Amendment in Russian App. Ser. No. 2012158142, dated Oct. 17, 2013, 48 pages (with English translation).
Amendment, Response to Office Action under 37 C.F.R. § 1.111 and Information Disclosure Statement for U.S. Appl. No. 13/624,278, filed Jun. 28, 2013, 23 pages.
Amendments received before examination for EP App. Ser. No. 01976786.2, dated Sep. 10, 2004, 126 pages.
Amendments to the specification filed on Mar. 26, 2012 for AU Patent Appl. No. 2010285740, 15 pages.
American Association for Cancer Research, "Redefining the Frontiers of Science," 94th Annual Meeting, vol. 44, 2nd Edition, Washington Convention Center, Washington, DC (Jul. 11-14, 2003), 3 pages.
Amino et al., "YM-231146, a Novel Orally Sioavailable Inhibitor of Vascular Endothelial Growth Factor Receptor-2, Is Effective against Paclitaxel Resistant Tumors", Biological and Pharmaceutical Bulletin. 28:2096-2101, 2005.
Anderson and Flora, "Preparation of Water-Soluble Compounds Through Salt Formation," Practice of Medicinal Chem., 1996, pp. 739-754.
Anderson et al., "Preparation of Water-soluble Compounds through Salt Formation. The Practice of Medicinal Chemistry," *Technomics*, 347-349 and 355-356 (Sep. 25, 1999).
Anonymous, "Scientific Discussion," EMEA, URL: htttp://www.ema.europa.eu/docs/en_GB/document_library/EPARScientific_Discussion/human/000406/WC500022203.pdf, 1-61 (2004) (XP007918143), 62 pages.
Antibodies: A Laboratory Manual, E. Harlow and D. Lane, ed. Cold Spring Harbor Laboratory (Cold Spring Harbour, NY, 1988), 190 pages.

(56) References Cited

OTHER PUBLICATIONS

Applicant Interview Summary Under 37 C.F.R § 1.133(b) for U.S. Appl. No. 12/439,339, dated May 31, 2013, 7 pages.
Applicant Observation for CN App. Ser. No. 200780017371.9, filed May 29, 2013, 6 pages (with English translation).
Approval of request for amendments for EP App. Ser. No. 04025700.8, dated Mar. 13, 2008, 1 page.
Argument and Amendment for JP App. Ser. No. 2008-556208, filed Mar. 21, 2013, 15 pages (with English translation).
Argument and Amendment for CN 200880002425.9 filed on Jul. 18, 2011, 8 pages with English translation.
Argument and Amendment for JP App. Ser. No. 2008-532141, filed Nov. 29, 2012, 12 pages (with English translation).
Argument and Amendment for JP. App. Ser. No. 2008-516724, filed Nov. 28, 2012, 22 pages (with English translation).
Argument and Amendment for JP. App. Ser. No. 2009-123432, dated Jun. 12, 2012, 12 pages (with English translation).
Argument and Amendment for JP. App. Ser. No. 2009-529019, dated Jul. 3, 2012, 14 pages (with English translation).
Argument Brief filed on Mar. 6, 2006 for KR App. Ser. No. 10-2003-7005506, 45 pages (with English translation).
Argument Brief filed on Mar. 8, 2006 for KR App. Ser. No. 10-2005-7020292, 42 pages (with English translation).
Argument Brief filed on Nov. 24, 2011 for KR App. Ser. No. 10-2007-7001347, 52 pages (with English translation).
Argument Brief filed on Oct. 25, 2005 for KR App. Ser. No. 10-2003-7005506, 20 pages (with English translation).
Argument filed on Apr. 19, 2005 for JP App. Ser. No. 2002-536056, 6 pages (with English translation).
Argument filed on Aug. 13, 2013 in JP App. Ser. No. 2009-540099, 10 pages (with English translation).
Argument filed on Aug. 6, 2013 for JP Patent Application No. 2009-551518, 18 pages (with English translation).
Argument filed on Mar. 23, 2009 for JP App. Ser. No. 2005-124034, 12 pages (with English translation).
Argument filed on May 21, 2009 for JP App. Ser. No. 2005-124034, 5 pages (with English translation).
Asai et al., "Mechanism of Ret Activation by a Mutation of Aspartic Acid 631 Identified in Sporadic Pheochromocytoma", Biochemical and Biophysical Research Communications, 255, 587-590 (1999).
Asano et al., "Inhibition of Tumor Growth and Metastasis by an Immunoneutralizing Monoclonal Antibody to Human Vascular Endothelial Growth Factor/Vascular Permeability Factor121", Cancer Research., 55, 5296-5301, 1995.
*Asu no Shinyaku* ("The New Drugs of Tomorrow"), editing/printing by Technomics, Inc., 81-83 (Dec. 2006) (English translation), 14 pages.
Australian (""AU"") Office Action dated Oct. 29, 2009 for corresponding AU Application No. 2006285673, 3 pages.
Australian ("AU") Notice of Allowance dated Nov. 22, 2010 for corresponding AU Application No. 2006285673, 3 pages.
Australian ("AU") Office Action dated May 19, 2010 for corresponding AU Application No. 2006285673, 2 pages.
Australian ("AU") Office Action dated May 7, 2009 for corresponding AU Application No. 2006285673, 2 pages.
Australian Office Action directed at Appl. No. 2007252506 dated Nov. 7, 2011, 5 pages.
Australian Office Action directed at Appl. No. 2007252506 dated Jan. 13, 2012, 2 pages.
Australian Office Action for App. Ser. No. 2008205847, dated Apr. 11, 2012, 2 pages.
Australian Office Action for App. Ser. No. 2008211952, dated Apr. 3, 2012, 2 pages.
Australian Office Action for Application No. 2006309551 dated Feb. 2, 2012, 2 pages.
Australian Office Action for Application No. AU2006309551 dated Apr. 28, 2011, 3 pages.
Australian Response to Office Action directed at Appl. No. 2007252506 filed on Jan. 4, 2012, 74 pages.
Australian Response to Office Action directed at Appl. No. 2007252506 filed on Mar. 2, 2012, 4 pages.
Australian Response to Office Action for Application No. 2006309551 filed on Jan. 27, 2012, 81 pages.
Bainbridge et al., "A peptide encoded by exon 6 of VEGF (EG3306) inhibits VEGF-induced angiogenesis in vitro and ischaemic retinal neovascularisation in vivo", Biochem Biophys Res Commun., 302, 793-799, 2003.
Baker et al., "Blockade of vascular endothelial growth factor receptor and epidermal growth factor receptor signaling for therapy of metastatic human pancreatic cancer," Cancer Res., 62:1996-2003 (2002).
Bankston et al., "A Scaleable synthesis of BAY 43/9006: A Potent Raf Kinase Inhibitor for the Treatment of Cancer", Organic Process Res Dev., 6:777-81 (2002).
Bartsch et al., "A RET double mutation in the germline of a kindred with FMTC", Exp. Clin Endocrinol Diabetes, 108, 128-132, 2000.
Bastin et al., "Salt Selection and Optimisation Procedures for Pharmaceutical New Chemical Entities," Organic Process Research & Development, 4(5):427-435 (2000) (XP002228592).
Beebe et al., "Pharmacological Characterization of CP-547,632, a Novel Vascular Endothelial Growth Factor Receptor-2 Tyrosine Kinase Inhibitor for Cancer Therapyl", Cancer Research. 63:7301-9, 2003.
Behr et al., Improved Treatment of Medullary Thyroid Cancer in a Nude Mouse Model by Combined Radioimmunochemotherapy: Doxorubicin Potentiates the Therapeutic Efficacy of Radiolabeled Antibodies in a RadioresistantTumorType, 57 Cancer Res. 5309-5319 (Dec. 1, 1997).
Bellone et al., "Growth Stimulation of Colorectal Carcinoma Cells via the c-kit Receptor is Inhibited by TGF-β-1," Journal of Cellular Physiology, 172:1-11 (1997).
Benjamin et al., "Selective ablation of immature blood vessels in established human tumors follows vascular endothelial growth factor withdrawal," J. Clin. Invest., 103(2):159-165 (1999).
Berdel et al., "Recombinant Human Stem Cell Factor Stimulates Growth of a Human Glioblastoma Cell Line Expressing c-kit Protooncogene," Cancer Res., 52:3498-3502 (1992).
Berge et al., "Pharmaceutical Salts," *Journal of Pharmaceutical Sciences*, 66(1):1-19 (Jan. 1977) (XP002550655).
Bergers et al., "Benefits of targeting both pericytes and endothelial cells in the tumor vasculature with kinase inhibitors," J. Clin. Invest., 111(9):1287-1295 (2003).
Berndt et al., "A New Hot Spot for Mutations in the ret Protooncogene Causing Familial Medually Thyroid Carcinoma and Multiple Endocrine Neoplasia Type 2A", Journal of Clinical Endocrinology and Metabolism, 83, 770-774 (1998).
Bernex et al., "Spatial and temporal patterns of c-kit-expressing cells in WlacZ/+ and WlacZ/WlacZ mouse embryos", Development 122:3023-3033 (1996).
Blume-Jensen et al., "Activation of the Human c-kit Product by Ligand-Induced Dimerization Mediates Circular Actin Reorganization and Chemotaxis," The EMBO Journal, 10(13):4121-4128 (1991).
Boissan et al., "c-Kit and c-kit mutations in mastocytosis and other hematological diseases," J. Leukocyte Biol., 67:135-148 (2000).
Bold et al., "New anilinophthalazines as potent and orally well absorbed inhibitors of the VEGF receptor tyrosine kinases useful as antagonists of tumor-driven angiogenesis", Journal of Medicinal Chemistry., 43:2310-2323 (2000).
Bonferoni et al, "Influence of medium on dissolution-erosion behavior of Na carboxymethylcellulose and on viscoelastic properties of gels," International journal of pharmaceutics, 1995, vol. 117, No. 1, pp. 41-48.
Bramhall, S., "The Matrix Metalloproteinases and Their Inhibitors in Pancreatic Cancer", International J. Pancreatol., 21, 1-12, 1997.
Brief communication to applicant for EP App. Ser. No. 01976786.2, dated Sep. 9, 2005, 1 page.
Brueggen et al., "Preclinical profile of ABP309, a potent $2^{nd}$ generation VEGF receptor tyrosine kinase inhibitor belonging to the class of aminonicotinamides," EORTC-NCI-AACR Symp Mol Targets Cancer Ther., 2, (Abstract 172), 2004, 2 pages.

(56) References Cited

OTHER PUBLICATIONS

Bruns et al., "Effect of the vascular endothelial growth factor receptor-2 antibody DC101 plus gemcitabine on growth, metastasis and angiogenesis of human pancreatic cancer growing orthotopically in nude mice," J. Cancer, 102:101-108 (2002).
Bussolino et al., "Role of Soluble Mediators in Angiogenesis," Eur. J. Cancer, 32A(14):2401-2412 (1996).
Cairns et al., "New antiallergic pyrano[3,2g]quinoline-2,8-dicarboxylic acids with potential for the topical treatment of asthma," J. Med. Chem., 28(12):1832-1842 (1985).
Canadian ("CA") Office Action dated Jan. 14, 2010 for corresponding CA Application No. 2,620,594, 3 pages.
Canadian ("CA") Office Action dated Jan. 6, 2011 for corresponding CA Application No. 2,620,594, 3 pages.
Canadian Office Action for App. Ser. No. 2426461, dated Dec. 6, 2007, 5 pages.
Canadian Office Action for App. Ser. No. 2426461, dated Feb. 10, 2010, 2 pages.
Canadian Office Action for App. Ser. No. 2426461, dated May 8, 2009, 2 pages.
Canadian Office Action for App. Ser. No. 2426461, dated Nov. 20, 2008, 3 pages.
CancerCare, "Types of Lung Cancer," Cancer Care, Inc. [online] [retrieved on Nov. 12, 2009]. Retrieved from the Internet: www.lungcancer.org/reading/types.php?printable=true (2009).
Cappellen et al., "Frequent activating mutations of FGFR3 in human bladder and cervix carcinomas," Nat. Genet., 23:18-20 (1999).
Carlomagno et al., "Point Mutation of the RET Proto-Oncogene in the TT Human Medullary Thyroid Carcinoma cell Line", Biochemical and Biophysical Research Communications, 207,1022-1028 (1995).
Carlomagno et al., "BAY 43/9006 inhibition of oncogenic RET mutants," J. Natl. Cancer Inst., 98(5):326-34 (2006).
Carlomagno et al., "ZD6474, an orally available inhibitor of KDR tyrosine kinase activity, efficiently blocks oncogenic RET kinases," Cancer Res., 62:7284-7290 (2002).
Carniti et al., "The RetC620R Mutation Affects Renal and Enteric Development in a mouse Model of Hirschprung's Disease", American Journal of Pathology, 168, 1262-1275, (2006).
Carter et al., "Inhibition of drug-resistant mutants of ABL, KIT and EGF receptor kinases", Proceedings of the National Academy of Sciences of the United States of America., 102, 11011-11016, 2005.
Cell Technology, Supplementary Volume, "Bio-Experiment Illustrated vol. 5, No Fear of Proteins", Visual Laboratory Notebook Series, Section 6, Immunostaining, pp. 127-163, Shujunsha, Co., Ltd., 1997 (Japanese).
Chen et al., "FGFR3 as a therapeutic target of the small molecule inhibitor PKC412 in hematopoietic malignancies," Oncogene, 24:8259-8267 (2005).
Chesi et al., "Activated fibroblast growth factor receptor 3 is an oncogene that contributes to tumor progression in multiple myeloma," Blood, 97:729-736 (2001).
Chesi et al., "Frequent translocation t(4;14)(p16.3;q32.3) in multiple myeloma is associated with increased expression and activating mutations of fibroblast growth factor receptor 3," Nat. Genet., 16:260-264 (1997).
Cheung et al., "Discovery of indazolylpyrimidines as potent inhibitors of VEGFR2 tyrosine kinase," Proceedings of the American Association for Cancer Research, 44, 9, (Abstract 40), 2003, 2 pages.
Chikahisa et al, "TSU-68 KDR/flk-1 inhibitor, can modulate the anti-tumor activity of paclitaxel by the induction of endothelial cell and tumor cell apoptosis," 61st Annual Meeting of the Japanese Cancer Association, 2002, 61(1374):443, 5 total pages (with English translation).
Chinese ("CN") Office Action dated Dec. 4, 2009 for corresponding CN Application No. 200680036592.6, 8 pages with English translation.
Chinese Office Action directed at Appl. No. 200780017371 .9 dated Oct. 20, 2010, 13 pages with English translation.
Chinese Office Action for App. Ser. No. 200780017371.9, dated Mar. 7, 2012, 8 pages with English translation.
Chinese Office Action for App. Ser. No. 200880002425.9, dated Mar. 7, 2012, 7 pages (with English translation).
Chinese Office Action for App. Ser. No. 200880003336.6, dated May 24, 2011, 24 pages (with English translation).
Chinese Office Action for App. Ser. No. 200880115011.7, dated Feb. 20, 2012, 10 pages (with English translation).
Chinese Office Action for App. Ser. No. 201080030508.6, dated Nov. 30, 2012, 13 pages, (with English translation).
Chinese Office Action for Application No. 200680041355.9 dated Mar. 5, 2010, 21 pages (with English translation).
Chinese Office Action for Application No. 200680041355.9 dated Aug. 24, 2010, 10 pages (with English translation).
Chinese Office Action for CN 200680020317.5 dated Aug. 3, 2012 with English translation, 11 pages.
Chinese Office Action with the English translation dated, Feb. 29, 2012, for Application No. 200680036592.6, 7 pages.
Chinese Response to Office Action directed at Appl. No. 200780017371 .9 filed on Feb. 24, 2011, 10 pages with English translation.
Chinese Response to Office Action for Application No. 200680041355.9 filed on Jul. 19, 2010, 4 pages with English translation.
Chinese Response to Office Action for Application No. 200680041355.9 filed on Nov. 8, 2010, 6 pages with English translation.
Chinese Response to the Chinese Decision of Rejection, filed on Feb. 7, 2013, for corresponding Chinese Application No. 200680036592.6, 27 pages.
Ciardiello et al., "ZD1839 (IRESSA), an EGFR-selective tyrosine kinase inhibitor, enhances taxane activity in bcl-2 overexpressing, multidrug-resistant MCF-7 ADR human breast cancer cells," Int. J. Cancer, 98:463-469 (2002).
CIPO Notice of Allowance for Appl. No. 2,620,594 dated May 3, 2012, 1 page.
Clark et al., "Safety and Pharmacokinetics of the Dual Action Raf Kinase and Vascular Endothelial Growth Factor Receptor Inhibitor, BAY43-9006, in Patients with Advanced Refractory Solid Tumors," Clin. Cancer Res., 11:5472-5480 (2005).
ClinicalTrials.gov, "A Study of E7080 Alone, and in Combination With Everolimus in Subjects With Unresectable Advanced or Metastatic Renal Cell Carcinoma Following One Prior Vascular Endothelial Growth Factor (VEGF)-Targeted Treatment," National Institutes of Health, Food and Drug Administration, National Library of Medicine, [online] [retrieved on Sep. 27, 2010]. Retrieved from the Internet: http://clinicaltrials.gov/ct2/show/NCT01136733, (May 26, 2010).
CN200780032071.8 Office Action dated Oct. 13, 2010, 29 pages with English translation.
CN200780032071.8 Response to Office Action filed on Feb. 16, 2011, 62 pages with English translation.
CN200880003336.6 Response to Office Action filed on Oct. 8, 2011, 10 pages.
Cohen et al., "Expression of Stem Cell Factor and c-kit in Human Neuroblastoma," Blood, 84(10):3465-3472 (1994).
Colombian Office Action for App. Ser. No. 12-022608, dated Oct. 7, 2013, 10 pages (with English translation).
Communication about intention to grant a European patent for EP App. Ser. No. 01976786.2, dated Sep. 4, 2006, 173 pages.
Communication about intention to grant a European patent for EP App. Ser. No. 04025700.8, dated Oct. 15, 2007, 392 pages.
Communication about intention to grant a European patent for EP App. Ser. No. 06023078.6, dated Jul. 18, 2008, 169 pages.
Communication about intention to grant a European patent for EP App. Ser. No. 05783232.1, dated Nov. 20, 2008, 70 pages.
Communication from the Examining Division for EP App. Ser. No. 01976786.2, dated Aug. 17, 2005, 4 pages.
Communication from the Examining Division for EP App. Ser. No. 01976786.2, dated Mar. 21, 2006, 3 pages.

(56) References Cited

OTHER PUBLICATIONS

Communication from the Examining Division for EP App. Ser. No. 01976786.2, dated Sep. 19, 2005, 4 pages.
Communication from the Examining Division for EP App. Ser. No. 04025700.8, dated Oct. 23, 2006, 2 pages.
Communication from the Examining Division for EP App. Ser. No. 05783232.1, dated Feb. 7, 2008, 1 pages.
Communication from the Examining Division for EP App. Ser. No. 06023078.6, dated Aug. 2, 2007, 1 page.
Communication from the Examining Division for EP App. Ser. No. 06023078.6, dated Sep. 26, 2007, 2 pages.
Communication regarding the expiry of opposition period for EP App. Ser. No. 01976786.2, dated Jan. 4, 2008, 1 page.
Communication regarding the expiry of opposition period for EP App. Ser. No. 04025700.8, dated May 7, 2009, 1 page.
Communication regarding the expiry of opposition period for EP App. Ser. No. 05783232.1, dated Feb. 19, 2010, 1 page.
Communication regarding the expiry of opposition period for EP App. Ser. No. 06023078.6, dated Nov. 4, 2009, 1 page.
Continuation Patent Application, Preliminarty Amendment and Information Disclosure Statement for U.S. Appl. No. 13/923,858, filed Jun. 21, 2013, 97 pages.
Corbin et al., "Sensitivity of oncogenic KIT mutants to the kinase inhibitors MLN518 and PD180970", Blood., 104, 3754-3757, 2004.
Corvi et al., "RET IPCM-1: a novel fusion gene in papillary thyroid carcinoma", Oncogene, 19: 4236-4242 (2000).
Croom et al., "Imatinib mesylate," *Drugs*, 63(5):513-522 (2003).
Da Silva et al., "A novel germ-line point mutation in RET exon 8 (Gly(533)Cys) in a large kindred with familial medullary thyroid carcinoma," *J. Clin. Endocrinol. Metab*., 88:5438-5443 (2003).
David et al., "A Phase I Trial of the Epidermal Growth Factor Receptor (EGFR)-Directed Bispecific Antibody (BsAB) MDX-447 in Patients with Solid Tumors. (Meeting abstract).", ASCO 18: 433, Abstract 1999.
De Lange et al., "Phase II trial of cisplatin and gemcitabine in patients with advanced gastric cancer," Annals of Oncology, 15:484-488 (2004).
Decision of Final Rejection issued in CN App. Ser. No. 200780017371.9, dated Jul. 3, 2013, 16 pages (with English translation).
Decision of Rejection dated Oct. 30, 2012 issued for corresponding Chinese Application No. 200680036592.6, 8 pages with full English language translation.
Decision to grant a European patent for EP App. Ser. No. 01976786.2, dated Feb. 1, 2007, 2 pages.
Decision to grant a European patent for EP App. Ser. No. 04025700.8, dated Jun. 5, 2008, 2 pages.
Decision to grant a European patent for EP App. Ser. No. 05783232.1, dated Mar. 19, 2009, 2 pages.
Decision to grant a European patent for EP App. Ser. No. 06023078.6, dated Dec. 4, 2008, 2 pages.
Deficiencies in sequence listing for EP App. Ser. No. 06023078.6, dated Dec. 5, 2006, 3 pages.
Demand for Appeal Trial filed in JP App. Ser. No. 2008-532141, filed Jul. 5, 2013, 10 pages (with English translation).
Deplanque et al., "Anti-Angiogenic Agents: Clinical Trial Design and Therapies in Development," *European Journal of Cancer*, 36:1713-1724 (2000).
Dermer, "Another Anniversary for the War on Cancer," *Bio/Technology*, 12:320 (1994).
Di Lorenzo et al., "Targeted Therapy in the Treatment of Metastatic Renal Cell Cancer", Oncology, 77(Suppl.1):122-131 (2010).
Di Raimondo et al., "Antiogenic Factors in multiple myeloma: higher levels in bone than in peripheral blood," *Haematologica*, 85:800-805 (2000).
Dias et al., "IL-12 Regulates VEGF and MMPs in a Murine Breast Cancer Model", International J. Cancer., 78, 361-5, 1998.
Dourisboure et al, "Penetrance and Clinical Manifestations of Non-Hotspot Germ line RET Mutation, C630R, in a Family with Medullary Thyroid Carcinoma", Thyroid, 15, 668-671, 2005.

Dupont et al., "Phase 1 study of VEGF Trap in patients with solid tumors and lymphoma," Proc. Am. Soc. Clin. Oncology, (Abstract 776), 2003, 2 pages.
Dvorakova et al., "Exon 5 of the RET proto-oncogene: A newly detected risk exon for familial medullary thyroid carcinoma, a novel germ-line mutation Gly321Arg", Journal of Endocrinological Investigation, 28, 905-909, 2005.
El-Abseri et al., "Chemoprevention of UV Light-Induced Skin Tumorigenesis by Inhibition of the Epidermal Growth Factor Receptor", Cancer Research., 64, 3958-3965, 2004.
Elisei et al., "Identification of a novel point mutation in the RET gene (Ala883Thr), which is associated with medullary thyroid carcinoma phenotype only in homozygous condition," J. Clin. Endocrinol. Metab., 89:5823-5827 (2004).
Emanuel et al., "A Vascular Endothelial Growth Factor Receptor-2 Kinase Inhibitor Potentiates the Activity of the Conventional Chemotherapeutic Agents Paclitaxel and Doxorubicin in Tumor Xenograft Models", Molecular Pharmacology., 66, 635-647, 2004.
EP Communication under Rule 71(3) EPC for Application No. 06832529.9 dated Nov. 25, 2011, 35 pages.
EP07806561.2 Office Action dated Dec. 9, 2011, 5 pages.
EP07806561.2 Office Action dated Feb. 7, 2011, 1 page.
EP07806561.2 Response to Office Action filed on Aug. 9, 2011, 134 pages.
Erber et al., "Combined inhibition of VEGF and PDGF signaling enforces tumor vessel regression by interfering with pericyte-mediated endothelial cell survival mechanisms," *FASEB J*., 18(2):338-340 (2004).
European Office Action for App. Ser. No. 04719054.1, dated Oct. 30, 2009, 5 pages.
European Office Action for App. Ser. No. 04807580.8, dated Apr. 18, 2011, 11 pages.
European Office Action for App. Ser. No. 04807580.8, dated Dec. 3, 2010, 7 pages.
European Office Action for App. Ser. No. 04807580.8, dated Oct. 25, 2011, 17 pages.
European Office Action for App. Ser. No. 04818213.3, dated Feb. 2, 2012, 5 pages.
European Office Action for App. Ser. No. 07743994.1, dated Oct. 10, 2012, 8 pages.
European Office Action for Application No. 06832529.9 dated Oct. 15, 2009, 1 page.
European Office Action for Application No. 06832529.9 dated Sep. 12, 2011, 3 pages.
European Response to EESR directed at Appl. No. 07743994.1-2123 filed on Nov. 23, 2010, 22 pages.
European Response to Office Action for Application No. 06832529.9 filed on Apr. 22, 2010, 82 pages.
European Response to Office Action for Application No. 06832529.9 filed on Oct. 4, 2011, 27 pages.
European Search Report dated Jul. 23, 2010 for European application No. 06782407, 8 pages.
European Search Report dated May 4, 2010 for European Application No. 07743994, 9 pages.
European Search Report directed at application No. 06768437.3, dated Oct. 11, 2010, 10 pages.
European Search Report directed at application No. 06832529.9, dated Jul. 29, 2009, 6 pages.
European Search Report directed at application No. 06833681.7, dated Nov. 24, 2010, 15 pages.
European Search Report directed at application No. 07806561.2, dated Jan. 19, 2011, 16 pages.
European Search Report directed at application No. 10015141.4, dated Sep. 9, 2011, 6 pages.
European Search Report for App. Ser. No. 03791389.4, dated Jul. 7, 2011, 5 pages.
European Search Report for App. U.S. Appl. No. 04025700.8, dated Jan. 13, 2005, 3 pages.
European Search Report for App. Ser. No. 04719054.1, dated Apr. 17, 2009, 4 pages.
European Search Report for App. Ser. No. 04818213.3, dated Jul. 30, 2007, 3 pages.

(56) References Cited

OTHER PUBLICATIONS

European Search Report for App. Ser. No. 05783232.1, dated Sep. 7, 2007, 5 pages.
European Search Report for App. Ser. No. 06023078.6, dated Mar. 16, 2007, 5 pages.
European Search Report for App. Ser. No. 06767145.3, dated May 23, 2011, 7 pages.
European Search Report for App. Ser. No. 10809938.3, dated Jan. 2, 2013, 5 pages.
European Search Report for EP 08704376.6 dated Jun. 14, 2012, 12 pages.
Examination Report dated Feb. 18, 2005 for NZ App. Ser. No. 525324, 1 page.
Examination Report dated Feb. 21, 2008 for AU App. Ser. No. 2006203099, 2 pages.
Examination Report dated Jan. 30, 2013 for AU App. Ser. No. 2009210098, 10 pages.
Examination Report dated Mar. 26, 2008 for AU App. Ser. No. 2006236039, 2 pages.
Examination Report dated May 4, 2006 for AU App. Ser. No. 2001295986, 2 pages.
Examination Report dated Nov. 24, 2012 for AU App. Ser. No. 2008325608, 3 pages.
Examination Report dated Oct. 13, 2003 for NZ App. Ser. No. 525324, 2 pages.
Examination Report dated Sep. 2, 2004 for NZ App. Ser. No. 525324, 1 page.
Examination Report dated Sep. 20, 2005 for AU App. Ser. No. 2001295986, 3 page.
Examination report from EP 04025700 dated Apr. 10, 2006, 3 pages.
Experimental Medicine, Supplementary Volume, "A New Handbook of Genetic Engineering", Section 4, Yodosha, 2003(Japanese).
Explanation of Circumstances Concerning Accelerated Examination filed May 10, 2012 for JP Patent Application No. 2011-527665, 18 pages (with English Translation).
Extended European Search Report dated Feb. 21, 2013 for EP App. Ser. No. 12195436.6, 8 pages.
Extended European Search Report for App. Ser. No. 08846814.5, dated Jun. 18, 2012, 11 pages.
Extended European Search Report dated Dec. 7, 2012 issued in connection with Corresponding European Application No. 06797249.7, 6 pages.
Ezzat et al., "Dual Inhibition of RET and FGFR4 Retains Medullary Thyroid Cancer Cell Growth," Clinical Cancer Research, Feb. 2005, 11:1336-1341.
Fargnoli et al., "Preclinical studies of BMS-582664, an alanine prodrug of BMS-540215, a potent, dual inhibitor of VEGFR-2 and FGFR-1 kinases," AACR American Association Cancer Research, 96th Annual Meeting, 46 (Abstract 3033), Anaheim, Orange County CA USA Apr. 16-20, 2005, 2 pages.
First Office Action dated Mar. 6, 2012 for the corresponding JP application, JP2007-542863, 17 pages and English translation.
Folkman et al., "Angiogenesis," *The Journal of Biological Chemistry*, 267(16):10931-10934 (1992).
Folkman et al., "Seminars in Medicine of the Beth Israel Hospital, Boston: Clinical Applications of Research on Angiogenesis," *The New England Journal of Medicine*, 333(26):1757-1763 (1995).
Folkman et al., "What is the Evidence That Tumors are Angiogenesis Dependent?," *Journal of the National Cancer Institute*, 82(1):4-6 (1990).
Folkman, "New Perspective in Clinical Oncology From Angiogenesis Research," J. Eur. J. Cancer, 32A(4):2534-2539 (1996).
Fong et al., "SU5416 is a Potent and Selective Inhibitor of the Vascular Endothelial Growth Factor Receptor (Flk-1/KDR) That Inhibits Tyrosine Kinase Catalysis, Tumor Vascularization, and Growth of Multiple Tumor Types", Cancer Research., 59, 99-106, 1999.
Forbes et al., "Dissolution kinetics and solubilities of p-aminosalicylic acid and its salts," *International Journal of Pharmaceutics*, 126:199-208 (1995).
Formality Requirement dated Jun. 18, 2003 for PH App. Ser. No. 1-2003-500266, 3 pages.
Freshney, R. Ian, "Culture of Animal Cells, A Manual of Basic Technique," *Alan R. Liss*, New York, 29-32 (1983).
Frings, "New Molecular Targeted Therapeutic Drugs Clinical Results of Bevacizumab in Non-Small Cell Lung Cancer (NSCLC)", Jap. J. Lung Cancer, Jun. 2006, 46(3):277-281 (with English Translation).
Fugazzola et al., "Molecular and biochemical analysis of RET/PTC4, a novel oncogenic rearrangement between RET and ELE1 genes, in a post-Chernobyl papillary thyroid cancer", Oncogene, 13, 1093-1097, 1996.
Fujii et al., "MP-412, a dual EGFR/HER2 tyrosine kinase inhibitor: 2. In vivo antitumor effects," Am. Assoc. Cancer Research, A3394, 2005, 2 pages.
Funahashi et al., "P-2123, Lenvatinib treatment of differentiated thyroid cancer (DTC): Analysis to identify biomarkers associated with response," the $71^{st}$ Annual Meeting of the Japanese Cancer Association, Sep. 19-21, 2012, p. 339.
Furitsu et al., "Identification of Mutations in the Coding Sequence of the Proto-Oncogene c-kit in a Human Mast Cell Leukemia Cell Line Causing Ligand-Independent Activation of c-kit Product," *J. Clin. Invest.*, 92:1736-1744 (1993).
Furitsu et al., "Stable medicinal compositions of quinolinecarboxamide derivative," Database Caplus Chemical Abstracts Service, Columbus, OH, US (2006) (XP002520305), 11 pages.
Furuta et al., "Synthesis and Biological Evaluation of Selective Inhibitors of PDGF Receptor Auto Phosphorylation," #64, *American Chemical Society, $226^{th}$ ACS National Meeting*, New York, NY (Sep. 7-11, 2003), 72 pages.
Gall-Istok et al., "Notes on the Synthesis of 4-Amino-6,7-Di-Sec-Butoxyquinoline,-6,7-Methylene-Dioxyquinoline and its N-Alkylaminoacetyl Derivatives," *Acta Chimica Hungarica*, 112(2):241-247 (1983).
Gardner et al., "In Vitro Activity Sorghum-Selective Fluorophenyl Urea Herbicides," *Pesticide Biochemistry and Physiology*, 24(3):285-297 (1985).
Gatzemeier et al., "Phase III comparative study of high-dose cisplatin versus a combination of paclitaxel and cisplatin in patients with advanced non-small-cell lung cancer," *J Clin. Oncol.*, 18(19):3390-3399 (2000).
Genitourinary Cancers, Prostate Cancer Genitourinary, http://www.merkmanuals.com/professional/print/sec17/ch241/ch241e.html Mar. 16, 2011, 7 pages.
Giles, "The vascular endothelial growth factor (VEGF) signaling pathway: a therapeutic target in patients with hematologic malignancies," Oncologist, 6(suppl 5):32-39 (2001).
Gingrich et al., "A New Class of Potent Vascular Endothelial Growth Factor Receptor Tyrosine . . . Clinical Candidate CEP-7055", Journal of Medicinal Chemistry., 46: 5375-88, 2003.
Golkar et al., "Mastocytosis," Lancet, 349:1379-1385 (1997).
Gould, "Salt Selection for Basic Drugs," *International Journal of Pharmaceutics*, 33:201-217, (1986) (XP025813036), 18 pages.
Grieco et al., "PTC is a Novel Rearranged Form of the ret Proto-Oncogene and is Frequentrly Detected in Vivo in Human Thyroid Papillary Carcinomas", Cell, 60: 557-563 (1990).
Guo et al., "Expression of gastric cancer-associated MG7 antigen in gastric cancer, precancerous lesions and H. pylori-associated gastric diseases", Word J. Gastroenterol, 8(6):1009-1013 (2002).
Guo et al., "In Vitro Pharmacological Characterization of TKI-28, a Broad-Spectrum Tyrosine Kinase Inhibitor with Anti-Tumor and Anti-Angiogenic Effects", Cancer Biol Ther., 4, p. 1125-1132, 2005.
Gura, "Cancer Models Systems for Identifying new drugs are often faulty," Science, 278:1041-1042 (1997).
Gutheil et al., Targeted Antiangiogenic Therapy for Cancer Using Vitaxin: A Humanized Monoclonal Antibody to the Integrin alphavbeta3 1 Clinical Cancer Research., 6, 3056-61, 2000.

(56) References Cited

OTHER PUBLICATIONS

Haleblian, "Characterization of habits and crystalline modification of solids and their pharmaceutical applications," *J. Pharm. Sci.*, 64(8):1269-1288 (1975).
Haller, "Chemotherapy for advanced pancreatic cancer," *Int. J. Radiation Oncol. Biol. Phys.*, 56:16-23 (2003).
Hamby et al., "Structure-Activity Relationships for a Novel Series of Pyrido[2,3-d]pyrimidine Tyrosine Kinase Inhibitors", Journal of Medicinal Chemistry., 40, 2296-2303, 1997.
Hamel et al., "The Road Less Travelled: c-kit and Stem Cell Factor," Journal of Neuro-Oncology, 35:327-333 (1997).
Hara et al., "Amplification of c-myc, K-sam, and c-met in Gastric Cancers: Detection by Fluorescence In Situ Hybridization", Laboratory Investigation, 78, 1143-1153, 1998.
Hattori et al., "Immunohistochemical detection of K-sam protein in stomach cancer," *Clin. Cancer Res.*, 2(8):1373-1381 (1996).
Hayek et al., "An In Vivo Model for Study of the Angiogenic Effects of Basic Fibroblast Growth Factor," *Biochemical and Biophysical Research Communications*, 147(2):876-880 (1987).
Haymo et al., "Pericytes in experimental MDA-MB231 tumor angiogenesis," Histochemistry and Cell Biology, 117(6):527-534 (2002) (abstract).
Heinemann, V., et al., "Comparison of the Cellular Pharmacokinetics and Toxicity of . . . 1-beta-d-Arabinofuranosylcytosine", Cancer Research, 48, 4024-4031, 1988.
Heinrich et al., "Kinase Mutations and Imatinib Response in Patients with Metastatic Gastrointestinal Stromal Tumor", Journal of Clinical Oncology, vol. 21, No. 23:4342-4349 (2003).
Heinrich et al., "Inhibition of c-kit receptor tyrosine kinase activity by STI 571, a selective tyrosine kinase inhibitor," *Blood*, 96(3):925-932 (2000) (XP001097629).
Heinrich et al., "Inhibition of KIT tyrosine kinase activity: a novel molecular approach to the treatment of KIT-positive malignancies," *J. Clin. Oncol.*, 20(6):1692-1703 (2002).
Hennequin et al., "Design and Structure-Activity Relationship of a New Class of Potent VEGF Receptor Tyrosine Kinase Inhibitors", Journal of Medicinal Chemistry., 42: 5369-5389, 1999.
Hennequin et al., "Novel 4-Anilinoquinazolines with C-7 Basic Side Chains: Design and Structure Activity Relationship of a Series of Potent, Orally Active, VEGF Receptor Tyrosine Kinase Inhibitors," J. Med. Chem., 45:1300-1312 (2002).
Herbst et al., "AMG 706 first in human, open-label, dose-finding study evaluating the safety and pharmacokinetics (PK) in subjects with advanced sold tumors," EORTC-NCI-AACR Symp Mol Targets Cancer Ther., 2, (Abstract 151), 2004, 1 page.
Hertel LW., et al., "Evaluation of the Antitumor Activity of Gemcitabine (2',2'-Difluoro-2'-deoxycytidine)", Cancer Research, 50, 4417-4422, 1990.
Hibi et al., "Coexpression of the Stem Cell Factor and the c-kit Genes in Small-Cell Lung Cancer," Oncogene, 6:2291-2296 (1991).
Highlights of Prescribing Information: GLEEVEC® (imatinib mesylate) Tablets for Oral Use (Initial U.S. Approval 2001; Label Revised Jan. 2012), 38 pages.
Hines et al., "Coexpression of the c-kit and Stem Cell Factor Genes in Breast Carcinomas," Cell Growth & Differentiation, 6:769-779 (1995).
Hogaboam et al., "Novel Role of Transmembrane SCF for Mast Cell Activation and Eotaxin Production in Mast Cell-Fibroblast Interactions," *J. Immunol.*, 160:6166-6171 (1998).
Hori et al., "Suppression of Solid Tumor Growth by Immunoneutralizing Monoclonal Antibody against Human Basic Fibroblast Growth Factor", Cancer Research., 51, 6180-4, 1991.
Hu-Lowe et al., "SU014813 is a novel multireceptor tyrosine kinase inhibitor with potent antiangiogenic and antitumor activity," AACR American Association Cancer Research., 96th Annual Meeting, 46, (Abstract 2031), Anaheim, Orange County, CA, USA Apr. 2005, 2 pages.
Hurwitz et al., "Bevacizumab plus irinotecan, fluorouracil, and leucovorin for metastatic colorectal cancer," N. Engl. J. Med., 350(23):2335-2342 (2004).
Huston et al., "Protein engineering of antibody binding sites: Recovery of specific activity in an anti-digoxin single-chain Fv analogue produced in *Escherichia coli*", Proc. Natl. Acad. Sci. USA 85: 5879-83, 1988.
Ikeda et al., "Changes in Phenotype and Proliferative Potential of Human Acute Myeloblastic Leukemia Cells in Culture with Stem Cell Factor," *Experimental Hematology*, 21:1686-1694 (1993).
Ikeda et al., "Expression and Functional Role of the Proto-Oncogene c-kit in Acute Myeloblastic Leukemia Cells," *Blood*, 78(11):2962-2968 (1991).
Inai et al., "Inhibition of vascular endothelial growth factor (VEGF) signaling in cancer causes loss of endothelial fenestrations, regression of tumor vessels, and appearance of basement membrane ghosts," *American Journal of Pathology*, 165:35-52 (2004).
Indian Office Action for App. Ser. No. 1571/CHENP/2007, dated Oct. 30, 2012, 2 pages.
Indian Office Action for IN App. Ser. No. 383/CHENP/2008, dated May 3, 2012, 2 pages.
Indian Office Action in App. Ser. No. 6415/CHENP/2008, dated Oct. 3, 2013, 2 pages.
Indian Patent Application No. 2572/CHENP/2006 filed Jul. 13, 2006, 1 page.
Information about decision on request for EP App. Ser. No. 06023078.6, dated Mar. 21, 2007, 1 page.
Inoue et al., "Molecular Target Therapy Targeting Angiogenesis Pathways," *The Nishinihon Journal of Urology*, 66:425-432 (2004).
International Preliminary Report on Patentability for International Application No. PCT/JP2010/063804 dated Mar. 13, 2012, 6 pages.
International Preliminary Report on Patentability for International Application No. PCT/JP2007/060560 dated Nov. 18, 2008, 6 pages with English translation.
International Preliminary Report on Patentability for International Application No. PCT/JP2006/312487, dated Dec. 24, 2007, 7 pages.
International Preliminary Report on Patentability for International Application No. PCT/JP2001/09221, dated Jan. 8, 2003, 9 pages.
International Preliminary Report on Patentability for International Application No. PCT/JP2004/003087, dated Feb. 13, 2006, 5 pages.
International Preliminary Report on Patentability for International Application No. PCT/JP2011/064430, dated Jan. 24, 2013, 6 pages.
International Preliminary Report on Patentability for International Application No. PCT/JP2005/016941, dated Mar. 20, 2007, 10 pages.
International Preliminary Report on Patentability for International Application No. PCT/JP2003/010964 dated Aug. 10, 2004, 7 pages.
International Preliminary Report on Patentability for International Application No. PCT/JP2007/060560, dated Dec. 10, 2008, 7 pages.
International Preliminary Report on Patentability for International Application No. PCT/JP2009/051244 dated Aug. 31, 2010, 12 pages (with English translation).
International Preliminary Report on Patentability for International Application No. PCT/JP2008/070321, dated May 11, 2010, 15 pages with English translation.
International Preliminary Report on Patentability for International Application No. PCT/JP2008/051697, dated Aug. 4, 2009, 18 pages.
International Preliminary Report on Patentability for International Application No. PCT/JP2007/067088 dated Mar. 3, 2009, 16 pages with English translation.
International Preliminary Report on Patentability for International Application No. PCT/JP2008/051024 dated Jul. 21, 2009, 15 pages with English translation.
International Preliminary Report on Patentability in International Application No. PCT/JP2006/315563 dated Feb. 5, 2008, 10 pages with English translation.
International Preliminary Report on Patentability in International Application No. PCT/JP2006/315698 dated Feb. 5, 2008, 17 pages English translation.
International Preliminary Report on Patentability in International Application No. PCT/JP2006/322514 dated May 7, 2008, 8 pages.
International Preliminary Report on Patentability in International Application No. PCT/JP2006/322516 dated May 7, 2008, 8 pages.
International Search Report and Written Opinion dated Sep. 14, 2010 for International Application No. PCT/JP2010/063804, 11 pages.

(56) References Cited

OTHER PUBLICATIONS

International Search Report dated Apr. 1, 2008 for International Application No. PCT/JP2008/051024, 6 pages.
International Search Report dated Jan. 20, 2009 for International Application No. PCT/JP2008/070321, 8 pages.
International Search Report dated Jan. 23, 2007 for International Application No. PCT/JP2006/322514, 10 pages.
International Search Report dated Jan. 23, 2007 for International Application No. PCT/JP2006/323881, 6 pages.
International Search Report dated Mar. 24, 2009 for International Application No. PCT/JP2009/051244, 6 pages.
International Search Report dated Mar. 4, 2008 for International Application No. PCT/JP2008/051697, 7 pages.
International Search Report dated Nov. 20, 2007 for International Application No. PCT/JP2007/067088, 6 pages.
International Search Report dated Oct. 17, 2006 for International Application No. PCT/JP2006/315698, 5 pages.
International Search Report dated Sep. 11, 2007 for International Application No. PCT/JP2007/060560, 6 pages.
International Search Report dated Sep. 4, 2007 for International Application No. PCT/JP2007/063525, 7 pages.
International Search Report dated Sep. 5, 2006 for International Application No. PCT/JP2006/315563, 2 pages.
International Search Report for International Application No. PCT/JP2001/09221, dated Jan. 15, 2002, 9 pages.
International Search Report for International Application No. PCT/JP2006/317307, dated Dec. 12, 2006, 3 pages.
International Search Report for International Application No. PCT/JP2004/003087, dated Jul. 13, 2004, 3 pages.
International Search Report for International Application No. PCT/JP2005/016941, dated Nov. 15, 2005, 4 pages.
International Search Report in International Application No. PCT/JP2006/322516 dated Jan. 23, 2007, 5 pages.
Invitation to declare maintenance of the application for EP App. Ser. No. 01976786.2, dated Jul. 12, 2004, 1 page.
Invitation to declare maintenance of the application for EP App. Ser. No. 05783232.1, dated Sep. 25, 2007, 1 page.
Invitation to declare maintenance of the application for EP App. Ser. No. 06023078.6, dated May 2, 2007, 1 page.
Israel 200090 Office Actions dated Jun. 22, 2010, 3 pages (with English translation).
Israel 200090 Response to Office Action filed on Oct. 12, 2010, 3 pages.
Israel Appl. No. 195282 IDS List filed on Jul. 1, 2010, 3 pages.
Israel Office Action directed at Appl. No. 195282 dated Jan. 26, 2010, 4 pages with English translation.
Israel Office Action directed at Appl. No. 205512 dated Nov. 13, 2011, 4 pages with English translation.
Israel Response (IDS List) to Office Action directed at Appl. No. 195282 filed on May 3, 2010, 6 pages with English translation.
Israeli Office Action dated Mar. 27, 2012 for Israeli Application No. 189589, 3 pages with English translation.
Israeli Office Action for App. Ser. No. 155447, dated Oct. 16, 2007, 3 pages (with English translation).
Israeli Office Action for App. Ser. No. 189677, dated Feb. 18, 2009, 2 pages (with English translation).
Israeli Office Action for App. Ser. No. 195282, dated Feb. 5, 2012, 3 pages (with English translation).
Israeli Office Action for App. Ser. No. 199907, dated Apr. 22, 2012, 3 pages (with English translation).
Israeli Office Action dated May 16, 2010 for corresponding Israeli Application No. 189589, 3 pages with English translation.
Itoh et al., "Preferential alternative splicing in cancer generates a K-sam messenger RNA with higher transforming activity," *Cancer Res.*, 54:3237-3241 (1994).
Jakeman et al., "Developmental Expression of Binding Sites and Messenger Ribonucleic Acid for Vascular Endothelial Growth Factor Suggests a Role for This Protein in Vasculogenesis and Angiogenesis," *Endocrinology*, 133(2):848-859 (1993).

Jang et al., "Mutations in Fibroblast Growth Factor Receptor 2 and Fibroblast Growth Factor Receptor 3 Genes Associated with Human Gastric and Colorectal Cancers", Cancer Research, 61:3541-3543 (2001).
Japanese Allowance for App. Ser. No. P2005-515330, dated Apr. 21, 2009, 2 pages.
Japanese Allowance for App. Ser. No. P2005-516605, dated Dec. 7, 2010, 5 pages (with English translation).
Japanese Classification of Gastric Carcinoma "Igan-Toriatsukai Kiyaku" (Jun. 1999, 13th ed.) and an English translation, 10 pages.
Japanese Decision to Grant a Patent dated Jan. 30, 2013 for Japanese Application No. 2007-533350, 3 pages with English translation.
Japanese Notice of Reasons for Rejection dated May 15, 2012 for Japanese Application No. 2007-533350, 6 pages with English translation.
Japanese Office Action dated Apr. 11, 2005 for App. Ser. No. 2002-536056, 6 pages (with English translation).
Japanese Office Action for App. Ser. No. 2007-522356, dated Feb. 8, 2011, 5 pages.
Japanese Office Action for App. Ser. No. P2005-516605, dated Nov. 4, 2009, 7 pages.
Japanese Office Action for App. Ser. No. P2008-516724, dated Oct. 9, 2012, 6 pages (with English translation).
Jhiang, "The RET proto-oncogene inn human cancers," *Oncogene*, 19:5590-5597 (2000).
Jiang, "ZD6474: an Agent That Selectively Targets Both VEGFR Tyrosine Kinase and EGFR Tyrosine Kinase", Jap. J. Lung Cancer, Jun. 2006, 46(3):283-288 (with English translation).
Jimenez et al., "Pheochromocytoma and medullary thyroid carcinoma: a new genotype-phenotype correlation of the RET protooncogene 891 germline mutation," *J. Clin. Endocrinol. Metab.*, 89:4142-4145 (2004).
Joao et al., "Somatic trinucleotide change encompassing codons 882 and 883 of the RET proto-oncogene in a patient with sporadic medullary thyroid carcinoma", European Journal of Endocrinology, 142,573-575, (2000).
Johnson et al., "Influence of ionic strength on matrix integrity and drug release from hydroxypropyl cellulose compacts," International journal of pharmaceutics, 1993, vol. 90, No. 2, pp. 151-159.
Johnson et al., "Paclitaxel plus carboplatin in advanced non-small-cell lung cancer: a phase II trial," *J. Clin. Oncol.*, 14(7):2054-2060 (1996).
Joly et al., "In vitro and in vivo characterization of exel-7647, a novel spectrum selective receptor tyrosine kinase inhibitor that modulates angiogenesis and tumor cell proliferation," EORTC-NCI-AACR Symp Mol Targets Cancer Ther., (Abstract 134), 2004, 1 page.
Jung et al., "Effects of combination anti-vascular endothelial growth factor receptor and anti-epidermal growth factor receptor therapies on the growth of gastric cancer in a nude mouse model," *Eur. J Cancer*, 38:1133-1140 (2002).
Juurikivi et al., "Inhibition of c-kit tyrosine kinase by imatinib mesylate induces apoptosis in mast cells in rheumatoid synovia: a potential approach to the treatment of arthritis," *Ann Rheum. Dis.*, 64:1126-1131 (2005).
Kanai et al., "Development Status and Future Prospects of Novel Molecular Target Drugs for Hepatocellular Carcinoma", Journal of the Japanese Society of Gastroenterology, 106:1727-1735 (2009).
Kanai et al., "Current status and future perspective of molecular targeted therapy for hepatocellular carcinoma," *Journal of the Japanese Society of Gastroenterology*, 106:1727-1735 (2009) (English translation).
Kanakura et al., "Expression, Function and Activation of the Proto-Oncogene c-kit Product in Human Leukemia Cells," *Leukemia and Lymphorma*, 10:35-41 (1993).
Kashuk et al., "Phenotype-genotype correlation in Hirschsprung disease is illuminated by comparative analysis of the RET protein sequence," *PNAS*, 102(25):8949-8954 (2005).
Kawano et al., "Presentation Abstract, Abstract No. 1619, Combination of VEGFR inhibitor lenvatinib (E7080) and Met/EphB4inhibitor golvatinib (E7050) overcomes VEGFR inhibitor—

(56) References Cited

OTHER PUBLICATIONS resistant tumor vascular", Annual Meeting 2013, Walter E. Washington Convention Center, Washington, D.C., Apr. 6-10, 2013, 1 page.
Kay et al., "Eosinophils and Eosinophil-Associated Cytokines in Allergic Inflammation," Int. Arch. Allergy Immunol., 113:196-199 (1997).
Kelly et al., "Randomized phase III trial of paclitaxel plus carboplatin versus vinorelbine plus cisplatin in the treatment of patients with advanced none-small-cell lung cancer: a Southwest Oncology Group trial," J. Clin. Oncol., 19(13):3210-3218 (2001).
Kibbe, Handbook of Pharmaceutical Excipients. Third Edition, 2000, pp. 6-1 through 6-6.
Kim et al., "RET Oligonucleotide Microarray for the Detection of RET Mutations in Multiple Endocrine Neoplasia Type 2 Syndromes", Clinical Cancer Research, 8,457-463, (2002).
Kim et al., "A phase II study of irinotecan plus cisplatin for patients with advanced stage IIIB or IV NSCLC previously treated with nonplatinum-based chemotherapy," Cancer, 107(4):799-805 (2006).
Kim et al., "An orally administered multitarget tyrosine kinase inhibitor, SU11248, is a novel potent inhibitor of thyroid oncogenic RET/papillary thyroid cancer kinases," J Clin. Endocrinol. Metlab., 91(10):4070-4076 (2006).
Kim, "Technology evaluation: Matuzumab, Merck KGaA", Curr Opin Mol Ther. 2004; 6(1):96-103.
Kinlaw et al., "Multiple endocrine neoplasia 2A due to a unique C6095 RET mutation presents with pheochromocytoma and reduced penetrance of medullary thyroid carcinoma", Clin Endocrinol, 69, 676-682, 2005.
Kitamura et al., "Regulation of Development, Survival and Neoplastic Growth of Mast Cells through the c-kit Receptor," Int. Arch Allergy Immunol., 107:54-56 (1995).
Kitteringham et al., "A Simple Method for the Synthesis of Unsymmetrical Ureas," Synthetic Communications, 30(11):1937-1943 (2000).
Kleespies et al., "Tyrosine kinase inhibitors and gemcitabine: New treatment options in pancreatic cancer,?" Drug Resistance Updates, 9:1-18 (2006).
Klugbauer and Rabes, "The transcription coactivator HT1 F1 and a related protein are fused to the RET receptor tyrosine kinase in childhood papillary thyroid carcinomas", Oncogene, 18: 4388-4393(1999).
Klugbauer et al., "A Novel Type of RET Rearrangement (PTC8) in Childhood Papillary Thyroid Carcinomas and Characterization of the Involved Gene (RFG8)", Cancer Research, 60: 7028-7032 (2000).
Klugbauer et al., "Detection of a Novel Type of RET Rearrangement (PTC5) in Thyroid Carcinomas after Chernobyl and Analysis of the Involved RET-fused Gene RFGS", Cancer Research, 58:198-203 (1998).
Ko, "Stomach Cancer," Cancer Supportive Care.com [published online Feb. 2003], [retrieved on Dec. 28, 2011]. Retrieved from the Internet: http://web.archive.org/web/20030224212825/http://www.cancersupportivecare.com/stomach.html.
Kolibaba et al., "Protein Tyrosine Kinases and Cancer," Biochimica et Biophysica Acta, 1333:F217-F248 (1997).
Korean ("KR") Notice of Allowance dated Aug. 25, 2010 corresponding KR Application No. 10-2008-7005195, 3 pages with English translation.
Korean ("KR") Office Action dated Dec. 24, 2009 for corresponding KR Application No. 10-2008-7005195, 7 pages with English translation.
Korean ("KR") Office Action dated May 29, 2010 for corresponding KR Application No. 10-2008-7005195, 6 pages with English translation.
Korean Office Action for App. Ser. No. 10-2003-7005506, dated Jan. 5, 2006, 5 pages (with English translation).
Korean Office Action for App. Ser. No. 10-2005-7020292, dated Dec. 8, 2005, 5 pages (with English translation).
Korean Office Action for App. Ser. No. 10-2007-7001347, dated Apr. 27, 2012, 6 pages (with English translation).
Korean Office Action for App. Ser. No. 10-2009-7005657, dated Sep. 30, 2013, 27 pages (with English translation).
Korean Office Action in KR App. Ser. No. 10-2008-7029472, dated Sep. 30, 2013, 27 pages (with English translation).
Kotva et al., "Substances with Antineoplastic Activity, LIII. N-($\delta$-(4-Pyrrolo[2,3-d]Pyrimidinylthio) Valeryl]} Amino Acids and Analogous Derivatives of Di- and Triglycine," Collection Czechoslov. Chem. Commun., 38:1438-1444 (1973).
Koyama et al, "Anti-tumor effect of E7080, a novel angiogenesis inhibitor," Folia Pharmacol. Japan., 2008, 132: 100-104 (with English translation).
Kruckeberg et al., "Pyrosequencing Technology as a Method for the Diagnosis of Multiple Endocrine Neoplasia Type 2", Clinical Chemistry, 50, 522-529, 2004.
Krystal et al., "Indolinone Tyrosine Kinase Inhibitors Block Kit Activation and Growth of Small Cell Lung Cancer Cells", Cancer Research., 61, 3660-3668, 2001.
Kubo et al., "A novel series of 4-phenoxyquinolines: potent and highly selective inhibitors of pdgf receptor autophosphorylation", Bioorganic and Medicinal Chemistry Letters., 7, 2935-2940, 1997.
Kubo et al., "Novel Potent Orally Active Selective VEGFR-2 Tyrosine Kinase Inhibitors: . . . ureas", Journal of Medicinal Chemistry., 48, 1359-1366, 2005.
Kumar et al., "Discovery and biological evaluation of GW654652: A pan inhibitor of VEGF receptors," Proceedings of the American Association for Cancer Research, 44, 9, (Abstract 39), 2003, 2 pages.
Laird et al., "SU6668 is a Potent Antiangiogenic and Antitumor Agent That Induces Regression of Established Tumors1", Cancer Research., 60, 4152-4160, 2000.
Lam et al., "High prevalence of RET proto-oncogene activation (RET/PTe) in papillary thyroid carcinomas", Eur J Endocrinology, 147: 741-745 (2002).
Lasota et al., "Mutations in Exons 9 and 13 of KIT Gene are Rare Events in Gastrointestinal Stromal Tumors," American Journal of Pathology, 157(4):1091-1095 (2000).
LeDoussal et al. "Bispecific-antibody-mediated targeting of radiolabeled bivalent haptens: theoretical, experimental and clinical results", Int. J. Cancer Suppl. 7: 58-62, 1992.
Lee et al., "In vivoTargetModulation and Biological Activity of CHIR-258, aMultitargeted Growth Factor Receptor Kinase Inhibitor, in Colon CancerModels", Clinical Cancer Research., 11, 3633-3641, 2005.
Lennartsson et al., The Stem Cell Factor Receptor/c-Kit as a Drug Target in Cancer, Current Cancer Drug Targets, 6:561-571 (2006).
Lesueur et al., "Polymorphisms in RET and its coreceptors and ligands as genetic modifiers of multiple endocrine neoplasia type 2A," Cancer Res., 66:1177-1180 (2006).
Leukemias, Hematology, and Oncology, http://www.merkmanuals.com/professional/print/sec11/ch142a.html. Mar. 16, 2011, 5 pages.
Lev et al., "A Specific Combination of Substrates is Involved in Signal Transduction by the Kit-Encoded Receptor," The EMBO Journal, 10(3):647-654 (1991).
Li et al., "Abrogation of c-kit/Steel factor-dependent tumorigenesis by kinase defective mutants of the c-kit receptor: c-kit kinase defective mutants as candidate tools for cancer gene therapy," Cancer Res., 56:4343-4346 (1996) (XP002522473).
Li et al., "ABT-869 a novel multi-targeted receptor tyrosine kinase inhibitor: characterization of FLT3 phosphorylation in a model of acute myelogenous leukemia," AACR American Association Cancer Research, 96th Annual Meeting, 46:1407, (Abstract 5981), Anaheim, Orange County CA USA Apr. 16-20, 2005, 2 pages.
Lin et al., "The vascular endothelial growth factor receptor tyrosine kinase inhibitor PTK787/ZK222584 inhibits growth and migration of multiple myeloma cells in the bone marrow microenvironment," Cancer Res., 62(17):5019-5026 (2002).
Liu et al., "Structure of Human Methionine Aminopeptidase-2 Complexed with Fumagillin", Science., 282, 1324-1327, 1998.
Logie et al., "Activating mutations of the tyrosine kinase receptor FGFR3 are associated with benign skin tumors in mice and humans," Human Mol. Genet., 14:1153-1160 (2005).

(56) References Cited

OTHER PUBLICATIONS

Longley et al., "Altered Metabolism of Mast-Cell Growth Factor (c-kit Ligand) in Cutaneous Mastocytosis," *The New England Journal of Medicine*, 328(18):1302-1307 (1993).
Longley et al., "Classes of c-KIT activating mutations: proposed mechanisms of action and implications for disease classification and therapy," *Leuk. Res.*, 25:571-576 (2001).
Longley et al., "Somatic c-KIT Activating Mutation in Urticaria Pigmentosa and Aggressive Mastocytosis: Establishment of Clonality in a Human Mast Cell Neoplasm," *Nature Genetics*, 12:312-314 (1996).
Lukacs et al., "Stem Cell Factor (c-kit Ligand) Influences Eosinophil Recruitment and Histamine Levels in Allergic Airway Inflammation," *J. Immunol.*, 156:3945-3951 (1996).
Machens et al., "Genotype-Phenotype Correlations in Hereditary Medullary Thyroid Carcinoma: Oncological Features and Biochemical Properties", Journal of Clinical Endocrinology and Metabolism, 86(3):1104-1109 (2001).
Maintenance of the application for EP App. Ser. No. 01976786.2, dated Sep. 6, 2004, 1 page.
Maintenance of the application for EP App. Ser. No. 05783232.1, dated Nov. 9, 2007, 1 pages.
Maintenance of the application for EP App. Ser. No. 06023078.6, dated Jun. 19, 2007, 1 page.
Masferrer et al., "COX-2 Inhibitors A New Class of Antiangiogenic Agents", Annals of N.Y. Acad. Science., 889:84-6, 1999.
Matsui et al., "E7080 (ER-203492-00), a Novel VEGF Receptor Tyrosine Kinase Inhibitor-I. Characterization as an Angiogenesis Inhibitor," Abstract # 51, *AACR*, Washington, USA (Jul. 11-14, 2003).
Matsui et al., "E7080 (ER-203492-00), a Novel VEGF Receptor Tyrosine Kinase Inhibitor-I. Characterization as an Angiogenesis Inhibitor," Abstract # 51, AACR, Toronto, Canada (Apr. 5-9, 2003).
Matsui et al., "E7080, a novel inhibitor that targets multiple kinases, has potent antitumor activities against stem cell factor producing human small cell lung cancer H146, based on angionenesis inhibition," *Int. J. Cancer*, 122:664-671 (2008).
Matsui et al., "E7080, a novel multi-receptor Tyrosine Kinase Inhibitor, inhibited in vitro / in vivo VRGG- and SCF-driven angiogenesis SCLC cell line," Abstract #146, *EORTC-NCI-AACR*, Geneva, Switzerland (Sep. 28-Oct. 1, 2004).
Matsui et al., "E7080, a novel multi-targeted tyrosine kinase inhibitor, exhibits anti-angiogenic activity via inhibition of KIT signaling in a small cell lung cancer xenograft model," *Eur. J. Cancer*, 2(8):47 (2004).
Matsui et al., "Quantitative analysis of the profile of tumor vessels may be useful as predictive biomarkers for E7080," Abstract #4631, *98th AACR annual meeting*, Los Angeles, CA, (Apr. 14-18, 2007).
Matsui et al., "VEGFRs inhibitor E7080 inhibits lymph node metastasis of human breast carcinoma, by preventing murine lymphatic endothelial cells from lymphangiogenesis," Abstract #PD12-8, *18th EORTC-NCI-AACR Symposium on "Molecular Targets and Cancer Therapeutics,"* Prague, Czech Republic (Nov. 7-10, 2006).
Matsui, "Extracellular matrix of linitis plastica as a possible new therapeutic target," Surgical Treatment, Sep. 2003, 89(3):301-306 (with English translation).
McCarty et al., "ZD6474, a vascular endothelial growth factor receptor tyrosine kinase inhibitor with additional activity against epidermal growth factor receptor tyrosine kinase, inhibits orthotopic growth and angiogenesis of gastric cancer," *Mol. Cancer Ther.*, 3(9):1041-1048 (2004).
McCulloch et al., "Astragalus-based Chinese herbs and platinum-based chemotherapy for advanced non-small-cell lung cancer: meta-analysis of randomized trials," *J. Clin. Oncol.*, 24(3):419-430 (2006).
Meltzer, "The Pharmacological Basis for the Treatment of Perennial Allergic Rhinitis and Non-Allergic Rhinitis with Topical Corticosteroids," *Allergy*, 52:33-40 (1997).
Mendel et al., "In vivo antitumor activity of SU11248, a novel tyrosine kinase inhibitor targeting vascular endothelial growth factor and platelet-derived growth factor receptors: determination of a pharmacokinetic/pharmacodynamic relationship," *Clin. Cancer Res.*, 9:327-337 (2003).
Metcalfe et al., "Lineage Commitment in the Progeny of Murine Hematopoietic Preprogenitor Cells: Influence of Thrombopoietin and Interleukin 5," *Proc. Nat'l Acad. Sci. USA*, 95:6408-6412 (1998).
Metcalfe et al., "Mast cells," *Physiol. Rev.*, 77(4):1033-1079 (1997).
Metcalfe, "Classification and Diagnosis of Mastocytosis: Current Status," *J. Invest. Dermatol.*, 96:2S-4S (1991).
Mexican Office Action in App. Ser. No. MX/a/2010/008187, dated Aug. 21, 2013, 6 pages (with English translation).
Micke et al., "Characterization of c-kit expression in small cell lung cancer: prognostic and therapeutic implications," *Clin. Cancer Res.*, 9:188-194 (2003).
Miknis et al., "AARY-334543, A potent, orally active small molecule inhibitor of EGFR and ErbB-2," Am. Assoc. Cancer Res. Abstract 3399, 2005, 2 pages.
Miller et al., "Paclitaxel plus bevacizumab versus paclitaxel alone for metastatic breast cancer," *N. Engl. J. Med.*, 357(26):2666-2676 (2007).
Milstein and Cuello, "Hybrid hybridomas and their use in immunohistochemistry", Nature 305: 537-9, 1983.
Mitchell al, "The influence of additives on the cloud point, disintegration and dissolution of hydroxypropylmethylcellulose gels and matrix tablets," International Journal of Pharmaceutics, 1990, vol. 66, No. 1/3, pp. 233-242.
Miyauchi et al., "Two Germline Missense Mutations of Co dons 804 and 806 of the RET proto-oncogene in the Same 15 Allele in a Patient with Multiple Endocrine Neoplasia Type 2B without Codon 915 Mutation", Japanese Journal of D Cancer Research, 90, 1-5, (1999).
Miyazaki et al., "Synthesis, Structure and Biological Activity Relationship of E7080 and its Derivatives as Novel and Potent Antiangiogenic Protein Tyrosine Kinase Inhibitors Including the VEGF Receptors, FGFR1 Receptor and Pdgf Receptor," AIMECS03, Kyoto, Japan (Oct. 14-17, 2003), 1 page.
Mohammadi et al., "Crystal structure of an angiogenesis inhibitor bound to the Fgf receptor tyrosine kinase domain", EMBO J., 17, 5896-5904, 1998.
Mologni et al., "Inhibition of RET tyrosine kinase by SU5416," *J. Mol. Endocrinol.*, 37(2):199-212 (2006).
Morgan et al., "Dynamic contrast-enhanced magnetic resonance imaging as a biomarker for the pharmacological response of PTK787/ZK 222584, an inhibitor of the vascular endothelial growth factor receptor tyrosine kinases, in patients with advanced colorectal cancer and liver metastases: results from two phase I studies," *J. Clin. Oncol.*, 21(21):3955-3964 (2003).
Morikawa et al., "Angiogenesis and Pericytes, " *The Cell*, 37(4):164-168 (2005) (English translation).
Morris et al., "An Integrated Approach to the Selection of optimal Salt Form for a New Drug Candidate," *International Journal of Pharmaceutics*, 105:209-217 (1994) (XP023724810).
Myers et al., "The Preparation and SAR of 4-(Anilino), 4-(Phenoxy), and 4-(Thiophenoxy)-Quinazolines: Inhibitors of p56lck and EGF-R Tyrosine Kinase Activity," *Bioorgan. & Med. Chem. Letters*, 7:417-420 (1997).
Naclerio et al., "Rhinitis and Inhalant Allergens," *JAMA*, 278(22):1842-1848 (1997).
Nagata et al., "Elevated Expression of the Proto-Oncogene c-kit in Patients with Mastocytosis," *Leukemia*, 12:175-181 (1998).
Nakamura et al., "KRN633: A Selective inhibitor of vascular endothelial growth factor receptor-2 tyrosine kinase that suppresses tumor angiogenesis and growth", Molecular Cancer Therapeutics., 2004, 3:1639-49.
Nakamura et al., "E7080 (ER-203492-00), a Novel VEGF Receptor Tyrosine Kinase Inhibitor-II. Effects on Growth of Human Tumor Xenografts and Life Span of Mice in Colon 38 Orthotopic Transplantation Model," Abstract #52, *AACR*, Toronto, Canada (Apr. 5-9, 2003).

(56) References Cited

OTHER PUBLICATIONS

Nakamura et al., "In vitro selectivity and potency of KRN951, a novel inhibitor of VEGF receptor tyrosine kinases," Proceedings of the American Association for Cancer Research, 45, 594, (Abstract 2571), 2004, 1 page.

Nakata et al., "Fusion of a Novel Gene, ELKS, to RET Due to Translocation t(1 0; 12) (q11; p13) in a Papillary Thyroid Carcinoma", Genes Chromosomes Cancer, 25: 97-103 (1999).

Naruse et al., "Antitumor activity of the selective epidermal growth factor receptor-tyrosine kinase inhibitor (EGFR-TKI) Iressa (ZD1839) in an EGFR-expressing multidrug-resistant cell line in vitro and in vivo," Int. J. Cancer, 98:310-315 (2002).

Naski et al., "Graded activation of fibroblast growth factor receptor 3 by mutations causing achondroplasia and thanatophoric dysplasia," Nat. Genet., 13:233-237 (1996).

Natali et al., "Breast Cancer is Associated with Loss of the c-kit Oncogene Product," Int. J. Cancer, 52:713-717 (1992).

NCBI GenBank Accession No. NM_000222, Coffey et al. (Feb. 11, 2008), 7 pages.

Nishikawa et al., "Cys611Ser mutation in RET proto-oncogene in a kindred with medullary thryroid carcinoma and Hirschsprung's disease", European Journal of Human Genetics, 11,364-368 (2003).

Nishio et al, "Phase 1 study of lenvatinib combined with carboplatin and paclitaxel in patients with non-small-cell lung cancer", British Journal of Cancer, 2013, 109:538-544.

Nocka et al., "Expression of c-kit gene products in known cellular targets of W mutations in normal and W mutant mice—evidence for an impaired c-kit kinase in mutant mice," Cold Spring Harbor Laboratory Press, 3:816-826 (1989) (XP002522472).

Non-Final Office Action in U.S. Appl. No. 10/577,531, dated Sep. 23, 2008, 17 pages.

Non-Final Office Action in U.S. Appl. No. 10/797,903, dated Aug. 20, 2009, 10 pages.

Non-Final Office Action in U.S. Appl. No. 10/797,903, dated Dec. 11, 2007, 12 pages.

Noriyuki et al., "Anti-tumor effect of E7080, a novel angiogenesis inhibitor," Database BIOSIS [Online] Biosciences Information Service, Philadelphia, PA, US: Database accession No. PREV200800475929, Aug. 2008, XP002677323, 1 page.

Notice of Acceptance dated Aug. 10, 2004 for ZA Patent App. No. 2003/3567, 1 page.

Notice of Acceptance dated Aug. 3, 2006 for AU App. Ser. No. 2001295986, 4 pages.

Notice of Acceptance dated May 13, 2008 for AU App. Ser. No. 2006236039, 4 pages.

Notice of Acceptance for AU App. Ser. No. 2009210098, dated Jun. 4, 2013, 3 pages.

Notice of Acceptance of Complete Specification dated Mar. 4, 2005 for NZ App. Ser. No. 525324, 1 page.

Notice of Allowability dated Nov. 28, 2007 for PH App. Ser. No. 1-2003-500266, 1 page.

Notice of Allowance dated Apr. 19, 2005 for RU App. Ser. No. 2003114740, 79 pages (with English translation).

Notice of Allowance dated Apr. 19, 2011 for JP App. Ser. No. 2007-522356, 5 pages.

Notice of Allowance dated Apr. 24, 2012 for U.S. Appl. No. 12/524,754, 10 pages.

Notice of Allowance dated Apr. 29, 2010 for AU App. Ser. No. 2005283422, 3 pages.

Notice of Allowance dated Aug. 2, 2005 for JP App. Ser. No. 2002-536056, 2 pages (with English translation).

Notice of Allowance dated Aug. 7, 2012 for Japanese App. Ser. No. P2007-529565, 6 pages (with English translation).

Notice of Allowance dated Dec. 15, 2006 for CN App. Ser. No. 01819710.8, 4 pages.

Notice of Allowance dated Dec. 26, 2007 for IL App. Ser. No. 155447, 2 pages (with English translation).

Notice of Allowance dated Feb. 15, 2013 for NZ App. Ser. No. 598291, 1 page.

Notice of Allowance dated Feb. 27, 2009 for U.S. Appl. No. 11/293,785, 4 pages.

Notice of Allowance dated Feb. 5, 2010 for CN App. Ser. No. 200580026468.7, 5 pages (with English translation).

Notice of Allowance dated Jul. 17, 2012 for JP App. Ser. No. P2011-527665, 4 pages (with English translation).

Notice of Allowance dated Jul. 21, 2009 for JP App. Ser. No. 2005-124034, 6 pages (with English translation).

Notice of Allowance dated Jun. 13, 2006 for U.S. Appl. No. 10/420,466, 2 pages.

Notice of Allowance dated Jun. 20, 2012 for EP App. Ser. No. 06782407.8, 35 pages.

Notice of Allowance dated Jun. 25, 2012 for EP App. Ser. No. 07806561.2, 7 pages.

Notice of Allowance dated Jun. 3, 2008 for U.S. Appl. No. 11/293,785, 6 pages.

Notice of Allowance dated Mar. 14, 2010 for IL App. Ser. No. 189677, 3 pages (with English translation).

Notice of Allowance dated Mar. 16, 2007 for U.S. Appl. No. 10/420,466, 3 pages.

Notice of Allowance dated Mar. 22, 2012 for U.S. Appl. No. 12/986,638, 12 pages.

Notice of Allowance dated Mar. 8, 2013 for CA App. Ser. No. 2627598, 1 page.

Notice of Allowance dated May 18, 2009 for U.S. Appl. No. 11/293,785, 4 pages.

Notice of Allowance dated May 6, 2013 for EP App. Ser. No. 04818213.3, 22 pages.

Notice of Allowance dated Nov. 14, 2011 for IL App. Ser. No. 181697, 4 pages (with English translation).

Notice of Allowance dated Nov. 19, 2008 for U.S. Appl. No. 11/293,785, 4 pages.

Notice of Allowance dated Nov. 2, 2012 for EP App. Ser. No. 06782407.8, 2 pages.

Notice of Allowance dated Nov. 2, 2012 for EP App. Ser. No. 07806561.2, 2 pages.

Notice of Allowance dated Oct. 14, 2010 for CA App. Ser. No. 2426461, 1 page.

Notice of Allowance dated Oct. 17, 2011 for CA App. Ser. No. 2579810, 1 page.

Notice of Allowance dated Oct. 18, 2006 for MX App. Ser. No. PA/a/2003/003362, 4 pages (with English translation).

Notice of Allowance dated Oct. 20, 2008 for TW App. Ser. No. 90125928, 4 pages (with English translation).

Notice of Allowance dated Oct. 31, 2008 for NO App. Ser. No. 20031731, 4 pages (with English translation).

Notice of Allowance dated Oct. 9, 2010 for CN App. Ser. No. 200710007097.9, 4 pages (with English translation).

Notice of Allowance dated Sep. 12, 2005 for U.S. Appl. No. 10/420,466, 2 pages.

Notice of Allowance dated Sep. 20, 2011 for JP App. Ser. No. 2006-535174, 4 pages.

Notice of Allowance dated Sep. 25, 2012 for U.S. Appl. No. 12/986,638, 56 page.

Notice of Allowance dated Sep. 4, 2012 in JP App. Ser. No. P2009-123432, 5 pages (with English translation).

Notice of Allowance for CN App. Ser. No. 200980103218.7, dated May 27, 2013, 4 pages (with English translation).

Notice of Allowance for JP App. Ser. No. 2008-516724, dated Jan. 22, 2013, 4 pages, with English translation.

Notice of Allowance for JP App. Ser. No. P2008-532141, dated Sep. 10, 2013, 5 pages (with English translation).

Notice of Allowance for U.S. Appl. No. 12/524,754, dated Jan. 18, 2013, 9 pages.

Notice of Allowance for U.S. Appl. No. 12/741,682, dated Feb. 19, 2013, 65 pages.

Notice of Allowance for U.S. Appl. No. 12/741,682, dated Jun. 19, 2013, 10 pages.

Notice of Allowance for U.S. Appl. No. 12/524,754 dated Oct. 9, 2012, 36 pages.

Notice of Allowance for U.S. Appl. No. 11/997,719, dated Sep. 13, 2013, 20 pages.

(56) References Cited

OTHER PUBLICATIONS

Notice of Allowance for U.S. Appl. No. 13/083,338, dated Jun. 4, 2013, 57 pages.
Notice of Allowance for U.S. Appl. No. 13/083,338, dated Sep. 26, 2013, 28 pages.
Notice of Allowance for U.S. Appl. No. 13/205,328, dated Jun. 10, 2013, 58 pages.
Notice of Allowance for U.S. Appl. No. 13/205,328, dated Oct. 3, 2013, 11 pages.
Notice of Allowance in EP App. Ser. No. 04818213.3, dated Sep. 19, 2013, 2 pages.
Notice of Allowance in U.S. Appl. No. 12/741,682, dated Oct. 21, 2013, 12 pages.
Notice of Allowance in U.S. Appl. No. 13/624,278, dated Sep. 16, 2013, 20 pages.
Notice of Allowance issued in CN App. Ser. No. 200880115011.7, dated Aug. 5, 2013, 4 pages (with English translation).
Notice of Allowance issued in CN App. Ser. No. 201080030508.6, dated Jul. 4, 2013, 4 pages (with English translation).
Notice of Allowance issued in EP App. Ser. No. 10015141.4, dated Jul. 1, 2013, 40 pages.
Notice of Allowance issued in IL App. Ser. No. 175363, dated Aug. 13, 2013, 2 pages (with English translation).
Notice of Allowance issued in JP App. Ser. No. P2008-556208, dated Jul. 9, 2013, 4 pages (with English translation).
Notice of Allowance issued in U.S. Appl. No. 12/524,754, dated Jul. 19, 2013, 11 pages.
Notice of decision for patent dated Apr. 17, 2006 for KR App. Ser. No. 10-2005-7020292, 4 pages (with English translation).
Notice of decision for patent dated Jun. 12, 2006 for KR App. Ser. No. 10-2003-7005506, 4 pages (with English translation).
Notice of Reasons for Rejection issued in JP App. Ser. No. P2009-540099, dated Jul. 2, 2013, 7 pages (with English translation).
Notice of Reasons for Rejection dated Nov. 13, 2012 issued for corresponding Japanese Application No. 2007-533350, 3 pages with full English language translation.
Notice Prior to Examination dated Jun. 29, 2008 for IL App. Ser. No. 189677, 3 pages (with English translation).
Notice Prior to Examination dated Mar. 9, 2009 for IL App. Ser. No. 181697, 3 pages (with English translation).
Notice Requesting Submission of Opinion in KR Application No. 10-2006-7013993 dated Jul. 31, 2007, 9 pages (with English translation).
Notification dated Apr. 25, 2008 for PH App. Ser. No. 1-2003-500266, 1 page.
Notification of Defects for IL App. Ser. No. 195282, dated Apr. 10, 2013, 4 pages (with English Translation).
Nugiel et al., "Synthesis and evaluation of indenopyrazoles as cyclin-dependent kinase inhibitors. 2. Probing the indeno ring substituent pattern," *J. Med. Chem.*, 45(24):5224-5232 (2002).
Nyati et al., "Radiosensitization by Pan ErbB Inhibitor CI-1033 in Vitro and in Vivo", Clinical Cancer Research., 10:691-700, 2004.
Ocqueteau et al., Expression of the CD117 antigen (C-Kit) on normal and myelomatous plasma cells, Br. J. Haematol., 95:489-493 (1996).
Office Action dated Apr. 11, 2013 for IL App. Ser. No. 217197, 4 pages (with English translation).
Office Action dated Apr. 16, 2013 for CA App. Ser. No. 2652442, 2 pages.
Office Action dated Apr. 27, 2010 for CN App. Ser. No. 200710007097.9, 7 pages (with English translation).
Office Action dated Apr. 28, 2009 for JP App. Ser. No. 2005-124034, 3 pages (with English translation).
Office Action dated Apr. 8, 2013 for U.S. Appl. No. 11/997,719, 55 pages.
Office Action dated Apr. 9, 2013 for CN App. Ser. No. 201080030508.6, 6 pages (with English translation).
Office Action dated Aug. 11, 2006 for CN App. Ser. No. 01819710.8, 6 pages (with English translation).
Office Action dated Aug. 8, 2003 for PH App. Ser. No. 1-2003-500266, 1 page.
Office Action dated Dec. 20, 2010 for IL App. Ser. No. 181697, 3 pages (with English translation).
Office Action dated Dec. 25, 2009 for CN App. Ser. No. 200710007097.9, 6 pages (with English translation).
Office Action dated Feb. 10, 2006 for CN App. Ser. No. 01819710.8, 8 pages (with English translation).
Office Action dated Jan. 27, 2009 for JP App. Ser. No. 2005-124034, 8 pages (with English translation).
Office Action dated Jul. 15, 2011 for CA App. Ser. No. 2579810, 2 pages.
Office Action dated Jul. 21, 2006 for PH App. Ser. No. 1-2003-500266, 1 pages.
Office Action dated Jul. 24, 2009 for CN App. Ser. No. 200710007096.4, 8 pages (with English translation).
Office Action dated Jul. 27, 2005 for KR App. Ser. No. 10-2003-7005506, 4 pages (with English translation).
Office Action dated Jun. 26, 2009 for CN App. Ser. No. 200580026468.7, 25 pages (with English translation).
Office Action dated Jun. 27, 2007 for PH App. Ser. No. 1-2003-500266, 1 page.
Office Action dated Jun. 5, 2012 for JP App. Ser. No. 2009-123432, 4 pages (with English translation).
Office Action dated Jun. 7, 2006 for MX App. Ser. No. PA/a/2003/003362, 6 pages (with English translation).
Office Action dated Mar. 14, 2013 for CN App. Ser. No. 200780017371.9, 9 pages (with English translation).
Office Action dated Mar. 21, 2007 for PH App. Ser. No. 1-2003-500266, 1 page.
Office Action dated Mar. 29, 2013 for U.S. Appl. No. 13/624,278, 73 pages.
Office Action dated Mar. 7, 2007 for NO App. Ser. No. 20031731, 3 pages (with English translation).
Office Action dated May 13, 2005 for CN App. Ser. No. 01819710.8, 8 pages (with English translation).
Office Action dated May 16, 2008 for NO App. Ser. No. 20031731, 2 pages (with English translation).
Office Action dated Nov. 13, 2012 for JP App. Ser. No. P2008-532141, 8 pages (with English translation).
Office Action dated Nov. 20, 2009 for CN App. Ser. No. 200580026468.7, 9 pages (with English translation).
Office Action dated Nov. 26, 2007 for MX App. Ser. No. PA/a/2005/013764, 6 pages (with English translation).
Office Action dated Oct. 11, 2007 for TW App. Ser. No. 90125928, 5 pages (with English translation).
Office Action dated Oct. 15, 2012 for IL App. Ser. No. 200090, 5 pages (with English translation).
Office Action dated Oct. 15, 2012 for NZ App. Ser. No. 598291, 2 pages.
Office Action dated Oct. 4, 2005 for MX App. Ser. No. PA/a/2003/003362, 8 pages (with English translation).
Office Action dated Oct. 4, 2007 for NO App. Ser. No. 20031731, 2 pages (with English translation).
Office Action dated Sep. 11, 2009 for CN App. Ser. No. 200710007097.9, 8 pages (with English translation).
Office Action dated Sep. 19, 2012 for CA App. Ser. No. 2627598, 3 pages.
Office Action dated Sep. 28, 2011 for KR App. Ser. No. 10-2007-7001347, 12 pages (with English translation).
Office Action dated Sep. 28, 2012 for CN App. Ser. No. 200780017371.9, 9 pages (with English translation).
Office Action dated Sep. 29, 2012 for CN App. Ser. No. 200980103218.7, 13 pages (with English translation).
Office Action dated Sep. 5, 2008 for NO App. Ser. No. 20031731, 2 pages (with English translation).
Office Action dated Sep. 5, 2012 for CN App. Ser. No. 200880003336.6, 12 pages (with English translation).
Office Action dated Sep. 5, 2012 for CN App. Ser. No. 200880115011.7, 6 pages (with English translation).
Office Action dated Sep. 7, 2007 for PH App. Ser. No. 1-2003-500266, 1 page.

(56) References Cited

OTHER PUBLICATIONS

Office Action directed at Israel Application No. 207089 dated Nov. 13, 2011, 4 pages (with English translation).
Office Action for Canadian Application No. 2,620,594, dated Aug. 15, 2011, 2 pages.
Office Action for EP App. Ser. No. 08846814.5, dated Apr. 16, 2013, 5 pages.
Office Action for IL 199907 dated Jun. 17, 2010, 3 pages with English translation.
Office Action for IL App. Ser. No. 175363, dated Jan. 2, 2013, 2 pages, with English translation.
Office Action for IL App. Ser. No. 200090, dated Jul. 24, 2013, 5 pages (with English translation).
Office Action for IL App. Ser. No. 205512, dated Dec. 20, 2012, 8 pages, with English translation.
Office Action for IL App. Ser. No. 207089, dated Jan. 6, 2013, 5 pages (with English translation).
Office Action for Indian Application No. 1908/DELNP/2008, dated Feb. 2, 2012, 2 pages.
Office Action for JP App. Ser. No. 2008-556208, dated Jan. 22, 2013, 8 pages, with English translation.
Office Action for JP App. Ser. No. P2008-532141, dated May 21, 2013, 4 pages (with English translation).
Office Action for JP App. Ser. No. P2009-551518, dated Jun. 18, 2013, 5 pages (with English translation).
Office Action for JP2007-542863 dated May 29, 2012, 8 pages with English translation.
Office Action for KR App. Ser. No. 10-2008-7013685, dated May 20, 2013, 10 pages (with English translation).
Office Action for PH App. Ser. No. 1-2011-502441 dated Oct. 1, 2013, 1 page.
Office Action for U.S. Appl. No. 12/039,381, dated Sep. 12, 2013, 15 pages.
Office Action for U.S. Appl. No. 13/083,338, dated Jan. 3, 2013, 9 pages.
Office Action for U.S. Appl. No. 13/238,085, dated Sep. 6, 2013, 10 pages.
Office Action for U.S. Appl. No. 12/439,339, dated May 23, 2013, 15 pages.
Office Action in Chinese Application No. 200710007097.9, dated Mar. 6, 2009, 5 pages.
Office Action in JP Application No. P2005-516605 dated Jun. 1, 2010, 3 pages.
Office Action issued for CN 200880002425.9 dated Mar. 2, 2011, 10 pages with English translation.
Office Action issued for EP 06768437.3 (EPO Form1224) dated Oct. 28, 2010, 47 pages.
Office Action issued for European Search Report for European Application No. 06782407 dated Sep. 29, 2011, 6 pages.
Office Action issued for Japanese Application No. 2007-529565 dated Dec. 13, 2011, 7 pages with English full translation.
Office Action issued for JP Appl. No. 2007-529565 dated May 8, 2012, 6 pages with English translation.
Office Action issued in MX App. Ser. No. MX/a/2012/002011, dated Jul. 17, 2013, 6 pages (with English translation).
Office Action dated Jan. 7, 2011, in U.S. Appl. No. 12/092,539, 12 pages.
Office Action, U.S. Appl. No. 11/347,749 dated Feb. 9, 2009, 6 pages.
Office Communication dated Sep. 13, 2004 for U.S. Appl. No. 10/420,466, 7 pages.
Office Letter Confirmation of Amendment After Allowance dated Jan. 11, 2011 for CA App. Ser. No. 2426461, 1 pages.
Office Letter re Notice of Allowance dated May 25, 2012 for ZA App. Ser. No. 201108697, 3 pages.
Official Letter and Notice of Allowance for AU App. Ser. No. 2008325608, dated Feb. 27, 2013, 7 pages.
Official Letter and Notice of Allowance for AU App. Ser. No. 2008211952, dated Jul. 10, 2012, 10 pages.

Official Letter re Grant of Request for Correction of Specification for SG App. Ser. No. 201108602-2, dated Aug. 8, 2012, 2 pages.
Ohe et al., "Randomized phase III study of cisplatin plus irinotecan versus carboplatin plus paclitaxel, cisplatin plus gemcitabine, and cisplatin plus vinorelbine for advanced non-small-cell lung cancer: Four-Arm Cooperative Study in Japan," *Ann Oncol.*, 18(2):317-323 (2007).
Okayama et al., "Activation of Eosinophils with Cytokines Produced by Lung Mast Cells," *Int Arch Allergy Immunol.*, 114(suppl 1):75-77 (1997).
Okayama et al., "Human Lung Mast Cells are Enriched in the Capacity to Produce Granulocyte-Macrophage Colony-Stimulating Factor in Response to IgE-Dependent Stimulation," *Eur. J. Immunol.*, 28:708-715 (1998).
Okura et al., "Effects of monoclonal anti-c-kit antibody (ACK2) on melanocytes in newborn mice," *J. Invest. Dermatol.*, 105(3):322-328 (1995).
Olaso et al., "DDR2 receptor promotes MMP-2-mediated proliferation and invasion by hepatic stellate cells," *J. Clin. Invest.*, 108(9):1369-1378 (2001).
Ozols et al., "Phase III trial of carboplatin and paclitaxel compared with cisplatin and paclitaxel in patients with optimally resected stage III ovarian cancer: a Gynecologic Oncology Group study," *J. Clin. Oncol.*, 21(17):3194-3200 (2003).
Pakistani Office Action for App. Ser. No. 94/2011, dated May 9, 2012, 2 pages.
Pandey et al., "Identification of Orally Active, Potent, and Selective 4-Piperazinylquinazolines as Antagonists of the Platelet-Derived Growth Factor Receptor Tyrosine Kinase Family", Journal of Medicinal Chemistry., 45, 3772-3793, 2002.
Partial European Search Report for App. Ser. No. 01976786.2, dated Apr. 6, 2004, 5 pages.
Paterson et al., "Preclinical studies of fibroblast growth factor receptor 3 as a therapeutic target in multiple myeloma," *British Journal of Haematology*, 124:595-603 (2004).
Paulus, "Preparation and Biomedical Applications of Bispecific Antibodies", Behring Inst. Mitt. 78: 118-132 (1985).
Paz et al., "Development of angiogenesis inhibitors to vascular endothelial growth factor receptor 2. Current status and future perspective," *Frontiers in Bioscience*, 10:1415-1439 (May 1, 2005).
Pearson, "Rapid and Sensitive Sequence Comparison with FASTP and FASTA", Methods in Enzymology 183 :63-98 (1990).
Petti et al., "Temporal quantitation of mutant Kit tyrosine kinase signaling attenuated by a novel thiophene kinase inhibitor OSI-930", Molecular Cancer Therapeutics., 4:1186-1197, 2005.
Plowright et al., "Ectopic expression of fibroblast growth factor receptor 3 promotes myeloma cell proliferation and prevents apoptosis," Blood, 95:992-998 (2000).
Podar et al., "GW654652, the pan-inhibitor of VEGF receptors, blocks the growth and migration of multiple myeloma cells in the bone marrow microenvironment", Blood.,103, 3474-3479, 2004.
Polverino et al, "AMG 706, an Oral, Multikinase Inhibitor that Selectively Targets Vascular Endothelial Growth Factor, Platelet-Derived Growth Factor, and Kit Receptors, Potently inhibits Angiogenesis and Induces Regression in Tumor Xenografts," Cancer Research, 66(17):8715-8721 (2006).
Preliminary Amendment and Response to Restriction Requirement in U.S. Appl. No. 12/439,339, filed Aug. 10, 2011, 24 pages.
Preliminary Amendment and Response to Restriction Requirement in U.S. Appl. No. 13/083,338, filed Apr. 30, 2012, 16 pages.
Preliminary Amendment dated Apr. 26, 2013 for U.S. Appl. No. 13/870,507, 10 pages.
Preliminary Amendment filed on Apr. 18, 2003 for U.S. Appl. No. 10/420,466, 376 pages.
Preliminary Amendment filed on Dec. 2, 2005 for U.S. Appl. No. 10/420,466, 36 pages.
Preliminary Amendment filed on Feb. 3, 2006 for U.S. Appl. No. 11/293,785, 33 pages.
Preliminary Amendment filed on May 23, 2003 for KR App. Ser. No.10-2003-7005506, 42 pages (with English translation).
Preliminary Amendment filed on Oct. 27, 2003 for U.S. Appl. No. 10/420,517, 41 pages.

(56) References Cited

OTHER PUBLICATIONS

Preliminary Amendment for U.S. Appl. No. 13/624,278, filed Sep. 21, 2012, 7 pages.
Pritzker, "Cancer Biomarkers: Easier Said Than Done," *Clinical Chemistry*, 48(8):1147-1150 (2002).
Reasons for Reexamination dated Sep. 11, 2012 for CN App. Ser. No. 200680020317.5, 7 pages (with English translation).
Reexamination filed on May 25, 2004 for TW App. Ser. No. 90125928, 59 pages (with English translation).
Reexamination filed on Nov. 25, 2004 for TW App. Ser. No. 90125928, 59 pages (with English translation).
Registered dated Feb. 24, 2009 for PH App. Ser. No. 1-2003-500266, 3 pages.
Rejection dated Apr. 26, 2004 for TW App. Ser. No. 90125928, 10 pages (with English translation).
Reply to communication from the Examining Division for EP App. Ser. 06023078.6, dated Feb. 4, 2008, 97 pages.
Reply to communication from the Examining Division for EP App. Ser. 06023078.6, dated Sep. 11, 2007, 10 pages.
Reply to communication from the Examining Division for EP App. Ser. No. 01976786.2, dated Jan. 25, 2006, 36 pages.
Reply to communication from the Examining Division for EP App. Ser. No. 01976786.2, dated Jul. 19, 2006, 124 pages.
Reply to communication from the Examining Division for EP App. Ser. No. 04025700.8, dated Feb. 15, 2007, 2 pages.
Reply to communication from the Examining Division for EP App. Ser. No. 04025700.8, dated Jan. 26, 2007, 232 pages.
Reply to communication from the Examining Division for EP App. Ser. No. 04025700.8, dated Sep. 12, 2006, 21 pages.
Reply to Examination Report dated Feb. 8, 2013 for EP App. Ser. No. 07743994.1, 4 pages.
Reply to official communication for EP App. Ser. No. 05783232.1, dated Apr. 30, 2008, 13 pages.
Reply to the invitation to remedy deficiencies for EP App. Ser. No. 06023078.6, dated Jan. 11, 2007, 3 pages.
Request for amendment of the text intended for grant and translation of claims for EP App. Ser. No. 04025700.8, dated Feb. 1, 2008, 41 pages.
Request for amendment of the text intended for grant and translation of claims for EP App. Ser. No. 06023078.6, dated Nov. 5, 2008, 19 pages.
Request for Continued Examination (RCE) transmittal for U.S. Appl. No. 12/864,817, filed Dec. 22, 2011, 1 page.
Request for correction of errors in filed documents for EP App. Ser. No. 06023078.6, dated Feb. 13, 2007, 4 pages.
Request for Examination in CA App. Ser. No. 2713930, dated Oct. 21, 2013, 8 pages.
Request for Re-Examination in CN App. Ser. No. 200780017371.9, dated Oct. 11, 2013, 9 pages (with English translation).
Request for Substantive Examination for ID App. Ser. No. W-00201201031, filed Jun. 3, 2013, 6 pages (with English translation).
Request for Substantive Examination for UA App. Ser. No. a201203132, filed Apr. 15, 2013, 16 pages (with English translation).
Request for Voluntary Amendments filed May 10, 2012, in Ukraine Patent Application No. A 2012 03132, 11 pages with English Abstract.
Request to Amend Complete Specification dated Feb. 15, 2013 for AU App. Ser. No. 2008325608, 23 pages.
Request to Amend Complete Specification dated May 9, 2013 for AU App. Ser. No. 2009210098, 22 pages.
Response and Amended Claims filed in EP App. Ser. No. 08846814.5, filed Aug. 1, 2013, 14 pages.
Response and Amended Claims filed in EP App. Ser. No. 10809938.3, filed Jul. 19, 2013, 7 pages.
Response and Amendment for CA App. Ser. No. 2652442, dated Sep. 5, 2013, 17 pages.
Response filed in in App. Ser. No. 1571/CHENP/2007, dated Oct. 30, 2013, 9 pages.
Response filed on Apr. 11, 2006 for CN App. Ser. No. 01819710.8, 4 pages (with English translation).
Response filed on Apr. 17, 2007 for PH App. Ser. No. 1-2003-500266, 1 page.
Response filed on Apr. 27, 2006 for AU App. Ser. No. 2001295986, 22 pages.
Response filed on Apr. 30, 2008 for PH App. Ser. No. 1-2003-500266, 1 page.
Response filed on Aug. 13, 2009 for CA App. Ser. No. 2426461, 4 pages.
Response filed on Aug. 14, 2006 for PH App. Ser. No. 1-2003-500266, 1 page.
Response filed on Aug. 18, 2008 for NO App. Ser. No. 20031731, 2 pages (with English translation).
Response filed on Aug. 21, 2006 for MX App. Ser. No. PA/a/2003/003362, 5 pages (with English translation).
Response filed on Aug. 26, 2004 for NZ App. Ser. No. 525324, 3 pages.
Response filed on Aug. 5, 2003 for PH App. Ser. No. 1-2003-500266, 1 page.
Response filed on Dec. 11, 2007 for TW App. Ser. No. 90125928, 54 pages (with English translation).
Response filed on Dec. 15, 2005 for MX App. Ser. No. PA/a/2003/003362, 9 page (with English translation).
Response filed on Dec. 4, 2007 for IL App. Ser. No. 155447, 35 pages (with English translation).
Response filed on Feb. 23, 2009 for CA App. Ser. No. 2426461, 31 pages.
Response filed on Feb. 26, 2008 for U.S. Appl. No. 11/293,785, 16 pages.
Response filed on Jan. 11, 2010 for CN App. Ser. No. 200580026468.7, 4 pages (with English translation).
Response filed on Jan. 21, 2005 for NZ App. Ser. No. 525324, 2 pages.
Response filed on Jan. 26, 2010 for CN App. Ser. No. 200710007097.9, 3 pages (with English translation).
Response filed on Jan. 26, 2011 for IL App. Ser. No. 181697, 5 pages (with English translation).
Response filed on Jul. 1, 2005 for U.S. Appl. No. 10/420,466, 14 pages.
Response filed on Jul. 2, 2009 for CN App. Ser. No. 200710007097.9, 4 pages (with English translation).
Response filed on Jul. 26, 2006 for AU App. Ser. No. 2001295986, 11 pages.
Response filed on Jul. 31, 2007 for Ph App. Ser. No. 1-2003-500266, 1 page.
Response filed on Jun. 22, 2010 for CN App. Ser. No. 200710007097.9, 3 pages (with English translation).
Response filed on Mar. 17, 2005 for RU App. Ser. No. 2003114740, 75 pages (with English translation).
Response filed on May 13, 2009 for IL App. Ser. No. 189677, 125 pages (with English translation).
Response filed on May 16, 2008 for CA App. Ser. No. 2426461, 79 pages.
Response filed on May 20, 2010 for CA App. Ser. No. 2426461, 23 pages.
Response filed on May 7, 2008 for NO App. Ser. No. 20031731, 2 pages (with English translation).
Response filed on May 8, 2008 for AU App. Ser. No. 2006236039, 2 pages.
Response filed on Nov. 19, 2009 for CN App. Ser. No. 200710007097.9, 9 pages (with English translation).
Response filed on Nov. 30, 2004 for RU App. Ser. No. 2003114740, 90 pages (with English translation).
Response filed on Oct. 13, 2008 for NO App. Ser. No. 20031731, 400 pages (with English translation).
Response filed on Oct. 15, 2007 for PH App. Ser. No. 1-2003-500266, 1 page.
Response filed on Oct. 8, 2004 for U.S. Appl. No. 10/420,466, 19 pages.
Response filed on Oct. 9, 2006 for CN App. Ser. No. 01819710.8, 2 pages (with English translation).

(56) References Cited

OTHER PUBLICATIONS

Response filed on Sep. 10, 2007 for NO App. Ser. No. 20031731, 60 pages (with English translation).
Response filed on Sep. 13, 2005 for CN App. Ser. No. 01819710.8, 7 pages (with English translation).
Response filed on Sep. 15, 2003 for PH App. Ser. No. 1-2003-500266, 1 page.
Response filed on Sep. 21, 2011 for CA App. Ser. No. 2579810, 16 pages.
Response filed on Sep. 23, 2009 for CN Patent Application No. 200580026468.7, 4 pages with English translation.
Response filed on Sep. 8, 2003 for PH App. Ser. No. 1-2003-500266, 1 page.
Response to AU OA for AU 2008211952 filed on Jun. 28, 2012, 36 pages.
Response to Australian Office Action filed on Apr. 29, 2010 for corresponding AU Application No. 2006285673, 11 pages.
Response to Australian Office Action filed on Jul. 28, 2010 for corresponding AU Application No. 2006285673, 6 pages.
Response to Australian Office Action filed on Oct. 16, 2009 for corresponding AU Application No. 2006285673, 14 pages.
Response to Canadian Office Action filed Feb. 13, 2012, in Canadian Application No. 2,620,594, 8 pages.
Response to Canadian Office Action filed on Apr. 12, 2011 for corresponding CA Application No. 2,620,594, 4 pages.
Response to Canadian Office Action filed on Jun. 21, 2010 for corresponding CA Application No. 2,620,594, 18 pages.
Response to Chinese Office Action filed on Jul. 11, 2012 for Chinese Patent Application No. 200680036592.6, 17 pages with English translation.
Response to Chinese Office Action filed on Mar. 5, 2010 for corresponding CN Application No. 200680036592.6, 11 pages with English translation.
Response to Chinese Office Action for CN 200680020317.5 dated Sep. 11, 2012, 7 pages with English translation.
Response to CN OA for CN200880003336.6 filed on May 3, 2012, 15 pages.
Response to EP OA for EP 07806561.2 filed on Apr. 18, 2012, 8 pages.
Response to IL OA for IL 195282 filed on May 28, 2012, 5 pages.
Response to Indian Office Action dated Feb. 2, 2012, dated Jun. 22, 2012, for Application No. 1908/DELNP/2008, 27 pages.
Response to Israeli Office Action filed on Sep. 7, 2010 for the corresponding Israeli Application No. 189589, 9 pages.
Response to Israeli Office Action, filed Jul. 24, 2012 for corresponding Israeli Patent Application No. 189589, 7 pages.
Response to Japanese Office Action dated Jul. 17, 2012 for Japanese Application No. 2007-533350, 12 pages with English translation.
Response to Japanese Office Action filed on Jan. 9, 2013 for corresponding Japanese Application JP-2007-533350, 6 pages.
Response to Korean Office Action filed on Feb. 24, 2010 for corresponding KR Application No. 10-2008-7005195, 31 pages with English translation.
Response to Korean Office Action filed on Jul. 29, 2010 for corresponding KR Application No. 10-2008-7005195, 26 pages with English translation.
Response to Notice of Allowability filed on Dec. 13, 2007 for PH App. Ser. No. 1-2003-500266, 1 page.
Response to Notice Prior to Examination filed in IL App. Ser. No. 217197, filed Jul. 31, 2013, 9 pages (with English translation).
Response to Notice Prior to Examination filed on Apr. 22, 2009 for IL App. Ser. No. 181697, 11 pages (with English translation).
Response to Notice Prior to Examination filed on Jan. 11, 2009 for IL App. Ser. No. 189677, 7 pages (with English translation).
Response to OA for EP 10015141 filed on Mar. 5, 2012, 47 pages.
Response to Office Action dated Feb. 7, 2013 for CN App. Ser. No. 201080030508.6, 17 pages (with English translation).
Response to Office Action dated Jul. 5, 2012 for CN App. Ser. No. 200880115011.7, 24 pages (with English translation).
Response to Office Action dated Nov. 30, 2012 for CN App. Ser. No. 200780017371.9, 4 pages (with English translation).
Response to Office Action directed at Australian Appl. No. 2006309551 filed on Mar. 28, 2012, 27 pages.
Response to Office Action filed on Jan. 25, 2013 for CA App. Ser. No. 2627598, 9 pages.
Response to Office Action filed on Jul. 11, 2012 for CN App. Ser. No. 200880003336.6 (with English translation), 10 pages.
Response to Office Action filed on May 29, 2012 for RU App. Ser. No. 2012103471 (with English translation), 7 pages.
Response to Office Action for EP 08704376.6 dated Jan. 2, 2013, 22 pages.
Response to Office Action for IL 199907 filed on Oct. 11, 2010, 4 pages with English translation.
Response to Office Action for Israeli App. Ser. No. 205512, filed on Mar. 11, 2012 (with English translation), 12 pages.
Response to Office Action for Israeli App. Ser. No. 207089, filed on Mar. 11, 2012, with English translation, 13 pages.
Response to Office Action for MX App. Ser. No. MX/a/2012/002011, dated Aug. 29, 2013, 12 pages (with English translation).
Response to Office Action for U.S. Appl. No. 13/322,961, dated Jan. 25, 2013, 22 pages.
Response to Office Action for U.S. Appl. No. 10/420,466 dated Jun. 29, 2005, 14 pages.
Response to Office Action under 37 C.F.R. §1.111 for U.S. Appl. No. 12/523,495, filed Dec. 7, 2011, 13 pages.
Response to Office Action under 37 C.F.R. §1.111 for U.S. Appl. No. 13/083,338, filed Sep. 6, 2012, 8 pages.
Response to Office Action under 37 C.F.R. §1.111 for U.S. Appl. No. 13/083,338, filed Apr. 8, 2011, 6 pages.
Response to Office Action under 37 C.F.R.S 1.111 and Information Disclosure Statement for U.S. Appl. No. 11/997,719, filed Jul. 3, 2013, 26 pages.
Response to Restriction Requirement for U.S. Appl. No. 11/997,543, filed Mar. 22, 2011, 4 pages.
Response to Restriction Requirement for U.S. Appl. No. 12/301,353, filed Nov. 23, 2010, 4 pages.
Response to Restriction Requirement for U.S. Appl. No. 12/524,754, filed Dec. 1, 2011, 2 pages.
Response to Restriction Requirement in U.S. Appl. No. 13/238,085, dated Oct. 4, 2013, 3 pages.
Response to the European Search Report for European Application No. 06782407 filed on Nov. 8, 2010, 105 pages.
Response to the Office Action for European Application No. 06782407 filed on Jan. 23, 2012, 17 pages.
Response to the Office Action issued for Japanese Application No. 2007-529565 filed on Feb. 3, 2012, 44 pages with English full translation.
Restriction Requirement for U.S. Appl. No. 12/092,539, dated Oct. 29, 2010, 8 pages.
Restriction Requirement for U.S. Appl. No. 12/301,353, dated Oct. 29, 2010, 11 pages.
Restriction Requirement for U.S. Appl. No. 12/439,339, dated Jul. 29, 2011, 10 pages.
Restriction Requirement for U.S. Appl. No. 12/524,754, dated Nov. 3, 2011, 11 pages.
Roberts et al., "Antiangiogenic and Antitumor Activity of a Selective PDGFR Tyrosine Kinase Inhibitor, CP-673,451", Cancer Research., 65, 957-966, 2005.
Ruggeri et al., "CEP-7055: A Novel, Orally Active Pan Inhibitor of Vascular Endothelial Growth Factor Receptor Tyrosine Kinases with Potent Antiangiogenic Activity and Antitumor Efficacy in Preclinical Modelsl", Cancer Research., 63, 5978-5991, 2003.
Ruggeri et al., "CEP-7055: An orally-active VEGF-R kinase inhibitor with potent anti-angiogenic activity and anti-tumor efficacy against human tumor xenograft growth," AACR American Association Cancer Research., 93rd Annual Meeting, 43:1080, Apr. 6-10, 2002, San Francisco, CA, USA, abstract 5347, 2 pages.
Russian Decision of Grant directed at Appl. No. 2008149948115(065561), 16 pages with English translation.
Russian Office Action dated Apr. 11, 2012 for App. Ser. No. 2012103471, 6 pages (with English translation).

(56) References Cited

OTHER PUBLICATIONS

Russian Office Action dated Jan. 19, 2005 for App. Ser. No. 2003114740 (with English translation), 3 pages.
Russian Office Action dated Jun. 29, 2004 for App. Ser. No. 2003114740 (with English translation), 16 pages.
Russian Office Action directed at Appl. No. 2008149948115(065561) dated May 24, 2011, 8 pages with English translation.
Russian Response to Office Action directed at Appl. No. 2008149948115(065561) filed on Jul. 27, 2011, 14 pages with English translation.
Salassidis et al., "Translocation t(1 0; 14) (q 11.2; q22.1) Fusing the Kinectin to the RET Gene Creates a Novel Rearranged Form (PTC8) of the RET Proto-Oncogene in Radiation-induced Childhood Papillary Thyroid Carcinoma", Cancer Research, 60: 2786-2789 (2000).
Salmon et al., "Anti-angiogenic treatment of gastrointestinal malignancies," *Cancer Invest.*, 23(8):712-726 (2005).
Salvatore et al., "Molecular profile ofhyalinizing trabecular tumours of the thyroid: High prevalence of RET/PTC rearrangements and absence of B-raf and N-raspoint mutations", European Journal of Cancer, 41: 816-821 (2005).
Sandler et al., "Phase III trial of gemcitabine plus cisplatin versus cisplatin alone in patients with locally advanced or metastatic non-small-cell lung cancer," *J. Clin. Oncol.*, 18(1):122-130 (2000).
Sanger et al., "DNA sequencing with chain-terminating inhibitors", Proc. Natl. Acad. Sci. USA 74: 5463 (1977).
Santoro et al., "Drug insight: Small-molecule inhibitors of protein kinases in the treatment of thyroid cancer," *Nat. Clin. Pract. Endocrinol. Metab.*, 2(1):42-52 (2006).
Santoro et al., "Minireview: RET: normal and abnormal functions," *Endocrinology*, 145:5448-5451 (2004).
Santoro et al., "Molecular Mechanisms of RET Activation in Human Cancer," *Ann. N.Y. Academy of Sciences*, 963:116-121 (2002).
Sattler et al., "Targeting c-Kit mutations: basic science to novel therapies," Leukemia Research, 2004, 28S1:S11-S20.
Scheijen et al., "Tryosine Kinase Oncogenes in Normal Hematopoiesis and Hematological Disease," *Oncogene*, 21:3314-3333 (2002).
Schlumberger et al., "A Phase 2 Trial of the Multi-Targeted Kinase Inhibitor Lenvatinib (E7080) in Advanced Medullary Thyroid Cancer (MTC)," 2012 ASCO Annual Meeting, Poster Presentation, Jun. 1-5, 2012.
Second Preliminary Amendment and Response to Restriction Requirement for U.S. Appl. No. 12/092,539, filed Nov. 22, 2010, 5 pages.
Sekido et al., "Preferential Expression of c-kit Protooncogene Transcripts in Small Cell Lung Cancer," Cancer Res., 51:2416-2418 (1991).
Shiang et al., "Mutations in the transmembrane domain of FGFR3 cause the most common genetic form of dwarfism, achondroplasia," *Cell.*, 78:335-342 (1994).
Shibata et al., "Rapid Communication Association of Epstein-Barr Virus with Undifferentiated Gastric Carcinomas with Intense Lymphoid Infiltration", American Journal of Pahthology 139(3):469-473 (1991).
Shimizu et al., "Orally active anti-proliferation agents: novel diphenylamine derivatives as FGF-R2 autophosphorylation inhibitors," *Bioorganic and Medicinal Chemistry Letters*, 14(4):875-879 (2004).
Shirai, et al., ""Role of llow-substituted hydroxypropylcellulose in dissociation and bioavalability of novel fine granule system for masking bitter taste," Biol. Pharm. Bull, 17(3): 427-431 (1994)."
Siegel et al., "Sorafenib: Where Do We Go from Here?," *Hepatology*, 52:360-369 (2010).
Siemeister et al., "ZK304709, the oral Multitarget Tumor Growth InhibitorTm, acts via inihibition of cell cycle progression and tumor-induced angiogenesis," Proceedings of the American Association for Cancer Research, 46, (Abstract 5842), 2005, 3 pages.
Sihto et al., "KIT and platelet-derived growth factor receptor alpha tyrosine kinase gene mutations and KIT amplifications in human solid tumors," Journal of Clinical Oncology, 23(1):49-57 (2005).
Spacey et al., "Indolocarbazoles, Potent and Selective Inhibitors of Platelet-Derived Growth Factor Receptor Autophosphorylation," *Biochemical Pharmacology*, 55:261-271 (1998).
St. Bernard et al., "Fibroblast Growth Factor Receptors as Molecular Targets in Thyroid Carcinoma," Endocrinology, Mar. 2005, 146(3):1145-1153.
Strohmeyer et al., "Expression of the hst-1 and c-kit Protoonocogenes in Human Testicular Germ Cell Tumors," *Cancer Res.*, 51:1811-1816 (1991).
Submission Document(s) Before the Patent Office for IL App. Ser. No. 200090, dated Dec. 23, 2012, 16 pages, with English translation.
Submission Document Before the Patent Office dated Apr. 22, 2013 for IL App. Ser. No. 207089, 7 pages (with English translation).
Submission Document Before the Patent Office dated Mar. 14, 2013 for IL App. Ser. No. 205512, 12 pages (with English translation).
Submission Document Before the Patent Office for CL App. Ser. No. 2012-00412, dated Aug. 31, 2012, 6 pages (with English translation).
Submission Document Before the Patent Office for EP App. Ser. No. 03791389.4, dated Dec. 20, 2012, 4 pages.
Submission Document Before the Patent Office for EP App. Ser. No. 08846814.5, dated Jan. 3, 2013, 102 pages.
Submission Document Before the Patent Office re Observation dated Feb. 16, 2013 for CN App. Ser. No. 200980103218.7, 6 pages (with English translation).
Submission Document Before the Patent Office re RCE in U.S. Appl. No. 13/205,328, dated Sep. 10, 2013, 1 page.
Submission Document re Petition on Oct. 2, 2013 in CL App. Ser. No. 2012-00412, 22 pages (with English translation).
Submission Documents re RCE and Information Disclosure Statement on Sep. 19, 2013 in U.S. Appl. No. 12/741,682, 19 pages.
Submission Documents RCE and Information Disclosure Statement o Oct. 18, 2013, in U.S. Appl. No. 12/524,754, 17 pages.
Submission Documents Before the Patent Office for CN App. Ser. No. 201080030508.6, dated May 27, 2013, 7 pages (with English translation).
Submission Documents Before the Patent Office for KR App. Ser. No. 10-2009-7017694, dated Jan. 18, 2013, 22 pages, with English translation.
Submission Documents Before the Patent Office for U.S. Appl. No. 12/741,682, dated May 17, 2013, 16 pages.
Submission Documents re New Claim Set Before the Patent Office for AR App. Ser. No. P110100513, dated Aug. 27, 2013, 8 pages (with English translation).
Submission Documents re Preliminary Amendment Before the Patent Office U.S. Appl. No. 14/002,018, dated Aug. 28, 2013, 9 pages.
Submission Documents re RCE Before the Patent Office for U.S. Appl. No. 13/083,338, dated Aug. 28, 2013, 20 pages.
Submission Documents re RCE Before the Patent Office for U.S. Appl. No. 12/524,754, dated Apr. 15, 2013, 17 pages.
Submission of Amendments and Complete Specification dated Apr. 10, 2013 for IN App. Ser. No. 1571/CHENP/2007, 15 pages.
Submission of Document Before the Patent Office re Request for Voluntary Amendments dated Jan. 30, 2013 for NZ App. Ser. No. 598291, 8 pages.
Submission of Document re Claims filed in Response to Second Office Action for CN App. Ser. No. 200880115011.7, filed on Nov. 20, 2012, 16 pages.
Submission of Document re Request for Examination in CO App. Ser. No. 12-022608, submitted on Jun. 12, 2012, 6 pages.
Submission of Documents before the Patent Office for CN App. Ser. No. 200980103218.7, dated Mar. 13, 2013, 6 pages (with English translation).
Submission of Documents before the Patent Office for CN App. Ser. No. 200880115011.7, dated Apr. 11, 2013, 10 pages (with English translation).
Submission of Documents Before the Patent Office for IL App. Ser. No. 175363, dated Feb. 27, 2013, 22 pages.

(56) References Cited

OTHER PUBLICATIONS

Submission of Documents re Amendment in UA App. Ser. No. a2012 03132, dated May 22, 2012, 11 pages (with English translation).
Submission of Documents re Claim 3 and Figure 3 for KR App. Ser. No. 10-2009-7005657, filed on Jul. 13, 2012, 5 pages.
Submission of Reference Materials in KR App. Ser. No. 10-2008-7013685, filed Jul. 5, 2013, 43 pages, (with English translation).
Sun et al., "Design, synthesis, and evaluations of substituted 3-[(3- or 4-carboxyethylpyrrol-2-yl)methylidenyl]indolin-2-ones as inhibitors of VEGF, FGF, and PDGF receptor tyrosine kinases", Journal of Medicinal Chemistry., 42:5120-5130 (1999).
Sun et al., "Discovery of 5-[5-Fluoro-2-oxo-1,2-dihydroindol-(3Z)-ylidenemethyl]-2,4-dimethyl-1H- pyrrole-3carboxylic acid . . . Tyrosine Kinase", Journal of Medicinal Chemistry., 46:1116-1119 (2003).
Sun et al., "Synthesis and Biological Evaluations of 3-Substituted Indolin-2-ones: A novel class of Tyrosine kinase inhibitors that exhibit selectivity toward particular receptor tyrosine kinases", Journal of Medicinal Chemistry., 41:2588-2603 (1998).
Supplementary European Search Report for App. Ser. No. 01976786.2, dated Jul. 6, 2004, 6 pages.
Supplementary European Search Report dated Jul. 5, 2012, in European Patent Application No. 08846814.5, 1 page.
Suzuki et al., "MP-412, a dual EGFR/HER2 tyrosine kinase inhibitor: 1. In vivo kinase inhibition profiled," Am. Assoc. Cancer Research, A3405, 2005, 2 pages.
Taguchi et al., "A novel orally active inhibitor of VEGF receptor tyrosine kinases KRN951: Anti-angiogenic and anti-tumor activity against human solid tumors," Proc Am Assoc Cancer Res., 45:1070-1071, Abstract 2575, 2004.
Takahashi et al., "A case of inoperable scirrhous gastric cancer that responded remarkably to a combination of TS-1+paclitaxel and showed complete loss of ascites," *Japanese Journal of Cancer and Chemotherapy*, 31(7):1093-1095 (2004).
Takeda et al., "AZD2171 shows potent anti-tumor activity against gastric cancer expressing variant K-SAM/FGFR2," Abstract #3785, *Proceeding of the American Association for Cancer Research*, 47:890 (2006).
Tan et al., "Randomized study of vinorelbine—gemcitabine versus vinorelbine—carboplatin in patients with advanced non-small cell lung cancer," *Lung Cancer*, 49(2):233-240 (2005).
Taniguchi et al., "Effect of c-kit Mutation on Prognosis of Gastrointestinal Stromal Tumors," *Cancer Res.*, 59:4297-4300 (1999).
The Pharmacology of Monoclonal Antibody, vol. 113, Chapter 11, Rosenburg and Moore ed., Springer Verlag (1994) pp. 269-315.
Third Office Action dated Feb. 25, 2013 for CN App. Ser. No. 200880115011.7, 6 pages (with English translation).
Thomas et al., "The Eosinophil and its Role in Asthma," *Gen. Pharmac.*, 27(4)593-597 (1996).
Thyroid Cancers, Endocrine and Metabolic Disorders, http://www.merkmanuals.com/professional/print/sec12/ch152/ch152j.html Mar. 16, 2011, 4 pages.
Tian et al., "Activating c-kit Gene Mutations in Human Germ Cell Tumors," American Journal of Pathology, 154(6):1643-1647 (1999).
Tohyama et al., "P-3111, Preclinical effect of lenvatinib on human thyroid cancer targeting angiogenesis and receptor tyrosine kinase signaling," The 71$^{st}$ Annual Meeting of the Japanese Cancer Association, Sep. 19-21, 2012, p. 502.
Tonary et al., "Lack of expression of c-KIT in ovarian cancers is associated with poor prognosis," *Int. J. Cancer*, 89:242-250 (2000).
Tong et al., "Vascular normalization by vascular endothelial growth factor receptor 2 blockade induces a pressure gradient across the vasculature and improves drug penetration in tumors," *Cancer Res.*, 64:3731-3736 (2004).
Toshiyuki et al., "Thermal recording materials with improved background stability," Database CA (Online) Chemical Abstracts Service, Columbus, OH, US (Feb. 20, 1996) (XP002443195), 1 page.
Transmittal of Information Disclosure Statement, Terminal Disclaimer, Request for Continued Examination, and Response to Office Action under 37 C.F.R. §1.116 for U.S. Appl. No. 11/997,719, filed Jul. 6, 2011, 15 pages.
Traxler et al., "AEE788; A dual family epidermal growth factor receptor/ErbB2 and vascular endothelial growth factor receptor tyrosine kinase inhibitor with antitumor and antiangiogenic activity," *Cancer Res.*, 64:4931-4941 (2004).
Trudel et al., "CHIR-258, a novel, multitargeted tyrosine kinase inhibitor for the potential treatment of t(4;14) multiple myeloma," *Blood*, 105:2941-2948 (2005).
Trudel et al., "Inhibition of fibroblast growth factor receptor 3 induces differentiation and apoptosis in t(4;14) myeloma," *Blood*, 103:3521-3528 (2004).
Tsou et al., "Optimization of 6,7-Disubstituted-4-(arylamino)quinoline-3-carbonitriles as Orally Active, Irreversible Inhibitors of Human Epidermal Growth Factor Receptor-2 Kinase Activity", Journal of Medicinal Chemistry., 48, 1107-1131, 2005.
Turner et al., "Fibroblast growth factor signaling: from development to cancer," *Nature Reviews, Cancer*, 10:116-129 (2010).
U.S. Notice of Allowance for U.S. Appl. No. 12/244,227, dated Oct. 22, 2010, 32 pages.
U.S. Office Action for U.S. Appl. No. 10/420,466, dated Apr. 13, 2005, 16 pages.
U.S. Office Action for U.S. Appl. No. 10/797,903, dated Apr. 1, 2010, 11 pages.
U.S. Office Action for U.S. Appl. No. 10/797,903, dated Sep. 1, 2010, 7 pages.
U.S. Office Action for U.S. Appl. No. 11/293,785, dated Sep. 4, 2007, 18 pages.
U.S. Office Action for U.S. Appl. No. 11/662,425, dated May 3, 2010, 16 pages.
U.S. Office Action for U.S. Appl. No. 11/662,425, dated Sep. 28, 2010, 35 pages.
U.S. Office Action for U.S. Appl. No. 11/997,543, dated Feb. 23, 2011, 9 pages.
U.S. Office Action for U.S. Appl. No. 11/997,543, dated May 19, 2011, 38 pages.
U.S. Office Action for U.S. Appl. No. 11/997,543, dated Nov. 9, 2011, 12 pages.
U.S. Office Action for U.S. Appl. No. 11/997,719, dated Apr. 6, 2011, 6 pages.
U.S. Office Action for U.S. Appl. No. 11/997,719, dated Sep. 3, 2010, 10 pages.
U.S. Office Action for U.S. Appl. No. 12/092,539, dated Jun. 28, 2011, 3 pages.
U.S. Office Action for U.S. Appl. No. 12/092,539, dated May 9, 2011, 10 pages.
U.S. Office Action for U.S. Appl. No. 12/094,492, dated Mar. 24, 2011, 16 pages.
U.S. Office Action for U.S. Appl. No. 12/301,353, dated Jan. 24, 2011, 10 pages.
U.S. Office Action for U.S. Appl. No. 12/400,562, dated Mar. 31, 2010, 11 pages.
U.S. Office Action for U.S. Appl. No. 12/439,339, dated Mar. 30, 2012, 6 pages.
U.S. Office Action for U.S. Appl. No. 12/439,339, dated Nov. 14, 2011, 44 pages.
U.S. Office Action for U.S. Appl. No. 12/523,495, dated Dec. 27, 2011, 11 pages.
U.S. Office Action for U.S. Appl. No. 12/523,495, dated Sep. 27, 2011, 37 pages.
U.S. Office Action for U.S. Appl. No. 12/524,754, dated Dec. 19, 2011, 53 pages.
U.S. Office Action for U.S. Appl. No. 12/741,682, dated Apr. 30, 2012, 50 pages.
U.S. Office Action for U.S. Appl. No. 12/864,817, dated Dec. 16, 2011, 4 pages.
U.S. Office Action for U.S. Appl. No. 12/864,817, dated May 19, 2011, 11 pages.
U.S. Office Action for U.S. Appl. No. 12/864,817, dated Nov. 3, 2011, 11 pages.

(56) References Cited

OTHER PUBLICATIONS

U.S. Office Action for U.S. Appl. No. 13/083,338, dated Apr. 12, 2012, 8 pages.
U.S. Office Action for U.S. Appl. No. 13/083,338, dated Jun. 8, 2012, 55 pages.
U.S. Office Action for U.S. Appl. No. 13/083,338, dated Nov. 23, 2012, 38 pages.
U.S. Office Action for U.S. Appl. No. 13/205,328, dated Jan. 12, 2012, 37 pages.
U.S. Office Action for U.S. Appl. No. 13/205,328, dated May 1, 2012, 21 pages.
U.S. Office Action for U.S. Appl. No. 13/322,961, dated Sep. 25, 2012, 62 pages.
Ueda et al., "VGA1155, a Novel Binding Antagonist of VEGF, Inhibits Angiogenesis In Vitro and In Vivo", Anticancer Research., 24, 3009-3017, 2004.
Ueda et al., "Deletion of the carboxyl-terminal exons of K-sam/FGFR2 by short homology-mediated recombination, generating preferential expression of specific messenger RNAs," Cancer Res., 59(24):6080-6086 (1999).
U.S. Office Action for U.S. Appl. No. 11/997,543, dated Sep. 30, 2013, 88 pages.
U.S. Response to Notice of Non-Compliant Amendment dated Jan. 13, 2005 for U.S. Appl. No. 10/420,466, 17 pages.
Van Dijk et al. "Induction of Tumor-Cell Lysis by B-Specific Monoclonal Antibodies Recognizing Renal-Cell Carcinoma and CD3 Antigen", Int. J. Cancer 43: 344-9, 1989.
Van Oers et al., "A simple and fast method for the simultaneous detection of nine fibroblast growth factor receptor 3 mutations in bladder cancer and voided urine," Clin. Cancer Res., 11:7743-7748 (2005).
Vippagunta et al., "Crystalline solids," Advanced Drug Delivery Reviews, 48:3-26 (2001).
Vogel et al., "Sensing extracellular matrix: an update on discoidin domain receptor function," Cell Signaling, 18:1108-1116 (2006).
Voluntary Amendment filed in CA App. Ser. No. 2704000, filed Aug. 6, 2013, 6 pages.
Voluntary Amendment filed on Aug. 11, 2010 for CN App. Ser. No. 200710007097.9, 12 pages (with English translation).
Voluntary Amendment filed on Aug. 19, 2010 for CA App. Ser. No. 2426461, 2 pages.
Voluntary Amendment filed on Aug. 30, 2006 for AU App. Ser. No. 2006203099, 16 pages.
Voluntary Amendment filed on Feb. 16, 2012 for BR Patent App. No. BR112012003592-4, 18 pages (with partial English translation).
Voluntary Amendment filed on Feb. 27, 2007 for AU App. Ser. No. 2006236039, 10 pages.
Voluntary Amendment filed on Feb. 9, 2010 for AU App. Ser. No. 2005283422, 12 pages.
Voluntary Amendment filed on Jul. 6, 2010 for AU App. Ser. No. 2005283422, 21 pages.
Voluntary Amendment filed on Sep. 10, 2010 for HU App. Ser. No. P0302603, 36 pages (with English translation).
Voluntary Amendment for Australian App. Ser. No. 2010285740, filed on Nov. 21, 2011, 3 pages.
Voluntary Amendment for Chinese counterpart of App. No. PCT/JP2010/063804, filed on Jan. 5, 2012, 8 pages (with English translation).
Voluntary Amendment for counterpart Canadian patent application, filed on Feb. 16, 2012, 3 pages.
Voluntary Amendment for Russian App. Ser. No. 2012103471, filed on Feb. 1, 2012, 3 pages (with English translation).
Voluntary Amendment for Thailand App. Ser. No. 1201000221, filed on Feb. 17, 2012, 8 pages.
Voluntary Brief Amendments for Venezuelan App. Ser. No. 2011-000193, filed on Dec. 21, 2011, 8 pages (with English translation).
Wakeling et al., "ZD1839 (Iressa): an orally active inhibitor of epidermal growth factor signaling with potential for cancer therapy," Cancer Res., 62(20)5749-5754 (2002).
Wakui, "Chemotherapy of scirrhous gastric cancer," Japanese Journal of Cancer and Chemotherapy, 21(14):2398-2406 (1994) (English abstract).
Wang et al., "A Convenient Set of Bidentate Pyridine Ligands for Combinatorial Synthesis," Tetrahedron Lett., 40:4779-1478 (1999).
Wang et al., "Phase II study of gemcitabine and carboplatin in patients with advanced non-small-cell lung cancer," Cancer Chemother Pharmacol., 60(4):601-607 (2007).
Wang et al., "The Expression of the Proto-Oncogene C-Kit in the Blast Cells of Acute Myeloblastic Leukemia," Leukemia, 3(10):699-702 (1989).
Wang, "Everolimus in renal cell carcinoma," Drugs of Today, Aug. 2010, 46(8), abstract, 1 page.
Waterman, M., "Computer Analysis of Nucleic Acid Sequences", Methods in Enzymology, 164:765-793 (1988).
Wedge et al., "ZD4190: An Orally Active Inhibitor of Vascular Endothelial Growth Factor Signaling with Broad-Spectrum Antitumor Efficacy", Cancer Research., 60, 970-975, 2000.
Wedge et al., "AZD2171: a highly potent, orally bioavailable, vascular endothelial growth factor receptor-2 tyrosine kinase inhibitor for the treatment of cancer," Cancer Res., 65(10):4389-4400 (2005).
Wedge et al., "Pharmacological Efficacy of ZD6474, a VEGF Receptor Tyrosine Kinase Inhibitor, in Rat," AACR American Association Cancer Research, 92nd Annual Meeting, 42:583, Mar. 2428, 2001, New Orleans, LA, USA, abstract 3126, 2 pages.
Wells et al., "Targeting the RET Pathway in Thyroid Cancer," Clin. Cancer Res., 15:7119-7123 (2009).
Werner et al., "Gastric adenocarcinoma: pathomorphology and molecular pathology," J. Cancer Res. Clin. Oncology, 127:207-216 (2001) (English abstract).
Wickman et al., "Further characterization of the potent VEGF/PDGF receptor tyrosine kinase inhibitor AG-013736 in preclinical tumor models for its antiangiogenesis and antitumor activity," Proceedings of the American Association for Cancer Research, 44, 865, (Abstract 3780), 2003, 1 page.
Wilbur, W.J. and Lipman, DJ., "Rapid similarity searches of nucleic acid and protein data banks", Natl. Acad. Sci, U.S.A. 80:726-730 (1983).
Wilhelm et al., "BAY 43/9006 Exhibits Broad Spectrum Oral Antitumor Activity and Targets the RAF/MEK/ERK Pathway and Receptor Tyrosine Kinases Involved in Tumor Progression and Angiogenesis", Cancer Research., 64:7099-7109 (2004).
Willett et al., "Direct evidence that the VEGF-specific antibody bevacizumab has antivascular effects in human rectal cancer," Nat. Med., 10(2):145-1147 (2004).
Wisniewski et al., "Characterization of Potent Inhibitors of the Bcr-Abl and the c-Kit Receptor Tyrosine Kinases", Cancer Research., 62, 4244-4255, 2002.
Wood et al., "A Unique Structure for Epidermal Growth Factor Receptor Bound to GW572016 (Lapatinib): Relationships among Protein Conformation, Inhibitor Off-Rate, and Receptor Activity in Tumor Cells", Cancer Research, 64, 6652-6659. 2004.
Wood et al., "PTK787/Zk 222584, a Novel and Potent Inhibitor of Vascular Endothelial Growth Factor Receptor Tyrosine Kinases, Impairs Vascular Endothelial Growth Factor-Induced Responses and Tumor Growth after Oral Administration", Cancer Research., 60, 2178-2189, 2000.
Wozniak et al., "Randomized trial comparing cisplatin with cisplatin plus vinorelbine in the treatment of advanced non-small-cell lung cancer: a Southwest Oncology Group study," J. Clin. Oncol., 16(7):2459-2465 (1998).
Written Amendment filed on Jun. 16, 2009 for JP App. Ser. No. 2009-123432, 12 pages (with English translation).
Written Amendment filed on Sep. 21, 2011 for JP App. Ser. No. 2011-527665, 2 pages (with English translation).
Written Statement filed on Jun. 16, 2009 for JP App. Ser. No. 2009-123432, 32 pages (with English translation).
Written Statement filed on Sep. 21, 2011 for JP App. Ser. No. 2011-527665, 2 pages (with English translation).

(56) References Cited

OTHER PUBLICATIONS

Wu et al., "A fully human monoclonal antibody against VEGFR-1 inhibits growth of human breast cancers," Proceedings of the American Association for Cancer Research, 45, 694, (Abstract 3005), 2004, 3 pages.
Wulff et al., "Luteal Angiogenesis: Prevention and Intervention by Treatment with Vascular Endothelial Growth Factor TrapA40", The Journal of Clinical Endocrinology & Metabolism. 86(7), 3377-3386, 2001.
Yamada et al., "New technique for staining," *Monthly Medical Technology Supplementary Volume* (Apr. 1999) (with English translation).
Yamamoto et al., "E7080 (ER-203492-00), a Novel VEGF Receptor Tyrosine Kinase Inhibitor-III. Significant prolongation of life span in mice transplanted with human ovarian carcinoma based on inhibition of VEGF signaling," Abstract #50, *AACR*, Toronto, Canada (Apr. 5-9, 2003).
Yamamoto et al., "E7080 a novel multitargeted tyrosine kinase inhibitor, has direct anti-tumor activity via inhibition of KIT signaling in small cell lung cancer," Abstract #4636, *AACR*, Orlando, FL, (Mar. 27-31, 2004).
Yamamoto et al., "E7080, an oral multi-targeted tyrosine kinase inhibitor, has direct anti-tumor efficacy via inhibition of KIT signaling in gastrointestinal stromal tumor (GIST)," Abstract #4038, *97th Annual Meeting AACR*, Washington, DC. (Apr. 1-5, 2006).
Yamamoto et al., "E7080, an oral multi-targeted tyrosine kinase inhibitor, has direct anti-tumor efficacy via inhibition of KIT signaling in small cell lung cancer," *Proceedings of the American Association for Cancer Research*,45:1070-1071 (Mar. 2004).
Yanagihara et al., "Development and biological analysis of peritoneal metastasis mouse models for human scirrhous stomach cancer," *Cancer Sci.*, 96(6):323-332 (2005).
Yigitbasi et al., "Tumor Cell and Endothelial Cell Therapy of Oral Cancer by Dual Tyrosine Kinase Receptor Blockade", Cancer Research, 64, 7977-7984, 2004.
Yu, "Amorphous Pharmaceutical Solids:Preparation Characterization and Stabilization," *Advanced Drug Delivery Reviews*, 48:27-42 (2001) (XP009065056).
Zhang et al., "Induction of apoptosis in EMT-6 breast cancer cell in line by a Sigma-2 selective ligand," Am. Assoc. Cancer Research, Abstract 5353, 2005, 2 pages.
Zhang et al., "Inhibition of both autocrine and paracrine growth and propagation of human myeloid leukemia with antibodies directed against VEGF receptor 2," Proceedings of the American Association for Cancer Research, 44, 1479, (Abstract 6454), 2003, 2 pages.
Zhang et al., "Overexpression of Platelet-Derived Growth Factor Receptor a in Endothelial Cells of Hepatocellular Carcinoma Associated with High Metastatic Potential," *Clin. Cancer Res.*, 11(24):8557-8563 (2005).
Zhou et al., "Correlation Research on VEGF Testing in Primary Gastric Cancer and Clinical Pathology Factor," *Journal of Practical Oncology*, 20(2):103-105 (Apr. 25, 2006) with English translation.
Zhu et al., "Fibroblast growth factor receptor 3 inhibition by short hairpin RNAs leads to apoptosis in multiple myeloma," *Mol. Cancer Ther.*, 4(5):787-798 (2005).
Zhu et al., "Inhibition of human leukemia in an animal model with human antibodies directed against vascular endothelial growth factor receptor 2. Correlation between antibody affinity and biological activity," *Leukemia*, 17:604-611 (2003).
Zieger et al., "Role of activating fibroblast growth factor receptor 3 mutations in the development of bladder tumors," *Clin. Cancer Res.*, 11:7709-7719 (2005).
Zimmermann et al., "Potent and Selective Inhibitors of the Abl-Kinase:Phenylamino-Pyrimidine (PAP) Derivatives", Bioorganic and Medicinal Chemistry Letters., 7(2):187-192, 1997.
Zimmermann, "Electrical Breakdown, Electropermeabilization and Electrofusion", Rev. Physiol. Biochem. Pharmacol. 105:176-260 (1986).
Almarsson et al., "High-Throughput Surveys of Crystal Form Diversity of Highly Polymorphic Pharmaceutical Compounds," Crystal Growth & Design, Sep. 10, 2003, 3(6):927-933.
Amendment filed in KR App. Ser. No. 10-2009-7017694, dated Feb. 28, 2014, 7 pages.
Appeal for Reversal in CO App. Ser. No. 12-022608, dated Jan. 28, 2014, 17 pages (with English translation).
Argument filed in KR App. Ser. No. 10-2009-7017694, dated Feb. 28, 2014, 48 pages.
Notice of Allowance in U.S. Appl. No. 12/524,754, dated Feb. 13, 2014, 18 pages.
Notice of Allowance in U.S. Appl. No. 12/741,682, dated Feb. 7, 2014, 11 pages.
Notice of Allowance in U.S. Appl. No. 13/083,338, dated Feb. 6, 2014, 15 pages.
Notice of Allowance in U.S. Appl. No. 13/205,328, dated Jan. 30, 2014, 11 pages.
Office Action in CA App. Ser. No. 2676796, dated Dec. 30, 2013, 5 pages.
Office Action in CN App. Ser. No. 200680020317.5, dated Mar. 4, 2014, 13 pages.
Office Action in EP App. Ser. No. 04807580.8, dated Mar. 18, 2014, 12 pages.
Office Action in EP App. Ser. No. 08704376.6, dated Feb. 24, 2014, 4 pages.
Office Action in KR App. Ser. No. 10-2009-7017694, dated Jan. 29, 2014, 26 pages (with English translation).
Office Action in PH App. Ser. No. 1-2011-502441, dated Feb. 19, 2014, 2 pages.
Office Action in U.S. Appl. No. 11/662,425, dated Feb. 27, 2014, 152 pages.
Office Action in U.S. Appl. No. 11/997,543, dated Mar. 11, 2014, 20 pages.
Office Action in U.S. Appl. No. 12/039,381, dated Jan. 9, 2014, 16 pages.
O'Reilly et al., "Hydrolysis of tert-Butyl Methyl Ether (MTBE) in Dilute Aqueous Acid," Environ. Sci. Technol., 2001, 35:3954-3961.
Patel et al., "The effect of excipients on the stability of levothyroxine sodium pentahydrate tablets," Int'l J Pharm., 2003, 264:35-43.
Response filed in PH App. Ser. No. 1-2011-502441, dated Feb. 28, 2014, 4 pages.
Response to Office Action in CN App. Ser. No. 200680020317.5 filed on Jan. 9, 2014, 7 pages (with English translation).
Response to Office Action in CN App. Ser. No. 201180030568.2 filed on Jan. 13, 2014, 46 pages (with English translation).
Response to Office Action in MX App. Ser. No. MX/a/2010/008187, dated Feb. 17, 2014, 7 pages (with English translation).
Response to Office Action in MX App. Ser. No. MX/a/2012/002011 filed on Jan. 16, 2014, 20 pages (with English translation).
Response to the Office Action issued for IN App. Ser. No. 6415/CHENP/2008 filed on Jan. 17, 2014, 16 pages.
Search Report in EP App. Ser. No. 11798224.9, dated Mar. 21, 2014, 1 page.
Search Report in EP App. Ser. No. 11798224.9, dated Mar. 4, 2014, 6 pages.
Stahl and Wermuth, "Handbook of Pharmaceutical Salts: Properties, selection, and use," 2002, pp. 117-122.
Submission documents re RCE filed in U.S. Appl. No. 12/741,682, dated Jan. 17, 2014, 1 page.
Submission documents re RCE in U.S. Appl. No. 12/439,339, dated Jan. 27, 2014, 1 page.
Submission documents re RCE in U.S. Appl. No. 12/524,754 filed Feb. 3, 2014, 1 page.
Winkler et al., "Kinetics of vascular normalization by VEGFR2 blockade governs brain tumor response to radiation: Role of oxygenation, angiopoietin-1, and matrix metalloproteinases," Cancer Cell, Dec. 2004, 6:553-563.
Written Submission regarding hearing in IN App. Ser. No. 1571/CHENP/2007 filed on Jan. 23, 2014, 8 pages.
Zhang et al., "Synergic antiproliferative effect of DNA methyltransferase inhibitor in combination with anticancer drugs in gastric carcinoma," Cancer Sci., Sep. 2006, 97(9):938-944.

(56) References Cited

OTHER PUBLICATIONS

Agnieszka et al., "Emergence of potential biomarkers of response to anti-angiogenic anti-tumor agents," International Journal of Cancer, Sep. 2010, 127(6):1251-1258.
Dietrich, "BRAF Inhibition in Refractory Hairy-Cell Leukemia," N Eng J Med., 366(21):2038-2040 (May 24, 2012).
FMC BioPolymer; http://www.Fmcbiopolymer.com/portals/pharm/contect/docs/fmc_alubra_brochurefinal.pdf; accessed Mar. 16, 2015, 6 pages.
Glen, "Pre-clinical investigation and clinical development of E7080, a multi-targeted tyrosine inhibitor: implications for melanoma," Ph.D. thesis submitted to the Faculty of Medicine, Division of Cancer Sciences and Molecular Pathology, University of Glasgow, Aug. 2010, 2 pages.
Goede, "Identification of serum angiopoietin-2 as a biomarker—for clinical outcome of colorectal cancer patients treated with bevacizumab-containing therapy," British Journal of Cancer, Oct. 2010, 103(9):1407-1414.
Helfrich et al., "Angiopoietin-2 Levels are Associated with Disease—Progression in Metastatic Malignant Melanoma," Clinical Cancer Research, Feb. 2009, 15(4):1384-1392.
Marchetti et al., "Clinical Features and Outcome of Patients with Non-Small-Cell Lung Cancer Harboring BRAF Mutations," J Clin Oncol., 29(26):3574-3579 (Aug. 8, 2011).
Notice of Allowance in IL App. Ser. No. 205512, dated Feb. 15, 2015, 5 pages (with English translation).
Notice of Allowance in KR App. Ser. No. 10-2010-7011023, dated Mar. 24, 2015, 3 pages (with English translation).
Notice of Allowance in MX App. Ser. No. MX/a/2012/014776, dated Mar. 18, 2015, 3 pages (with English translation).
Office Action in CA App. Ser. No. 2704000, dated Mar. 27, 2015, 3 pages.
Office Action in CL App. Ser. No. 2012-00412, dated Jan. 28, 2015, 17 pages (with English translation).
Office Action in EP App. Ser. No. 12774278.1, dated Mar. 9, 2015, 6 pages.
Office Action in HU App. Ser. No. P0302603, dated Apr. 7, 2015, 4 pages (with English translation).
Office Action in IL App. Ser. No. 223695, dated Feb. 16, 2015, 5 pages (with English translation).
Office Action in JP App. Ser. No. P2012-521531, dated Mar. 3, 2015, 6 pages (with English translation).
Office Action in MX App. Ser. No. MX/a/2013/009931, dated Apr. 9, 2015, 3 pages (with English translation).
Office Action in NO App. Ser. No. 20063383, dated Apr. 15, 2015, 2 pages (with English translation).
Office Action in PH App. Ser. No. 1-2011-502441, dated May 8, 2015, 2 pages.
Office Action in RU App. Ser. No. 2012158142, dated Feb. 12, 2015, 21 pages (with English translation).
Office Action in U.S. Appl. No. 12/039,381, dated Feb. 26, 2015, 13 pages.
Office Action in U.S. Appl. No. 13/870,507, dated Apr. 1, 2015, 82 pages.
Official Notification in CO App. Ser. No. 12-022608, dated Jan. 6, 2015, 8 pages (with English translation).
Park, "Serum Angiopoietin-2 as a Clinical Market for Lung Cancer," Chest, Jul. 2007, 132(1):7 pages.
Reply to Restriction Requirement in U.S. Appl. No. 13/870,507, dated Jan. 27, 2015, 3 pages.
Response in Reexamination and Invalidation Procedure in CN App. Ser. No. 200780017371.9, dated Jan. 19, 2015, 8 pages (with English translation).
Response to Examiner's Report in CL App. Ser. No. 2012-00412, dated Mar. 30, 2015, 16 pages (with English translation).
Response to Office Action in EP App. Ser. No. 10809938.3, dated Apr. 13, 2015, 12 pages.
Response to office action in EP App. Ser. No. 12786619.2, dated May 12, 2015, 99 pages.
Response to Office Action in RU App. Ser. No. 2012158142, dated Apr. 13, 2015, 11 pages (with English translation).
Response to Office Action in U.S. Appl. No. 13/923,858, filed Apr. 1, 2015, 12 pages.
Search Report in EP App. Ser. No. 12793322.4, dated May 26, 2015, 9 pages.
Submission Document in EP App. Ser. No. 09705712.9, dated Feb. 24, 2015, 196 pages.
Submission Documents in EG App. Ser. No. PCT 283/2012, dated Jan. 18, 2015, 26 pages (with English translation).
Submission Documents in TW App. Ser. No. 100104281, dated Mar. 9, 2015, 12 pages (with English translation).
Yamada et al., "Phase 1 Dose-Escalation Study and Biomarker Analysis of E7080 in Patients with Advanced Solid Tumors," Clinical Cancer Research, Mar. 2011, 17(8):2528-2537 (with supplementary Data).
Zurita et al., "A cytokine and angiogenic factor (CAF) analysis in-plasma for selection of sorafenib therapy in patients with metastatic renal cell carcinoma," Annals of oncology, Apr. 2011, 23(1):46-52.
Zurita et al., "Circulating biomarkers for vascular-endothelial growth factor inhibitors in renal cell carcinoma," Cancer, May 2009, 115(S10):2346-2354.
Australian Notice of Allowance in Application No. 2012246490, dated Jul. 25, 2016, 3 pages.
Australian Office Action in Application No. 2012246490, dated Apr. 20, 2016, 3 pages.
Australian Office Action in Application No. 2012246490, dated Feb. 5, 2016, 3 pages.
Australian Response to Examination Report in Application No. 2012246490, dated Jul. 15, 2016, 30 pages.
Canadian Notice of Allowance in Application No. 2704000, dated Jul. 7, 2016, 1 page.
Canadian Notice of Allowance in Application No. 2828946, dated Feb. 22, 2016, 1 page.
Canadian Office Action in Application No. 2713930, dated Mar. 7, 2016, 5 pages.
Canadian Response to Office Action in Application No. 2704000, dated May 19, 2016, 11 pages.
Canadian Response to Office Action in Application No. 2802644, dated Apr. 18, 2016, 9 pages.
Canadian Submission Documents in Application No. 2828946, dated Feb. 5, 2016, 6 pages.
Chemical & Engineering News, "The Top Pharmaceuticals That Changed the World," 83, [cited: Mar. 29, 2016], Jun. 20, 2005, 3 pages.
Chinese Office Action in Application No. 201510031628.2, dated Jun. 2, 2016, 11 pages, with English translation.
European Office Action in Application No. 08846814.5, dated Apr. 29, 2016, 28 pages.
European Response to Office Action in Application No. 12786619.2, dated Apr. 15, 2016, 41 pages.
European Response to Office Action in Application No. 12793322.4, dated Apr. 8, 2016, 10 pages.
European Search Report in Application No. 13865671.5, dated May 23, 2016, 7 pages.
European Submission Documents in Application No. 13865671.5, dated Jul. 7, 2016, 3 pages.
European Submission Documents in Application No. 14727633.1, dated Jul. 18, 2016, 8 pages.
Ferrara, "Vascular Endothelial Growth Factor: Basic Science and Clinical Progress," Endocrine Reviews, 25(4):581-611, Aug. 2004.
Folkman, "What is the evidence that tumors are angiogenesis dependent," J Nat Can Inst 82(1), 1990.
Herbst and Khuri et al., "Mode of action of docetaxel—a basis for combination with novel anticancer agents," Cancer Treat Rev, 29:407-415, 2003.
Indian Office Action in Application No. 5022/CHENP/2009, dated Jun. 28, 2016, 7 pages.
Indonesian Office Action in Application No. W-00201201031, dated Mar. 14, 2016, 4 pages, with English translation.

(56) References Cited

OTHER PUBLICATIONS

International Adjuvant Lung Cancer Trial Collaborative Group, "Cisplatin-Based Adjuvant Chemotherapy in Patients with Completely Resec," The New England Journal of Medicine, 350(4):351-360, Jan. 22, 2004.
Israeli Office Action in Application No. 227558, dated Mar. 13, 2016, 5 pages, with English translation.
Israeli Submission Documents in Application No. 242519, dated Apr. 13, 2016, 4 pages, with English translation.
Isreali Notice of Allowance in Application No. 217197, dated Jun. 26, 2016, 3 pages, with English translation.
Jain, "Normalizing tumor vasculature with anti-angiogenic therapy: A new paradigm for combination therapy," Nature Medicine 7(9):987-989, Sep. 2001.
Japanese Notice of Allowance in Application No. P2012-521531, dated Mar. 1, 2016, 6 pages, with English translation.
Japanese Notice of Allowance in Application No. P2013-515178, dated May 17, 2016, 6 pages, with English translation.
Japanese Office Action in Application No. P2014-513691, dated Jun. 21, 2016, 4 pages, with English translation.
Japanese Office Action in Application No. P2014-513691, dated Mar. 8, 2016, 6 pages, with English translation.
Johnson et al., "Randomized phase II trial comparing bevacizumab plus carboplatin and paclitaxel with carboplatin and paclitaxel alone in preiously untreated locally advanced or metastatic non-small-cell lung cancer," J Clin Oncol 22(11):2184-2191, Jun. 1, 2004.
Norwegian Office Action in Application No. 20063383, dated Mar. 15, 2016, 6 pages, with English translation.
Norwegian Submission Documents in Application No. 20063383, dated Jun. 15, 2016, 181 pages.
Ohe et al, "Randomized phase III study of cisplatin plus irinotecan versus carboplatin plus paclitaxel, cisplatin plus gemcitabine, and cisplatin plus vinorelbine for advanced non-small-cell lung cancer: Four-Arm Cooperative Study in Japan," Annals of Oncology 18(2):317-323, Nov. 1, 2006.
Peruvian Office Action in Application No. 2081-2011, dated Mar. 23, 2016, 12 pages, with English translation.
Peruvian Submission Documents in Application No. 2081-2011, dated May 27, 2016, 20 pages.
Pisters et al, "Induction chemotherapy before surgery for early-stage lung cancer: A novel approach," J Thoracic Cardiovasc Surg 119(3):429-439, Mar. 2000.
Remington, "The Science and Practice of Pharmacy," Remington, 20th Edition, 2000, pp. 1123-1124.
Russian Office Action in Application No. 2015148193, dated Jan. 27, 2016, 4 pages, with English translation.
Russian Office Action in Application No. 2015148193, dated May 10, 2016, 3 pages, with English translation.
Russian Submission Documents in Application No. 2015148193, dated Apr. 27, 2016, 10 pages, with English translation.
Sandler et al, "Paclitaxel-carboplatin alone or with bevacizumab for non-small-cell lung cancer," N Engl J Med, 355(24):2542-2550, Dec. 14, 2006.
Stinchcombe "Targeted therapy of advanced non-small cell lung cancer: the role of bevacizumab," Biologics: Targets & Therapy 1(3):185-194, 2007.
Stinchcombe and Scoinski, "Bevacizumab in the treatment of non-small-cell lung cancer," Oncogene 26:3691-3698, May 28, 2007.
U.S. Notice of Allowance in U.S. Appl. No. 13/870,507, dated Jul. 26, 2016, 13 pages.
U.S. Notice of Allowance in U.S. Appl. No. 14/438,366, dated Feb. 12, 2016, 7 pages.
U.S. Notice of Panel Decision from Pre-Appeal Brief Review in U.S. Appl. No. 12/039,381, dated Mar. 4, 2016, 2 pages.
U.S. Office Action in U.S. Appl. No. 13/870,507, dated Feb. 17, 2016, 28 pages.
U.S. Office Action in U.S. Appl. No. 14/117,276, dated May 20, 2016, 11 pages.
U.S. Office Action in U.S. Appl. No. 14/862,349, dated Mar. 10, 2016, 11 pages.
U.S. Response to Office Action in U.S. Appl. No. 13/870,507, dated May 17, 2016, 12 pages.
Yamamoto et al., "Plasma biomarkers predictive for disease control duration in the phase I study of E7080, a multitarget kinase inhibitor," ASCO Annual Meeting Proceedings(Post Meeting Edition), Journal of Clinical Oncology, 27:15S, 2009, 1 page.
Amended claims in EP App. Ser. No. 04807580.8, dated Jun. 16, 2014, 7 pages.
Amended Claims in MY App. Ser. No. PI2011700172, dated in Jul. 3, 2014, 15 pages.
Amendment filed in KR App. Ser. No. 10-2008-7029472, dated May 1, 2014, 14 pages (with English translation).
Amendment filed in KR App. Ser. No. 10-2009-7005657, dated May 7, 2014, 15 pages (with English translation).
Besson et al., "PTEN/MMAC1/TEP1 in signal transduction and tumorigenesis," EP J Biochem., 1999, 263:605-611.
Comments re Board of Appeal in EP App. Ser. No. 04807580.8, dated Jul. 7, 2014, 3 pages.
Dankort et al., "Braf V660E cooperaties with Pten loss to induce metastic melanoma," Nature Genetics, 2009, 41(5):544-552.
Davies et al., "Mutations of the BRAF gene in human cancer," Nature, Jun. 27, 2002, 417:949-954.
Finn et al., "A multicenter, open-label, phase 3 trial to compare the efficacy and safety of lenvatinib (E7080) versus sorafenib in first-line treatment of subjects with unresectable hepatocellular carinoma," Am Soc Clin Oncol Annual Meeting Abstract, May 31, 2014, 5 pages.
Fujii et al., "Angiogenesis Inhibitor/Kekkan Shinsei Sogaiyaku," Clin Gastroenterol., May 25, 2004, 19:220-227.
Havel et al., "E7080 (lenvatinib) in addition to best supportive care (BSC) versus (BSC) alone in third-line or greater nonsquamous, non-small cell lung cancer (NSCLC)," Am Soc Clin Oncol Annual Meeting Abstract, May 31, 2014, abstract 8043, 4 pages.
Ikuta et al., "E7080, a Multi-Tyrosine Kinase Inhibitor, Suppresses the Progression of Malignant Pleural Mesothelioma with Different Proangiogenic Cytokine Production Profiles," Clin Cancer Res., Nov 24, 2009, 15(23):7229-7237.
International Preliminary Report on Patentability in PCT App. Ser. No. PCT/US2012/040183, dated Apr. 3, 2014, 9 pages.
Matsui et al., "Multi-Kinase Inhibitor E7080 Suppresses Lymph Node and Lung Metastases of Human Mammary Breast Tumor MDA-MB-231 via Inhibition of Vascular Endothelial Growth Factor-Receptor (VEGF-R) 2 and VEGF-R3 Kinase," Clin Cancer Res., 2008, 14:5459-5465.
Matsui et al., "Mechanism of antitumor activity of E7080, a selective VEGFR and FGFR tyrosine kinase inhibitor (TKI), in combination with selective mutant BRAF inhibition," J Clin Oncol., May 20, 2011, 29(15), Suppl., ASCO Meeting Abstracts, Part 1, Abstract No. 8567, 2 pages.
Nakazawa et al., "Maximizing the efficacy of anti-angiogenesis cancer therapy: A multi-targeting strategy by tyrosine kinase inhibitors," AACR Annual Meeting 2014, Presentation Abstract and Poster, Apr. 5-9, 2014, 2 pages.
Nakazawa, "Combination strategy of lenvatinib: Maximizing its anti-angiogenesis efficacy," Tsukuba Res Laboratory, Eisai Co., Ltd., Ibaraki, Japan, Jun. 27, 2014, 10 pages.
Notice of Allowance in CA App. Ser. No. 2652442, dated Apr. 16, 2014, 1 page.
Notice of Allowance in IL App. Ser. No. 195282, dated Aug. 11, 2014, 5 pages (with English translation).
Notice of Allowance in KR App. Ser. No. 10-2009-7017694, dated Jul. 28, 2014, 3 pages (with English translation).
Notice of Allowance in MX App. Ser. No. MX/a/2010/008187, dated Jul. 17, 2014, 3 pages (with English translation).
Notice of Allowance in UA App. Ser. No. a201203132, dated Mar. 21, 2014, 6 pages.
Notice of Allowance in U.S. Appl. No. 11/997,719, dated Jun. 5, 2014, 14 pages.
Notice of Allowance in U.S. Appl. No. 12/439,339, dated Apr. 1, 2014, 17 pages.

(56) References Cited

OTHER PUBLICATIONS

Notice of Allowance in U.S. Appl. No. 12/741,682, dated May 15, 2014, 13 pages.
Notice of Allowance in U.S. Appl. No. 13/083,338, dated Jul. 10, 2014, 22 pages.
Notice of Allowance in U.S. Appl. No. 13/205,328, dated May 8, 2014, 10 pages.
Notice of Allowance in U.S. Appl. No. 13/624,278, dated Jun. 25, 2014, 57 pages.
Notice of Allowance in VN App. Ser. No. 1-2011-03484, dated Apr. 28, 2014, 2 pages.
Office Action in CA App. Ser. No. 2771403, dated Jul. 16, 2014, 3 pages.
Office Action in CN App. Ser. No. 201180030568.2, dated Mar. 24, 2014, 8 pages (with English translation).
Office Action in EP App. Ser. No. 03791389.4, dated Jun. 10, 2014, 4 pages.
Office Action in EP App. Ser. No. 08846814.5, dated Jun. 4, 2014, 4 pages.
Office Action in JP App. Ser. No. P2009-540099, dated Mar. 25, 2014, 6 pages (with English translation).
Office Action in KR App. Ser. No. 10-2008-7029472, dated Mar. 28, 2014, 6 pages (with English translation).
Office Action in KR App. Ser. No. 10-2009-7005657, dated Mar. 28, 2014, 6 pages (with English translation).
Office Action in MX App. Ser. No. MX/a/2010/008187, dated Apr. 28, 2014, 4 pages (with English translation).
Office Action in MX App. Ser. No. MX/a/2012/002011, dated Apr. 28, 2014, 10 pages (with English translation).
Office Action in MX App. Ser. No. MX/a/2012/014776, dated Apr. 4, 2014, 22 pages (with English Translation).
Office Action in RU App. Ser. No. 2012103471, dated May 20, 2014, 5 pages (with English translation).
Office Action in U.S. Appl. No. 11/662,425, dated Jun. 5, 2014, 30 pages.
Office Action in U.S. Appl. No. 12/039,381, dated May 29, 2014, 78 pages.
Office Action in U.S. Appl. No. 12/864,817, dated Aug. 15, 2014, 79 pages.
Office Action in U.S. Appl. No. 13/805,826, dated Apr. 2, 2014, 8 pages.
Office Action in U.S. Appl. No. 13/805,826, dated Jul. 1, 2014, 88 pages.
Office Action in U.S. Appl. No. 13/923,858, dated Apr. 18, 2014, 64 pages.
Office Action in U.S. Appl. No. 14/002,018, dated Apr. 14, 2014, 28 pages.
Office Action in U.S. Appl. No. 14/002,018, dated Jul. 25, 2014, 14 pages.
Office Action in U.S. Appl. No. 14/002,018, dated Jun. 9, 2014, 19 pages.
Official Notification in EP App. Ser. No. 04807580.8, dated Jun. 16, 2014, 1 pages.
Official Notification in EP App. Ser. No. 04807580.8, dated Jun. 27, 2014, 17 pages.
Request for accelerated examination in KR App. Ser. No. 10-2012-7003846, dated Jun. 18, 2014, 29 pages (with English translation).
Response filed in VN App. Ser. No. 1-2011-03484, dated Feb. 28, 2014, 40 pages (with English translation).
Response to Notice of Allowance in U.S. Appl. No. 13/205,328, dated Jul. 8, 2014, 7 pages.
Response to Office Action filed in EP App. Ser. No. 04807580.8, dated May 16, 2014, 13 pages.
Response to Office Action in CA App. Ser. No. 2676796, dated Jun. 27, 2014, 18 pages.
Response to Office Action in CN App. Ser. No. 201180030568.2 filed on May 14, 2014, 10 pages (with English translation).
Response to Office Action in EP App. Ser. No. 03791389.4, dated Jul. 25, 2014, 75 pages.
Response to Office Action in EP App. Ser. No. 08704376.6, dated Apr. 30, 2014, 73 pages.
Response to Office Action in EP App. Ser. No. 08846814.5, dated Jul. 24, 2014, 71 pages.
Response to Office Action in JP App. Ser. No. P2009-540099, dated Apr. 28, 2014, 9 pages (with English Translation).
Response to Office Action in MX App. Ser. No. MX/a/2010/008187, dated Jun. 25, 2014, 5 pages (with English translation).
Response to Office Action in MX App. Ser. No. MX/a/2012/014776, dated Jun. 20, 2014, 16 pages (with English translation).
Response to Office Action in RU App. Ser. No. 2012103471, dated Jul. 21, 2014, 7 pages (with English translation).
Response to Office Action in SG App. Ser. No. 201108602-2, dated May 22, 2014, 37 pages.
Response to Office Action in U.S. Appl. No. 11/662,425, filed May 20, 2014, 8 pages.
Response to Office Action in U.S. Appl. No. 12/039,381, dated Apr. 3, 2014, 7 pages.
Response to Office Action in U.S. Appl. No. 13/805,826, dated Aug. 8, 2014, 9 pages.
Response to Office Action in U.S. Appl. No. 13/923,858, dated Aug. 8, 2014, 24 pages.
Response to Office Action in U.S. Appl. No. 14/002,018, dated Jul. 18, 2014, 8 pages.
Response to Office Action in U.S. Appl. No. 14/002,018, filed May 28, 2014, 7 pages.
Response to Restriction Response in U.S. Appl. No. 13/805,826, dated Jun. 2, 2014, 2 pages.
Schlumberger et al., "A phase 3, multicenter, double-blind, placebo-controlled trial of lenvatinib (E7080) in patients with 131I-refractory differentiated thyroid cancer (SELECT)," Am Soc Clin Oncol., Annual Meeting Abstract LBA6008, 2012, 4 pages.
Search Report in EP App. Ser. No. 09705712.9, dated Aug. 7, 2014, 6 pages.
Search Report in EP App. Ser. No. 12774278.1, dated Aug. 14, 2014, 8 pages.
Shumaker et al., "Effect of lenvatinib (E7080) on the QTc interval: results from a thorough QT study in healthy volunteers," Cancer Chemother Pharmacol., published online Mar. 23, 2014, 9 pages.
Sondergaard et al., Differential sensitivity of melanoma cell lines with BRAFV600E mutation to the specific Raf inhibitor PLX4032, J Translational Med., 2010, 8:39, 11 pages.
Submission Document re RCE in U.S. Appl. No. 12/741,682, dated Aug. 14, 2014, 1 page.
Submission Documents re RCE filed in U.S. Appl. No. 12/524,754, dated May 13, 2014, 1 page.
Submission Documents re RCE filed in U.S. Appl. No. 12/741,682, dated May 6, 2014, 1 page.
Submission Documents re RCE filed in U.S. Appl. No. 13/083,338, dated May 6, 2014, 1 page.
Submission documents re RCE in U.S. Appl. No. 13/205,328, dated Apr. 28, 2014, 1 page.
Submission in EP App. Ser. No. 04807580.8, dated Jun. 13, 2014, 18 pages.
Tahara et al., "Lenvatinib in Radioactive Iodine-refractory Differentiated Thyroid Cancer: Results of the Phase 3 trial (SELECT trial),"01-18-1, Abstract and Presentation Document, 12th Annual Meeting of Japanese Society of Medical Oncology, Jul. 17, 2014, 21 pages.
Vergote et al., "Prognostic and prediction role of circulating angiopoietin-2 in multiple solid tumors: An analysis of approximately 500 patients treated with lenvatinib across tumor types," Am Soc Clin Oncol Annual Meeting Abstract, May 31, 2014, abstract 11061, 3 pages.
Wang et al., "KRAS, BRAF, PIK3CA mutations and Pten Expression in Human Colorectal Cancer-Relationship with Metastatic Colorectal Cancer," Ann Oncol., 2010, 21(Supp 6):V164.
Yamori et al., "Current Treatment of Solid Tumors New Approaches of Treatment, Drug Treatment, Kinase Inhibitors/Kokeigan no Saishin Chiryo Chiryo no Aratana Torikumi Yakubutsu Ryoho Kinase Inhibitors," JP J Clin Med., Jun. 1, 2010, 68(6):1059-1066.

(56) References Cited

OTHER PUBLICATIONS

Yang et al., "RG7204 (PLX4032), a Selective BRAF V600E Inhibitor, Displays Potent Antitumor in Activity Preclinical Melanoma Models," Cancer Res., 2010, 70(13):5518-5527.
Yokota, "ASCO report: Gastrointestinal Cancer field/ASCO Hokoku Shokakigan Ryoiki," Gan Bunshi Hyoteki Chiryo, 2010, 8(4):271-283.
Certificate of Correction in U.S. Appl. No. 12/524,754, dated Aug. 11, 2015, 1 page.
Certificate of Correction in U.S. Appl. No. 12/741,682, dated Aug. 4, 2015, 2 pages.
Certificate of Correction in U.S. Appl. No. 13/624,278, dated Aug. 18, 2015, 1 page.
Decision to Grant European Patent in EP App. Ser. No. 10809938.3, dated Jan. 8, 2016, 2 pages.
International Preliminary Report on Patentability in International App. No. PCT/JP2013/084052, dated Jul. 2, 2015, 7 pages.
International Search Report and Written Opinion in International Application No. PCT/JP2014/063134, dated Sep. 9, 2014, 8 pages.
Kato et al., "Effects of lenvatinib on tumor-associated macrophages enhance antitumor activity of PD-1 signal Inhibitors," Eisai Co., Ltd, poster, Nov. 6, 2015, 1 page.
Kharkyevitch, "Farmakologiya," Third ed (revised and supplemented), Moscow, "Meditsina," 1987, 5 pages (with English Translation).
Kumar et al., "Survival and Failure Outcomes in Primary Thyroid Lymphomas: A Single Centre Experience of Combined Modality Approach," Journal of Thyroid Research, vol. 2013, Jun. 18, 2013, 6 pages.
"Molecular Targets and Cancer Therapeutics ," Poster Session A. A92, Nov. 6, 2015, p. 64 (134 total pages).
Mototsugu, "mTOR inhibitors," Nippohn Rinsho, Jun. 2010, 68(6):1067-1072 (with English abstract).
Notice of Allowance in AU App. Ser. No. 2011270165, dated Dec. 14, 2015, 3 pages.
Notice of Allowance in CA App Ser. No. 2676796, dated Oct. 8, 2015, 1 page.
Notice of Allowance in CN App. Ser. No. 201280010898.X, dated Sep. 2, 2015, 4 pages (with English translation).
Notice of Allowance in EP App. Ser. No. 07743994.1, dated May 8, 2015, 51 pages.
Notice of Allowance in EP App. Ser. No. 10809938.3, dated Sep. 3, 2015, 30 pages.
Notice of Allowance in EP App. Ser. No. 11798224.9, dated Sep. 29, 2015, 37 pages.
Notice of Allowance in EP App. Ser. No. 12774278.1, dated Jun. 29, 2015, 34 pages.
Notice of Allowance in HU App. Ser. No. P0302603, dated Aug. 19, 2015, 5 pages (with English translation).
Notice of Allowance in JP App. Ser. No. 2011-206481, dated Aug. 4, 2015, 7 pages (with English translation).
Notice of Allowance in MK App. Ser. No. P/2015/231, dated Oct. 13, 2015, 2 pages (with English translation).
Notice of Allowance in MX App. Ser. No. MX/a/2013/009931, dated Jun. 29, 2015, 3 pages.
Notice of Allowance in RU App. Ser. No. 2012158142, dated May 5, 2015, 15 pages (with English translation).
Notice of Allowance in TW App. Ser. No. 100104281, dated Jun. 9, 2015, 4 pages (with English translation).
Notice of Allowance in U.S. Appl. No. 14/438,366, dated Dec. 18, 2015, 5 pages.
Notice of Appeal, Pre-appeal Brief Request for Review and Petition for Extension of Time in U.S. Appl. No. 13/923,858, dated Nov. 25, 2015, 8 pages.
Notice of Panel Decision from Pre-Appeal Brief Review in U.S. Appl. No. 13/923,858, dated Jan. 7, 2016, 2 pages.
Noy et al., "Tumor-Associated Macrophages 41:49-61 From Mechanisms to Therapy," Immunity, Jul. 2014, 41:49-61.
Office Action in AU App. Ser. No. 2011270165, dated Nov. 6, 2015, 3 pages.
Office Action in BR App. Ser. No. PI0418200-6, dated Jun. 16, 2015, 1 page.
Office Action in CA App. Ser. No. 2,704,000, dated Jan. 14, 2016, 3 pages.
Office Action in CA App. Ser. No. 2,704,000, dated Jul. 14, 2015, 3 pages.
Office Action in CA App. Ser. No. 2,713,930, dated Sep. 15, 2015, 3 pages.
Office Action in CA App. Ser. No. 2,828,946, dated Nov. 30, 2015, 4 pages.
Office Action in CA App. Ser. No. 2802644, dated Oct. 23, 2015, 6 pages.
Office Action in CN App. Ser. No. 200780017371.9, dated May 15, 2015, 17 pages (with English translation).
Office Action in CN App. Ser. No. 201280010898.X, dated Mar. 30, 2015, 13 pages (with English translation).
Office Action in EP App. Ser. No. 12786619.2, dated Dec. 8, 2015, 4 pages.
Office Action in IL App. Ser. No. 217197, dated Oct. 25, 2015, 4 pages (with English translation).
Office Action in IL App. Ser. No. 223695, dated Aug. 25, 2015, 6 pages (with English translation).
Office Action in IL App. Ser. No. 227558, dated Aug. 2, 2015, 5 pages (with English translation).
Office Action in IL App. Ser. No. 238463, dated Oct. 28, 2015, 6 pages (with English translation).
Office Action in JP App. Ser. No. 2011-206481, dated Jun. 2, 2015, 7 pages (with English translation).
Office Action in JP App. Ser. No. 2012-521531, dated Sep. 29, 2015, 4 pages (with English translation).
Office Action in JP App. Ser. No. 2013-510994, dated Jun. 9, 2015, 6 pages (with English translation).
Office Action in JP. App. Ser. No. 2013-510994, dated Jul. 28, 2015, 5 pages (with English translation).
Office Action in MX App. Ser. No. MX/a/2014/010594, dated Oct. 13, 2015, 8 pages (with English translation).
Office Action in RU App. Ser. No. 2013140169, dated Nov. 6, 2015, 9 pages (with English translation).
Office Action in U.S. Appl. No. 12/039,381, dated Oct. 7, 2015, 22 pages.
Office Action in U.S. Appl. No. 13/923,858, dated Jul. 29, 2015, 15 pages.
Office Action in U.S. Appl. No. 14/438,366, dated Sep. 28, 2015, 8 pages.
Official Notification in HU App. Ser. No. P0302603, dated Nov. 26, 2015, 4 pages (with English translation).
Prior Art Submission and List of Corresponding Applications in IL App. Ser. No. 227558, dated Nov. 30, 2015, 3 pages (with English translation).
Rectification for a Voluntary Amendment in CN App. Ser. No. 201510031628.2, dated Oct. 10, 2015, 5 pages (with English translation).
Ren, Xiubao, "Advances in Medical Therapy for Melanoma," Journal of Practical Oncology, Dec. 2010, 2(25):137-140 (with English translation).
Request for Examination and Voluntary Amendment in TH App. Ser. No. 0401005163, dated Aug. 21, 2015, 29 pages (with English translation).
Request for Examination filed in NO App. Ser. No. 20063383, dated Jun. 19, 2015, 8 pages (with English translation).
Request for Examination in KR App. Ser. No. 10-2012-7033886, dated Aug. 26, 2015, 12 pages (with English translation).
Request to Enter PPH and Amended Claims in MX App. Ser. No. MX/a/2014/010594, dated Oct. 8, 2015, 10 pages (with English translation).
Response filed in CA App. Ser. No. 2713930, dated Jun. 22, 2015, 8 pages.
Response filed in CN App. Ser. No. 201280010898.X, dated Jun. 15, 2015, 12 pages (with English translation).
Response filed in U.S. Appl. No. 13/870,507, dated Jun. 18, 2015, 13 pages.
Response in AU App. Ser. No. 2011270165, dated Dec. 4, 2015, 5 pages.

(56) References Cited

OTHER PUBLICATIONS

Response to Final Rejection in U.S. Appl. No. 12/039,381, dated Dec. 22, 2015, 10 pages.
Response to Official Action in CA App. Ser. No. 2,704,000, dated Dec. 24, 2015, 11 pages.
Schlumberger et al., "Lenvatinib versus Placebo in Radioiodine-Refractory Thyroid Cancer," N Engl J Med., Feb. 12, 2015, 372(7):621-630.
Search Report in EP App. Ser. No. 12793322.4, dated Sep. 10, 2015, 13 pages.
Section 18 Submission in IL App. Ser. No. 223695, dated May 4, 2015, 4 pages (with English translation).
Sharma et al., "Thyroid Cancer," Feb. 18, 2015, pp. 1-16.
Submission Document in HU App. Ser. No. P0302603, dated Jul. 7, 2015, 45 pages (with English translation).
Submission Document in PH App Ser. No. 1-2011-502441, dated May 22, 2015, 25 pages.
Submission of Amended Claims in IL App. Ser. No. 223695, dated Dec. 24, 2015, 6 pages (with English translation).
Submission of Amended specification in IL App. Ser. No. 217197, dated Dec. 24, 2015, 5 pages (with English translation).
Submission of Relevant Patent in MX App. Ser. No. MX/a/2014/010594, dated Sep. 24, 2015, 2 pages (with English translation).
Tahara et al, "Comprehensive Analysis of Serum Biomarkers and Tumor Gene Mutations Associated With Clinical Outcomes in the Phase 3 Study of (E7080) Lenvatinib in Differentiated Cancer of the Thyroid (SELECT)", The presentation document, presented at European Society for Medical Oncology 2014 Congress, Sep. 26-30, 2014, 18 pages.
Tahara et al., "Comprehensive Analysis of Serum Biomarkers and Tumor Gene Mutations Associated With Clinical Outcomes in the Phase 3 Study of (E7080) Lenvatinib in Differentiated Cancer of the Thyroid (SELECT),", 12th Annual Meeting of Japanese Society of Medical Oncology, Jul. 17, 2014, Abstract (Document is 6 total pages).
Vianna et al., "The histological rarity of thyroid cancer", Brazilian Journal of Otorhinolaryngology, 2012, 78(4):48-51.
Voluntary Amendment (Specification) in AU App. Ser. No. 2010285740, dated Nov. 20, 2015, 11 pages.
Amendment and Response filed in U.S. Appl. No. 11/997,543, dated Dec. 19, 2013, 38 pages.
Amendment filed in EP App. Ser. No. 12793322.4, dated Nov. 28, 2013, 6 pages.
Amendment filed in KR App. Ser. No. 10-2008-7029472, dated Nov. 20, 2013, 81 pages (with English translation).
Amendment filed in KR App. Ser. No. 10-2013-7020616, dated Nov. 22, 2013, 22 pages (with English translation).
International Preliminary Report on Patentability in International App. Ser. No. PCT/JP2012/062509, dated Nov. 28, 2013, 11 pages.
Notice of Allowance in IL App. Ser. No. 200090, dated Nov. 18, 2013, 5 pages (with English translation).
Notice of Allowance in KR App. Ser. No. 10-2008-7013685, dated Nov. 29, 2013, 3 pages (with English translation).
Office Action in CN App. Ser. No. 200680020317.5, dated Nov. 28, 2013, 8 pages (with English translation).
Office Action in CO App. Ser. No. 12-022608, dated Dec. 17, 2013, 12 pages (with English translation).
Office Action in IL App. Ser. No. 207089, dated Nov. 25, 2013, 6 pages (with English translation).
Office Action in IN App. Ser. No. 1571/CHENP/2007, dated Dec. 9, 2013, 2 pages.
Office Action in MX App. Ser. No. MX/a/2010/008187, dated Dec. 5, 2013, 8 pages (with English translation).
Office Action in MX App. Ser. No. MX/a/2012/002011, dated Nov. 21, 2013, 8 pages (with English translation).
Office Action in VN App. Ser. No. 1-2011-03484, dated Dec. 31, 2013, 2 pages (with English translation).
Preliminary Amendment filed in U.S. Appl. No. 14/117,276, dated Nov. 12, 2013, 11 pages.
Response filed in CA App. Ser. No. 2652442, dated Jan. 8, 2014, 5 pages.
Response filed in KR App. Ser. No. 10-2009-7005657, dated Nov. 21, 2013, 46 pages (with English translation).
Submission documents re RCE filed in U.S. Appl. No. 11/997,719, dated Dec. 11, 2013, 10 pages.
Submission documents re RCE filed in U.S. Appl. No. 13/083,338, dated Dec. 2, 2013, 5 pages.
Submission documents re RCE filed in U.S. Appl. No. 13/205,328, dated Dec. 30, 2013, 1 page.
Submission documents re RCE filed in U.S. Appl. No. 13/624,278, dated Dec. 13, 2013, 10 pages.
Amended Claims in BR App. Ser. No. BR112012003592-4, dated Oct. 23, 2014, 12 pages (with English translation).
Amended Drawing in IL App. Ser. No. 217197, dated Oct. 22, 2014, 4 pages (with English translation).
Amended Drawing in PH App. Ser. No. 1-2011-502441, dated Oct. 17, 2014, 2 pages.
Amended drawings in EP App. Ser. No. 10809938.3, dated Nov. 11, 2014, 14 pages.
Amended set of Claims in EP App. Ser. No. 11798224.9, dated Sep. 19, 2014, 53 pages.
Amendment and Request for Continued Examiner (RCE) in U.S. Appl. No. 13/083,338, dated Oct. 10, 2014, 5 pages.
Amendment in IN App. Ser. No. 2371/CHENP/2012, dated Oct. 30, 2014, 2 pages.
Amendment in KR App. Ser. No. 10-2010-7011023, dated Oct. 21, 2014, 31 pages.
Amendment in KR App. Ser. No. 10-2010-7018835, dated Dec. 1, 2014, 18 pages (with English translation).
Amendment in KR App. Ser. No. 10-2012-7003846, dated Nov. 26, 2014, 20 pages (with English translation).
Amendment in TW App. Ser. No. 100104281, dated Oct. 22, 2014, 8 pages.
Amendment in U.S. Appl. No. 11/662,425, dated Sep. 2, 2014, 6 pages.
Anderson et al, "Clinical, Safety, and Economic Evidence in Radioactive Iodine-Refractory Differentiated Thyroid Cancer: A Systematic Literature Review", Thyroid, 23(4):392-407, 2013.
Application for Patent Term Adjustment in U.S. Appl. No. 12/439,339, dated Dec. 18, 2014, 8 pages.
Asano et al., "Broad-spectrum preclinical combination activity of eribulin combined with various anticancer agents in human breast cancer, lung cancer, ovarian cancer, and melanoma xenograft models," European J Cancer, 50(Suppl 6):20, Nov. 19, 2014.
Bajwa et al., "Antimalarials. 1. Heterocyclic Analogs of N-Substituted Naphthalenebisoxazines," J Med Chem., 16(2):134-138, Aug. 9, 1972.
Brose et al, "Sorafenib in radioactive iodine-refractory, locally advanced or metastatic differentiated thyroid cancer: a randomised, double-blind, phase 3 trial", The Lancet, 384:319-328, Jul. 26, 2014.
Burwell, Jr, "The Cleavage of Ethers," Chem Rev., 54(4):615-685, Feb. 26, 1954.
Carey, "Organic Chemistry 4e: Chapter 24: Phenols," McGraw Hill, http://www.mhhe.com/physsci/chemistry/carey/student/olc/ch24reactionsarylethers.html. Accessed Oct. 3, 2014, 2000, 4 pages.
Correction Request in CO App. Ser. No. 12-022608, dated Dec. 24, 2014, 3 pages (with English translation).
Elisei et al., "Subgroup Analyses of a Phase 3 Multicenter, Double-Blind, Placebo-Controlled Trial of Lenvatinib (E7080) in Patients with 131I-Refractory Differentiated Thyroid Cancer," Poster, No. 1033P, presented at European Society for Medical Oncology 2014 Congress, Sep. 26-30, 2014, 1 page.
Erdem et al, "Correlation of E-cadherin, VEGF, COX-2 expression to prognostic parameters in papillary thyroid carcinoma", Experimental Mole Pathol., 90:312-317, Feb. 16, 2011.
Extended Search Report in EP App. Ser. No. 12786619.2, dated Nov. 25, 2014, 6 pages.
Gild et al, "Multikinase inhibitors: a new option for the treatment of thyroid cancer", Nature Reviews Endocrinol., 7:617-624, Oct. 2011.

(56) References Cited

OTHER PUBLICATIONS

Kremer, "Lenvatinib Advisory Board", The presentation document, American Society of Clinical Oncology, Annual meeting 2014, May 31, 2014, 138 pages.
Notice of Allowance in AU App. Ser. No. 2010285740, dated Nov. 19, 2014, 1 page.
Notice of Allowance in CA App. Ser. No. 2771403, dated Oct. 22, 2014, 1 page.
Notice of Allowance in CN App. Ser. No. 201180030568.2, dated Sep. 9, 2014, 4 pages (with English translation).
Notice of Allowance in EP App. Ser. No. 04807580.8, dated Dec. 15, 2014, 103 pages.
Notice of Allowance in EP App. Ser. No. 08704376.6, dated Aug. 19, 2014, 62 pages.
Notice of Allowance in EP App. Ser. No. 08846814.5, dated Jan. 8, 2015, 36 pages.
Notice of Allowance in IL App. Ser. No. 207089, dated Nov. 10, 2014, 5 pages (with English translation).
Notice of Allowance in JP App. Ser. No. P2009-540099, dated Oct. 21, 2014, 6 pages (with English translation).
Notice of Allowance in KR App. Ser. No. 10-2008-7029472, dated Sep. 16, 2014, 3 pages (with English translation).
Notice of Allowance in KR App. Ser. No. 10-2009-7005657, dated Sep. 19, 2014, 3 pages (with English translation).
Notice of Allowance in KR App. Ser. No. 10-2010-7018835, dated Jan. 20, 2015, 3 pages (with English translation).
Notice of Allowance in KR App. Ser. No. 10-2012-7003846, dated Feb. 3, 2015, 3 pages.
Notice of Allowance in RU App. Ser. No. 2012103471, dated Dec. 19, 2014, 12 pages (with English translation).
Notice of Allowance in U.S. Appl. No. 11/662,425, dated Oct. 21, 2014, 49 pages.
Notice of Allowance in U.S. Appl. No. 11/997,719, dated Dec. 2, 2014, 21 pages.
Notice of Allowance in U.S. Appl. No. 12/524,754, dated Sep. 18, 2014, 35 pages.
Notice of Allowance in U.S. Appl. No. 12/741,682, dated Oct. 6, 2014, 11 pages.
Notice of Allowance in U.S. Appl. No. 13/083,338, dated Dec. 5, 2014, 19 pages.
Notice of Allowance in U.S. Appl. No. 13/624,278, dated Oct. 31, 2014, 14 pages.
Notice of Allowance in U.S. Appl. No. 13/805,826, dated Dec. 17, 2014, 15 pages.
Notice of Allowance in U.S. Appl. No. 14/002,018, dated Oct. 24, 2014, 70 pages.
Notice of Appeal in U.S. Appl. No. 11/662,425, dated Sep. 5, 2014, 11 pages.
Notice of Appeal in U.S. Appl. No. 12/039,381, dated Aug. 29, 2014, 9 pages.
Office Action in AU App. Ser. No. 2010285740, dated Aug. 22, 2014, 3 pages.
Office Action in CA App. Ser. No. 2676796, dated Jan. 29, 2015, 5 pages.
Office Action in CA App. Ser. No. 2704000, dated Nov. 4, 2014, 3 pages.
Office Action in CA App. Ser. No. 2713930, dated Jan. 30, 2015, 5 pages.
Office Action in CL App. Ser. No. 2012-00412, dated Sep. 3, 2014, 22 pages.
Office Action in CN App. Ser. No. 200780017371.9, dated Dec. 11, 2014, 9 pages (with English translation).
Office Action in CN App. Ser. No. 201280010898.X, dated Aug. 11, 2014, 14 pages (with English translation).
Office Action in EP App. Ser. No. 03791389.4, dated Dec. 2, 2014, 5 pages.
Office Action in EP App. Ser. No. 10809938.3, dated Oct. 16, 2014, 5 pages.
Office Action in EP Application No. 07743994.1, dated Sep. 9, 2014, 8 pages.
Office Action in EP Application No. 10809938.3, dated Feb. 10, 2015, 4 pages.
Office Action in IL App. Ser. No. 205512, dated Sep. 22, 2014, 5 pages (with English translation).
Office Action in IL App. Ser. No. 217197, dated Oct. 22, 2014, 4 pages (with English translation).
Office Action in KR App. Ser. No. 10-2010-7011023, dated Sep. 3, 2014, 14 pages (with English translation).
Office Action in KR App. Ser. No. 10-2010-7018835, dated Sep. 30, 2014, 6 pages (with English translation).
Office Action in KR App. Ser. No. 10-2012-7003846, dated Oct. 7, 2014, 7 pages.
Office Action in MX App. Ser. No. MX/a/2012/014776, dated Oct. 15, 2014, 15 pages (with English translation).
Office Action in MX App. Ser. No. MX/a/2013/009931, dated Sep. 5, 2014, 15 pages (with English translation).
Office Action in RU App. Ser. No. 2012103471, dated Sep. 16, 2014, 5 pages (with English translation).
Office Action in TW App. Ser. No. 100104281, dated Dec. 9, 2014, 13 pages (with English translation).
Office Action in U.S. Appl. No. 11/662,425, dated Sep. 17, 2014, 3 pages.
Office Action in U.S. Appl. No. 13/805,826, dated Sep. 23, 2014, 25 pages.
Office Action in U.S. Appl. No. 13/870,507, dated Dec. 12, 2014, 10 pages.
Office Action in U.S. Appl. No. 13/923,858, dated Dec. 5, 2014, 67 pages.
Official Notification in CA App. Ser. No. 2771403, dated Dec. 16, 2014, 1 page.
Official Notification re Decision on Petition in U.S. Appl. No. 11/997,719, dated Sep. 23, 2014, 1 page.
Official Notification re Interview Summary in U.S. Appl. No. 13/805,826, dated Dec. 1, 2014, 3 pages.
Official Notification re Interview Summary in U.S. Appl. No. 14/002,018, dated Oct. 6, 2014, 2 pages.
Pacini, "38th Annual Meeting of the European Thyroid Association", European Thyroid Association, Santiago de Compostela, Spain, Aug. 15, 2014, p. 73-p. 226.
Payment of Final Fee and Amendment after Allowance in CA App. Ser. No. 2771403, dated Nov. 24, 2014, 3 pages.
Reply to final office action in U.S. Appl. No. 13/805,826, dated Nov. 26, 2014, 7 pages.
Reply to Final Office Action in U.S. Appl. No. 14/002,018, dated Oct. 1, 2014, 6 pages.
Reply to Notice of Allowance in U.S. Appl. No. 11/662,425, dated Jan. 20, 2015, 5 pages.
Request for Continued Examination (RCE) in U.S. Appl. No. 13/624,278, dated Sep. 24, 2014, 1 page.
Request for Continued Examination (RCE) in U.S. Appl. No. 11/997,719, dated Aug. 29, 2014, 1 page.
Response in EP App. Ser. No. 12774278.1, dated Oct. 13, 2014, 4 pages.
Response to Communication in EP App. Ser. 07743994.1, dated Dec. 22, 2014, 62 pages.
Response to Examiner's Substantive Report in CL App. Ser. No. 2012-00412, dated Nov. 28, 2014, 39 pages (with English translation).
Response to office action in AU App. Ser. No. 2010285740, dated Oct. 28, 2014, 14 pages.
Response to Office Action in CA App. Ser. No. 2704000, dated Dec. 19, 2014, 13 pages.
Response to Office Action in CA App. Ser. No. 2771403, dated Sep. 10, 2014, 11 pages.
Response to office action in CN App. Ser. No. 201280010898.X, dated Nov. 25, 2014, 7 pages (with English translation).
Response to office action in IL App. Ser. No. 217197, dated Nov. 26, 2014, 7 pages (with English translation).
Response to Office Action in MX App. Ser.No. MX/a/2012/014776, dated Jan. 7, 2015, 20 pages (with English translation).
Response to Office Action in MX App. Ser. No. MX/a/2013/009931, dated Dec. 9, 2014, 24 pages (with English translation).

(56) References Cited

OTHER PUBLICATIONS

Response to office action in RU App. Ser. No. 2012103471, dated Nov. 18, 2014, 17 pages (with English translation).
Robinson et al, "Characterization of Tumor Size Changes Over Time From the Phase 3 Study of (E7080) Lenvatinib in Differentiated Cancer of the Thyroid (SELECT)", The Poster, No. 1031P, presented at European Society for Medical Oncology 2014 Congress, Sep. 26-30, 2014, 1 page.
Schlumberger et al., "Lenvatinib versus Placebo in Radioiodine-Refractory Thyroid Cancer," N Engl J Med., 372(7):621-630, Feb. 12, 2015.
Search Report in EP App. Ser. No. 12786619.2, dated Dec. 15, 2014, 6 pages.
Sennino and McDonald, "Controlling escape from angiogenesis inhibitors", Nature Rev Cancer, 12:699-709, Oct. 2012.
Stjepanovic and Capdevila, "Multikinase inhibitors in the treatment of thyroid cancer: specific role of lenvatinib," Biologics: Targets and Therapy, 8:129-139, Aug. 2014.
Submission Document in CL App. Ser. No. 2012-00412, dated Aug. 12, 2014, 2 pages (with English translation).
Submission Document in MX App. Ser. No. MX/a/2014/010594, dated Sep. 4, 2014, 70 pages (with English translation).
Submission Document in MY App. Ser. No. PI2011700172, dated Nov. 4, 2014, 3 pages.
Submission Document re figures in AR App. Ser. No. P110100513, dated Oct. 22, 2014, 3 pages.
Submission of Claims in IL App. Ser. No. 223695, dated Jan. 17, 2015, 16 pages.
Tahara et al, "Comprehensive Analysis of Serum Biomarkers and Tumor Gene Mutations Associated With Clinical Outcomes in the Phase 3 Study of (E7080) Lenvatinib in Differentiated Cancer of the Thyroid (Select)", The presentation document, presented at European Society for Medical Oncology 2014 Congress, Sep. 26-30, 2014, 24 pages.
Takahashi et al, "Phase II Study of Lenvatinib, A Multitargeted Tyrosine Kinase Inhibitor, In Patients With All Histologic Subtypes of Advanced Thyroid Cancer (Differentiated, Medullary, and Anaplastic)", The Poster, presented at the European Society for Medical Oncology 2014 Congress, Sep. 26-30, 2014, 1 page.
Tamura et al., "Molecular Characterization of Undifferentiated-Type Gastric Carcinoma," Laboratory Investigation, 81(4):593-598, Apr. 2001.
Tohyama et al, "Antitumor Activity of Lenvatinib (E7080): An Angiogenesis Inhibitor That Targets Multiple Receptor Tyrosine Kinases in Preclinical Human Thyroid Cancer Models," J Thyroid Res, 2014:1-13, Sep. 10, 2014.
Voluntary Amendment in ID App. Ser. No. W-00201201031, dated Nov. 5, 2014, 2 pages (with English translation).
Voluntary Amendment in MX App. Ser. No. MX/a/2014/010594, dated Oct. 23, 2014, 4 pages (with English translation).
Wells Jr et al, "Vandetanib in Patients With Locally Advanced or Metastatic Medullary Thyroid Cancer: A Randomized, Double-Blind Phase III Trial", J Clinical Oncol., 30(2):134-141, Jan. 10, 2012, corrections published Aug. 20, 2013, p. 3049.
Wirth et al, "Treatment-Emergent Hypertension and Efficacy in the Phase 3 Study of (E7080) Lenvatinib in Differentiated Cancer of the Thyroid (Select)", The Poster, No. 1030P, presented at the European Society for Medical Oncology 2014 Congress, Sep. 26-30, 2014, 1 page.
Yamamoto et al., "Lenvatinib, an angiogenesis inhibitor targeting VEGFR/FGFR, shows broad antitumor activity in human tumor xenograft models associated with microvessel density and pericyte coverage," Vascular Cell, 6(18):1-13, 2014.
Zhong et al., "Mechanisms underlying the synergistic effect of SU5416 and cisplatin on cytotoxicity in human ovarian tumor cells," Inter'l J Oncol., 25(2):445-451, 2001.
Auburn University, "Thyroid Cancer," (as of Feb. 25, 2006, using Wayback machine), Feb. 25, 2006, 8 pages.
Board of Appeal of the European Patent Office, "Decision—T1212/01 3.3.2," dated Feb. 3, 2015, 55 pages.
Chinese Submission Documents in Application No. 201380054667.3, dated Nov. 17, 2016, 8 pages (English Translation).
Chinese Submission Documents in Application No. 201480026871.9, dated Nov. 14, 2016, 11 pages (English Translation).
Chinese Submission Documents in Application No. 201510031628.2, dated Nov. 29, 2016, 8 pages (English Translation).
European Submission Documents in Application No. 08846814.5, dated Mar. 7, 2017, 18 pages.
European Submission Documents in Application No. 14727633.1, dated Feb. 2, 2017, 12 pages.
Indian Submission Documents in Application No. 5022/CHENP/2009, dated Sep. 23, 2016, 9 pages (English Translation).
Indonesia Submission Documents in Application No. W-00201201031, dated Aug. 11, 2016, 13 pages (English Translation).
Indonesia Submission Documents in Application No. W-00201201031, dated Dec. 9, 2016, 4 pages (English Translation).
Israeli Submission Documents in Application No. 223695, dated Dec. 22, 2016, 5 pages (English Translation).
Israeli Submission Documents in Application No. 227558, dated Jul. 12, 2016, 6 pages (English translation).
Klein et al, "Vascular endothelial growth factor gene and protein: strong expression in thyroiditis and thyroid carcinoma", Journal of endocrinology, Nov. 30, 1999, 41-49.
Korean Submission Documents in Application No. 10-2013-7020616, dated Feb. 13, 2017, 47 pages (English Translation).
Matsui et al, "A novel multi-targeted tyrosine kinase inhibitor, exhibits anti-angiogenic activity via inhibition of KIT signaling in a small cell lung cancer xenograft model", European Journal of Cancer, Sep. 29, 2004, p. 47.
Mexican Submission Documents in Application No. MX/a/2014/010594, dated Oct. 20, 2016, 15 pages (English Translation).
Nakamura et al., "In Vitro selectivity and potency ofKRN951, a novel inhibitor of VEGF receptor tyrosine kinases", Cancer Research, cited Jul. 13, 2016, 2 pages.
Notice of Allowance in Canadian Application No. 2802644, dated Aug. 5, 2016, 1 page.
Notice of Allowance in European Patent Application No. 12786619.2, dated Sep. 30, 2016, 155 pages.
Notice of Allowance in Indonesian Patent Application No. W-00201201031, dated Dec. 28, 2016, 5 pages (English Translation).
Notice of Allowance in Japanese Patent Application No. P2014-513691, dated Oct. 4, 2016, 6 pages.
Notice of Allowance in Korean Patent Application No. 10-2012-7033886, dated Oct. 18, 2016, 3 pages (English Translation).
Notice of Allowance in Mexican Patent Application No. MX/a/2014/010594, dated Nov. 17, 2016, 3 pages (English Translation).
Office Action in Australian Patent Application No. 2013364953, dated Feb. 16, 2017, 3 pages.
Office Action in Chilean Patent Application No. 2012-00412, dated Jan. 23, 2017, 4 pages (English Translation).
Office Action in Chinese Patent Application No. 201380054667.3, dated Jul. 18, 2016, 18 pages (English Translation).
Office Action in Chinese Patent Application No. 201380054667.3, dated Feb. 14, 2017, 9 pages (English Translation.
Office Action in Chinese Patent Application No. 201480026871.9, dated Feb. 21, 2017, 10 pages (English Translation).
Office Action in European Patent Application No. 08846814.5, dated Sep. 28, 2016, 14 pages.
Office Action in European Patent Application No. 13865671.5, dated Mar. 7, 2017, 4 pages.
Office Action in European Patent Application No. 14727633.1, dated Oct. 13, 2016, 4 pages.
Office Action in Indian Patent Application No. 1511/CHENP/2009, dated Feb. 27, 2017, 7 pages (English Translation).
Office Action in Indian Patent Application No. 6415/CHENO/2008, dated Jan. 19, 2017, 5 pages (English Translation).
Office Action in Jordan Patent Application No. 55/2011, dated Feb. 16, 2017, 2 pages (English Translation).
Office Action in Korean Patent Application No. 10-2013-7020616, dated Dec. 19, 2016, 12 pages (English Translation).

(56) References Cited

OTHER PUBLICATIONS

Office Action in Mexican Patent Application No. MX/a/2014/010594, dated Aug. 17, 2016, 10 pages (English Translation).
Office Action in Yemen Patent Application No. 592/2011, dated Jan. 16, 2017, 2 pages (English Translation).
Official Notification in Australian Application No. 200583422, dated Oct. 20, 2016, 1 pages.
Official Notification in Australian Patent Application No. 2005283422, dated Jul. 14, 2016, 8 pages.
Official Notification in European Patent Application No. 07743994.1, dated Jul. 22, 2016, 18 pages.
Peruvian Office Action in Application No. 2081-2011, dated Jul. 15, 2016, 12 pages (English Translation).
Ramsden, "Angiogenesis in the thyroid gland," Journal of endocrinology, Apr. 11, 2000, 475-480.
Russian Submission Documents in Application No. 2015148193, dated Aug. 8, 2016, 16 pages (English Translation).
Soh et al, "Neutralizing vascular endothelial growth factor activity inhibits thyroid cancer growth in vivo", Surgery, 2000:1059-1066.
U.S. Submission Documents in U.S. Appl. No. 14/117,276, dated Jul. 18, 2016, 3 pages.
Vergote et al., "A phase II trial of lenvatinib in patients with advanced or recurrent endometrial cancer: Angiopoietin-2 as a predictive marker for clinical outcomes," J. Clin. Oncol, vol. 31, No. 15 supplement 5520, May 20, 2013, XP002728918.
Vieira et al, "Expression of vascular endothelial growth factor (VEGF) and its receptors in thyroid carcinomas of follicular origin: a potential autocrine loop", European Journal of Endocrinology, 2005;153 :701-709.
Went et al, "Prevalence of KIT Expression in Human Tumor", Journal of Clinical Oncology, Nov. 15, 2004, 4514-4522.

\* cited by examiner

Gene mutation and progression free survival

BIOMARKERS FOR PREDICTING AND ASSESSING RESPONSIVENESS OF THYROID AND KIDNEY CANCER SUBJECTS TO LENVATINIB COMPOUNDS

FIELD OF THE INVENTION

The present invention relates generally to biomarkers and thyroid and kidney cancer.

BACKGROUND OF THE INVENTION

A number of kinase inhibitors have been developed as antitumor agents. For example, a group of compounds having inhibitory activity against receptor tyrosine kinases, such as vascular endothelial growth factor receptor (VEGFR), are known to inhibit angiogenesis and are regarded as a new class of antitumor agents. Lenvatinib mesylate (also known as E7080) is an oral tyrosine kinase inhibitor targeting VEGFR1-3, fibroblast growth factor receptor (FGFR) 1-4, rearranged during transfection receptor (RET), KIT, and platelet-derived growth factor receptor (PDGFR). In phase I clinical studies of lenvatinib mesylate, response to treatment was observed in thyroid, kidney and endometrial cancers, as well as melanoma.

Unfortunately, most anti-tumor treatments are associated with undesirable side effects, such as profound nausea, vomiting, or severe fatigue. Also, while anti-tumor treatments have been successful, they do not produce significant clinical responses in all patients who receive them resulting in undesirable side effects, delays, and costs associated with ineffective treatment. Therefore, biomarkers that can be used to predict the response of a subject to an antitumor agent prior to administration thereof are greatly needed. In addition, it is useful to have biomarkers that can be used to evaluate whether therapy comprising an antitumor agent is effective.

SUMMARY

The present application is based, at least in part, on the identification of biomarkers that are predictive of a thyroid or a kidney cancer subject's responsiveness to a therapy comprising lenvatinib or a pharmaceutically acceptable salt thereof (e.g., lenvatinib mesylate). The presence of a mutation in one or more of genes is a useful predictor of responsiveness to a therapy comprising lenvatinib or a pharmaceutically acceptable salt thereof (e.g., lenvatinib mesylate). For example, a mutation(s) in one or more of the genes NRAS, KRAS, VHL, BRAF, ERBB2, PTEN, and MET is indicative that a given thyroid or kidney cancer subject will respond to a therapy comprising lenvatinib or a pharmaceutically acceptable salt thereof (e.g., lenvatinib mesylate). In addition, the ratio of thyroglobulin levels pre- and post-treatment with a therapy comprising lenvatinib or a pharmaceutically acceptable salt thereof can be useful in determining the likelihood that a subject having differentiated thyroid cancer will respond to continued therapy with the lenvatinib compound. Furthermore, the expression level of certain proteins (e.g., those listed in Table 3) either prior to or post-treatment, or the ratio of the expression level post/pre-treatment compared to a control, can also be a useful predictor of responsiveness to a therapy comprising lenvatinib or a pharmaceutically acceptable salt thereof (e.g., lenvatinib mesylate). Also, the combination of these two classes biomarkers (mutations and blood biomarkers) or three classes biomarkers (mutations, thyroglobulin, and blood biomarkers) can provide for even stronger predictions of the likelihood that a subject having thyroid or kidney cancer will respond to a therapy comprising lenvatinib or a pharmaceutically acceptable salt thereof (e.g., lenvatinib mesylate).

The application also provides methods for evaluating whether to continue treatment with lenvatinib or a pharmaceutically acceptable salt thereof (e.g., lenvatinib mesylate) for a subject having thyroid or kidney cancer. Low or high levels of certain proteins (e.g., those listed in Table 3) before and/or after treatment with the therapy can be useful in evaluating whether to continue treatment with lenvatinib or a pharmaceutically acceptable salt thereof (e.g., lenvatinib mesylate). For example, lower ratios of thyroglobulin levels (post/pre-treatment with lenvatinib or a pharmaceutically acceptable salt thereof (e.g., lenvatinib mesylate)) compared to control ratios from samples of patients who are known to not respond to such therapy can be useful in assessing/evaluating whether the test subject will benefit from continued therapy comprising lenvatinib or a pharmaceutically acceptable salt thereof (e.g., lenvatinib mesylate).

Thus, the biomarkers and compositions described herein are useful, for example, in identifying and/or selecting a patient or a subset of patients having thyroid or kidney cancer that could benefit from treatment with lenvatinib or a pharmaceutically acceptable salt thereof (e.g., lenvatinib mesylate). In addition, the methods described herein are useful, for example, in selecting appropriate treatment modalities (e.g., therapy comprising lenvatinib or a pharmaceutically acceptable salt thereof (e.g., lenvatinib mesylate)) for a subject suffering from, suspected of having, or at risk of developing a thyroid or kidney cancer. Also, the methods allow a health care practitioner to determine whether to continue with a therapy comprising lenvatinib or a pharmaceutically acceptable salt thereof (e.g., lenvatinib mesylate) or change therapies and use a different treatment.

In one aspect, the disclosure provides a method of predicting the response of a subject having, suspected of having, or at risk of developing, a thyroid cancer or a kidney cancer to a therapy comprising lenvatinib or a pharmaceutically acceptable salt thereof. The method involves providing a biological sample obtained from the subject and detecting the presence of a mutation in at least one gene selected from the group consisting of RAS, VHL, and BRAF in the biological sample. The presence of a mutation in the at least one gene is predictive that the subject will respond to a therapy comprising lenvatinib or a pharmaceutically acceptable salt thereof. In one embodiment, RAS is KRAS or NRAS. In one embodiment, the mutation in at least one gene is a mutation listed in Table 1. In another embodiment, the mutation in at least one gene is a mutation listed in Table 2. In another embodiment, the mutation in RAS is selected from the group consisting of KRAS Q61R, KRAS G12R, NRAS Q61P, and NRAS Q61R. In another embodiment, the method of this aspect further involves detecting the presence of a mutation in at least one gene selected from the group consisting of ERBB2, PTEN, and MET in the biological sample, wherein the presence of a mutated RAS and a mutation in at least one of ERBB2, PTEN, and MET is even more strongly predictive that the subject will respond to a therapy comprising lenvatinib or a pharmaceutically acceptable salt thereof. In one embodiment, the method further comprises the step of determining the expression level of at least one gene selected from the group consisting of ANGPT2, VEGFA, FLT4, CCL3, and CCL4.

In a second aspect, the application provides another method of predicting the response of a subject having, suspected of having, or at risk of developing, a differentiated thyroid cancer to a therapy comprising lenvatinib or a pharmaceutically acceptable salt thereof. This method can also be used to evaluate/assess the benefit of continued administration of a therapy comprising lenvatinib or a pharmaceutically acceptable salt thereof. The method involves providing a first blood sample obtained from the subject before the therapy comprising lenvatinib or a pharmaceutically acceptable salt thereof; providing a second blood sample obtained from the subject after initiation of the therapy comprising lenvatinib or a pharmaceutically acceptable salt thereof, measuring the concentration of thyroglobulin in the first blood sample and the second blood sample; and calculating the ratio (second/first) of the concentrations of thyroglobulin. A reduced ratio, as compared to a control, of the concentration of thyroglobulin in the blood samples is predictive that the subject will respond to a therapy comprising lenvatinib or a pharmaceutically acceptable salt thereof, and an increased ratio, as compared to a control, of the concentration of thyroglobulin in the blood samples is predictive that the subject will respond less effectively to the therapy comprising lenvatinib or a pharmaceutically acceptable salt thereof than a subject having a reduced ratio, as compared to a control, of the concentration of thyroglobulin in the blood samples. In one embodiment, the second blood sample is obtained from the subject 1 week to 9 months after the initiation of the therapy comprising lenvatinib or a pharmaceutically acceptable salt thereof. In another embodiment, the second blood sample is obtained from the subject 2 weeks to 9 months after the initiation of the therapy comprising lenvatinib or a pharmaceutically acceptable salt thereof. In another embodiment, the second blood sample is obtained from the subject 4 weeks to 6 months after the initiation of the therapy comprising lenvatinib or a pharmaceutically acceptable salt thereof. In a further embodiment, the second blood sample is obtained from the subject 4 days to 2 weeks after the initiation of the therapy comprising lenvatinib or a pharmaceutically acceptable salt thereof.

In a third aspect, the disclosure provides another method of predicting the response of a subject having, suspected of having, or at risk of developing, a thyroid cancer or a kidney cancer to a therapy comprising lenvatinib or a pharmaceutically acceptable salt thereof. This method involves providing a biological sample obtained from the subject before the therapy comprising lenvatinib or a pharmaceutically acceptable salt thereof; and measuring the concentration of at least one protein selected from the group consisting of ANGPT2, VEGFA, IFNG, KDR (soluble VEGFR2), FLT4 (soluble VEGFR3), IL6, PDGFAB, CSF3 (G-CSF), CCL3 (MIP-1α), CCL4 (MIP-1β), FGF2, and IL13 in the biological sample. A reduced concentration, as compared to a control, of ANGPT2, VEGFA, IFNG, or soluble KDR (soluble VEGFR2), and/or an increased concentration, as compared to a control, of IL-6, IL-13, PDGFAB, CSF3 (G-CSF), CCL3 (MIP-1α), CCL4 (MIP-1β), FLT4 (soluble VEGFR3), or FGF2 is indicative that the subject will respond to the therapy comprising lenvatinib or a pharmaceutically acceptable salt thereof. In one embodiment, the concentration of at least two genes is measured. In one embodiment, the two genes are selected from the group consisting of VEGFA, ANGPT2, and CSF3; or IL13, CCL3 and CCL4. In another embodiment, the concentration of at least three genes is measured. In yet another embodiment, the concentration of at least four genes is measured.

In a fourth aspect, the disclosure provides another method of predicting the response of a subject having, suspected of having, or at risk of developing, a thyroid cancer or a kidney cancer to a therapy comprising lenvatinib or a pharmaceutically acceptable salt thereof. This method can also be used to evaluate/assess the benefit of continued administration of a therapy comprising lenvatinib or a pharmaceutically acceptable salt thereof. The method involves providing a biological sample obtained from the subject after initiation of the therapy comprising lenvatinib or a pharmaceutically acceptable salt thereof; and measuring the concentration of at least one protein selected from the group consisting of ANGPT2, IL13, VEGFA, IL6, PGF, IL10, CXCL12, and CCL5 in the biological sample. A reduced concentration, as compared to a control, of ANGPT2, IL13, VEGFA, IL6, or PGF, and an increased concentration, as compared to a control, of IL10, CXCL12 or CCL5 is indicative that the subject will respond to the therapy comprising lenvatinib or a pharmaceutically acceptable salt thereof. In one embodiment, the sample is obtained about 15 days after initiation of the therapy comprising lenvatinib or a pharmaceutically acceptable salt thereof. In one embodiment, the sample is obtained about 29 days or any first day of each treatment cycle (four weeks per cycle) after initiation of the therapy comprising lenvatinib or a pharmaceutically acceptable salt thereof.

In a fourth aspect, the disclosure provides another method of predicting the response of a subject having, suspected of having, or at risk of developing, a thyroid cancer or a kidney cancer to a therapy comprising lenvatinib or a pharmaceutically acceptable salt thereof. This method can also be used to evaluate/assess the benefit of continued administration of a therapy comprising lenvatinib or a pharmaceutically acceptable salt thereof. The method involves providing a first biological sample obtained from the subject before the therapy comprising lenvatinib or a pharmaceutically acceptable salt thereof; providing a second biological sample obtained from the subject after initiation of the therapy comprising lenvatinib or a pharmaceutically acceptable salt thereof, measuring the concentration of at least one protein selected from the group consisting of CCL5, FLT3LG, IL12(p40), EGF, PDGF-BB, PDGF-AA, CSF2, FLT1, TEK, HGF, VEGFA, IL6, CSF3, FIGF, IL1RN, CCL11, IL1A, TGFA, PGF, PDGF-AB, IL10, and FGF2, in the first and the second biological samples; and calculating the ratio (second/first) of the concentrations of the protein. A reduced ratio, as compared to a control, of the concentration of CCL5, FLT3LG, IL12(p40), EGF, PDGF-BB, PDGF-AA, CSF3, FLT1, TEK, HGF, VEGFA, or IL6, and an increased ratio, as compared to a control, of the concentration of CSF2, FIGF, IL1RN, CCL11, IL1A, TGFA, PGF, PDGF AB, IL10, or FGF2 is predictive that the subject will respond to the therapy comprising lenvatinib or a pharmaceutically acceptable salt thereof. In one embodiment, the sample is obtained about 15 days after initiation of the therapy comprising lenvatinib or a pharmaceutically acceptable salt thereof. In one embodiment, the sample is obtained about 29 days or any first day of each treatment cycle (four weeks per cycle) after initiation of the therapy comprising lenvatinib or a pharmaceutically acceptable salt thereof.

In a fifth aspect, the disclosure provides a method of treating a thyroid or kidney cancer, the method including the step of administering to a subject in need thereof an effective amount of a therapy comprising lenvatinib or a pharmaceutically acceptable salt thereof, wherein the subject has been identified as having a mutation that is associated with responsiveness to this therapy, and/or expressing a level or having an expression ratio of a biomarker that is associated with responsiveness to this therapy, and/or, for the case of thyroid cancer, having an expression ratio of thyroglobulin that is associated with responsiveness to this therapy.

In a sixth aspect, the disclosure provides a method of predicting responsiveness of a subject having, suspected of having, or at risk of developing a thyroid or kidney cancer. The method involves assessing the mutational status of NRAS and the pre-treatment concentrations of ANGPT2 in a biological sample(s) obtained from the subject. In one embodiment, the presence of a mutation in NRAS (e.g., a NRAS mutation listed in Table 1 or 2) and concentrations of ANGPT2 when entered into the following prediction formula: $(0.000751)*(Ang2)+(2.69)*D(NRAS,WT)-(3.92)<0.716$, where function D is defined in detailed description section, that satisfy the formula, are even more strongly predictive of the subject being responsive to a therapy comprising lenvatinib or a pharmaceutically acceptable salt thereof (e.g., lenvatinib mesylate) than a subject having either of these biomarkers individually (slopes, insertions and cut-off value in the formula can be differently optimized when a different population of the sample is analyzed.).

In a seventh aspect, the disclosure provides a method of predicting responsiveness of a subject having, suspected of having, or at risk of developing a thyroid or kidney cancer. The method involves assessing the mutational status of NRAS or KRAS and the pre-treatment concentrations of ANGPT2 in a biological sample(s) obtained from the subject. In one embodiment, the presence of a mutation in NRAS or KRAS (e.g., a NRAS mutation or a KRAS mutation listed in Table 1 or 2) and concentrations of ANGPT2 when entered into the following prediction formula: $(0.000869)*(ANG290)+(2.16)*D(KRASNRAS,WT)-(2.24)<0.508$, that satisfy the formula, are even more strongly predictive of the subject being responsive to a therapy comprising lenvatinib or a pharmaceutically acceptable salt thereof (e.g., lenvatinib mesylate) than a subject having either of these biomarkers individually (slopes, insertions and cut-off value in the formula can be differently optimized when a different population of the sample is analyzed.).

The following embodiments are envisaged for all of the above aspects. In one embodiment the lenvatinib or a pharmaceutically acceptable salt thereof is lenvatinib mesylate. In one embodiment, the thyroid cancer is a differentiated thyroid cancer. In another embodiment, the thyroid cancer is a medullary thyroid cancer. In one embodiment, the thyroid cancer is a papillary thyroid cancer. In another embodiment, the thyroid cancer is a follicular thyroid cancer. In another embodiment, the thyroid cancer is a Hürthle-cell thyroid cancer. In a certain embodiment, the thyroid cancer is an advanced radioiodine-refractory differentiated thyroid cancer. In one embodiment, the kidney cancer is renal cell carcinoma. In certain embodiments, the subject is a human. In some embodiments, the biological sample is selected from the group consisting of a blood sample, circulating tumor cells, circulating DNA, a plasma sample, a serum sample, a urine sample, a thyroid sample, a thyroid nodule sample, a kidney sample, and a tumor sample. In some embodiments, the method further includes communicating the test results to the subject's health care provider. In certain embodiments, the method further includes modifying the subject's medical record to indicate that the subject is likely or not likely to respond to a therapy comprising lenvatinib or a pharmaceutically acceptable salt thereof. In specific embodiments, the record is created on a computer readable medium. In certain embodiments, the method further includes prescribing a therapy comprising lenvatinib or a pharmaceutically acceptable salt thereof for the subject if the biomarker expression profile is predictive that the subject will respond to a therapy comprising lenvatinib or a pharmaceutically acceptable salt thereof. In some embodiments, the method further includes administering to the subject a therapy comprising lenvatinib or a pharmaceutically acceptable salt thereof. In some embodiments, the method further comprises selecting a subject having, or at risk of developing, a cancer that would benefit from treatment comprising lenvatinib or a pharmaceutically acceptable salt thereof.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description, and from the claims.

DETAILED DESCRIPTION

Figure 1:
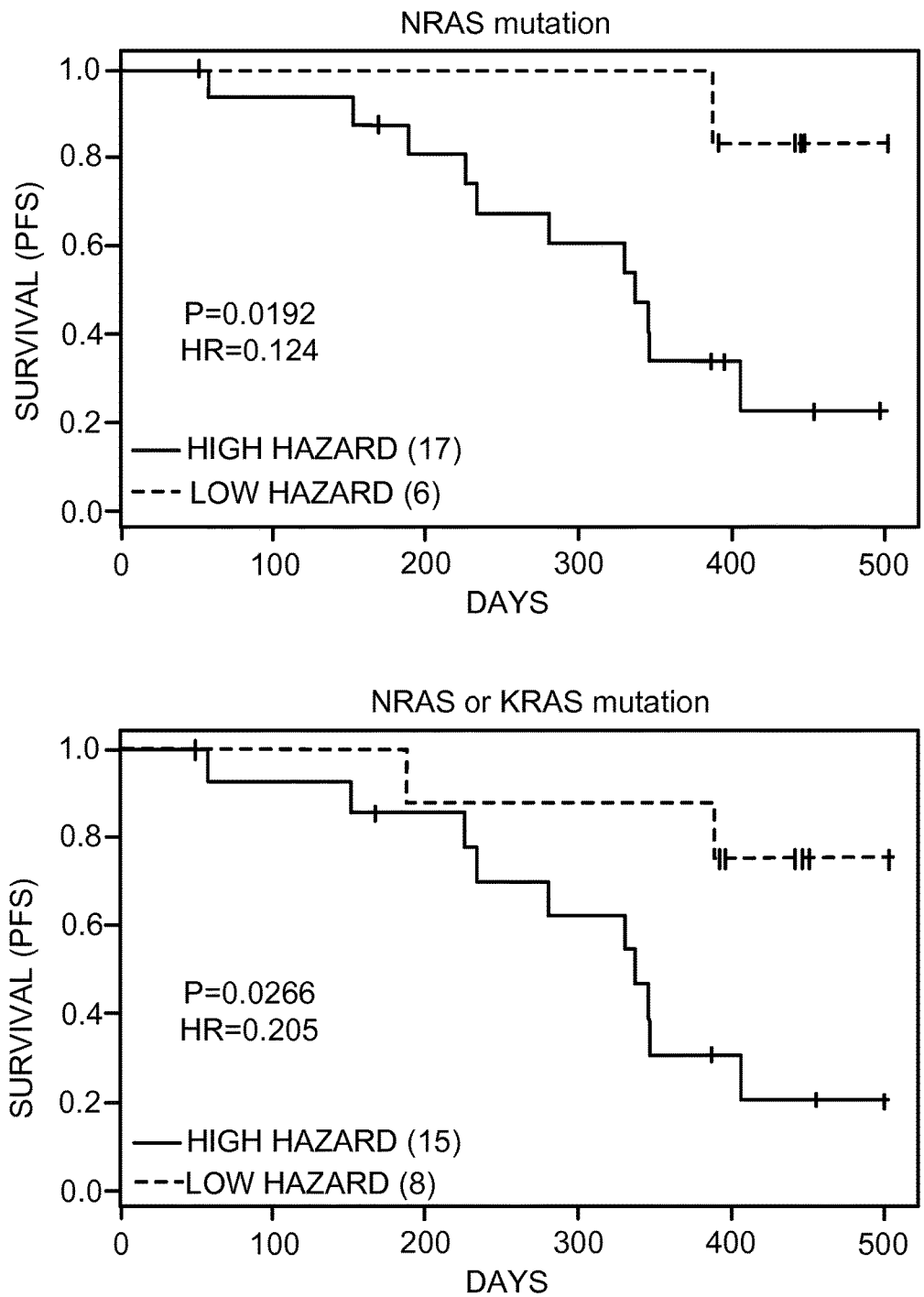
FIG. 1 is a schematic diagram of progression free survival (PFS) of patients with mutations in NRAS alone or with mutations in either NRAS or KRAS. Log rank test analysis demonstrated that patients with mutations in NRAS alone, or with mutations in either NRAS or KRAS had better PFS than those patients who were wild type for NRAS or KRAS.

This disclosure provides methods and compositions for predicting the response of a thyroid or kidney cancer subject (such as a human patient) to a therapy comprising lenvatinib or a pharmaceutically acceptable salt thereof (e.g., lenvatinib mesylate). The disclosure provides predictive biomarkers (e.g., protein expression levels and/or gene mutations) to identify those subjects having, suspected of having, or at risk of developing, thyroid (e.g., differentiated thyroid cancer) or kidney cancer (e.g., renal cell carcinoma), for whom administering a therapy comprising lenvatinib or a pharmaceutically acceptable salt thereof (e.g., lenvatinib mesylate) is likely to be effective or ineffective. In addition, the disclosure provides biomarkers that are useful to evaluate/assess continued treatment of thyroid or kidney cancer subjects with a therapy comprising lenvatinib or a pharmaceutically acceptable salt thereof (e.g., lenvatinib mesylate). The biomarkers, compositions, and methods described herein are useful in selecting appropriate therapeutic modalities (e.g., a lenvatinib or a pharmaceutically acceptable salt thereof (e.g., lenvatinib mesylate) therapy) for subjects suffering from thyroid cancer or kidney cancer. Furthermore, this application provides methods of selecting patients having, suspected of having, or at risk of developing, thyroid or kidney cancer that could benefit from a therapy comprising lenvatinib or a pharmaceutically acceptable salt thereof (e.g., lenvatinib mesylate) as well as methods of treatment.

Definitions

The term "circulating tumor cells" (CTCs) refers to cells that have detached from a primary tumor and circulate in the bloodstream. CTCs may constitute seeds for subsequent growth of additional tumors (metastasis) in different tissues (Kitago et al., Clin. Chem., 55(4):757:764 (2009)).

The term "circulating DNA" refers to DNA that is present in increased amounts in plasma or serum of cancer patients. Cancer patients have higher levels of circulating DNA than healthy controls (Leon et al., Cancer Res., 37: 646-650 (1977); Chuang et al., Head & Neck, 229-234 (2010)).

The term "decreased/reduced expression level" means an expression level that is lower than the expression level in a control.

The term "elevated expression level" means an expression level that is higher than the expression level in a control.

The term "lenvatinib" refers to 4-(3-chloro-4(cyclopropylaminocarbonyl)aminophenoxy)-7-methoxy-6-quinolinecarboxamide. This compound is disclosed in Example 368 (see, column 270) of U.S. Pat. No. 7,253,286. U.S. Pat. No. 7,253,286 is incorporated by reference in its entirety herein. Lenvatinib mesylate is also referred to as E7080.

The terms "nucleic acid" and "polynucleotide" are used interchangeably herein, and refer to both RNA and DNA, including cDNA, genomic DNA, synthetic DNA, and DNA (or RNA) containing nucleic acid analogs. Polynucleotides can have any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs.

The term "pharmaceutically acceptable salt" is not particularly restricted as to the type of salt. Examples of such salts include, but are not limited to, inorganic acid addition salt such as hydrochloric acid salt, sulfuric acid salt, carbonic acid salt, bicarnobate salt, hydrobromic acid salt and hydriodic acid salt; organic carboxylic acid addition salt such as acetic acid salt, maleic acid salt, lactic acid salt, tartaric acid salt and trifluoroacetic acid salt; organic sulfonic acid addition salt such as methanesulfonic acid salt, hydroxymethanesulfonic acid salt, hydroxyethanesulfonic acid salt, benzenesulfonic acid salt, toluenesulfonic acid salt and taurine salt; amine addition salt such as trimethylamine salt, triethylamine salt, pyridine salt, procaine salt, picoline salt, dicyclohexylamine salt, N,N'-dibenzylethylenediamine salt, N-methylglucamine salt, diethanolamine salt, triethanolamine salt, tris(hydroxymethylamino)methane salt and phenethylbenzylamine salt; and amino acid addition salt such as arginine salt, lysine salt, serine salt, glycine salt, aspartic acid salt and glutamic acid salt. In one embodiment, the pharmaceutically acceptable salt is a methanesulfonic acid salt ("mesylate"). The methanesulfonic acid salt form (i.e., the mesylate) of 4-(3-chloro-4-(cyclopropylaminocarbonyl)aminophenoxy)-7-methoxy-6-quinolinecarboxamide is disclosed in U.S. Pat. No. 7,612,208, which is incorporated by reference herein in its entirety.

"Polypeptide" and "protein" are used interchangeably herein and mean any peptide-linked chain of amino acids, regardless of length or post-translational modification. Typically, a polypeptide described herein is "isolated" when it constitutes at least 60%, by weight, of the total protein in a preparation, e.g., 60% of the total protein in a sample. In some embodiments, a polypeptide described herein consists of at least 75%, at least 90%, or at least 99%, by weight, of the total protein in a preparation.

The term "responds/responsive to a therapy" means that the subject administered with the therapy shows a positive response to the therapy provided. Non-limiting examples of such a positive response are: a decrease in tumor size, a decrease in metastasis of a tumor, or an increased period of survival after treatment.

The term "subject" means a mammal, including but not limited to, a human, a chimpanzee, an orangutan, a gorilla, a baboon, a monkey, a mouse, a rat, a pig, a horse, a dog, and a cow.

Mutations Associated with Responsiveness to Therapy Comprising Lenvatinib or a Pharmaceutically Acceptable Salt Thereof Mutations in certain genes such as NRAS, KRAS, VHL, or BRAF are predictive of the responsiveness of a subject to a therapy comprising lenvatinib or a pharmaceutically acceptable salt thereof (e.g., lenvatinib mesylate). Non-limiting examples of such mutations are listed in Tables 1 and 2 in the context of the amino acid sequence of the protein encoded by the respective genes.

TABLE 1

Mutational Biomarkers

| Gene | Mutation |
| --- | --- |
| BRAF | V600E |
| BRAF | V600K |
| BRAF | K601E |
| BRAF | V600R |
| BRAF | D594G |
| BRAF | V600D |
| BRAF | V600M |
| BRAF | G469A |
| BRAF | V600A |
| BRAF | V600G |
| BRAF | G466V |
| BRAF | G469V |
| BRAF | V600_K601 > E |
| BRAF | L597S |
| BRAF | L597V |
| BRAF | G464E |
| BRAF | G464V |
| BRAF | D594N |
| BRAF | F595L |
| BRAF | L597Q |
| BRAF | A598_T599insV |
| BRAF | G469R |
| BRAF | G469S |
| BRAF | L597R |
| BRAF | G466E |
| BRAF | G469E |
| BRAF | Y472S |
| BRAF | T599I |
| BRAF | K601N |
| BRAF | K601del |
| BRAF | A598V |
| BRAF | T599_R603 > I |
| BRAF | T599_V600 > IAL |
| BRAF | Q612* |
| KRAS | G12D |
| KRAS | G12V |
| KRAS | G13D |
| KRAS | G12C |

TABLE 1-continued

Mutational Biomarkers

| Gene | Mutation |
|---|---|
| KRAS | G12A |
| KRAS | G12S |
| KRAS | G12R |
| KRAS | G13C |
| KRAS | Q61H |
| KRAS | G13S |
| KRAS | Q61L |
| KRAS | G13R |
| KRAS | Q61R |
| KRAS | A146T |
| KRAS | G12F |
| KRAS | G13V |
| KRAS | G13A |
| KRAS | Q61K |
| KRAS | L19F |
| KRAS | Q61P |
| KRAS | G13G |
| KRAS | Q61E |
| KRAS | A146V |
| KRAS | V14I |
| KRAS | A59T |
| KRAS | G12G |
| KRAS | G12N |
| KRAS | K117N |
| KRAS | G10_AllinsG |
| KRAS | G12L |
| KRAS | Q22K |
| NRAS | Q61R |
| NRAS | Q61K |
| NRAS | G12D |
| NRAS | G13D |
| NRAS | Q61L |
| NRAS | G12S |
| NRAS | Q61H |
| NRAS | G12C |
| NRAS | G13R |
| NRAS | G12V |
| NRAS | G13V |
| NRAS | G12A |
| NRAS | G13C |
| NRAS | Q61P |
| NRAS | G13A |
| NRAS | G12R |
| NRAS | A18T |
| NRAS | Q61E |
| NRAS | G60E |
| NRAS | G13S |
| NRAS | G12G |
| NRAS | G13G |
| NRAS | Q61Q |
| NRAS | S65C |
| NRAS | A11T |
| NRAS | T58I |
| NRAS | R68T |
| VHL | P81S |
| VHL | S68* |
| VHL | L89H |
| VHL | F148fs*11 |
| VHL | S65L |
| VHL | R161* |
| VHL | S80R |
| VHL | V130L |
| VHL | L158V |
| VHL | S72fs*87 |
| VHL | S65* |
| VHL | L158Q |
| VHL | I151S |
| VHL | Q96* |
| VHL | V62fs*5 |
| VHL | E70* |
| VHL | L85P |
| VHL | S183* |
| VHL | G114C |
| VHL | H115N |
| VHL | L169P |
| VHL | F76del |
| VHL | A56fs*11 |
| VHL | A149fs*25 |
| VHL | E160K |
| VHL | Q132* |
| VHL | Q195* |
| VHL | P172fs*30 |
| VHL | L153P |
| VHL | Y175fs*27 |
| VHL | Q164* |
| VHL | G144fs*15 |
| VHL | L128fs*31 |
| VHL | V74D |
| VHL | Y175* |
| VHL | L184P |
| VHL | N78K |
| VHL | P99fs*60 |
| VHL | R167Q |
| VHL | I180N |
| VHL | W88* |
| VHL | Y156fs*3 |
| VHL | L135fs*24 |
| VHL | Y185fs*17 |
| VHL | R167W |
| VHL | L118P |
| VHL | C77* |
| VHL | Y98* |
| VHL | L89P |
| VHL | L163P |
| VHL | H115Y |
| VHL | Y175fs*27 |
| VHL | R82P |
| VHL | L158P |
| VHL | N90I |
| VHL | T157fs*2 |
| VHL | D126G |
| VHL | L89R |
| VHL | P86H |
| VHL | L135fs*24 |
| VHL | C162Y |
| VHL | F148fs*11 |
| VHL | G144fs*14 |
| VHL | P61P |
| VHL | F136fs*23 |
| VHL | S168fs*2 |
| VHL | D187fs*27 |
| VHL | R107fs*52 |
| VHL | T133fs*26 |
| VHL | W117* |
| VHL | R177* |
| VHL | Q73* |
| VHL | W88R |
| VHL | N141fs*3 |
| VHL | R161P |
| VHL | E189K |
| VHL | I151T |
| VHL | Y98fs*61 |
| VHL | V137fs*7 |
| VHL | F119L |
| VHL | C162R |
| VHL | Q164P |
| VHL | A149fs*26 |
| VHL | G144* |
| VHL | L128P |
| VHL | S111N |
| VHL | G114R |
| VHL | S80N |
| VHL | V155L |
| VHL | N131fs*28 |
| VHL | R58fs*9 |
| VHL | W117R |
| VHL | N78I |
| VHL | R108fs*51 |
| VHL | P172fs*30 |
| VHL | E10G |
| VHL | E12K |
| VHL | L153fs*6 |

TABLE 1-continued

Mutational Biomarkers

| Gene | Mutation |
|---|---|
| VHL | L101L |
| VHL | V87_W88del |
| VHL | L128R |
| VHL | M1I |
| VHL | G39S |
| VHL | E134* |
| VHL | K171N |
| VHL | P138R |
| VHL | G114S |
| VHL | G104fs*55 |
| VHL | G104fs*55 |
| VHL | W117* |
| VHL | G104fs*55 |
| VHL | L163fs*7 |
| VHL | I180fs*22 |
| VHL | P81fs*78 |
| VHL | D121E |
| VHL | S139fs*20 |
| VHL | N141fs*18 |
| VHL | R167fs*3 |
| VHL | H115fs*44 |
| VHL | S65fs*2 |
| VHL | S38F |
| VHL | P40S |
| VHL | E41V |
| VHL | E51Q |
| VHL | P95R |
| VHL | V62fs*68 |
| VHL | N131fs*28 |
| VHL | N131fs*27 |
| VHL | V137fs*22 |
| VHL | S139S |
| VHL | P146fs*13 |
| VHL | V166G |
| VHL | D187_L188del |
| VHL | L188Q |
| VHL | M1fs*20 |
| VHL | T157T |
| VHL | S111S |
| VHL | W88C |
| VHL | D179fs*23 |
| VHL | N150fs*9 |
| VHL | V155fs*4 |
| VHL | N150fs*9 |
| VHL | N78S |
| VHL | N174fs*28 |
| VHL | N90fs*69 |
| VHL | Y98F |
| VHL | T124fs*35 |
| VHL | V155fs*4 |
| VHL | V166D |
| VHL | Y175D |
| VHL | N193fs*22 |
| VHL | W88R |
| VHL | Y98* |
| VHL | A122E |
| VHL | P146P |
| VHL | G104fs*23 |
| VHL | D121G |
| VHL | C162W |
| VHL | R200W |
| VHL | T157I |
| VHL | P86L |
| VHL | V142fs*17 |
| VHL | E160* |
| VHL | N78H |
| VHL | V155M |
| VHL | V142fs*17 |
| VHL | L101P |
| VHL | P154L |
| VHL | I151N |
| VHL | F136V |
| VHL | N131fs*2 |
| VHL | P86S |
| VHL | S111G |
| VHL | I151M |

TABLE 1-continued

Mutational Biomarkers

| Gene | Mutation |
|---|---|
| VHL | Y185* |
| VHL | R182R |
| VHL | P59fs*8 |
| VHL | L169L |
| VHL | E186* |
| VHL | C162F |
| VHL | L188P |
| VHL | K196fs*18 |
| VHL | N131K |
| VHL | S68P |
| VHL | I109N |
| VHL | R113* |
| VHL | S65W |
| VHL | D121Y |
| VHL | E160fs*10 |

Key to Selected Mutations:
V600_K601 > E = amino acids VK are replaced by E;
A598_T599insV = insertion of V between A598 and T599;
K601del = deletion of K601;
Q612* = substitution of Q612 to stop codon; and
F148fs*11 = frameshift occurred at F148 and a stop codon appeared after 11 amino acids.

TABLE 2

Additional Mutational Biomarkers

| Gene | Mutation |
|---|---|
| BRAF | D594V |
| BRAF | D594G |
| BRAF | F468C |
| BRAF | F595L |
| BRAF | G464R |
| BRAF | G464V |
| BRAF | G464E |
| BRAF | G466R |
| BRAF | G469S |
| BRAF | G469E |
| BRAF | G469A |
| BRAF | G469V |
| BRAF | G469R |
| BRAF | G596R |
| BRAF | K601E |
| BRAF | K601N |
| BRAF | L597Q |
| BRAF | L597V |
| BRAF | L597S |
| BRAF | L597R |
| BRAF | T599I |
| BRAF | V600E |
| BRAF | V600K |
| BRAF | V600R |
| BRAF | V600L |
| BRAF | D587A |
| BRAF | D587E |
| BRAF | D594E |
| BRAF | E586K |
| BRAF | F595S |
| BRAF | G466V |
| BRAF | G469A |
| BRAF | I592M |
| BRAF | I592V |
| BRAF | K601del |
| BRAF | N581S |
| BRAF | R444W |
| BRAF | S605F |
| BRAF | S605N |
| BRAF | T599_V600insTT |
| BRAF | V471F |
| BRAF | V600A |
| BRAF | V600D |
| BRAF | V600M |
| KRAS | A59T |

TABLE 2-continued

Additional Mutational Biomarkers

| Gene | Mutation |
|---|---|
| KRAS | G12A |
| KRAS | G12C |
| KRAS | G12D |
| KRAS | G12F |
| KRAS | G12R |
| KRAS | G12S |
| KRAS | G12V |
| KRAS | G13V |
| KRAS | G13D |
| KRAS | Q61E |
| KRAS | Q61K |
| KRAS | Q61H |
| KRAS | Q61L |
| KRAS | Q61R |
| KRAS | Q61P |
| KRAS | A146T |
| KRAS | G13A |
| KRAS | G13R |
| KRAS | L19F |
| KRAS | Q22K |
| NRAS | A18T |
| NRAS | G12C |
| NRAS | G12R |
| NRAS | G12S |
| NRAS | G12V |
| NRAS | G12A |
| NRAS | G12D |
| NRAS | G13C |
| NRAS | G13R |
| NRAS | G13S |
| NRAS | G13V |
| NRAS | G13A |
| NRAS | G13D |
| NRAS | Q61E |
| NRAS | Q61K |
| NRAS | Q61H |
| NRAS | Q61L |
| NRAS | Q61P |
| NRAS | A18T |
| VHL | F148fs*11 |
| VHL | L158Q |
| VHL | L85P |
| VHL | L89H |
| VHL | P81S |
| VHL | R161* |
| VHL | R167W |

The presence in a subject of any one or more of the mutations listed in Table 1 and/or Table 2 is predictive that the subject will respond to a therapy comprising lenvatinib or a pharmaceutically acceptable salt thereof (e.g., lenvatinib mesylate). In the interest of brevity, every possible combination of mutations from Table 1 and Table 2 suitable for use in the invention is not expressly listed herein. Nevertheless, it should be understood that every such combination is contemplated and is within the scope of the invention. The subject can have a single mutation (e.g., NRAS Q61P) or multiple mutations in the same gene (e.g., NRAS G12D and NRAS Q61R); or single mutations in multiple genes (e.g., BRAF V600E, NRAS Q61R, KRAS G12R, and VHL P81S); or multiple mutations in multiple genes (e.g., NRAS G12D, NRAS Q61P, KRAS G12R, and KRAS Q61R); or a mixture of single mutations in certain genes and multiple mutations in other genes (e.g., BRAF V600E; NRAS Q61P, NRAS G13V; KRAS G12R, KRAS Q61R; and VHL P81S). As few as one mutation listed in Table 1 or Table 2 is useful in predicting responsiveness to a therapy comprising lenvatinib or a pharmaceutically acceptable salt thereof (e.g., lenvatinib mesylate). In certain embodiments, the mutation(s) is/are in NRAS. Non-limiting examples of NRAS mutations that are predictive of responsiveness to a therapy comprising lenvatinib or a pharmaceutically acceptable salt thereof (e.g., lenvatinib mesylate) are NRAS Q61P and NRAS Q61R. In other embodiments, the mutation(s) is/are in NRAS and/or KRAS. Non-limiting examples of KRAS mutations that are predictive of responsiveness to a therapy comprising lenvatinib or a pharmaceutically acceptable salt thereof (e.g., lenvatinib mesylate) are KRAS G12R and KRAS Q61R. In other embodiments, the mutation(s) is/are in NRAS and/or KRAS and/or VHL. A non-limiting example of a VHL mutation that is predictive of responsiveness to a therapy comprising lenvatinib or a pharmaceutically acceptable salt thereof (e.g., lenvatinib mesylate) is P81S. In yet other embodiments, the mutation(s) is/are in NRAS and/or KRAS and/or BRAF. A non-limiting example of a BRAF mutation that is predictive of responsiveness to a therapy comprising lenvatinib or a pharmaceutically acceptable salt thereof (e.g., lenvatinib mesylate) is BRAF V600E. In another embodiment, the mutation(s) is/are in NRAS and/or KRAS and/or BRAF and/or VHL.

One or more mutations in genes other than, or in addition to, NRAS, KRAS, VHL and/or BRAF can also be predictive of responsiveness to a therapy comprising lenvatinib or a pharmaceutically acceptable salt thereof (e.g., lenvatinib mesylate). Non-limiting examples of such genes include ERBB2, PTEN and MET. Non-limiting examples of mutations in these genes that can be predictive of responsiveness to a therapy comprising lenvatinib or a pharmaceutically acceptable salt thereof (e.g., lenvatinib mesylate) include ERBB2 S779_P780insVGS, PTEN N323fs*2 and MET T1010I.T992I.

In one embodiment, the subject has, is suspected of having, or is at risk of developing a thyroid cancer (e.g., differentiated thyroid cancer such as papillary or follicular thyroid cancer). In another embodiment, the subject has, is suspected of having, or is at risk of developing a kidney cancer (e.g., renal cell carcinoma).

Nucleic acid isolated from biological samples obtained from the subject can be analyzed for the presence of one or more of the mutations listed in Table 1 and/or Table 2. Methods of identifying mutations in a nucleic acid are well known in the art. One method of assessing whether a subject has a mutation in any of the genes of interest is the method described in Example 1, specifically, the use of Sequenom's OncoCarta™ mutation panels. Other non-limiting methods for determining if a gene or nucleic acid of interest contains a mutation include: Sanger sequencing (chain-termination method), massively parallel signature sequencing (MPSS), Polony sequencing, 454 pyrosequencing, Illumina sequencing, SOLiD sequencing, ion semiconductor sequencing, DNA nanoball sequencing, and the simultaneous multiple mutation detection (SMMD) system utilizing an electrochemical array chip and ferrocenyl-naphthalene diimide (FND) (see, Wakai et al., *Nucl. Acids. Res.,* 32(18): e141 (2004).

The proteins of interest can also be isolated from the biological samples from the subject and analyzed for the presence of mutations such as those disclosed above. Methods of protein sequencing are well known in the art. Non-limiting examples of such methods include mass spectrometry and the Edman degradation reaction. Protein sequencing can be carried out in both the form of whole-protein analysis or analysis of enzymatically produced peptides by mass spectrometry (see, Chait, *Science.* 314 (579065-6 (2006)). Tandem mass spectrometry (MS/MS), such as collision-induced dissociation (CID) (4), is a key technique for protein or peptide sequencing. In this method, gas-phase peptide/protein ions which are generated by ion source are internally heated by multiple collisions with rare gas atoms. This leads to peptide backbone fragmentation of the C—N bond resulting in a generation of series of fragment ions. The sequence information can be read from the series of fragment ions.

The biological samples that are used to obtain the nucleic acid or protein for analysis include, but are not limited to, a blood sample, a plasma sample, a serum sample, circulating tumor cells, circulating DNA, a urine sample, a thyroid tissue sample, a thyroid nodule sample, a renal tissue sample, or a tumor sample.

Thyroglobulin as a Biomarker for Responsiveness to Therapy Comprising Lenvatinib or a Pharmaceutically Acceptable Salt Thereof In addition to the mutation biomarkers described above, thyroglobulin can also be used as an effective biomarker. Thyroglobulin is the major protein found in the thyroid colloid and is central to thyroid physiology, functioning both as a pro-hormone and a storage site for thyroid hormones. The expression level of thyroglobulin can be used to determine whether a subject (e.g., one having, suspected of having, or at risk of developing differentiated thyroid cancer) will be more likely or less likely to respond to a therapy comprising lenvatinib or a pharmaceutically acceptable salt thereof (e.g., lenvatinib mesylate). In addition, the expression level of thyroglobulin can also be used to assess or evaluate whether a subject already being administered a therapy comprising lenvatinib or a pharmaceutically acceptable salt thereof (e.g., lenvatinib mesylate) should continue or terminate the therapy.

To assess whether a subject will respond effectively to a therapy comprising lenvatinib or a pharmaceutically acceptable salt thereof or to evaluate continued treatment with this therapy the following method can be employed. A biological sample (e.g., blood, serum, or plasma sample) is obtained from the subject both prior to and after administration of lenvatinib or a pharmaceutically acceptable salt thereof (e.g., lenvatinib mesylate). The ratio of the expression level of thyroglobulin in the two samples (concentration of thyroglobulin after administration of lenvatinib or a pharmaceutically acceptable salt thereof/concentration of thyroglobulin before administration of lenvatinib or a pharmaceutically acceptable salt thereof) is calculated. If the ratio of the samples from the test subject is less than the control, the subject is determined to be likely to respond to lenvatinib or a pharmaceutically acceptable salt thereof (e.g., lenvatinib mesylate), whereas if the ratio of the samples from the test subject is greater than or about the same as (at least 90% but less than 100% of) that of the control, the subject is determined to be less likely to respond to lenvatinib or a pharmaceutically acceptable salt thereof (e.g., lenvatinib mesylate). If the subject is predicted to respond to treatment, the therapy with lenvatinib or a pharmaceutically acceptable salt thereof is recommended to be continued. In the context of the above assay, the term "control" means samples obtained pre- and post-treatment with lenvatinib or a pharmaceutically acceptable salt thereof from the same source (e.g., blood, serum or plasma sample) as that of the test samples and that are taken at the same, or substantially the same, time points from a control subject(s) as the test samples, from a subject (or subjects) who has not responded to treatment with lenvatinib or a pharmaceutically acceptable salt thereof (e.g., lenvatinib mesylate). The term "control" includes samples obtained in the past (pre- and post-treatment with the therapy) and used as a reference for future comparisons to test samples taken from subjects for which therapeutic responsiveness is to be predicted. For example, the "control" may be pre-established by an analysis of thyroglobulin expression pre- and post-treatment with lenvatinib or a pharmaceutically acceptable salt thereof (e.g., lenvatinib mesylate) in one or more subjects that have not responded to treatment with lenvatinib or a pharmaceutically acceptable salt thereof (e.g., lenvatinib mesylate). This pre-established reference ratio (which may be an average or median ratio taken from multiple subjects that have not responded to the therapy) may then be used for the "control" ratio in the comparison with the test sample.

The "control" may alternatively be pre-established by an analysis of thyroglobulin expression in one or more subjects that have responded to treatment with lenvatinib or a pharmaceutically acceptable salt thereof (e.g., lenvatinib mesylate). This pre-established reference ratio (which may be an average or median ratio taken from multiple subjects that have responded to the therapy) may then be used as the "control" ratio in the comparison with the test sample. In such a comparison, the subject is predicted to respond to a therapy comprising lenvatinib or a pharmaceutically acceptable salt thereof (e.g., lenvatinib mesylate) if the ratio of thyroglobulin levels is comparable to or lower than, for example is lower than, the same as, or about the same as (at least 90% but less than 100% of), the pre-established reference ratio.

In the above method, the first biological sample can be taken at any time point prior to treatment with the therapy lenvatinib or a pharmaceutically acceptable salt thereof (e.g., lenvatinib mesylate). For example, the first biological sample may be taken minutes, hours, days, weeks, or months before initiation of the therapy, or substantially at the same time as the initiation of the therapy. The second biological sample can also be taken from the subject at any time point after initiation of treatment with the therapy lenvatinib or a pharmaceutically acceptable salt thereof (e.g., lenvatinib mesylate). For example, the second biological sample can be taken minutes, hours, days, weeks, or months after treatment with the therapy lenvatinib or a pharmaceutically acceptable salt thereof. Non-limiting examples of the time points when the second biological sample is taken include: 1 week to 9 months, 2 weeks to 9 months, 3 weeks to 9 months after, 4 weeks to 9 months after, 1 day to 2 weeks after, 2 days to 2 weeks after, 3 days to 2 weeks after, 4 days to 2 weeks after, 5 days to 2 weeks after, 6 days to 2 weeks after, 1 week to 2 weeks after, 1 week to 3 weeks after, 1 week to 4 weeks after, and 1 week to 5 weeks after, initiation of treatment with the therapy lenvatinib or a pharmaceutically acceptable salt thereof.

The thyroglobulin levels can be determined either by measuring the levels of mRNA or protein levels. Methods of measuring mRNA and protein levels are well known in the art (see, e.g., Sambrook J, Fritsch E F, Maniatis T, eds. (1989). Molecular Cloning: A Laboratory Manual, 2nd ed. (Woodbury, N.Y.: Cold Spring Harbor Laboratory Press; Real-time PCR applications guide. Bio-Rad Bulletin 5279 (catalog #170-9799)).

In certain embodiments, a subject is determined to respond to lenvatinib or a pharmaceutically acceptable salt thereof (e.g., lenvatinib mesylate), if the subject shows a partial response post treatment with the therapy. "Partial Response" means at least 30% decrease in the sum of the longest diameter (LD) of target lesions, taking as reference the baseline summed LD. In some embodiments, a subject is determined to respond to lenvatinib or a pharmaceutically acceptable salt thereof (e.g., lenvatinib mesylate), if the subject shows tumor shrinkage post-treatment with the therapy. "Tumor shrinkage" (TS) means percent change of sum of diameters of target lesions, taking as reference the baseline sum diameters. In other embodiments, a subject is determined to respond to lenvatinib or a pharmaceutically acceptable salt thereof (e.g., lenvatinib mesylate), if the subject shows progression free survival. "Progression Free Survival" (PFS) refers to the period from start date of treatment to the last date before entering Progressive Disease (PD) status. PD means at least 20% increase in the sum of the LD of target lesions, taking as reference the smallest summed LD recorded since the treatment started, or the appearance of one or more new lesions.

A larger decrease in thyroglobulin levels post-treatment from pre-treatment levels compared to a control (e.g., pre- and post-treatment samples obtained from a subject who is not responsive to a therapy comprising lenvatinib or a pharmaceutically acceptable salt thereof) is predictive of a partial response to a therapy comprising lenvatinib or a pharmaceutically acceptable salt thereof (e.g., lenvatinib mesylate) in differentiated thyroid cancer patients.

A decrease in thyroglobulin levels about 28 days (e.g., 24, 25, 26, 27, 28, 29, 30, 31, 32, 33, 34 days) after treatment with a therapy comprising lenvatinib or a pharmaceutically acceptable salt thereof (e.g., lenvatinib mesylate) is predictive of progression free survival in differentiated thyroid cancer patients.

A decrease in thyroglobulin levels about 56 days after, about 84 days after, about 112 days after, and about 140 days after treatment with a therapy comprising lenvatinib or a pharmaceutically acceptable salt thereof (e.g., lenvatinib mesylate) is predictive of tumor shrinkage in differentiated thyroid cancer patients.

Cytokine, Chemokine, and Angiogenic Factors as Biomarkers for Responsiveness to Therapy Comprising Lenvatinib or a Pharmaceutically Acceptable Salt Thereof A number of genes have been identified whose expression levels (e.g., mRNA or protein expression levels) are useful in predicting responsiveness of a subject to a therapy comprising lenvatinib or a pharmaceutically acceptable salt thereof (e.g., lenvatinib mesylate). These genes as identified by Gene ID, related URL, protein ID and UniProtKB Accession Nos. are listed in Table 3.

TABLE 3

List of Blood Biomarkers

| Official Gene Symbol | Gene ID | URL | Alternative Symbol* | UniProtKB Accession No. |
|---|---|---|---|---|
| ANGPT1 | 284 | www.ncbi.nlm.nih.gov/gene/284 | Ang-1/Ang1 | Q5HYA0 |
| ANGPT2 | 285 | www.ncbi.nlm.nih.gov/gene/285 | Ang-2/ANG-2/Ang2/ANG2 (90)/ANG290 | O15123 |
| CCL11 | 6356 | www.ncbi.nlm.nih.gov/gene/6356 | Eotaxin | P51671 |
| FGF2 | 2247 | www.ncbi.nlm.nih.gov/gene/2247 | FGF-2/FGF2(79)/FGF279 | P09038 |
| FGF23 | 8074 | www.ncbi.nlm.nih.gov/gene/8074 | FGF-23 | Q9GZV9 |
| FGF4 | 2249 | www.ncbi.nlm.nih.gov/gene/2249 | FGF4 (75)/FGF475 | P08620 |
| CSF2 | 1437 | www.ncbi.nlm.nih.gov/gene/1437 | GM-CSF/GMCSF | P04141 |
| IFNG | 3458 | www.ncbi.nlm.nih.gov/gene/3458 | IFN-g/IFN-γ | P01579 |
| IL10 | 3586 | www.ncbi.nlm.nih.gov/gene/3586 | IL-10 | P22301 |
| IL12A (p35) | 3592 | www.ncbi.nlm.nih.gov/gene/3592 | IL12A | P29459 |
| IL12B (p40) | 3593 | www.ncbi.nlm.nih.gov/gene/3593 | IL12B/IL12(p40)/IL-12(p40) | P29460 |
| IL13 | 3596 | www.ncbi.nlm.nih.gov/gene/3596 | IL-13 | P35225 |
| IL17A | 3605 | www.ncbi.nlm.nih.gov/gene/3605 | IL-17 | Q16552 |
| IL1A | 3552 | www.ncbi.nlm.nih.gov/gene/3552 | IL-1a/IL-1α | P01583 |
| IL1B | 3553 | www.ncbi.nlm.nih.gov/gene/3553 | IL-1b/IL-1β | P01584 |
| IL2 | 3558 | www.ncbi.nlm.nih.gov/gene/3558 | IL-2 | P60568 |
| IL5 | 3567 | www.ncbi.nlm.nih.gov/gene/3567 | IL-5 | P05113 |
| IL6 | 3569 | www.ncbi.nlm.nih.gov/gene/3569 | IL-6 | P05231 |
| IL8 | 3576 | www.ncbi.nlm.nih.gov/gene/3576 | IL-8 | P10145 |
| CXCL10 | 3627 | www.ncbi.nlm.nih.gov/gene/3627 | IP-10 | P02778 |
| CCL2 | 6347 | www.ncbi.nlm.nih.gov/gene/6347 | MCP-1 | P13500 |
| CCL3 | 6348 | www.ncbi.nlm.nih.gov/gene/6348 | MIP-1a/MIP1a/MIP-1α | P10147 |
| CCL4 | 6351 | www.ncbi.nlm.nih.gov/gene/6351 | MIP-1b/MIP1b/MIP-1β | P13236 |
| CCL5 | 6352 | www.ncbi.nlm.nih.gov/gene/6352 | RANTES | P13501 |
| CD40LG | 959 | www.ncbi.nlm.nih.gov/gene/959 | sCD40L | P29965 |
| CXCL12 | 6387 | www.ncbi.nlm.nih.gov/gene/6387 | SDF-1a/SDF1a | P48061 |
| KDR | 3791 | www.ncbi.nlm.nih.gov/gene/3791 | sVEGFR2 | P35968 |
| TEK | 7010 | www.ncbi.nlm.nih.gov/gene/7010 | Tie-2 | Q02763 |
| TNF | 7124 | www.ncbi.nlm.nih.gov/gene/7124 | TNFa/TNF-α | P01375 |
| FIGF | 2277 | www.ncbi.nlm.nih.gov/gene/2277 | VEGFD (78) | O43915 |
| EGF | 1950 | www.ncbi.nlm.nih.gov/gene/1950 | EGF (80) | P01133 |
| FLT3LG | 2323 | www.ncbi.nlm.nih.gov/gene/2323 | FLT3 LG (89) | P49771 |
| CSF3 | 1440 | www.ncbi.nlm.nih.gov/gene/1440 | G-CSF/GCSF | P09919 |
| HGF | 3082 | www.ncbi.nlm.nih.gov/gene/3082 | HGF (86) | P14210 |
| IL15 | 3600 | www.ncbi.nlm.nih.gov/gene/3600 | IL-15 | P40933 |
| IL1RN | 3557 | www.ncbi.nlm.nih.gov/gene/3557 | IL-1ra | P18510 |
| IL4 | 3565 | www.ncbi.nlm.nih.gov/gene/3565 | IL-4 | P05112 |
| IL7 | 3574 | www.ncbi.nlm.nih.gov/gene/3574 | IL-7 | P13232 |
| PDGFA | 5154 | www.ncbi.nlm.nih.gov/gene/5154 | PDGFA | P04085 |

TABLE 3-continued

List of Blood Biomarkers

| Official Gene Symbol | Gene ID | URL | Alternative Symbol* | UniProtKB Accession No. |
| --- | --- | --- | --- | --- |
| PDGFB | 5155 | www.ncbi.nlm.nih.gov/gene/5155 | PDGFB | P01127 |
| PGF | 5228 | www.ncbi.nlm.nih.gov/gene/5228 | PGF (91) | P49763 |
| FLT1 | 2321 | www.ncbi.nlm.nih.gov/gene/2321 | sVEGFR1 | P17948 |
| FLT4 | 2324 | www.ncbi.nlm.nih.gov/gene/2324 | sVEGFR3 | P35916 |
| TGFA | 7039 | www.ncbi.nlm.nih.gov/gene/7039 | TGFa/TGF-α | P01135 |
| VEGFA | 7422 | www.ncbi.nlm.nih.gov/gene/7422 | VEGF/VEGFA (100)/VEGFA100 | P15692 |

*Other alternate symbols
PDGF-AA (alternative symbol PDGFAA); homo dimer of PDGFA
PDGF-AB (alternative symbol PDGFAB); hetero dimer of PDGFA and PDGFB
PDGF-BB (alternative symbol PDGFBB); homo dimer of PDGFB
IL-12p70; hetero dimer of IL12A(p35) and IL12B(p40)

A low expression (e.g., mRNA or protein expression) level (compared to a control) of certain genes listed in Table 3 is indicative/predictive that a subject will respond to a therapy comprising lenvatinib or a pharmaceutically acceptable salt thereof (e.g., lenvatinib mesylate). For example, low concentrations (compared to a control) of ANGPT2, VEGFA, IFNG, and KDR in a biological sample obtained from a subject prior to treatment with the therapy are predictive that a given subject will respond to a therapy comprising lenvatinib or a pharmaceutically acceptable salt thereof (e.g., lenvatinib mesylate). In this context, the term "control" includes a sample (from the same tissue) obtained from a subject who is known to not respond to a therapy comprising lenvatinib or a pharmaceutically acceptable salt thereof (e.g., lenvatinib mesylate). The term "control" also includes a sample obtained in the past and used as a reference for future comparisons to test samples taken from subjects for which therapeutic responsiveness is to be predicted. For example, the "control" expression level for a particular gene in a particular cell type or tissue may be pre-established by an analysis of gene expression in one or more subjects that have not responded to treatment with lenvatinib or a pharmaceutically acceptable salt thereof (e.g., lenvatinib mesylate). This pre-established reference value (which may be an average or median expression level taken from multiple subjects that have responded to the therapy) may then be used for the "control" expression level in the comparison with the test sample. The "control" expression level for a particular gene in a particular cell type or tissue may alternatively be pre-established by an analysis of gene expression in one or more subjects that have responded to treatment with lenvatinib or a pharmaceutically acceptable salt thereof (e.g., lenvatinib mesylate). This pre-established reference value (which may be an average or median expression level taken from multiple subjects that have responded to the therapy) may then be used as the "control" expression level in the comparison with the test sample. In such a comparison, the subject is predicted to respond to a therapy comprising lenvatinib or a pharmaceutically acceptable salt thereof (e.g., lenvatinib mesylate) if the expression level of the gene being analyzed is comparable to or lower than, for example is lower than, the same as, or about the same as (at least 85% but less than 100% of), the pre-established reference.

A high expression (e.g., mRNA or protein expression) level (compared to a control) of certain genes listed in Table 3 is predictive that a subject will respond to a therapy comprising lenvatinib or a pharmaceutically acceptable salt thereof (e.g., lenvatinib mesylate). For example, high concentrations (compared to a control) of PDGF-AB, FGF2, CSF3, IL6, IL13, FLT4, CCL3, and CCL4 in a biological sample obtained from a subject prior to treatment with the therapy are predictive that a given subject will respond to a therapy comprising lenvatinib or a pharmaceutically acceptable salt thereof (e.g., lenvatinib mesylate). In this context, the term "control" is identical to that described in the paragraph above, except that when the "control" expression level for a particular gene in a particular cell type or tissue is alternatively pre-established by an analysis of gene expression in one or more subjects that have responded to treatment with lenvatinib or a pharmaceutically acceptable salt thereof (e.g., lenvatinib mesylate), the subject is predicted to respond to a therapy comprising lenvatinib or a pharmaceutically acceptable salt thereof (e.g., lenvatinib mesylate) if the expression level of the gene being analyzed is comparable to or higher than, for example is higher than, the same as, or about the same as (at least 85% but less than 100% of), the pre-established reference.

It is also envisaged that subjects be administered with lenvatinib or a pharmaceutically acceptable salt thereof (e.g., lenvatinib mesylate) for short periods of time to determine whether the administered therapy will be effective for the subject. The determination of effectiveness of the therapy is made based on the expression (e.g., mRNA or protein expression) levels of certain genes in biological samples obtained from these subjects at different time points post-treatment. Based on the expression levels of these genes, one can predict whether the subject will respond to continued treatment. Thus, these methods are useful in assessing or evaluating whether it is advisable to continue administration of lenvatinib or a pharmaceutically acceptable salt thereof (e.g., lenvatinib mesylate). For example, low concentrations (compared to a control) of certain genes, e.g., ANGPT2 and/or IL13 about 5 days to about 18 days after initiation of therapy comprising lenvatinib or a pharmaceutically acceptable salt thereof (e.g., lenvatinib mesylate) are predictive that the subject will have a beneficial clinical outcome (e.g., tumor response and/or tumor shrinkage) upon continued therapy with lenvatinib compounds. Similarly, high concentrations (compared to a control) of certain genes, e.g., IL10 and/or CXCL12 about 5 days to about 18 days after initiation of therapy comprising lenvatinib or a pharmaceutically acceptable salt thereof (e.g., lenvatinib mesylate) are also predictive that the subject will have a beneficial clinical outcome (e.g., tumor response and/or tumor shrinkage) upon continued therapy with lenvatinib compounds.

In addition, low concentrations (compared to a control) of certain genes, e.g., VEGFA, IL6, and/or PGF about 5 weeks (e.g., 3 weeks, 4 weeks, 5 weeks, 6 weeks, 7 weeks) after initiation of therapy comprising lenvatinib or a pharmaceutically acceptable salt thereof (e.g., lenvatinib mesylate) are predictive that the subject will have a beneficial clinical outcome (e.g., tumor response and/or tumor shrinkage) upon continued therapy with lenvatinib compounds. Also, high concentrations (compared to a control) of certain genes, e.g., CCL5 about 5 weeks (e.g., 3 weeks, 4 weeks, 5 weeks, 6 weeks, 7 weeks) after initiation of therapy comprising lenvatinib or a pharmaceutically acceptable salt thereof (e.g., lenvatinib mesylate) are predictive that the subject will have a beneficial clinical outcome (e.g., tumor response and/or tumor shrinkage) upon continued therapy with lenvatinib compounds.

The ratio of the expression (e.g., mRNA or protein expression) level of certain genes post-treatment over pre-treatment with lenvantib or a pharmaceutically acceptable salt thereof (compared to a control) can also be useful in predicting whether a subject will have a beneficial clinical outcome (e.g., best overall response, tumor shrinkage, progression free survival) upon continued therapy with lenvatinib compounds. For example, a reduced ratio, as compared to a control, of the expression level of certain genes, e.g., CCL5, FLT3LG, IL12(p40), EGF, PDGF-BB, PDGF-AA, CSF3, FLT1, TEK, HGF, VEGFA, or IL6 is indicative that the subject will respond to the therapy comprising lenvatinib or a pharmaceutically acceptable salt thereof. In addition, an increased ratio, as compared to a control, of the concentration of certain genes, e.g., CSF2, FIGF, IL1RN, CCL11, IL1A, TGFA, PGF, PDGF AB, IL10, or FGF2 is predictive that the subject will respond to the therapy comprising lenvatinib or a pharmaceutically acceptable salt thereof.

A reduced ratio (compared to a control) of the expression level of certain genes, e.g., CCL5, FLT3LG based on expression about 5 days to about 18 days after initiation of therapy comprising lenvatinib or a pharmaceutically acceptable salt thereof (e.g., lenvatinib mesylate) and the expression level of the same gene prior to initiation of this therapy is indicative that the subject will have progression free survival.

An increased ratio (compared to a control) of the expression level of certain genes, e.g., CSF3 or FGF2 based on expression about 5 days to about 18 days after initiation of therapy comprising lenvatinib or a pharmaceutically acceptable salt thereof (e.g., lenvatinib mesylate) and the expression level of the same gene prior to initiation of this therapy is indicative that the subject will have tumor response.

An increased ratio (compared to a control) of the expression level of certain genes, e.g., CSF3, IL10 or FGF2 based on expression about 5 days to about 18 days after initiation of therapy comprising lenvatinib or a pharmaceutically acceptable salt thereof (e.g., lenvatinib mesylate) and the expression level of the same gene prior to initiation of this therapy is indicative that the subject will show tumor shrinkage.

An increased ratio (compared to a control) of the expression level of certain genes, e.g., FIGF, ILIRN, PDGFAB or IL10 based on expression about 5 days to about 18 days after initiation of therapy comprising lenvatinib or a pharmaceutically acceptable salt thereof (e.g., lenvatinib mesylate) and the expression level of the same gene prior to initiation of this therapy is indicative that the subject will have progression free survival.

A reduced ratio of the expression level of certain genes, e.g., FLT3LG, IL12, EGF, PDGFBB, PDGFAA, CSF3, or FLT1 based on expression about 5 weeks (e.g., 3 weeks, 4 weeks, 5 weeks, 6 weeks, 7 weeks) after initiation of therapy comprising lenvatinib or a pharmaceutically acceptable salt thereof (e.g., lenvatinib mesylate) and the expression level of the same gene prior to initiation of this therapy is indicative that the subject will have progression free survival.

An increased ratio of the expression level of certain genes, e.g., CCL11 based on expression about 5 weeks (e.g., 3 weeks, 4 weeks, 5 weeks, 6 weeks, 7 weeks) after initiation of therapy comprising lenvatinib or a pharmaceutically acceptable salt thereof (e.g., lenvatinib mesylate) and the expression level of the same gene prior to initiation of this therapy is indicative that the subject will exhibit tumor response.

An increased ratio of the expression level of certain genes, e.g., IL1A or TGFA based on expression about 5 weeks (e.g., 3 weeks, 4 weeks, 5 weeks, 6 weeks, 7 weeks) after initiation of therapy comprising lenvatinib or a pharmaceutically acceptable salt thereof (e.g., lenvatinib mesylate) and the expression level of the same gene prior to initiation of this therapy is predictive that the subject will exhibit tumor shrinkage.

A reduced ratio of the expression level of certain genes, e.g., FLT1, TEK, VEGFA, or IL6 based on expression about 5 weeks (e.g., 3 weeks, 4 weeks, 5 weeks, 6 weeks, 7 weeks) after initiation of therapy comprising lenvatinib or a pharmaceutically acceptable salt thereof (e.g., lenvatinib mesylate) and the expression level of the same gene about 5 days to about 18 days after initiation of this therapy is indicative that the subject will exhibit tumor shrinkage.

A reduced ratio of the expression level of certain genes, e.g., TEK, HGF, or VEGFA based on expression about 5 weeks (e.g., 3 weeks, 4 weeks, 5 weeks, 6 weeks, 7 weeks) after initiation of therapy comprising lenvatinib or a pharmaceutically acceptable salt thereof (e.g., lenvatinib mesylate) and the expression level of the same gene about 5 days to about 18 days after initiation of this therapy is predictive that the subject will show the best overall response.

An increased ratio of the expression level of certain genes, e.g., PGF based on expression about 5 weeks (e.g., 3 weeks, 4 weeks, 5 weeks, 6 weeks, 7 weeks) after initiation of therapy comprising lenvatinib or a pharmaceutically acceptable salt thereof (e.g., lenvatinib mesylate) and the expression level of the same gene about 5 days to about 18 days after initiation of this therapy is indicative that the subject will exhibit tumor shrinkage, whereas an increased ratio under the same conditions of e.g., FGF2 is predictive of the subject exhibiting a tumor response.

The progression free survival observed above can be, for example, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, or 24 months, or about 4 months, about 5 months, about 6 months, about 7 months, about 8 months, about 9 months, about 10 months, about 11 months, about 12 months, about 13 months, about 14 months, about 15 months, about 15 months, about 17 months, about 18 months, about 19 months, about 20 months, about 21 months, about 22 months, about 23 months, or about 24 months.

In determining whether the ratio is increased or decreased comparison is made to a control. In this context, the term "control" includes samples obtained from the same source (e.g., blood, serum or plasma sample) as that of the test samples and that are taken at the same, or substantially the same, time points as the test samples, from a subject (or subjects) who has not responded to treatment with lenvatinib or a pharmaceutically acceptable salt thereof (e.g., lenvatinib mesylate). The term "control" includes samples obtained in the past (pre- and post-treatment with the therapy) and used as a reference for future comparisons to test samples taken from subjects for which therapeutic responsiveness is to be predicted. For example, the "control" may be a pre-established ratio of the expression of the gene of interest pre- and post-treatment with lenvatinib or a pharmaceutically acceptable salt thereof (e.g., lenvatinib mesylate) in one or more subjects that have not responded to treatment with lenvatinib or a pharmaceutically acceptable salt thereof (e.g., lenvatinib mesylate). This pre-established reference ratio (which may be an average or median ratio taken from multiple subjects that have not responded to the therapy) may then be used for the "control" ratio in the comparison with the test sample.

The "control" may alternatively be pre-established by an analysis of expression of the gene of interest in one or more subjects who have responded to treatment with lenvatinib or a pharmaceutically acceptable salt thereof (e.g., lenvatinib mesylate). This pre-established reference ratio (which may be an average or median ratio taken from multiple subjects that have responded to the therapy) may then be used as the "control" ratio in the comparison with the test sample. In such a comparison, the subject is predicted to respond to a therapy comprising lenvatinib or a pharmaceutically acceptable salt thereof (e.g., lenvatinib mesylate) if the ratio of expression levels of the gene is comparable to, for example, the same as or about the same as (at least 90% but less than 100% of), the pre-established reference ratio.

Combinatorial Methods

Any of the above biomarkers may be assessed in combination to determine whether a subject will respond to, or benefit from continued, administration of a therapy comprising lenvatinib or a pharmaceutically acceptable salt thereof (e.g., lenvatinib mesylate). For example, any one or more of the mutation biomarkers may be assessed in combination with thyroglobulin expression ratios and/or expression levels or expression ratios of cytokine, chemokine, or angiogenic factors, and/or histological analysis. In some instances, a mutational biomarker(s) is assessed in combination with histological analysis. In other cases, a mutational biomarker(s) is assessed in combination with thyroglobulin expression ratios. In some instances, a mutational biomarker(s) is assessed in combination with expression levels or expression ratios of one or more cytokine, chemokine, or angiogenic factors. In one embodiment, the mutational status of NRAS is assessed in the biological sample obtained from the subject and considered in combination with pre-treatment concentrations of ANGPT2. In another embodiment, the mutational status of NRAS or KRAS is assessed in the biological sample obtained from the subject and considered in combination with pre-treatment concentrations of ANGPT2. Such combinatorial biomarker analyses provide even stronger predictive value than studying individual biomarkers, and are useful, for example, in predicting responsiveness of a subject to a therapy comprising lenvatinib or a pharmaceutically acceptable salt thereof (e.g., lenvatinib mesylate).

Statistical analysis can be used to determine which markers when used in combination are better associated with a desired clinical outcome than the individual markers. A non-limiting example of such an analysis is provided in Example 4 of this application.

The combination of the expression levels of VEGFA and ANGPT2 prior to initiation of a therapy comprising lenvatinib or a pharmaceutically acceptable salt thereof (e.g., lenvatinib mesylate) ("pre-treatment") can be a better predictor of response to the therapy than each of these individual blood biomarkers. For example, if the pre-treatment concentrations of VEGFA and ANGPT2 in a subject when entered into the following prediction formula:

$$(0.000261)*(Ang2)+(0.00126)*(VEGFA100)-(1.09)<-0.24$$

render this formula true (i.e. if the value is <−0.24 (e.g., −1.0)), then the subject is predicted to have a stronger clinical outcome (e.g., progression free survival) after taking the therapy comprising lenvatinib or a pharmaceutically acceptable salt thereof (e.g., lenvatinib mesylate) than subjects whose concentrations of these factors do not satisfy the formula (slopes, insertions and cut-off value in the formula can be differently optimized when different population of the sample is analyzed.). For another example, if the pre-treatment concentrations of VEGFA, ANGPT2, and GCSF in a subject when entered into the following prediction formula:

$$(0.000591)*(ANG290)+(-0.0178)*(GCSF)+(0.00142)*(VEGFA100)-(-0.671)<0.651$$

render this formula true (i.e. if the value is <0.651), then the subject is predicted to have a stronger clinical outcome (e.g., progression free survival) after taking the therapy comprising lenvatinib or a pharmaceutically acceptable salt thereof (e.g., lenvatinib mesylate) than subjects whose pre-treatment concentrations of these factors do not satisfy the formula (slopes, insertions and cut-off value in the formula can be differently optimized when different population of the sample is analyzed.).

For further example, if the pre-treatment concentrations of IL13 and MIP1a in a subject when entered into the following prediction formula:

$$(-0.0459)*(IL13)+(0.0459)*(MIP1a)-(0.0395)<0.268$$

render this formula true (i.e. if the value is <0.268), then the subject is predicted to have a stronger clinical outcome (e.g., progression free survival) after taking the therapy comprising lenvatinib or a pharmaceutically acceptable salt thereof (e.g., lenvatinib mesylate) than subjects whose concentrations of these factors do not satisfy the formula (slopes, insertions and cut-off value in the formula can be differently optimized when different population of the sample is analyzed.).

For further example, if the pre-treatment concentrations IL13, MIP1a, and MIP1b in a subject when entered into the following prediction formula:

$$(-0.0353)*(IL13)+(0.0713)*(MIP1a)+(-0.0154)*(MIP1b)-(0.188)<0.222$$

render this formula true (i.e. if the value is <0.222), then the subject is predicted to have a stronger clinical outcome (e.g., progression free survival) after taking the therapy comprising lenvatinib or a pharmaceutically acceptable salt thereof (e.g., lenvatinib mesylate) than subjects whose pre-treatment concentrations of these factors do not satisfy the formula (slopes, insertions and cut-off value in the formula can be differently optimized when different population of the sample is analyzed.).

The combination of a mutation(s) and the expression levels of VEGFA and MIP1b prior to initiation of a therapy comprising lenvatinib or a pharmaceutically acceptable salt thereof (e.g., lenvatinib mesylate) ("pre-treatment") can also be a better predictor of response to the therapy than each of these individual mutational and blood biomarkers. For example, if the sample from the subject has a mutation in NRAS (e.g., one of those listed in Table 1 or 2) and the pre-treatment concentrations of VEGFA and MIP1b in a subject when entered into the following prediction formula:

$$(-0.025)*(MIP1b)+(-0.00616)*(VEGFA100)+(3.32)*D(NRAS,WT)-(-0.52)<1.81$$

(The function D(g, s) is 1 when mutation status of gene(s) g is status s, and 0 when g is not s. The status s can be "WT" (wild type) or "MU" (mutation). For the case of multiple-genes, mutation status is "MU" if one or more genes have mutation and "WT" only for the case that all genes are wild-type) render this formula true (i.e. if the value is <1.81 (e.g., 1.0)), then the subject is predicted to have a stronger clinical outcome (e.g., progression free survival) with the therapy comprising lenvatinib or a pharmaceutically acceptable salt thereof (e.g., lenvatinib mesylate) than subjects who have wild type NRAS and whose pre-treatment concentrations of VEGFA and MIP1b do not satisfy the formula (slopes, insertions and cut-off value in the formula can be differently optimized when different population of the sample is analyzed.).

For another example, if the sample from the subject has a mutation in NRAS (e.g., one of those listed in Table 1 or 2) and the pre-treatment concentrations of VEGFA, MIP1b, and sVEGFR3 in a subject when entered into the following prediction formula:

$$(-0.0494)*(MIP1b)+(-0.000472)*(sVEGFR3)+(-0.0119)*(VEGFA100)+(4.66)*D(NRAS,WT)-(-5.9)<3.55$$

render this formula true (i.e. if the value is <3.55 (e.g., 3.0)), then the subject is predicted to have a stronger clinical outcome (e.g., progression free survival) with the therapy comprising lenvatinib or a pharmaceutically acceptable salt thereof (e.g., lenvatinib mesylate) than subjects who have wild type NRAS and whose pre-treatment concentrations of VEGFA, MIP1b, and sVEGFR3 do not satisfy the formula (slopes, insertions and cut-off value in the formula can be differently optimized when different population of the sample is analyzed.).

For further example, if the sample from the subject has a mutation in NRAS (e.g., one of those listed in Table 1 or 2) and the pre-treatment concentrations of VEGFA, MIP1b, sVEGFR3, and Ang2 in a subject when entered into the following prediction formula:

$$(0.00148)*(Ang2)+(-0.0606)*(MIP1b)+(-0.000917)*(sVEGFR3)+(-0.0177)*(VEGFA100)+(6.58)*D(NRAS,WT)-(-5.78)<3.97$$

render this formula true (i.e. if the value is <3.97 (e.g., 3.0)), then the subject is predicted to have a stronger clinical outcome (e.g., progression free survival) with the therapy comprising lenvatinib or a pharmaceutically acceptable salt thereof (e.g., lenvatinib mesylate) than subjects who have wild type NRAS and whose pre-treatment concentrations of VEGFA, MIP1b, sVEGFR3, and Ang2 do not satisfy the formula (slopes, insertions and cut-off value in the formula can be differently optimized when different population of the sample is analyzed.).

For further example, if the sample from the subject has a mutation in NRAS (e.g., one of those listed in Table 1 or 2) and the pre-treatment concentrations of Ang2 in a subject when entered into the following prediction formula:

$$(0.000751)*(Ang2)+(2.69)*D(NRAS,WT)-(3.92)<0.716$$

render this formula true (i.e. if the value is <0.716 (e.g., 0.5)), then the subject is predicted to have a stronger clinical outcome (e.g., progression free survival) with the therapy comprising lenvatinib or a pharmaceutically acceptable salt thereof (e.g., lenvatinib mesylate) than subjects who have wild type NRAS and whose pre-treatment concentrations of Ang2 do not satisfy the formula (slopes, insertions and cut-off value in the formula can be differently optimized when different population of the sample is analyzed.).

For a further example, if the sample from the subject has a mutation in NRAS (e.g., one of those listed in Table 1 or 2) and the pre-treatment concentrations of ANG2(90) in a subject when entered into the following prediction formula:

$$(0.000972)*(ANG290)+(2.75)*D(NRAS,WT)-(2.96)<0.633$$

render this formula true (i.e. if the value is <0.633 (e.g., 0.5)), then the subject is predicted to have a stronger clinical outcome (e.g., progression free survival) with the therapy comprising lenvatinib or a pharmaceutically acceptable salt thereof (e.g., lenvatinib mesylate) than subjects who have wild type NRAS and whose pre-treatment concentrations of ANG2(90) do not satisfy the formula (slopes, insertions and cut-off value in the formula can be differently optimized when different population of the sample is analyzed.).

For another example, if the sample from the subject has a mutation in NRAS or KRAS (e.g., one of those listed in Table 1 or 2) and the pre-treatment concentrations of ANG2 (90) in a subject when entered into the following prediction formula:

$$(0.000869)*(ANG290)+(2.16)*D(KRASNRAS,WT)-(2.24)<0.508$$

render this formula true (i.e. if the value is <0.508 (e.g., 0.4)), then the subject is predicted to have a stronger clinical outcome (e.g., progression free survival) with the therapy comprising lenvatinib or a pharmaceutically acceptable salt thereof (e.g., lenvatinib mesylate) than subjects who have wild type NRAS or KRAS and whose pre-treatment concentrations of ANG2(90) do not satisfy the formula (slopes, insertions and cut-off value in the formula can be differently optimized when different population of the sample is analyzed.).

For another example, if the sample from the subject has a mutation in NRAS, KRAS, or BRAF (e.g., one of those listed in Table 1 or 2) and the pre-treatment concentrations of MIP1a in a subject when entered into the following prediction formula:

$$(-0.0281)*(MIP1a)+(2.19)*D(BRAFKRASNRAS,WT)-(-0.41)<-0.0348$$

render this formula true (i.e. if the value is <-0.0348 (e.g., -1.0)), then the subject is predicted to have a stronger clinical outcome (e.g., progression free survival) with the therapy comprising lenvatinib or a pharmaceutically acceptable salt thereof (e.g., lenvatinib mesylate) than subjects who have wild type NRAS or KRAS or BRAF and whose pre-treatment concentrations of MIP1a do not satisfy the formula (slopes, insertions and cut-off value in the formula can be differently optimized when different population of the sample is analyzed.).

For another example, if the sample from the subject has a mutation in NRAS, KRAS, or BRAF (e.g., one of those listed in Table 1 or 2) and the pre-treatment concentrations of IL6, VEGFA, MIP1a, and MIP1b in a subject when entered into the following prediction formula:

$$(0.126)*(IL6)+(-0.193)*(MIP1a)+(-0.0775)*(MIP1b)+(-0.0514)*(VEGFA100)+(7.94)*D(BRAFKRASNRAS,WT)-(-14.4)<4.69$$

render this formula true (i.e. if the value is <4.69 (e.g., 3.0)), then the subject is predicted to have a stronger clinical outcome (e.g., progression free survival) with the therapy comprising lenvatinib or a pharmaceutically acceptable salt thereof (e.g., lenvatinib mesylate) than subjects who have wild type NRAS or KRAS or BRAF and whose pre-treatment concentrations of IL6, VEGFA, MIP1a, and MIP1b do not satisfy the formula (slopes, insertions and cut-off value in the formula can be differently optimized when different population of the sample is analyzed.).

Biological Samples

Suitable biological samples for the methods described herein include any biological fluid, cell, tissue, or fraction thereof, which includes analyte biomolecules of interest such as nucleic acid (e.g., DNA or mRNA) or protein. A biological sample can be, for example, a specimen obtained from a subject (e.g., a mammal such as a human) or can be derived from such a subject. For example, a sample can be a tissue section obtained by biopsy, or cells that are placed in or adapted to tissue culture. A biological sample can also be a biological fluid such as urine, blood, plasma, serum, saliva, semen, sputum, cerebral spinal fluid, tears, or mucus, or such a sample absorbed onto a substrate (e.g., glass, polymer, paper). A biological sample can also include a thyroid tissue sample, a renal tissue sample, a tumor sample, circulating tumor cells, and circulating DNA. In specific embodiments, the biological sample is a tumor cell(s) or a cell(s) obtained from a region of the subject suspected of containing a tumor or a pre-cancerous lesion. For example, the biological sample may be a thyroid tumor sample or a renal tumor sample. A biological sample can be further fractionated, if desired, to a fraction containing particular cell types. For example, a blood sample can be fractionated into serum or into fractions containing particular types of blood cells such as red blood cells or white blood cells (leukocytes). If desired, a sample can be a combination of samples from a subject such as a combination of a tissue and fluid sample.

The biological samples can be obtained from a subject, e.g., a subject having, suspected of having, or at risk of developing, a cancer. In certain embodiments, the subject has a thyroid cancer. In some embodiments, the subject has a differentiated thyroid cancer (e.g., papillary thyroid cancer, follicular thyroid cancer). In other embodiments, the subject has a medullary thyroid cancer. In certain embodiments, the subject has a kidney cancer. In some embodiments, the subject has a renal cell carcinoma. Any suitable methods for obtaining the biological samples can be employed, although exemplary methods include, e.g., phlebotomy, swab (e.g., buccal swab), or fine needle aspirate biopsy procedure. Non-limiting examples of tissues susceptible to fine needle aspiration include lymph node, lung, thyroid, breast, skin, and liver. Samples can also be collected, e.g., by microdissection (e.g., laser capture microdissection (LCM) or laser microdissection (LMD)).

Methods for obtaining and/or storing samples that preserve the activity or integrity of molecules (e.g., nucleic acids or proteins) in the sample are well known to those skilled in the art. For example, a biological sample can be further contacted with one or more additional agents such as appropriate buffers and/or inhibitors, including nuclease, protease and phosphatase inhibitors, which preserve or minimize changes in the molecules (e.g., nucleic acids or proteins) in the sample. Such inhibitors include, for example, chelators such as ethylenediamine tetraacetic acid (EDTA), ethylene glycol bis(P-aminoethyl ether) N,N,N1,N1-tetraacetic acid (EGTA), protease inhibitors such as phenylmethylsulfonyl fluoride (PMSF), aprotinin, leupeptin, antipain and the like, and phosphatase inhibitors such as phosphate, sodium fluoride, vanadate and the like. Appropriate buffers and conditions for isolating molecules are well known to those skilled in the art and can be varied depending, for example, on the type of molecule in the sample to be characterized (see, for example, Ausubel et al. Current Protocols in Molecular Biology (Supplement 47), John Wiley & Sons, New York (1999); Harlow and Lane, Anti-bodies: A Laboratory Manual (Cold Spring Harbor Laboratory Press (1988); Harlow and Lane, Using Antibodies: A Laboratory Manual, Cold Spring Harbor Press (1999); Tietz Textbook of Clinical Chemistry, 3rd ed. Burtis and Ashwood, eds. W.B. Saunders, Philadelphia, (1999)). A sample also can be processed to eliminate or minimize the presence of interfering substances. For example, a biological sample can be fractionated or purified to remove one or more materials that are not of interest. Methods of fractionating or purifying a biological sample include, but are not limited to, chromatographic methods such as liquid chromatography, ion-exchange chromatography, size-exclusion chromatography, or affinity chromatography. For use in the methods described herein, a sample can be in a variety of physical states. For example, a sample can be a liquid or solid, can be dissolved or suspended in a liquid, can be in an emulsion or gel, or can be absorbed onto a material.

Assessing Expression of Biomarkers

Gene expression can be detected as, e.g., protein or mRNA expression of a target gene. That is, the presence or expression level (amount) of a gene can be determined by detecting and/or measuring the level of mRNA or protein expression of the gene. In some embodiments, gene expression can be detected as the activity of a protein encoded by a gene such as a gene depicted in Table 3.

A variety of suitable methods can be employed to detect and/or measure the level of mRNA expression of a gene. For example, mRNA expression can be determined using Northern blot or dot blot analysis, reverse transcriptase-PCR (RT-PCR; e.g., quantitative RT-PCR), in situ hybridization (e.g., quantitative in situ hybridization) or nucleic acid array (e.g., oligonucleotide arrays or gene chips) analysis. Details of such methods are described below and in, e.g., Sambrook et al., Molecular Cloning: A Laboratory Manual Second Edition vol. 1, 2 and 3. Cold Spring Harbor Laboratory Press: Cold Spring Harbor, N.Y., USA, November 1989; Gibson et al. (1999) *Genome Res.*, 6(10):995-1001; and Zhang et al. (2005) *Environ. Sci. Technol.*, 39(8):2777-2785; U.S. Publication No. 2004086915; European Patent No. 0543942; and U.S. Pat. No. 7,101,663; the disclosures of each of which are incorporated herein by reference in their entirety.

In one example, the presence or amount of one or more discrete mRNA populations in a biological sample can be determined by isolating total mRNA from the biological sample (see, e.g., Sambrook et al. (supra) and U.S. Pat. No. 6,812,341) and subjecting the isolated mRNA to agarose gel electrophoresis to separate the mRNA by size. The size-separated mRNAs are then transferred (e.g., by diffusion) to a solid support such as a nitrocellulose membrane. The presence or amount of one or more mRNA populations in the biological sample can then be determined using one or more detectably-labeled-polynucleotide probes, complementary to the mRNA sequence of interest, which bind to and thus render detectable their corresponding mRNA populations. Detectable-labels include, e.g., fluorescent (e.g., umbelliferone, fluorescein, fluorescein isothiocyanate, rhodamine, dichlorotriazinylamine fluorescein, dansyl chloride, allophycocyanin (APC), or phycoerythrin), luminescent (e.g., europium, terbium, Qdot™ nanoparticles supplied by the Quantum Dot Corporation, Palo Alto, Calif.), radiological (e.g., 125I, 131I, 35S, 32P, 33P, or 3H), and enzymatic (horseradish peroxidase, alkaline phosphatase, beta-galactosidase, or acetylcholinesterase) labels.

In another example, the presence or amount of discrete populations of mRNA (e.g., mRNA encoded by one or more genes depicted in Table 3) in a biological sample can be determined using nucleic acid (or oligonucleotide) arrays (e.g., an array described below under "Arrays and Kits"). For example, isolated mRNA from a biological sample can be amplified using RT-PCR with, e.g., random hexamer or oligo(dT)-primer mediated first strand synthesis. The amplicons can be fragmented into shorter segments. The RT-PCR step can be used to detectably-label the amplicons, or, optionally, the amplicons can be detectably-labeled subsequent to the RT-PCR step. For example, the detectable-label can be enzymatically (e.g., by nick-translation or kinase such as T4 polynucleotide kinase) or chemically conjugated to the amplicons using any of a variety of suitable techniques (see, e.g., Sambrook et al., supra). The detectably-labeled-amplicons are then contacted with a plurality of polynucleotide probe sets, each set containing one or more of a polynucleotide (e.g., an oligonucleotide) probe specific for (and capable of binding to) a corresponding amplicon, and where the plurality contains many probe sets each corresponding to a different amplicon. Generally, the probe sets are bound to a solid support and the position of each probe set is predetermined on the solid support. The binding of a detectably-labeled amplicon to a corresponding probe of a probe set indicates the presence or amount of a target mRNA in the biological sample. Additional methods for detecting mRNA expression using nucleic acid arrays are described in, e.g., U.S. Pat. Nos. 5,445,934; 6,027,880; 6,057,100; 6,156,501; 6,261,776; and 6,576,424; the disclosures of each of which are incorporated herein by reference in their entirety.

Methods of detecting and/or for quantifying a detectable label depend on the nature of the label. The products of reactions catalyzed by appropriate enzymes (where the detectable label is an enzyme; see above) can be, without limitation, fluorescent, luminescent, or radioactive or they may absorb visible or ultraviolet light. Examples of detectors suitable for detecting such detectable labels include, without limitation, x-ray film, radioactivity counters, scintillation counters, spectrophotometers, colorimeters, fluorometers, luminometers, and densitometers.

The expression of a gene can also be determined by detecting and/or measuring expression of a protein encoded by the gene. Methods of determining protein expression are well known in the art. A generally used method involves the use of antibodies specific for the target protein of interest. For example, methods of determining protein expression include, but are not limited to, western blot or dot blot analysis, immunohistochemistry (e.g., quantitative immunohistochemistry), immunocytochemistry, enzyme-linked immunosorbent assay (ELISA), enzyme-linked immunosorbent spot (ELISPOT; Coligan, J. E., et al., eds. (1995) Current Protocols in Immunology. Wiley, New York), or antibody array analysis (see, e.g., U.S. Publication Nos. 20030013208 and 2004171068, the disclosures of each of which are incorporated herein by reference in their entirety). Further description of many of the methods above and additional methods for detecting protein expression can be found in, e.g., Sambrook et al. (supra).

In one example, the presence or amount of protein expression of a gene (e.g., a gene depicted in Table 3) can be determined using a western blotting technique. For example, a lysate can be prepared from a biological sample, or the biological sample itself, can be contacted with Laemmli buffer and subjected to sodium-dodecyl sulfate polyacrylamide gel electrophoresis (SDS-PAGE). SDS-PAGE-resolved proteins, separated by size, can then be transferred to a filter membrane (e.g., nitrocellulose) and subjected to immunoblotting techniques using a detectably-labeled antibody specific to the protein of interest. The presence or amount of bound detectably-labeled antibody indicates the presence or amount of protein in the biological sample.

In another example, an immunoassay can be used for detecting and/or measuring the protein expression of a gene (e.g., a gene depicted in Table 3). As above, for the purposes of detection, an immunoassay can be performed with an antibody that bears a detection moiety (e.g., a fluorescent agent or enzyme). Proteins from a biological sample can be conjugated directly to a solid-phase matrix (e.g., a multi-well assay plate, nitrocellulose, agarose, sepharose, encoded particles, or magnetic beads) or it can be conjugated to a first member of a specific binding pair (e.g., biotin or streptavidin) that attaches to a solid-phase matrix upon binding to a second member of the specific binding pair (e.g., streptavidin or biotin). Such attachment to a solid-phase matrix allows the proteins to be purified away from other interfering or irrelevant components of the biological sample prior to contact with the detection antibody and also allows for subsequent washing of unbound antibody. Here as above, the presence or amount of bound detectably-labeled antibody indicates the presence or amount of protein in the biological sample.

There is no particular restriction as to the form of the antibody and the present disclosure includes polyclonal antibodies, as well as monoclonal antibodies. The antiserum obtained by immunizing animals, such as rabbits with a protein of the invention, as well polyclonal and monoclonal antibodies of all classes, human antibodies, and humanized antibodies produced by genetic recombination, are also included.

An intact protein or its partial peptide may be used as the antigen for immunization. As partial peptides of the proteins, for example, the amino (N)-terminal fragment of the protein and the carboxy (C)-terminal fragment can be given.

A gene encoding a protein of interest or a fragment thereof is inserted into a known expression vector, and, by transforming the host cells with the vector described herein, the desired protein or a fragment thereof is recovered from outside or inside the host cells using standard methods. This protein can be used as the sensitizing antigen. Also, cells expressing the protein, cell lysates, or a chemically synthesized protein of the invention may be also used as a sensitizing antigen.

The mammal that is immunized by the sensitizing antigen is not restricted; however, it is preferable to select animals by considering the compatibility with the parent cells used in cell fusion. Generally, animals belonging to the orders rodentia, lagomorpha, or primates are used. Examples of animals belonging to the order of rodentia that may be used include, for example, mice, rats, and hamsters. Examples of animals belonging to the order of lagomorpha that may be used include, for example, rabbits. Examples of animals belonging to the order of primates that may be used include, for example, monkeys. Examples of monkeys to be used include the infraorder catarrhini (old world monkeys), for example, *Macaca fascicularis*, rhesus monkeys, sacred baboons, and chimpanzees.

Well-known methods may be used to immunize animals with the sensitizing antigen. For example, the sensitizing antigen is injected intraperitoneally or subcutaneously into mammals. Specifically, the sensitizing antigen is suitably diluted and suspended in physiological saline, phosphate-buffered saline (PBS), and so on, and mixed with a suitable amount of general adjuvant if desired, for example, with Freund's complete adjuvant. Then, the solution is emulsified and injected into the mammal. Thereafter, the sensitizing antigen suitably mixed with Freund's incomplete adjuvant is preferably given several times every 4 to 21 days. A suitable carrier can also be used when immunizing and animal with the sensitizing antigen. After the immunization, the elevation in the level of serum antibody is detected by usual methods.

Polyclonal antibodies against the proteins of the present disclosure can be prepared as follows. After verifying that the desired serum antibody level has been reached, blood is withdrawn from the mammal sensitized with antigen. Serum is isolated from this blood using conventional methods. The serum containing the polyclonal antibody may be used as the polyclonal antibody, or according to needs, the polyclonal antibody-containing fraction may be further isolated from the serum. For example, a fraction of antibodies that specifically recognize the protein of the invention may be prepared by using an affinity column to which the protein is coupled. Then, the fraction may be further purified by using a Protein A or Protein G column in order to prepare immunoglobulin G or M.

To obtain monoclonal antibodies, after verifying that the desired serum antibody level has been reached in the mammal sensitized with the above-described antigen, immunocytes are taken from the mammal and used for cell fusion. For this purpose, splenocytes can be mentioned as preferable immunocytes. As parent cells fused with the above immunocytes, mammalian myeloma cells are preferably used. More preferably, myeloma cells that have acquired the feature, which can be used to distinguish fusion cells by agents, are used as the parent cell.

The cell fusion between the above immunocytes and myeloma cells can be conducted according to known methods, for example, the method by Milstein et al. (Galfre et al., *Methods Enzymol.* 73:3-46, 1981).

The hybridoma obtained from cell fusion is selected by culturing the cells in a standard selection medium, for example, HAT culture medium (medium containing hypoxanthine, aminopterin, and thymidine). The culture in this HAT medium is continued for a period sufficient enough for cells (non-fusion cells) other than the objective hybridoma to perish, usually from a few days to a few weeks. Then, the usual limiting dilution method is carried out, and the hybridoma producing the objective antibody is screened and cloned.

Other than the above method for obtaining hybridomas, by immunizing an animal other than humans with the antigen, a hybridoma producing the objective human antibodies having the activity to bind to proteins can be obtained by the method of sensitizing human lymphocytes, for example, human lymphocytes infected with the EB virus, with proteins, protein-expressing cells, or lysates thereof in vitro and fusing the sensitized lymphocytes with myeloma cells derived from human, for example, U266, having a permanent cell division ability.

The monoclonal antibodies obtained by transplanting the obtained hybridomas into the abdominal cavity of a mouse and extracting ascites can be purified by, for example, ammonium sulfate precipitation, protein A or protein G column, DEAE ion exchange chromatography, an affinity column to which the protein of the present disclosure is coupled, and so on.

Monoclonal antibodies can be also obtained as recombinant antibodies produced by using the genetic engineering technique (see, for example, Borrebaeck C. A. K. and Larrick, J. W., THERAPEUTIC MONOCLONAL ANTIBODIES, Published in the United Kingdom by MACMILLAN PUBLISHERS LTD (1990)). Recombinant antibodies are produced by cloning the encoding DNA from immunocytes, such as hybridoma or antibody-producing sensitized lymphocytes, incorporating into a suitable vector, and introducing this vector into a host to produce the antibody. The present disclosure encompasses such recombinant antibodies as well.

Antibodies or antibody fragments specific for a protein encoded by one or more biomarkers can also be generated by in vitro methods such as phage display.

Moreover, the antibody of the present disclosure may be an antibody fragment or modified-antibody, so long as it binds to a protein encoded by a biomarker of the invention. For instance, Fab, F (ab') 2, Fv, or single chain Fv (scFv) in which the H chain Fv and the L chain Fv are suitably linked by a linker (Huston et al., *Proc. Natl. Acad. Sci. USA*, 85:5879-5883, (1988)) can be given as antibody fragments. Specifically, antibody fragments are generated by treating antibodies with enzymes, for example, papain or pepsin. Alternatively, they may be generated by constructing a gene encoding an antibody fragment, introducing this into an expression vector, and expressing this vector in suitable host cells (see, for example, Co et al., *J. Immunol.*, 152:2968-2976, 1994; Better et al., *Methods Enzymol.*, 178:476-496, 1989; Pluckthun et al., *Methods Enzymol.*, 178:497-515, 1989; Lamoyi, *Methods Enzymol.*, 121:652-663, 1986; Rousseaux et al., *Methods Enzymol.*, 121:663-669, 1986; Bird et al., *Trends Biotechnol.*, 9:132-137, 1991).

The antibodies may be conjugated to various molecules, such as polyethylene glycol (PEG), fluorescent substances, radioactive substances, and luminescent substances. Methods to attach such moieties to an antibody are already established and conventional in the field (see, e.g., U.S. Pat. Nos. 5,057,313 and 5,156,840).

Examples of methods that assay the antigen-binding activity of the antibodies include, for example, measurement of absorbance, enzyme-linked immunosorbent assay (ELISA), enzyme immunoassay (EIA), radioimmunoassay (RIA), and/or immunofluorescence. For example, when using ELISA, a protein encoded by a biomarker of the invention is added to a plate coated with the antibodies of the present disclosure, and then, the antibody sample, for example, culture supernatants of antibody-producing cells, or purified antibodies are added. Then, secondary antibody recognizing the primary antibody, which is labeled by alkaline phosphatase and such enzymes, is added, the plate is incubated and washed, and the absorbance is measured to evaluate the antigen-binding activity after adding an enzyme substrate such as p-nitrophenyl phosphate. As the protein, a protein fragment, for example, a fragment comprising a C-terminus, or a fragment comprising an N-terminus may be used. To evaluate the activity of the antibody of the invention, BIAcore (Pharmacia) may be used.

By using these methods, the antibody of the invention and a sample presumed to contain a protein of the invention are contacted, and the protein encoded by a biomarker of the invention is detected or assayed by detecting or assaying the immune complex formed between the above-mentioned antibody and the protein.

Mass spectrometry based quantitation assay methods, for example, but not limited to, multiple reaction monitoring (MRM)-based approaches in combination with stable-isotope labeled internal standards, are an alternative to immunoassays for quantitative measurement of proteins. These approaches do not require the use of antibodies and so the analysis can be performed in a cost- and time-efficient manner (see, for example, Addona et al., *Nat. Biotechnol.*, 27:633-641, 2009; Kuzyk et al., *Mol. Cell Proteomics*, 8:1860-1877, 2009; Paulovich et al., *Proteomics Clin. Appl.*, 2:1386-1402, 2008). In addition, MRM offers superior multiplexing capabilities, allowing for the simultaneous quantification of numerous proteins in parallel. The basic theory of these methods has been well-established and widely utilized for drug metabolism and pharmacokinetics analysis of small molecules.

Methods for detecting or measuring gene expression (e.g., mRNA or protein expression) can optionally be performed in formats that allow for rapid preparation, processing, and analysis of multiple samples. This can be, for example, in multi-welled assay plates (e.g., 96 wells or 386 wells) or arrays (e.g., nucleic acid chips or protein chips). Stock solutions for various reagents can be provided manually or robotically, and subsequent sample preparation (e.g., RT-PCR, labeling, or cell fixation), pipetting, diluting, mixing, distribution, washing, incubating (e.g., hybridization), sample readout, data collection (optical data) and/or analysis (computer aided image analysis) can be done robotically using commercially available analysis software, robotics, and detection instrumentation capable of detecting the signal generated from the assay. Examples of such detectors include, but are not limited to, spectrophotometers, luminometers, fluorimeters, and devices that measure radioisotope decay. Exemplary high-throughput cell-based assays (e.g., detecting the presence or level of a target protein in a cell) can utilize ArrayScan® VTI HCS Reader or KineticScan® HCS Reader technology (Cellomics Inc., Pittsburg, Pa.).

In some embodiments, the expression level of two genes, three genes, four genes, five genes, six genes, seven genes, eight genes, nine genes, 10 genes, 11 genes, 12 genes, 13 genes, 14 genes, 15 genes, 16 genes, 17 genes, 18 genes, 19 genes, 20 genes, 21 genes, 22 genes, 23 genes, at least 24 genes, at least 25 genes or more, or at least two genes, at least three genes, at least four genes, at least five genes, at least six genes, at least seven genes, at least eight genes, at least nine genes, at least 10 genes, at least 11 genes, at least 12 genes, at least 13 genes, at least 14 genes, at least 15 genes, at least 16 genes, at least 17 genes, at least 18 genes, at least 19 genes, at least 20 genes, at least 21 genes, at least 22 genes, at least 23 genes, at least 24 genes, or at least 25 genes or more can be assessed and/or measured.

To aid in detecting the presence or level of expression of one or more of the genes depicted in Table 3, any part of the nucleic acid sequence of the genes can be used, e.g., as hybridization polynucleotide probes or primers (e.g., for amplification or reverse transcription). The probes and primers can be oligonucleotides of sufficient length to provide specific hybridization to an RNA, DNA, cDNA, or fragments thereof derived from a biological sample. Depending on the specific application, varying hybridization conditions can be employed to achieve varying degrees of selectivity of a probe or primer towards target sequence. The primers and probes can be detectably-labeled with reagents that facilitate detection (e.g., fluorescent labels, chemical labels (see, e.g., U.S. Pat. Nos. 4,582,789 and 4,563,417), or modified bases).

Standard stringency conditions are described by Sambrook, et al. (supra) and Haymes, et al. Nucleic Acid Hybridization, A Practical Approach, IRL Press, Washington, D.C. (1985). In order for a nucleic acid molecule to serve as a primer or probe it need only be sufficiently complementary in sequence to be able to form a stable double-stranded structure under the particular hybridization conditions (e.g., solvent and salt concentrations) employed.

Hybridization can be used to assess homology between two nucleic acid sequences. A nucleic acid sequence described herein, or a fragment thereof, can be used as a hybridization probe according to standard hybridization techniques. The hybridization of a probe of interest (e.g., a probe containing a portion of a nucleotide sequence described herein or its complement) to DNA, RNA, cDNA, or fragments thereof from a test source is an indication of the presence of DNA or RNA corresponding to the probe in the test source. Hybridization conditions are known to those skilled in the art and can be found in Current Protocols in Molecular Biology, John Wiley & Sons, N.Y., 6.3.1-6.3.6, 1991. Moderate hybridization conditions are defined as hybridization in 2× sodium chloride/sodium citrate (SSC) at 30° C., followed by a wash in 1×SSC, 0.1% SDS at 50° C. Highly stringent conditions are defined as hybridization in 6×SSC at 45° C., followed by a wash in 0.2×SSC, 0.1% SDS at 65° C.

Primers can be used in in a variety of PCR-type methods. For example, polymerase chain reaction (PCR) techniques can be used to amplify specific sequences from DNA as well as RNA, including sequences from total genomic DNA or total cellular RNA. The PCR primers are designed to flank the region that one is interested in amplifying. Primers can be located near the 5' end, the 3' end or anywhere within the nucleotide sequence that is to be amplified. The amplicon length is dictated by the experimental goals. For qPCR, the target length is closer to 100 bp and for standard PCR, it is near 500 bp. Generally, sequence information from the ends of the region of interest or beyond is employed to design oligonucleotide primers that are identical or similar in sequence to opposite strands of the template to be amplified. PCR primers can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair.

In addition, the nucleic acid sequences or fragments thereof (e.g., oligonucleotide probes) can be used in nucleic acid arrays (such as the nucleic acid arrays described below under "Arrays") for detection and/or quantitation of gene expression.

Cut-Off Values

As noted above, the methods described herein can involve, assessing the expression level (e.g., mRNA or protein expression level) of one or more genes (e.g., one or more genes depicted in Table 3), wherein the expression level of one or more of the genes predicts the response of a subject to treatment comprising a lenvatinib or a pharmaceutically acceptable salt thereof (e.g., lenvatinib mesylate). "Assessing" can include, e.g., comparing the expression of one or more genes in a test biological sample with a known or a control expression level (e.g., in a reference biological sample) of the particular gene(s) of interest. For example, the expression level of one or more genes in a test biological sample can be compared to the corresponding expression levels in a subject who has responded or failed to respond to lenvatinib or a pharmaceutically acceptable salt thereof (e.g., lenvatinib mesylate), or an average or median expression level of multiple (e.g., two, three, four, five, six, seven, eight, nine, 10, 15, 20, 25, 30, 35, or 40 or more) subjects, of the same species, who have responded or have failed to respond to lenvatinib or a pharmaceutically acceptable salt thereof (e.g., lenvatinib mesylate). Assessing can also include determining if the expression level of one or more genes (e.g., one or more genes as depicted in Table 3) falls within a range of values predetermined as predictive of responsiveness of a subject to a therapy comprising lenvatinib or a pharmaceutically acceptable salt thereof (e.g., lenvatinib mesylate). In some embodiments, assessing can be, or include, determining if the expression of one or more genes (e.g., one or more of the genes depicted in Table 3) falls above or below a predetermined cut-off value. A cut-off value is typically an expression level of a gene, or ratio of the expression level of a gene with the expression level of another gene, above or below which is considered predictive of responsiveness of a subject to a therapy comprising lenvatinib or a pharmaceutically acceptable salt thereof (e.g., lenvatinib mesylate). Thus, in accordance with the methods (and compositions) described herein, a reference expression level of a gene (e.g., a gene depicted in Table 3) is identified as a cut-off value, above or below of which is predictive of responsiveness to a therapy comprising lenvatinib or a pharmaceutically acceptable salt thereof (e.g., lenvatinib mesylate). Some cut-off values are not absolute in that clinical correlations can still remain significant over a range of values on either side of the cutoff, however, it is possible to select an optimal cut-off value (e.g. varying H-scores) of expression levels of genes for a particular sample types. Cut-off values determined for use in the methods described herein can be compared with, e.g., published ranges of expression levels but can be individualized to the methodology used and patient population. It is understood that improvements in optimal cut-off values could be determined depending on the sophistication of statistical methods used and on the number and source of samples used to determine reference level values for the different genes and sample types. Therefore, established cut-off values can be adjusted up or down, on the basis of periodic re-evaluations or changes in methodology or population distribution.

The reference expression level of one or more genes can be determined by a variety of methods. The reference level can be determined by comparison of the expression level of a gene of interest in, e.g., populations of subjects (e.g., patients) that are responsive to a therapy comprising lenvatinib or a pharmaceutically acceptable salt thereof (e.g., lenvatinib mesylate) or not responsive to a therapy comprising lenvatinib or a pharmaceutically acceptable salt thereof. This can be accomplished, for example, by histogram analysis, in which an entire cohort of patients are graphically presented, wherein a first axis represents the expression level of a gene and a second axis represents the number of subjects in the cohort whose sample contain one or more expression levels at a given amount. Determination of the reference expression level of a gene can then be made based on an amount which best distinguishes these separate groups. The reference level can be a single number, equally applicable to every subject, or the reference level can vary, according to specific subpopulations of subjects. For example, older subjects can have a different reference level than younger subjects for the same metabolic disorder. In addition, a subject with more advanced disease (e.g., a more advanced form of a disease treatable by lenvatinib or a pharmaceutically acceptable salt thereof (e.g., lenvatinib mesylate)) can have a different reference value than one with a milder form of the disease.

Creating A Response Profile

The methods described herein can also be used to generate a lenvatinib (e.g., lenvatinib mesylate) therapy response profile for a subject. The profile can include information that indicates whether one or more of the mutations such as those listed in Tables 1 and 2 are present in a sample from the subject; and/or information that indicates the expression level of one or more genes (e.g., one or more genes depicted in Table 3); and/or the expression ratio of thyroglobulin in a sample (e.g., plasma, serum) of the subject post/pre-treatment with lenvatinib or a pharmaceutically acceptable salt thereof; and/or the histological analysis of any tumors (e.g., whether a thyroid cancer is a FTC or PTC). A lenvatinib therapy response profile can include the expression level of one or more additional genes and/or other proteomic markers, serum markers, or clinical markers. The response profiles described herein can contain information on the expression or expression level of at least two, at least three, at least four, at least five, at least six, at least seven, at least eight, at least nine, at least 10, at least 11, at least 12, at least 13, at least 14, at least 15, at least 16, at least 17, at least 18, at least 19, at least 20, at least 21, at least 22, at least 23, at least 24, or at least 25 genes listed in Table 3. The response profiles described herein can also contain information on the presence of mutations (if any) and the nature of the mutation(s) in any one or more of the following genes: NRAS, KRAS, VHL, BRAF, ERBB2, PTEN and MET. The resultant information (lenvatinib therapy response profile) can be used for predicting the response of a subject (e.g., a human patient) to a treatment comprising lenvatinib or a pharmaceutically acceptable salt thereof (e.g., lenvatinib mesylate). In addition, the response profiles can be used in predicting the response of a subject to a variety of therapies and/or a variety of disease states since, e.g., the expression levels of one or more of the genes (e.g., one or more of the genes depicted in Table 3), the mutations, the thyroglobulin levels, and/or the histological data examined can be indicative of such responses or disorders, whether or not physiologic or behavioral symptoms of the disorder have become apparent.

It is understood that a lenvatinib (e.g., lenvatinib mesylate) response profile can be in electronic form (e.g., an electronic patient record stored on a computer or other electronic (computer-readable) media such as a DVD, CD, or floppy disk) or written form. The lenvatinib (e.g., lenvatinib mesylate) response profile can also include information for several (e.g., two, three, four, five, 10, 20, 30, 50, or 100 or more) subjects (e.g., human patients). Such multi-subject response profiles can be used, e.g., in analyses (e.g., statistical analyses) of particular characteristics of subject cohorts.

Responsiveness of a subject to a therapy comprising lenvatinib or a pharmaceutically acceptable salt thereof (e.g., lenvatinib mesylate) can be classified in several ways and classification is dependent on the subject's disease (e.g., thyroid cancer, a kidney cancer, or any other of the diseases treatable by therapy comprising lenvatinib or a pharmaceutically acceptable salt thereof (e.g., lenvatinib mesylate)), the severity of the disease, and the particular medicament the subject is administered. In the simplest sense, responsiveness is any decrease in the disease state as compared to pre-treatment, and non-responsiveness is the lack of any change in the disease state as compared to pre-treatment. Responsiveness of a subject (e.g., a human) with a cancer can be classified based on one or more of a number of objective clinical indicia such as, but not limited to, tumor size, Clinical Benefit (CB), Overall Survival (OS), Progression Free Survival (PFS), Disease Control Rate (DCR), Time-To-Response (TTR), Tumor Shrinkage (TS), or Tumor Response (TR).

"Clinical benefit" refers to having one of the following statuses—Complete Response (CR), Partial Response (PR); or Stable Disease (SD) with 6 months or more progression free survival (PFS). "Complete Response" means complete disappearance of all target lesions. "Partial Response" means at least 30% decrease in the sum of the longest diameter (LD) of target lesions, taking as reference the baseline summed LD. "Progressive Disease" (PD) means at least 20% increase in the sum of the LD of target lesions, taking as reference the smallest summed LD recorded since the treatment started, or the appearance of one or more new lesions. "Stable Disease" means neither sufficient shrinkage of the target lesions to qualify for PR nor sufficient increase to qualify for progressive disease (PD), taking as reference the smallest summed LD since the treatment started.

"Overall Survival" (OS) is defined as the time from randomization until death from any cause. "Randomization" means randomization of a patient into a test group or a control group when therapy plan for a patient is determined.

"Progression Free Survival" (PFS) refers to the period from start date of treatment to the last date before entering PD status.

"Disease Control Rate" (DCR) is defined as CR or PR or SD for 7 weeks.

"Time-To-Response" (TTR) is defined as the time from the date of initiation of treatment to the date when criteria for response (CR or PR) are first met.

"Tumor shrinkage" (TS) means percent change of sum of diameters of target lesions, taking as reference the baseline sum diameters.

"Tumor response" (TR) compares subjects with "Partial Response" (PR) with subjects with either Stable Disease (SD) or Progressive Disease (PD).

Methods of Treatment

The methods disclosed herein enable the assessment of a subject for responsiveness to lenvatinib or a pharmaceutically acceptable salt thereof (e.g., lenvatinib mesylate). A subject who is likely to respond to lenvatinib or a pharmaceutically acceptable salt thereof (e.g., lenvatinib mesylate) can be administered lenvatinib or a pharmaceutically acceptable salt thereof (e.g., lenvatinib mesylate).

The methods of this disclosure also enable the classification of subjects into groups of subjects that are more likely to benefit, and groups of subjects that are less likely to benefit, from treatment with lenvatinib or a pharmaceutically acceptable salt thereof (e.g., lenvatinib mesylate). The ability to select such subjects from a pool of subjects who are being considered for treatment with lenvatinib or a pharmaceutically acceptable salt thereof (e.g., lenvatinib mesylate) is beneficial for effective treatment.

The methods of this disclosure can also be used to determine whether to continue treatment with lenvatinib or a pharmaceutically acceptable salt thereof (e.g., lenvatinib mesylate) after administering this therapy for a short period of time and determining based on the expression profile of one or more of the biomarkers described above post-treatment or post-treatment versus pre-treatment whether this therapy is more likely or less likely to benefit the patient.

Lenvatinib or a pharmaceutically acceptable salt thereof (e.g., lenvatinib mesylate) shows potent anti-tumor effects in xenograft models of various tumors by inhibiting angiogenesis. The subjects who are considered for treatment with lenvatinib or a pharmaceutically acceptable salt thereof (e.g., lenvatinib mesylate) include, but are not limited to, subjects having, suspected of having, or likely to develop a thyroid cancer or a kidney cancer (e.g., renal cell carcinoma).

In one embodiment, the subject to be treated with lenvatinib or a pharmaceutically acceptable salt thereof (e.g., lenvatinib mesylate) has, is suspected of having, or is likely to develop a thyroid cancer. Thyroid cancer is a cancerous tumor or growth located within the thyroid gland. It is the most common endocrine cancer and is one of the few cancers that has increased in incidence rates over recent years. It occurs in all age groups from children through seniors. The American Cancer Society estimates that there were about 44,670 new cases of thyroid cancer in the U.S. in 2010. Of these new cases, about 33,930 were in women and about 10,740 in men. About 1,690 people (960 women and 730 men) died of thyroid cancer in 2010. Many patients, especially in the early stages of thyroid cancer, do not experience symptoms. However, as the cancer develops, symptoms can include a lump or nodule in the front of the neck, hoarseness or difficulty speaking, swollen lymph nodes, difficulty swallowing or breathing, and pain in the throat or neck. There are several types of thyroid cancer: papillary, follicular, medullary, anaplastic, and variants. Papillary carcinoma is the most common type accounting for approximately 85% of all thyroid cancers, and usually affects women of childbearing age. It spreads slowly and is the least dangerous type of thyroid cancer. Follicular carcinoma accounts for about 10% of all cases and is more likely to come back and spread. Medullary carcinoma is a cancer of nonthyroid cells that are normally present in the thyroid gland. This form of the thyroid cancer tends to occur in families. It requires different treatment than other types of thyroid cancer. Anaplastic carcinoma (also called giant and spindle cell cancer) is the most dangerous form of thyroid cancer. It is rare, and does not respond to radioiodine therapy. Anaplastic carcinoma spreads quickly and invades nearby structures such as the windpipe (trachea), causing breathing difficulties. Variants include tall cell, insular, columnar, and Hurthle cell. Lenvatinib or a pharmaceutically acceptable salt thereof (e.g., lenvatinib mesylate) can be used to treat a subject having, suspected of having, or likely to develop any of the above-described thyroid cancers. In certain embodiments, the subject to be treated with lenvatinib or a pharmaceutically acceptable salt thereof (e.g., lenvatinib mesylate) has, is suspected of having, or is likely to develop a differentiated thyroid cancer. In other embodiments, the subject to be treated with lenvatinib or a pharmaceutically acceptable salt thereof (e.g., lenvatinib mesylate) has, is suspected of having, or is likely to develop a medullary thyroid cancer. In one embodiment, the subject to be treated with lenvatinib or a pharmaceutically acceptable salt thereof (e.g., lenvatinib mesylate) has, is suspected of having, or is likely to develop a papillary thyroid cancer. In another embodiment, the subject to be treated with lenvatinib or a pharmaceutically acceptable salt thereof (e.g., lenvatinib mesylate) has, is suspected of having, or is likely to develop a follicular thyroid cancer. In another embodiment, the subject to be treated with lenvatinib or a pharmaceutically acceptable salt thereof (e.g., lenvatinib mesylate) has, is suspected of having, or is likely to develop a Hürthle-cell thyroid cancer.

In one embodiment, the subject to be treated with lenvatinib or a pharmaceutically acceptable salt thereof (e.g., lenvatinib mesylate) has, is suspected of having, or is likely to develop a kidney cancer. Kidney cancer is usually defined as a cancer that originates in the kidney. The two most common types of kidney cancer, reflecting their location within the kidney, are renal cell carcinoma (RCC, also known as hypernephroma) and urothelial cell carcinoma (UCC) of the renal pelvis. Other, less common types of kidney cancer include: Squamous cell carcinoma, Juxtaglomerular cell tumor (reninoma), Angiomyolipoma, Renal oncocytoma, Bellini duct carcinoma, Clear-cell sarcoma of the kidney, Mesoblastic nephroma, Wilms' tumor, and mixed epithelial stromal tumor. RCC is a kidney cancer that originates in the lining of the proximal convoluted tubule, the very small tubes in the kidney that filter the blood and remove waste products. RCC is the most common type of kidney cancer in adults, responsible for approximately 80% of cases. It is also known to be the most lethal of all the genitourinary tumors. Initial treatment is most commonly a radical or partial nephrectomy and remains the mainstay of curative treatment. Where the tumor is confined to the renal parenchyma, the 5-year survival rate is 60-70%, but this is lowered considerably where metastases have spread. It is resistant to radiation therapy and chemotherapy, although some cases respond to immunotherapy. Lenvatinib or a pharmaceutically acceptable salt thereof (e.g., lenvatinib mesylate) can be used to treat a subject having, suspected of having, or likely to develop any of the above-described kidney cancers. In a specific embodiment, the subject to be treated with lenvatinib or a pharmaceutically acceptable salt thereof (e.g., lenvatinib mesylate) has, is suspected of having, or is likely to develop a renal cell carcinoma.

If the subject is more likely to respond to a therapy comprising lenvatinib or a pharmaceutically acceptable salt thereof (based on presence of mutational biomarkers and/or expression levels/ratios of the biomarkers described above), the subject can then be administered an effective amount of the lenvatinib compound (e.g., lenvatinib mesylate). An effective amount of the compound can suitably be determined by a health care practitioner taking into account, for example, the characteristics of the patient (age, sex, weight, race, etc.), the progression of the disease, and prior exposure to the drug. If the subject is less likely to respond to a therapy comprising lenvatinib or a pharmaceutically acceptable salt thereof (e.g., lenvatinib mesylate), the subject can then be optionally administered a therapy that does not comprise lenvatinib. These therapies include, but are not limited to, radioactive iodine, doxorubicin, carboplatin, cisplatin, paclitaxel, sorafenib, docetaxel, trastumab, interleukin-2, interferon, everolimus, sunitinib, pazopanib, vandetanib, and "standard of care" treatment (i.e., prevailing standard of care as determined by the health care practitioner or as specified in the clinical study) such as investigational drugs and chemotherapy.

Subjects of all ages can be affected by disorders treatable by lenvatinib or a pharmaceutically acceptable salt thereof (e.g., lenvatinib mesylate). Therefore, a biological sample used in a methods described herein can be obtained from a subject (e.g., a human) of any age, including a child, an adolescent, or an adult, such as an adult having, or suspected of having, a disease (e.g., papillary thyroid cancer, renal cell carcinoma) treatable by lenvatinib or a pharmaceutically acceptable salt thereof (e.g., lenvatinib mesylate).

The methods can also be applied to individuals at risk of developing a cancer treatable by lenvatinib or a pharmaceutically acceptable salt thereof (e.g., lenvatinib mesylate). Such individuals include those who have (i) a family history of (a genetic predisposition for) such disorders or (ii) one or more risk factors for developing such disorders.

After classifying or selecting a subject based on whether the subject will be more likely or less likely to respond to lenvatinib or a pharmaceutically acceptable salt thereof (e.g., lenvatinib mesylate), a medical practitioner (e.g., a doctor) can administer the appropriate therapeutic modality to the subject. Methods of administering lenvatinib therapies are well known in the art.

It is understood that any therapy described herein (e.g., a therapy comprising a lenvatinib or a therapy that does not comprise a lenvatinib) can include one or more additional therapeutic agents. That is, any therapy described herein can be co-administered (administered in combination) with one or more additional therapeutic agents such as, but not limited to, doxorubicin, carboplatin, cisplatin, paclitaxel, docetaxel, trastumab, interleukin-2, interferon and everolimus. Furthermore, any therapy described herein can include one or more agents for treating, for example, pain, nausea, and/or one or more side-effects of a therapy comprising lenvatinib or a pharmaceutically acceptable salt thereof (e.g., lenvatinib mesylate).

Combination therapies (e.g., co-administration of a therapy comprising lenvatinib or a pharmaceutically acceptable salt thereof (e.g., lenvatinib mesylate) and one or more additional therapeutic agents) can be, e.g., simultaneous or successive. For example, lenvatinib or a pharmaceutically acceptable salt thereof (e.g., lenvatinib mesylate) and one or more additional therapeutic agents can be administered at the same time or a lenvatinib compound (e.g., lenvatinib mesylate) can be administered first in time and the one or more additional therapeutic agents administered second in time. In some embodiments, the one or more additional therapeutic agents can be administered first in time and lenvatinib or a pharmaceutically acceptable salt thereof (e.g., lenvatinib mesylate) administered second in time.

In cases where the subject predicted to respond to a lenvatinib (e.g., lenvatinib mesylate) therapy has been previously administered one or more non-lenvatinib therapies, the therapy comprising lenvatinib or a pharmaceutically acceptable salt thereof (e.g., lenvatinib mesylate) can replace or augment a previously or currently administered therapy. For example, upon treating with the therapy comprising lenvatinib or a pharmaceutically acceptable salt thereof (e.g., lenvatinib mesylate), administration of the one non-lenvatinib therapies can cease or diminish, e.g., be administered at lower levels. Administration of the previous therapy can be maintained while the therapy comprising lenvatinib or a pharmaceutically acceptable salt thereof (e.g., lenvatinib mesylate) is administered. In some embodiments, a previous therapy can be maintained until the level of the therapy comprising lenvatinib or a pharmaceutically acceptable salt thereof (e.g., lenvatinib mesylate) reaches a level sufficient to provide a therapeutic effect.

Arrays

Nucleic acid arrays including the nucleic acid biomarkers disclosed herein are useful in, e.g., detecting gene expression and/or measuring gene expression levels. The arrays are also useful for e.g., in predicting the response of a subject to a therapy comprising lenvatinib or a pharmaceutically acceptable salt thereof (e.g., lenvatinib mesylate), for identifying subjects who can benefit from a therapy comprising lenvatinib or a pharmaceutically acceptable salt thereof (e.g., lenvatinib mesylate), and for steering subjects who would not likely benefit from a therapy comprising lenvatinib or a pharmaceutically acceptable salt thereof (e.g., lenvatinib mesylate) to other cancer therapies.

An array is an orderly arrangement of samples where matching of known and unknown DNA samples is done based on base pairing rules (e.g., Adenosine pairs with Thymine or Uracil; Guanosine pairs with Cytosine). A typical microarray experiment involves the hybridization of an mRNA, a cDNA molecule, or fragments thereof, to a DNA template from which it is originated or derived. Many DNA samples are used to construct an array. An array experiment makes use of common assay systems such as microplates or standard blotting membranes. The sample spot sizes are typically less than 200 microns in diameter and the array usually contains thousands of spots. Thousands of spotted samples known as probes (with known identity) are immobilized on a substrate (e.g., a microscope glass slides, silicon chips, nylon membrane). The spots can be DNA, cDNA, or oligonucleotides. These are used to determine complementary binding of the unknown sequences thus allowing parallel analysis for gene expression and gene discovery. An experiment with a single DNA chip can provide information on thousands of genes simultaneously. An orderly arrangement of the probes on the support is important as the location of each spot on the array is used for the identification of a gene. The amount of mRNA bound to each site on the array indicates the expression level of the various genes that are included on the array. By using an array containing many DNA samples, one can determine, in a single experiment, the expression levels of hundreds or thousands of genes by measuring the amount of mRNA bound to each site on the array. With the aid of a computer, the amount of mRNA bound to the spots on the microarray can be precisely measured, generating a profile of gene expression in the cell.

The two main DNA microarray platforms that are generally used are cDNA and oligonucleotide microarrays. cDNA microarrays are made with long double-stranded DNA molecules generated by enzymatic reactions such as PCR (Schena, M. et al., *Science*, 270:467-470 (1995)), while oligonucleotide microarrays employ oligonucleotide probes spotted by either robotic deposition or in situ synthesis on a substrate (Lockhart, D. J. et al., *Nat. Biotechnol.*, 14,1675-1680 (1996)).

Kits

This application also provides kits. In some embodiments, the kits include probes that can be used to identify or detect any of the biomarkers of Table 3. In some embodiments, the kits include primers that can be used to amplify the region containing any of the mutations listed in Table 1 and/or Table 2. In some embodiments, the kits include any of the nucleic acid arrays described herein. In certain embodiments, the kits include antibodies that can be used to detect thyroglobulin or to detect any of the biomarkers of Table 3 or their expression or expression levels. In some embodiments, the kits include probes and antibodies that can be used to identify or detect any of the biomarkers of Table 3 or their expression or expression levels. The kits can, optionally, contain instructions for detecting and/or measuring the level of one or more genes in a biological sample.

The kits can optionally include, e.g., a control biological sample or control labeled-amplicon set containing known amounts of one or more amplicons recognized by nucleic acid probes of the array. In some instances, the control can be an insert (e.g., a paper insert or electronic medium such as a CD, DVD, or floppy disk) containing expression level ranges of one or more genes predictive of a response to a therapy comprising lenvatinib or a pharmaceutically acceptable salt thereof (e.g., lenvatinib mesylate).

In some embodiments, the kits can include one or more reagents for processing a biological sample. For example, a kit can include reagents for isolating a protein from a biological sample and/or reagents for detecting the presence and/or amount of a protein in a biological sample (e.g., an antibody that binds to the protein that is the subject of the detection assay and/or an antibody that binds the antibody that binds to the protein).

In some embodiments, the kits can include a software package for analyzing the results of, e.g., a microarray analysis or expression profile.

The kits can also include one or more antibodies for detecting the protein expression of any of the genes described herein. For example, a kit can include (or in some cases consist of) a plurality of antibodies capable of specifically binding to one or more proteins encoded by any of the genes depicted in Table 3 and optionally, instructions for detecting the one or more proteins and/or a detection antibody comprising a detectably-labeled antibody that is capable of binding to at least one antibody of the plurality. In some embodiments, the kits can include antibodies that recognize one, at least two, at least three, at least four, at least five, at least six, at least seven, at least eight, at least nine, at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45 or 46 proteins encoded by genes depicted in Table 3.

The kits described herein can also, optionally, include instructions for administering a therapy comprising lenvatinib or a pharmaceutically acceptable salt thereof (e.g., lenvatinib mesylate), where the expression level of one or more genes detectable by the array predicts that a subject will respond to a therapy comprising lenvatinib or a pharmaceutically acceptable salt thereof (e.g., lenvatinib mesylate).

The following are examples of the practice of the invention. They are not to be construed as limiting the scope of the invention in any way.

EXAMPLES

Example 1: Mutation Status as Predictive Biomarkers for Responsiveness to Therapy Comprising E7080

Purpose:

Tumor response and prolonged disease stabilization were observed in differentiated thyroid cancer patients treated in phase II with E7080 (lenvatinib). This experiment was directed at identifying amino acid mutations that are useful in predicting whether subjects respond to treatment with E7080 using three criteria of response: best overall response, tumor shrinkage, and progression free survival.

Materials and Methods:

Tissue samples were obtained at surgery before the patients had received any therapy comprising E7080 and were routinely processed with formalin fixed, paraffin embedded tissues (FFPE). The protocol that was used was approved by the institutional review board, and informed consent was obtained from each subject. Tumor tissue samples from 27 patients, for which tissues were available, were used for mutation analysis. DNA was isolated from FFPE tumor blocks collected from patients participating in the trial. Genomic DNA was extracted from two to five 10 micron unstained sections by deparaffinization and Qiagen DNA Mini Kit Tissue Protocol with minor modification. For mutation detection, the SEQUENOM® (San Diego, Calif.) platform and the OncoCarta™ Panel v1.0 and OncoCarta™ Panel v3.0 were used (see, www.sequenom.com/Files/Genetic-Analysis—Graphics/All-Application—PDFs/Assay-Explorer2010_1110-Web/). Sequenom's OncoCarta™ Panels are a set of pre-designed and pre-validated assays for efficient mutation screening. The OncoCarta™ Panel v1.0 genes and the number of mutations (in parentheses) are: ABL1 (14); AKT1 (7); AKT2 (2); BRAF (25); CDK4 (2); EGFR (40); ERBB2 (9); FGFR1 (2); FGRF3 (7); FLT3 (3); HRAS (10); JAK2 (1); KIT (32); KRAS (16); MET (5); NRAS (19); PDGFRA (11); PIK3CA (14); and RET (6). The OncoCarta™ Panel v3.0 genes and the number of mutations (in parentheses) are: ABL1 (2) AKT1 (1); APC (12); BRAF (19); CDKN2A (7); CSF1R (6); CTTNB1 (28); EGFR (32); ERBB2 (2); FLT3 (3); HRAS (2); JAK3 (3); KIT (3); KRAS (5); MET (6); MLH1 (1); MYC (6); PDGFRA (11); PIK3CA (4); PTEN (14); RB1 (11); RET (13); SRC (1); STK11 (12); P53 (7); and VH1 (7). OncoCarta™ Panel v3.0 genes and the number of mutations (in parentheses) are: ABL1 (2) AKT1 (1); APC (12); BRAF (19); CDKN2A (7); CSF1R (6); CTTNB1 (28); EGFR (32); ERBB2 (2); FLT3 (3); HRAS (2); JAK3 (3); KIT (3); KRAS (5); MET (6); MLH1 (1); MYC (6); PDGFRA (11); PIK3CA (4); PTEN (14); RB1 (11); RET (13); SRC (1); STK11 (12); P53 (7); and VH1 (7).

DNA was amplified using the OncoCarta™ PCR primer pools, unincorporated nucleotides were inactivated by shrimp alkaline phosphatase (SAP), and a single base extension reaction was performed using extension primers that hybridize immediately adjacent to the mutations and a custom mixture of nucleotides. Salts were removed by the addition of a cation exchange resin. Multiplexed reactions were spotted onto the SpectroChipII, and mutations, if present, were resolved by MALDI-TOF on the Compact Mass Spectrometer (Sequenom®, San Diego, Calif.). The OncoCarta™ Panel v1.0 (Sequenom®, San Diego, Calif.) consists of 24 pools of primer pairs and 24 pools of extension primers, and has the capacity to detect 225 mutations in 19 genes. The OncoCarta™ Panel v 3.0 consists of 24 pools of primer pairs and 24 pools of extension primers, and has the capacity to detect 218 mutations in 26 genes. Each pool consists of 5-9 primer pairs in the PCR reaction. Two types of assays have been designed in the OncoCarta panel, referred to as simple and complex. The simple assays are those in which a single assay is able to detect the amino acid changes at that codon. The complex assays are those that require more than one assay to identify codon changes or deletions and insertion, and thus are able to detect multiple different amino acid substitutions or deletions. An example of a complex assay involves the use of the KRAS_1 and KRAS_2 assays, which interrogates 2 different nucleotide positions within codon 12 and together identify all codon 12 amino acid changes. In the KRAS G12R mutation, the mutant allele has the codon CGT (Arginine) in contrast to the wild type allele which has the GGT (Glycine) codon. So, the first nucleotide of codon 12 needs to be "C" and second nucleotide needs to be "G". The KRAS_2 assay reveals which nucleotide is incorporated into the first nucleotide of the codon 12, and the KRAS_1 assay is for the second nucleotide. Together, the data from these two assays detects the G12R substitution. For the BRAF V600E mutation (GTG to GAG), BRAF_16 assay (for the first nucleotide of the codon 600) identifies "G" and BRAF_15 (for the second nucleotide) identifies "A". For the VHL P81S mutation, the mutant allele has TCG (Serine) whereas the wild type allele has CCG (Proline). The VHL_498 assay reveals which nucleotide is incorporated into the first nucleotide of the codon 81. For the KRAS Q61R mutation, the KRAS_7 assay discriminates the mutant allele (CGA, Arginine) from the wild type allele (CAA, Glutamine) by examining nucleotide variation in the second position of the codon. In the case of NRAS codon 61, there are three known mutations, Q61L (CAA to CTA), Q61R (CAA to CGA) and Q61P (CAA to CCA). The NRAS_6 assay detects nucleotide variation in the second position of the codon. Even more complex assays are also included in OncoCarta™, which interrogate insertions and deletions within the EGFR gene.

Data analysis was performed using MassArray Type Analyzer software (Sequenom®), which facilitates visualization of data patterns as well as the raw spectra. All mutations from the Onco mutation report were reviewed manually to identify "real" mutant peaks from salt peaks or other background peaks.

The period during which a patient takes E7080 was artificially divided into different Cycles for ease of evaluation and tracking. Patients received E7080 at a dose of 24 mg oral once daily in 28 day cycles. For analysis purposes, assessments of clinical outcomes were performed at the time of the 9 month and at 14 month minimum follow-up. For the E7080 Thyroid Cancer trial, each Cycle is 28 days (4 weeks) so Day 1-28 is cycle 1; Day 29 is Day 1 of Cycle 2; and Day 57 is Day 1 of Cycle 3. Blood samples were collected for pharmacokinetic (PK) analysis on Cycle 1 Days 1 and 8, Cycle 2 Day 1, and Cycle 3 Day 1. A total of 9 samples per patient were collected as follows: Cycle 1 Day 1: immediately prior to the dose of E7080, and at 0.5 and 2 hours following the first dose of E7080 (post-dose); Cycle 1 Day 8: immediately prior to the dose of E7080; Cycle 2 Day 1: immediately prior to the dose of E7080, 0.5 and 2 hours post-dose; Cycle 3 Day 1: immediately prior to the dose of E7080 and 2 hours post-dose. For analysis of progression free survival, PK parameter was used as a covariate in Cox proportional hazards model.

The three criteria of response: best overall response, tumor shrinkage, and progression free survival are defined below.

"Best Overall Response" (BOR) refers to having one of the following statuses—Complete Response (CR), Partial Response (PR), Stable Disease (SD) or Progressive Disease (PD).

"Clinical benefit" (CB) refers to having one of the following statuses—Complete Response (CR), Partial Response (PR); or Stable Disease (SD) with 6 months or more progression free survival (PFS).

"Complete Response" means complete disappearance of all target lesions.

"Partial Response" means at least 30% decrease in the sum of the longest diameter (LD) of target lesions, taking as reference the baseline summed LD.

"Progressive Disease" (PD) means at least 20% increase in the sum of the LD of target lesions, taking as reference the smallest summed LD recorded since the treatment started, or the appearance of one or more new lesions.

"Stable Disease" means neither sufficient shrinkage of the target lesions to qualify for PR nor sufficient increase to qualify for progressive disease (PD), taking as reference the smallest summed LD since the treatment started.

"Progression Free Survival" (PFS) refers to the period from start date of treatment to the last date before entering PD status.

"Tumor shrinkage" (TS) means percent change of sum of diameters of target lesions, taking as reference the baseline sum diameters.

Results:

A total of 443 mutations among 33 genes were tested using OncoCarta™ Panel v1.0 and OncoCarta™ Panel v3.0 mutation panel and mutations were found in 16 of the 23 subjects we examined. From 27 patients, 23 patient samples were analyzed using OncoCarta™ Panel v1.0 and using OncoCarta™ Panel v3.0. 12 mutations among 10 genes were identified and are listed in Table 4. 7 patients were wild type for all genes tested.

TABLE 4

Summary of Mutations Found in DTC Patients

| No of patient | BRAF | NRAS | KRAS | VHL | Other.mutation |
|---|---|---|---|---|---|
| 1 | WT | Q61P | WT | P81S | ERBB2 (S779_P780insVGS) |
| 2 | WT | Q61R | WT | P81S | PTEN (N323fs*2) |
| 3 | WT | Q61R | WT | WT | |
| 4 | WT | Q61R | WT | WT | |
| 5 | WT | Q61R | WT | WT | |
| 6 | WT | Q61R | WT | P81S | |
| 7 | V600E | WT | WT | WT | |
| 8 | V600E | WT | WT | WT | myc (A59V) |
| 9 | V600E | WT | WT | WT | |
| 10 | V600E | WT | WT | WT | |
| 11 | WT | WT | WT | P81S | |
| 12 | WT | WT | 061R | WT | |
| 13 | WT | WT | G12R | WT | |
| 14 | WT | WT | WT | WT | PI3KCA (E545A.E545G) |
| 15 | WT | WT | WT | WT | TP53 (R248W) |
| 16 | WT | WT | WT | WT | MET (T1010I.T992I) |

Best overall response was significantly better in patients whose tumor had mutations in any of KRAS, NRAS, BRAF, VHL-1 genes (Fishers exact test) as shown in Table 5. For example, 8 out of 8 patients with either an NRAS or KRAS mutation had partial response (PR), while only 5 out of 14 patients had PR without mutations in NRAS and KRAS.

TABLE 5

Mutation and Best Overall Response (BOR)

| Mutation (any of gene) | | BOR p-value (fisher's exact) | |
|---|---|---|---|
| BRAF.NRAS | | 0.038 | |
| KRAS.NRAS | | 0.007 | |
| BRAF.KRAS.NRAS | | 0.010 | |
| BRAF.VHL | | 0.042 | |
| BRAF.KRAS.VHL | | 0.034 | |
| KRAS.NRAS.VHL | | 0.020 | |
| BRAF.KRAS.NRAS.VHL | | 0.012 | |
| mutation (any of gene) | BOR | WT | MU |
| BRAF.NRAS | PR | 5 | 8 |
| | SD | 6 | 1 |
| | PD | 2 | 0 |
| KRAS.NRAS | PR | 5 | 8 |
| | SD | 7 | 0 |
| | PD | 2 | 0 |
| BRAF.KRAS.NRAS | PR | 3 | 10 |
| | SD | 6 | 1 |
| | PD | 2 | 0 |
| BRAF.VHL | PR | 10 | 6 |
| | SD | 5 | 0 |
| | PD | 0 | 2 |
| BRAF.KRAS.VHL | PR | 8 | 8 |
| | SD | 5 | 0 |
| | PD | 0 | 2 |
| KRAS.NRAS.VHL | PR | 5 | 8 |
| | SD | 7 | 0 |
| | PD | 1 | 1 |
| BRAF.KRAS.NRAS.VHL | PR | 3 | 10 |
| | SD | 6 | 1 |
| | PD | 1 | 1 |

*Tumor size of 1 wild type patient was not evaluable

Patients with mutations in either NRAS, either NRAS or KRAS, or either BRAF, KRAS, or NRAS, had a larger decrease of tumor size indicated as percent change in tumor shrinkage, compared with patients that were wild type for NRAS, KRAS and BRAF (see, Table 6).

TABLE 6

Mutation and % of Maximum Tumor Shrinkage

| Gene (any of gene) | Wild type* | Mutation | % of tumor shrinkage (Median) wild type | mutation | p value |
|---|---|---|---|---|---|
| NRAS | 16 | 6 | −35.5 | −45.5 | 0.042 |
| KRAS, NRAS | 14 | 8 | −31.0 | −44.5 | 0.022 |

*Tumor size of 1 wild type patient was not evaluable

The association of gene mutations with progression free survival of treated patients was analyzed first by performing Logrank test and then using Cox proportional hazards model with or without covariates. The covariate used are the following PK parameters: cycle 1 day 1 Cmax (E7080 concentration 2 hr after dosing on cycle 1 day 1: MAX1); cycle 1 day 1 Ctrough (E7080 concentration before dosing on cycle 1 day 8: MIN1); cycle 2 day1 Cmax (E7080 concentration 2 hrs after dosing on cycle 2 day 1: MAX2); cycle 2 day 1 Ctrough (E7080 concentration before dosing on cycle 2 day 1: MIN2). The Logrank test demonstrated that patients with mutations in NRAS alone or with mutations in either NRAS or KRAS had better progression free survival than those patients who were wild type for NRAS or KRAS (FIG. 1). Cox proportional hazards model also demonstrated that patients with mutations in either NRAS, KRAS, or VHL and mutations in either NRAS, KRAS, or BRAF had better progression free survival than those who did not have mutations based on cox proportion hazard test with a covariate of cycle 1 day 1 Ctrough (MIN1), since wild type set as 1 and mutation set as 0 and coefficients lower than 0 makes lower hazard for mutation (see, Table 7).

TABLE 7

Gene Mutation and Progression Free Survival

| Mutation (any of gene) | n | Coef | p value | pK MIN1 |
|---|---|---|---|---|
| KRAS.NRAS | 23 | −1.586 | 0.043 | |
| NRAS | 23 | −2.091 | 0.047 | |
| BRAF.KRAS.NRAS | 23 | −1.428 | 0.032 | 0.037 |
| KRAS.NRAS | 23 | −2.629 | 0.021 | 0.007 |
| KRAS.NRAS.VHL | 23 | −1.700 | 0.043 | 0.018 |

Conclusion:

Mutations in a small set of genes, such as anyone or a combination of NRAS, KRAS, BRAF, and VHL in thyroid tumors are useful in predicting the clinical response of a patient presenting with, suspected of having, or at risk of developing, thyroid cancer to a therapy comprising E7080.

Example 2: Thyroglobulin as a Biomarker for Therapy Comprising E7080 in Thyroid Tumors Purpose:

This experiment was directed at determining whether changes in thyroglobulin levels are predictive of whether patients respond to treatment with E7080 using three criteria of clinical response: tumor response, tumor shrinkage, and progression free survival.

Material and Methods:

The serum for the thyroglobulin assays was collected within 72 hours prior to Day 1 of all cycles. 24 mg of E7080 was administered orally, daily continuously in 28-day cycles. Serum samples from 58 patients were used for thyroglobulin measurements. 6 mL of blood was drawn into red top tubes and let to clot at room temperature for at least 30 min. Within 60 minutes of sample collection, the tubes were centrifuged for 15 minutes at 20-25° C. at 1000×g. The supernatant was drawn without disturbing the pellet, put into sample tubes with serum filter and shipped frozen to the central lab for testing on the day of collection. The level of thyroglobulin was detected by a solid-phase, chemiluminescent immunometric assay (IMMULITE 2000 Thyroglobulin Assay System, Siemens) following standard operating procedure. In brief, serum thyroglobulin was captured by beads coated with anti-thyroglobulin antibody and detected using anti-thyroglobulin antibody linked to alkaline phosphatase. The level of serum thyroglobulin was calculated from a standard curve generated with lyophilized thyroglobulin. Serum thyroglobulin was stable for up to 2 months when stored frozen for the assay. The sensitivity of this assay was 0.2 ng/ml.

Results:

From 58 patient samples, 50 pre- and post-treatment blood samples at maximum were used for these analyses. Dramatic changes in thyroglobulin levels were observed 29 days after the start of treatment with E7080. Thyroglobulin levels significantly decreased 48 days (within 2 cycles) after treatment with E7080 and the decrease continued to cycle 8.

Figure 2:
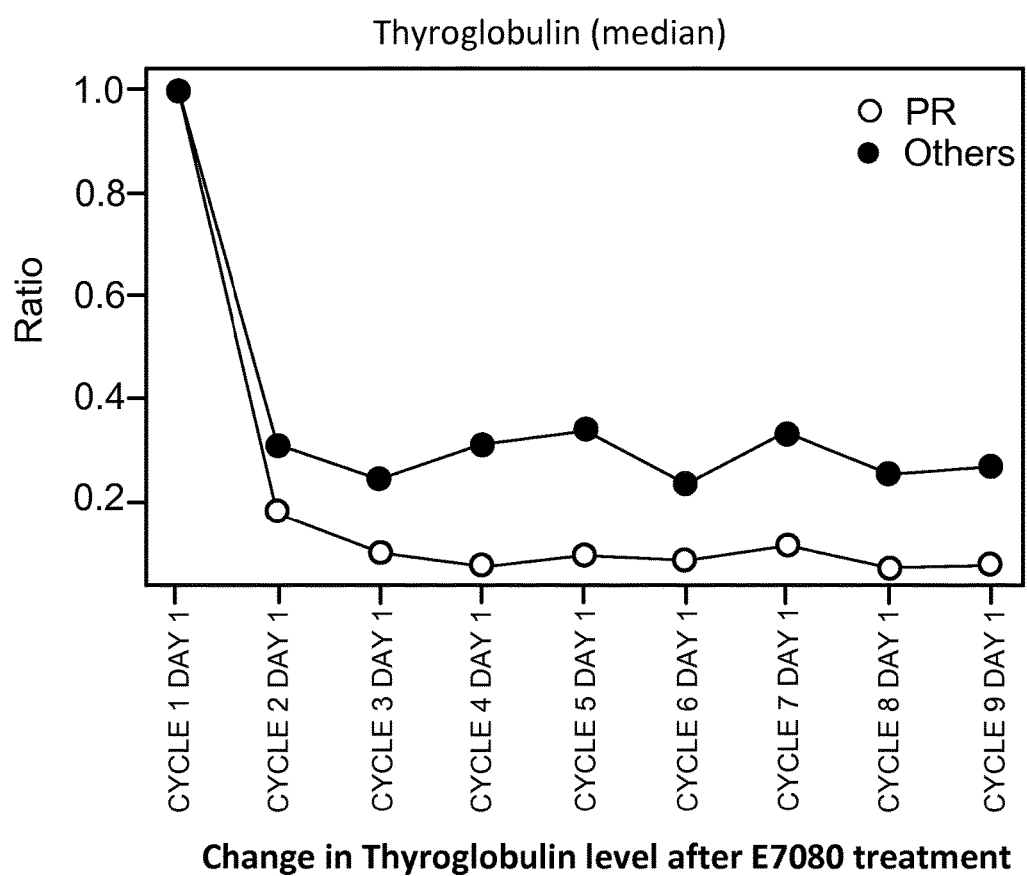
FIG. 2 is a schematic diagram of the change in thyroglobulin levels after E7080 treatment. "PR" refers to median values among groups of patients showing partial response to E7080 therapy. "Others" refers to median values among groups of patients having stable disease or progressive disease after E7080 therapy.

Changes in thyroglobulin levels in groups of patient, who have partial response (PR) with E7080, was significantly lower than those in groups of patients, who have either stable disease (SD) or progressive disease (PD) (Mann Whitney U test, FIG. 2; ○ median of PR groups, ● median of Others—SD or PD and Table 8, top). Also changes in thyroglobulin levels were associated with tumor shrinkage after completion of cycle 2 (56 days after treatment) (Spearman's rank correlation test, Table 8, middle). Cox proportional hazard test demonstrated that progression free survival of patients was associated with changes in thyroglobulin levels 28 days after treatment with E7080, indicating larger decrease predict longer PFS (Table 8, bottom).

TABLE 8

Changes in Thyroglobulin Levels After E7080 Treatment (a) Large decrease of thyroglobulin level in group of patients with PR

| Factor | Time point | n | PR group median | PR group IQR | Other group Median | Other group IQR | p value |
|---|---|---|---|---|---|---|---|
| Thyroglobulin | CYCLE2 DAY 1/CYCLE1 DAY 1 | 49 | 0.195 | 0.233 | 0.288 | 0.460 | 0.154 |
|  | CYCLE3 DAY 1/CYCLE1 DAY 1 | 44 | 0.109 | 0.144 | 0.221 | 0.243 | 0.034 |
|  | CYCLE4 DAY 1/CYCLE1 DAY 1 | 44 | 0.079 | 0.112 | 0.227 | 0.390 | 0.007 |
|  | CYCLE5 DAY 1/CYCLE1 DAY 1 | 42 | 0.106 | 0.119 | 0.332 | 0.403 | 0.019 |
|  | CYCLE6 DAY 1/CYCLE1 DAY 1 | 40 | 0.078 | 0.133 | 0.198 | 0.235 | 0.044 |

(b) Association of large decrease of thyroglobulin level to % of tumor shrinkage

| Factor | Time point | maximum tumor shrinkage Correlation (r) | p value |
|---|---|---|---|
| Thyroglobulin | CYCLE2 DAY 1/CYCLE1 DAY 1 | 0.163 | 0.280 |
|  | CYCLE3 DAY 1/CYCLE1 DAY 1 | 0.342 | 0.026 |
|  | CYCLE4 DAY 1/CYCLE1 DAY 1 | 0.467 | 0.002 |
|  | CYCLE5 DAY 1/CYCLE1 DAY 1 | 0.443 | 0.004 |
|  | CYCLE6 DAY 1/CYCLE1 DAY 1 | 0.358 | 0.023 |

(c) Association of a change of thyroglobulin level to PFS after 1 cycle treatment with E7080

| Factor | Time & category | n | Coef | p-value |
|---|---|---|---|---|
| Thyroglobulin | CYCLE2 DAY 1/CYCLE1 DAY 1 | 49 | 0.995 | 0.039 |

Conclusion:

Changes in thyroglobulin levels following E7080 therapy are associated to tumor response, decrease of tumor size, and progression free survival and may be used to predict clinical response as early as 4 weeks after treatment with E7080. Thus, thyroglobulin levels are helpful in assessing whether to continue therapy comprising E7080.

Example 3: Cytokine, Chemokine, and Angiogenic Factors (Blood Biomarkers) as Predictive and Response Biomarkers of E7080

Purpose:

Angiogenesis is regulated by signaling through multiple growth factor receptors, such as VEGF and FGF receptor. VEGF receptor signaling is also associated with immune cell function. The purpose of this analysis was to measure cytokine, chemokine and angiogenic factors (collectively referred to herein as "blood biomarkers") in serum samples obtained from patients in clinical trials at both pre- and post-treatment with E7080 and to identify blood biomarkers which can be used to predict whether patients will respond to treatment with E7080. For these analyses, three criteria of response were employed, namely: tumor response, % of tumor shrinkage and progression free survival.

"Tumor response" (TR) compares subjects with "Partial Response" (PR) with subjects with either Stable Disease (SD) or Progressive Disease (PD).

Materials and Methods:

Patients received E7080 at a dose of 24 mg oral once daily in 28 day cycles. Serum samples were collected at Cycle 1 Day 1 (pre-treatment), Cycle 1 Day 8 and Cycle 2 Day 8 (i.e., day 36 post-treatment). 7.5 mL of blood was drawn into serum stainless steel tube (SST) and let to clot at room temperature for at least 30 min. Within 60 minutes of sample collection, the tubes were centrifuged for 10 minutes at 20-25° C. at 1400×g. The supernatant was drawn without disturbing the pellet and the serum was mixed and divided into two sample tubes and stored frozen (−70° C.) at an upright position until further treatment for analysis. Serum samples from 58 patients were used for blood biomarker analysis. Serum from Cycle 1 day 1 (baseline), cycle 1 day 8, and cycle 2 day 8 were used in this analysis. The association of progression free survival with or without a covariate was analyzed. The covariates used are the following PK parameters: cycle 1 day 1 Cmax (E7080 concentration 2 hr after dosing on cycle 1 day 1: MAX1); cycle 1 day 1 Ctrough (E7080 concentration before dosing on cycle1 day 8: MIN1); cycle 2 day 1 Cmax (E7080 concentration 2 hrs after dosing on cycle 2 day 1: MAX2); cycle 2 day 1 Ctrough (E7080 concentration before dosing on cycle 2 day 1: MIN2). Serum samples were tested in batch format where all timepoints from the same subject were assayed on the same day. On the day of assay, samples were removed from −80° C. and allowed to thaw and reach room temperature. The serum samples were tested using the following commercial assay kits as per the manufacturer's instructions: Human Soluble Tie-2 ELISA (R&D Systems Cat. No. DTE200), Human Angiopoietin-1 ELISA (R&D Systems Cat. No. DANG10), Human FGF23 ELISA, Human SDF-1a ELISA. Human Angiopoietin-2 ELISA (R&D Systems Cat. No. DANG20), Human Soluble Receptor Multiplex (Millipore Cat. No. HSCR-32K; sVEGF R1, sVEGF R2 and sVEGF R3 only), Human Cytokine/Chemokine Panel I Multiplex (Millipore Cat. No. MPXHCYTO-60K; IL-1α, IL-1β, IL-1ra, IL-2, IL-4, IL-5, IL-6, IL-7, IL-8, IL-10, IL-12p40, IL-12p70, IL-13, IL-15, IL-17, sCD40L, EGF, Eotaxin, FGF-2, G-CSF, GM-CSF, IFN-γ, IP-10, MCP-1, MIP-1α, MIP-1β, PDGF-AA, RANTES, TGF-α, TNF-α and VEGF only) and Human Growth Factor Multiplex (Origene TruPLEX Cat. No. AM100096; PDGF-AB, PDGF-BB, FGF4, VEGFD, FGF2, EGF, HGF, FLT3LG, ANGPT2, PGF and VEGFA).

The ELISA plates were measured using a Molecular Devices UVmax kinetic microplate reader with SoftMax Pro 5.2 software. The multiplex assays were performed using the Bio-Rad Bio-Plex system with Bio-Plex Manager 4.1 software. Final protein concentrations (pg/mL) were calculated from the standard curve for each assay. Depending on the assay, serum samples may have been diluted in assay buffer prior to testing. In these cases, protein concentrations were multiplied by the dilution factor.

Results and Discussion:

From 58 patient samples, between 27 and 49 pre- and post-treatment blood samples were used for analyses. Significant change in levels of 23 factors among 46 factors tested in 50 assays were observed at both, or either, cycle 1 day 8 or cycle 2 day 8 in the serum from patients treated with E7080 compared to pre-treatment levels (cycle 1 day 1 (baseline)) (Table 9).

TABLE 9

Change in Levels of Blood Biomarkers After E7080 Treatment

| Factor | Time point Pre | Time point Post | Number Pre | Number Post | Base line median | Base line IQR | Post Treatment median | Post Treatment IQR | Fold change median | Fold change IQR | P value |
|---|---|---|---|---|---|---|---|---|---|---|---|
| EGF | CYCLE 1 DAY 1 | CYCLE 2 DAY 8 | 42 | 44 | 119.9 | 128.5 | 75.9 | 76.6 | 0.808 | 0.735 | 3.70E−02 |
| Eotaxin | CYCLE 1 DAY 1 | CYCLE 1 DAY 8 | 49 | 49 | 128.2 | 75.9 | 154.7 | 117.5 | 1.171 | 0.313 | 3.20E−05 |
| | CYCLE 1 DAY 1 | CYCLE 2 DAY 8 | 44 | 44 | 128.2 | 75.9 | 177 | 123.9 | 1.363 | 0.54 | 1.10E−06 |
| G-CSF | CYCLE 1 DAY 1 | CYCLE 1 DAY 8 | 49 | 49 | 51.2 | 34.5 | 67.1 | 46.3 | 1.25 | 0.57 | 3.80E−04 |
| | CYCLE 1 DAY 1 | CYCLE 2 DAY 8 | 44 | 44 | 51.2 | 34.5 | 61.3 | 53.8 | 1.215 | 1.011 | 8.80E−03 |
| IL-6 | CYCLE 1 DAY 1 | CYCLE 1 DAY 8 | 37 | 49 | 9.9 | 23.3 | 17.3 | 34.9 | 1.824 | 2.759 | 2.10E−03 |
| | CYCLE 1 DAY 1 | CYCLE 2 DAY 8 | 34 | 44 | 9.9 | 23.3 | 15 | 34.4 | 1.299 | 2.069 | 1.90E−02 |
| IL-7 | CYCLE 1 DAY 1 | CYCLE 1 DAY 8 | 27 | 49 | 3.3 | 15.7 | 6.4 | 14.5 | 1 | 0.507 | 3.80E−02 |
| IL-8 | CYCLE 1 DAY 1 | CYCLE 1 DAY 8 | 48 | 49 | 26.1 | 24.9 | 31.7 | 28.4 | 1.164 | 0.66 | 1.20E−02 |
| | CYCLE 1 DAY 1 | CYCLE 2 DAY 8 | 43 | 44 | 26.1 | 24.9 | 31.4 | 20.3 | 1.205 | 0.799 | 7.80E−03 |
| IL-17 | CYCLE 1 DAY 1 | CYCLE 1 DAY 8 | 39 | 49 | 9.3 | 30.7 | 14.4 | 52.2 | 1.025 | 0.378 | 4.70E−02 |
| IP-10 | CYCLE 1 DAY 1 | CYCLE 1 DAY 8 | 49 | 49 | 387.7 | 313 | 474.3 | 443.1 | 1.249 | 0.41 | 2.70E−05 |
| | CYCLE 1 DAY 1 | CYCLE 2 DAY 8 | 44 | 44 | 387.7 | 313 | 602.8 | 538.5 | 1.382 | 0.719 | 9.40E−04 |
| MCP-1 | CYCLE 1 DAY 1 | CYCLE 2 DAY 8 | 44 | 44 | 582.7 | 323.3 | 618.0 | 342.1 | 1.086 | 0.431 | 4.10E−03 |
| TGFa | CYCLE 1 DAY 1 | CYCLE 1 DAY 8 | 45 | 49 | 12.2 | 12.0 | 14.6 | 9.9 | 1.157 | 0.706 | 2.80E−02 |
| VEGF | CYCLE 1 DAY 1 | CYCLE 1 DAY 8 | 48 | 49 | 622 | 1845.8 | 741.4 | 1918.7 | 1.29 | 0.517 | 1.20E−04 |
| Ang-2 | CYCLE 1 DAY 1 | CYCLE 1 DAY 8 | 49 | 49 | 2717 | 1697.8 | 1812 | 1150 | 0.665 | 0.298 | 3.10E−13 |
| | CYCLE 1 DAY 1 | CYCLE 2 DAY 8 | 44 | 44 | 2717 | 1697.8 | 1533 | 729 | 0.618 | 0.379 | 1.60E−11 |
| Tie-2 | CYCLE 1 DAY 1 | CYCLE 1 DAY 8 | 49 | 49 | 33675 | 10817.5 | 31685 | 11800 | 0.917 | 0.166 | 9.40E−06 |
| | CYCLE 1 DAY 1 | CYCLE 2 DAY 8 | 44 | 44 | 33675 | 10817.5 | 26220 | 6845 | 0.766 | 0.143 | 9.10E−09 |
| sVEGFR1 | CYCLE 1 DAY 1 | CYCLE 1 DAY 8 | 43 | 49 | 345.2 | 539.7 | 300 | 341 | 0.92 | 0.361 | 6.00E−03 |
| | CYCLE 1 DAY 1 | CYCLE 2 DAY 8 | 38 | 44 | 345.2 | 539.7 | 341.5 | 444.9 | 0.805 | 0.66 | 3.50E−02 |
| sVEGFR2 | CYCLE 1 DAY 1 | CYCLE 1 DAY 8 | 49 | 49 | 26778.4 | 9033.4 | 18823.1 | 6482.8 | 0.676 | 0.23 | 7.40E−13 |
| | CYCLE 1 DAY 1 | CYCLE 2 DAY 8 | 44 | 44 | 26778.4 | 9033.4 | 13352.1 | 4041.9 | 0.499 | 0.167 | 5.70E−13 |
| sVEGFR3 | CYCLE 1 DAY 1 | CYCLE 2 DAY 8 | 39 | 44 | 6226.6 | 4858.8 | 4030.9 | 6017.5 | 0.843 | 0.327 | 1.80E−03 |
| EGF (80) | CYCLE 1 DAY 1 | CYCLE 2 DAY 8 | 38 | 41 | 879.6 | 753.5 | 875.8 | 823.7 | 1.17 | 0.653 | 4.70E−02 |

TABLE 9-continued

Change in Levels of Blood Biomarkers After E7080 Treatment

| Factor | Time point | | Number | | Base line | | Post Treatment | | Fold change | | |
|---|---|---|---|---|---|---|---|---|---|---|---|
| | Pre | Post | Pre | Post | median | IQR | median | IQR | median | IQR | P value |
| HGF (86) | CYCLE 1 DAY 1 | CYCLE 1 DAY 8 | 46 | 48 | 1201.8 | 651.4 | 1339.3 | 1335.9 | 1.096 | 0.572 | 2.70E−02 |
| FLT3 LG (89) | CYCLE 1 DAY 1 | CYCLE 1 DAY 8 | 48 | 48 | 80.4 | 56.5 | 71.1 | 50.6 | 0.885 | 0.249 | 5.40E−03 |
| ANG2 (90) | CYCLE 1 DAY 1 | CYCLE 1 DAY 8 | 48 | 48 | 928.2 | 748.9 | 688.6 | 442.3 | 0.671 | 0.218 | 3.20E−12 |
| | CYCLE 1 DAY 1 | CYCLE 2 DAY 8 | 41 | 41 | 928.2 | 748.9 | 600.6 | 373.9 | 0.586 | 0.327 | 2.90E−09 |
| PGF (91) | CYCLE 1 DAY 1 | CYCLE 1 DAY 8 | 48 | 48 | 16.1 | 8.5 | 35.9 | 37.2 | 2.306 | 1.769 | 1.70E−09 |
| | CYCLE 1 DAY 1 | CYCLE 2 DAY 8 | 41 | 41 | 16.1 | 8.5 | 46.0 | 55.1 | 3.05 | 2.717 | 3.00E−11 |
| VEGFA (100) | CYCLE 1 DAY 1 | CYCLE 1 DAY 8 | 48 | 48 | 125.9 | 142.4 | 202.1 | 204.5 | 1.28 | 0.838 | 9.40E−08 |
| | CYCLE 1 DAY 1 | CYCLE 2 DAY 8 | 41 | 41 | 125.9 | 142.4 | 212.5 | 191.4 | 1.426 | 0.941 | 3.20E−04 |
| SDF-1a | CYCLE 1 DAY 1 | CYCLE 1 DAY 8 | 49 | 49 | 2582.6 | 957.7 | 3129.0 | 1161.8 | 1.21 | 0.172 | 5.30E−12 |
| | CYCLE 1 DAY 1 | CYCLE 2 DAY 8 | 43 | 43 | 2582.6 | 957.7 | 3529.5 | 970 | 1.345 | 0.246 | 6.80E−13 |

It was next assessed whether changes in expression levels of these factors was associated with clinical outcomes (tumor response; PR and others (SD or PD), tumor shrinkage, and PFS).

TABLE 10

Concentration and Ratio of Blood Biomarkers and Tumor Response

| | | PR | | others | | |
|---|---|---|---|---|---|---|
| Factor | Time point | Median | IQR | Median | IQR | p. value |
| IFN-g | CYCLE 1 DAY 1 | 7.9 | 14.1 | 21.2 | 60.2 | 0.013 |
| Ang-2 | | 2530.5 | 914.5 | 3399 | 2288 | 0.032 |
| ANG2 (90) | | 829.5 | 541.3 | 1032.9 | 1113.4 | 0.032 |
| ANG2 (90) | CYCLE 1 DAY 8 | 591.7 | 329.3 | 799.3 | 505.6 | 0.043 |
| SDF-1a | | 3294 | 1271.3 | 2915 | 866.2 | 0.042 |
| IL-6 | CYCLE 2 DAY 8 | 8.2 | 17.8 | 33.9 | 33.7 | 0.026 |
| FGF-2 | CYCLE 1 DAY 8/CYCLE 1 DAY 1 | 1.189 | 0.821 | 0.952 | 0.397 | 0.021 |
| GM-CSF | | 1.037 | 0.641 | 0.945 | 0.459 | 0.044 |
| Eotaxin | CYCLE 2 DAY 8/CYCLE 1 DAY 1 | 1.541 | 0.464 | 1.242 | 0.411 | 0.008 |
| IP-10 | | 1.547 | 0.616 | 1.151 | 0.606 | 0.039 |
| Tie-2 | CYCLE 2 DAY 2/CYCLE 1 DAY 8 | 0.791 | 0.159 | 0.852 | 0.206 | 0.023 |
| FGF2 (79) | | 1.132 | 1.051 | 0.978 | 0.391 | 0.043 |
| GM-CSF | | 1.051 | 0.547 | 0.876 | 0.439 | 0.07 |
| HGF (86) | | 0.789 | 0.318 | 1.087 | 0.491 | 0.004 |
| VEGFA (100) | | 0.899 | 0.521 | 1.172 | 0.422 | 0.011 |

Median concentrations of 4 factors (IFN-g, ANG-2, SDF-1a and IL-6) in 5 assays at pre-treatment or either 1 week or 5 weeks after treatment with E7080 were significantly different in patients who responded to E7080 treatment (PR group) compared with the "others" group (patients with SD or PD) (Table 10, Mann-Whitney U test). For example, concentrations of IFN-g and ANG-2 at pre-treatment was significantly lower than that seen in patients who had either SD or PD, indicating that low concentrations of IFN-g and ANG-2 before the commencement of treatment with E7080 are predictive of a beneficial tumor response to E7080. Changes in the expression levels of 3 factors (FGF2, Eotaxin, IP-10) were increased in PR group at either cycle 1 day 8 or cycle 2 day 8, while the by expression level of these 3 factors were decreased in the "others" groups. Interestingly, GM-CSF expression levels were decreased only in others groups at cycle 2 day 8 compared to either cycle 1 day 1 or cycle 1 day 8. In addition, expression levels of Tie-2, HGF, and VEGF were significantly decreased in PR groups at cycle 2 day 8 more than in the "others" group compared to cycle 1 day 8. These results demonstrated that changes in expression levels of blood biomarkers were associated with and therefore can be to predict tumor responses to therapy comprising E7080.

Next, the factors associated with tumor shrinkage were investigated (Pearson's correlation coefficient test, Table 11).

TABLE 11

Concentration and Ratio of Blood Biomarkers and % of Maximum Tumor Shrinkage

| Factor | Time point | correlation (r) | p value |
|---|---|---|---|
| ANG2(90) | CYCLE1 DAY1 | 0.309 | 0.033 |
| PDGF AB(68) | | −0.420 | 0.011 |
| Ang-2 | | 0.341 | 0.012 |
| sVEGFR2 | | 0.289 | 0.036 |
| VEGF | | 0.276 | 0.048 |
| IL-10 | CYCLE1 DAY8 | −0.315 | 0.035 |
| SDF-1a | | −0.354 | 0.009 |
| IL-13 | | 0.399 | 0.048 |
| PGF(91) | CYCLE2 DAY8 | 0.305 | 0.040 |
| VEGFA(100) | | 0.300 | 0.043 |
| RANTES | | −0.311 | 0.045 |
| VEGF | | 0.292 | 0.047 |
| FGF-2 | CYCLE1 DAY8/CYCLE1 DAY1 | −0.347 | 0.021 |
| IL-10 | | −0.38 | 0.020 |
| GM-CSF | | −0.369 | 0.032 |
| IL-1a | CYCLE2 DAY8/CYCLE1 DAY1 | −0.468 | 0.028 |
| TGFa | | −0.348 | 0.030 |
| IL-6 | CYCLE2 DAY8/CYCLE1 DAY1 | 0.392 | 0.017 |
| Tie-2 | DAY8 | 0.352 | 0.019 |
| PGF(91) | | −0.314 | 0.046 |

TABLE 11-continued

Concentration and Ratio of Blood Biomarkers
and % of Maximum Tumor Shrinkage

| Factor | Time point | correlation (r) | p value |
|---|---|---|---|
| sVEGFR1 | | 0.332 | 0.032 |
| VEGFA(100) | | 0.319 | 0.035 |

Concentration of 4 factors (ANG-2, PDGF-AB, sVEGFR2, and VEGF) in 5 assays were significantly associated with tumor shrinkage at pre-treatment. These studies indicated that lower concentrations of these 4 factors can predict larger tumor shrinkage, while higher concentration of PDGF-AB might predict larger tumor shrinkage. Concentration of 3 factors (IL-13, PGF, and VEGF) in 4 assays at either 1 week or 5 weeks after treatments with E7080 were significantly associated with tumor shrinkage. These studies showed that lower concentrations of these IL-13, PGF, and VEGF are predictive of larger tumor shrinkage at indicated time points. Higher concentration of 3 factors (IL-10, SDF1a, and RANTES) in 3 assays at either 1 week or 5 weeks after treatments of E7080 are predictive of larger tumor shrinkage. Increase expression levels (indicating high ratio) of FGF2, IL10, GMCSF at cycle 1 day 8 compared to cycle 1 day 1 were significantly associated with tumor shrinkage and are predictive of larger tumor shrinkage. At cycle 2 day 8 compared to cycle 1 day 1, a high ratio of IL1a and TGFa is predictive of larger tumor shrinkage. A low ratio of the expression of 4 factors (IL-6, Tie-2, sVEGFR1, and VEGF) at cycle 2 day 8 compared to cycle 1 day 8 was associated with larger tumor shrinkage. A high ratio of the expression of PGF at cycle 2 day 8 compared to cycle 1 day 8 was associated with larger tumor shrinkage.

Cox proportional hazard model was performed to identify blood biomarkers that predict progression free survival by either concentrations or ratio (changes in expression levels) of factors. Pharmacokinetic (PK) parameter was used as a covariate in Cox proportional hazards model. Low concentrations of ANG-2 and VEGF at cycle 1 day1, or a low ratio of IL-12(p40) at cycle 2 day 8 compared to cycle 1 day 1 were significantly associated to longer PFS, indicating that these factors can be used as biomarkers for prediction or response to E7080 therapy (Table 12). Cox proportional hazard model with PK parameter demonstrated that high concentrations of 7 factors (GCSF, MIP1b, FGF2, MIP1a, IL6, IL13, and sVEGFR3) at pre-treatment can be predictive of longer PFS; whereas, low concentrations of ANG-2 at pre-treatment can be predictive of longer PFS. Cox proportional hazard model with PK parameter demonstrated that low ratios of 7 factors (FLT3LG, RANTES, GCSF, sVEGFR1, EGF, PDGF-BB, PDGF-AA) are predictive of better PFS and that high ratios of 4 factors (VEGFD, IL10, IL1RA, PDGF-AB) are predictive of better PFS.

TABLE 12

Concentration and Ratio of Blood Biomarker and Progression Free Survival

| Factor | Time | Coef | P value | MAX1 | MAX2 | MIN1 | MIN2 |
|---|---|---|---|---|---|---|---|
| Ang-2 | CYCLE1 DAY1 | 2.70E−04 | 0.017 | | | | |
| VEGFA (100) | | 1.40E−03 | 0.02 | | | | |
| IL-12(p40) | CYCLE2 DAY8/CYCLE1 DAY1 | 1.90E−01 | 0.046 | | | | |
| Ang-2 | CYCLE1 DAY1 | 3.30E−04 | 0.004 | 0.006 | 0.006 | | |
| G-CSF | | −1.60E−02 | 0.045 | 0.01 | 0.007 | | |
| ANG2 (90) | | 6.50E−04 | 0.021 | 0.003 | 0.01 | | |
| MIP-1b | | −1.10E−02 | 0.048 | 0.007 | 0.006 | | |
| FGF-2 | | −1.10E−02 | 0.049 | 0.003 | 0.004 | | |
| MIP-1a | | −2.60E−02 | 0.033 | 0.003 | 0.009 | | |
| IL-6 | | −3.00E−02 | 0.018 | 0.002 | 0.002 | | |
| IL-13 | | −3.00E−02 | 0.033 | 0.047 | | | 0.049 |
| sVEGFR3 | | −1.00E−04 | 0.045 | 0.001 | 0.003 | 0.023 | |
| FLT3 LG (89) | CYCLE1 DAY8/CYCLE1 DAY1 | 1.70E+00 | 0.022 | | | 0.049 | |
| VEGFD (78) | | −1.20E+00 | 0.043 | 0.006 | 0.006 | | |
| RANTES | | 2.50E+00 | 0.018 | 0.006 | 0.014 | | |
| IL-10 | | −8.60E−01 | 0.05 | 0.014 | 0.019 | | |
| IL-1ra | | −8.30E−01 | 0.033 | 0.028 | 0.008 | | |
| PDGF AB (68) | | −2.00E+00 | 0.043 | | | 0.018 | 0.031 |
| G-CSF | CYCLE2 DAY8/CYCLE1 DAY1 | 2.20E−01 | 0.021 | 0.025 | | | |
| FLT3 LG (89) | | 6.40E−01 | 0.029 | 0.002 | 0.008 | | |
| sVEGFR1 | | 9.30E−01 | 0.038 | | | 0.042 | |
| EGF (80) | | 1.10E+00 | 0.036 | 0.006 | 0.01 | | |
| PDGF BB (73) | | 4.40E−01 | 0.044 | | | 0.018 | |
| PDGF-AA | | 2.30E+00 | 0.014 | 0.011 | 0.003 | | |

Conclusion:

Concentration and changes in expression levels of cytokines, chemokine and angiogenic factors are associated to tumor response, tumor shrinkage and progression free survival and can be used to predict clinical response to E7080 treatment.

Example 4: Multivariate Analysis to Develop Biomarkers Combining Two or More than 3 Factors for Prediction of Clinical Outcomes Purpose:

The purpose of this analysis was to identify combinations of factors, such as mutations, thyroglobulin, blood biomarkers that better associate with clinical outcomes, such as progression free survival (PFS) than a single factor and to predict those clinical outcomes.

Materials and Methods:

All factors (i.e., mutations, thyroglobulin, cytokine, chemokine and angiogenic factors) were used as independent variables of interest, that is, as biomarker candidates. PFS was used as a dependent variable, that is, as one of the clinical outcomes, in this analysis. Firstly, all factors were screened according to p-values calculated by Cox proportional hazards model with single factor. Secondly, all combinations of the screened factors were tested by Cox proportional hazards model to find significant factors in all combinations of the factors. Combinations in which all factors were significant were chosen for further analysis. Hazard functions of the combinations of factors defined by their coefficients were obtained from this analysis. Each patient has his/her own hazard value for each model, so that patients can be assigned into two groups when a threshold of hazard is given for a model. After grouping patients, log rank test of progression free survival was performed to test difference of survival curves between two groups (low hazard and high hazard). The best threshold of hazard for each model of combination of factors was identified by sweeping threshold to calculate log rank test p-values and finding a threshold that minimized the smoothed curve constructed from the p-values, which was similar to the approach described in U. Abel, J. Berger and H. Wiebelt, "CRITLEVEL: An Exploratory Procedure for the Evaluation of Quantitative Prognostic Factors", Methods Inf. Medicine, 23(3):154-6(1984). The best thresholds of the models divided patients into high and low hazard groups. Patients are predicted as longer PFS when their hazard value is lower than the threshold.

Results and Discussion:

To find biomarkers to predict PFS at pre-treatment, we analyzed the data, which was available before the treatment. Cox proportional hazards model demonstrated 4 types of combination in two groups of biomarkers. One group is ANG-2, VEGF, GCSF and another group is IL13, MIP1a, and MIP1b. Hazard ratio determined by prediction models indicated that combination of VEGF and ANG-2 (Hazard ratio=0.386) predicted PFS better than each single factors (VEGF; 0.552, ANG-2; Hazard ratio=0.545). Addition of GCSF to VEGF and ANG-2 did not caused further decrease of Hazard ratio (0.413). Combination of IL13 and MIP1a showed low hazard ratio ($1.0\times10^{-9}$) in our prediction model and addition of MIP1b did not affect Hazard ratio further (Table 13).

Next we examined if the combination of gene mutation and blood biomarker predicted PFS better than gene mutation alone. Cox proportional hazards model demonstrated 3 groups of combination among 3 gene mutations (Table 14), such as:

Group (1): NRAS mutation (mu)

a. plus ANG-2;

b. plus VEGF, MIP1b;

c. plus VEGF, MIP1b, sVEGFR3;

d. NRAS mu plus ANG-2, VEGF, MIP1b, sVEGFR3;

Group (2): NRAS mu or KRAS mu plus ANG-2; and

Group (3): NRAS mu or KRAS mu or VHL mu a. plus MIP1a;

b. plus IL6, VEGF, MIP1a, MIP1b.

For example, hazard ratio determined by the prediction models indicated that combination of NRAS mu and ANG-2 (hazard ratio=0.085) predicted PFS better than mutation alone (NRAS; hazard ratio=0.124). Also combination of any of NRAS mu or KRAS mu and ANG-2 (Hazard ratio=0.083) had lower hazard ratio than mutation only (KRAS mu or NRAS mu; hazard ratio=0.205). Combination of any of BRAF mu or NRAS mu or KRAS mu and IL6, VEGF, MIP1a, MIP1b had lower hazard ratio (hazard ratio=1.9 E-10) than mutation only (hazard ratio=0.086) (Table 14).

TABLE 13

Predictive Biomarker Using Combination of Blood Biomarkers at Pre-Treatment

| | Cox proportional hazards model (P value) | | | | | Logrank test | | | | |
|---|---|---|---|---|---|---|---|---|---|---|
| VEGFA | ANG-2 | GCSF | IL13 | MIP1a | MIP1b | Low Gr N | High Gr N | p value | HR* | Prediction Model |
| 0.02 | | | | | | 15 | 36 | 0.198 | 0.552 | (0.0014) * (VEGFA100) − (0.279) < −0.15 |
| | 0.017 | | | | | 27 | 26 | 0.108 | 0.545 | (0.000267) * (Ang2) − (0.854) < −0.128 |
| 0.037 | 0.026 | | | | | 23 | 28 | 0.021 | 0.386 | (0.000261) * (Ang2) + (0.00126) * (VEGFA100) − (1.09) < −0.24 |
| 0.016 | 0.028 | 0.034 | | | | 25 | 26 | 0.027 | 0.413 | (0.000591) * (ANG290) + (−0.0178) * (GCSF) + (0.00142) * (VEGFA100) − (−0.671) < 0.651 |
| | | | 0.009 | 0.005 | | 7 | 18 | 0.015 | 1.00E−09 | (−0.0459) * (IL13) + (0.0459) * (MIP1a) − (0.0395) < 0.268 |
| | | | 0.031 | 0.001 | 0.049 | 12 | 13 | 0.002 | 0.121 | (−0.0353) * (IL13) + (0.0713) * (MIP1a) + (−0.0154) * (MIP1b) − (0.188) > 0.222 |

TABLE 14

Predictive Biomarker Using Combination of Gene Mutation and Blood Biomarkers at Pre-Treatment

| Cox proportional hazards model (p value) | | | | | | | | | Logrank test | | | | |
|---|---|---|---|---|---|---|---|---|---|---|---|---|---|
| Mutation (any of gene) | | | | | | | | | N | | | | |
| NRAS | KRAS, NRAS | BRAF, KRAS, NRAS | VEGFA | ANG-2 | MIP1a | MIp1b | sVEGFR3 | IL-6 | Low Gr | High Gr | p-value | HR* | Prediction Model |
| 0.047 | | | | | | | | | 6 | 17 | 1.90E−02 | 0.124 | D(NRAS, MU) |
| 0.011 | | | 0.044 | | | 0.035 | | | 14 | 6 | 1.70E−04 | 0.097 | (−0.025) * log10(MIP1b) + (.00616) * log10(VEGFA100) + (3.32) * D(NRAS, WT)−(−0.52) < 1.81 |
| 0.003 | | | 0.01 | | 0.004 | 0.016 | | | 14 | 6 | 8.70E−06 | 0.054 | (−0.0494) * log10(MIP1b) + (−0.000472) * log10(sVEGFR3) + (−0.0119) * log10(sVEGFA100) + (4.66) * D(NRAS, WT) − (.5.9) < 3.55 |
| 0.003 | | | 0.006 | 0.017 | 0.007 | 0.005 | | | 12 | 8 | 2.00E−06 | 2.60E−10 | (0.00148) * log10(Ang2) + (−0.0606) * log10(MIP1b) + (−0.000917) * log10(MIP1b) − (−0.0177) * log10(VEGFA100) + (6.58) * D(NRAS, WT) − (−5.78) < 3.97 |
| 0.015 | | | | 0.049 | | | | | 13 | 8 | 5.10E−04 | 0.115 | (0.000751) * log10(ANg2) + (2.69) * D(NRAS, WT) − (3.92) < 0.716 |
| 0.013 | | | | 0.028 | | | | | 14 | 7 | 2.80E−04 | 0.085 | (0.000972) * log10(Ang290) + (2.75) * D(NARS, WT) − (2.96) < 0.633 |
| | 0.043 | | | | | | | | 8 | 15 | 2.70E−02 | 0.205 | D(KRASNRAS, MU) |
| | 0.010 | | | 0.044 | | | | | 13 | 8 | 2.20E−04 | 0.083 | (0.000869) * log10(ANG290) + (2.16) * D(KRASNRAS, WT) − (2.24) < 0.508 |
| | | 0.004 | | | 0.044 | | | | 11 | 9 | 2.60E−04 | 0.086 | (−0.0281) * log10(MIP1a) + (2.19) * D(BRAFKRASNRAS, WT) − (−0.41) < −0.0348 |
| | | 0.010 | 0.017 | | 0.015 | 0.016 | | 0.019 | 10 | 5 | 3.30E−05 | 1.90E−10 | (0.126) * log10(IL6) + (−0.193) * log10(MIP1a) + (−0.0775) * log10(MIP1b) + (−0.0514) * log10(VEGFA100) + (7.94) * D(BRAFKRASNRAS, WT) − (−14.4) < 4.69 |

Conclusion:

Combination of biomarkers, either gene mutations or blood biomarkers or combination among blood biomarkers predicted PFS better than as a single biomarker based on prediction models after determining combinations of them using the Cox proportional hazard model. Biomarker combinations that were found by this analysis may be used to predict clinical outcomes such as PFS with E7080 and response to E7080 treatment.

Example 5: Mutation Status as Predictive Biomarkers for RCC Patients' Responsiveness to Therapy Comprising E7080 Either Alone or in Combination with Everolimus Purpose:

Tumor response and prolonged disease stabilization are observed in renal cell carcinoma patients (RCC) treated in a phase II study with E7080 (methanesulfonic acid salt of lenvatinib) alone or in combination with Everolimus. This experiment is directed at identifying amino acid mutations that are useful in predicting whether RCC subjects respond, or fail to respond, to treatment with E7080 using three criteria of response: best overall response, tumor shrinkage, and progression free survival.

Materials and Methods:

Tissue samples are obtained at surgery before the patients had received any therapy comprising E7080 and were routinely processed with formalin fixed, paraffin embedded tissues (FFPE). The protocol that is used is approved by the institutional review board, and informed consent is obtained from each subject. Tumor tissue samples from X patients, for which tissues are available, will be used for mutation analysis. DNA is isolated from FFPE tumor blocks collected from patients participating in the trial. Genomic DNA is extracted from two to five 10 micron unstained sections by deparaffinization and Qiagen DNA Mini Kit Tissue Protocol with minor modification. For mutation detection, a sequencing technology such as the SEQUENOM® (San Diego, Calif.) platform and the OncoCarta™ Panel v1.0 and OncoCarta™ Panel v3.0 described in Example 1, semiconductor sequencing such as Ion Torrent PGM, High Resolution Melt Analysis, or classical Sanger sequencing is used.

The period during which a patient takes E7080 is artificially divided into different Cycles for ease of evaluation and tracking. Patients receive E7080 at a dose of 24 mg orally once daily in 28 day cycles either alone or in combination with everolimus (E7080 and/or everolimus). For the E7080 Renal cell Carcinoma trial, each Cycle is 28 days (4 weeks) so Day 1-28 is cycle 1; Day 29 is Day 1 of Cycle 2; and Day 57 is Day 1 of Cycle 3. Blood samples are collected for pharmacokinetic (PK) analysis on Cycle 1 Days 1, Cycle 2 Day 1, and Cycle 3 Day 1. A total of 6 samples per patient are collected as follows: Cycle 1 Day 1: immediately prior to the dose of E7080, and 2 to 8 hours following the first dose of E7080 (post-dose); Cycle 2 Day 1: immediately prior to the dose of E7080 and 2 to 8 hours following the first dose of E7080 (post-dose); Cycle 3 Day 1: immediately prior to the dose of E7080 and 2 to 8 hours following the first dose of E7080 (post-dose). For analysis of progression free survival, PK parameter is used as a covariate in Cox proportional hazards model.

The four criteria of response: best overall response, tumor response, tumor shrinkage, and progression free survival are defined below.

"Best Overall Response" (BOR) refers to having one of the following statuses—Complete Response (CR), Partial Response (PR), Stable Disease (SD) or Progressive Disease (PD) an association of BOR to gene mutation is analyzed by Fisher's exact test.

"Clinical benefit" (CB) refers to having one of the following statuses—Complete Response (CR), Partial Response (PR); or Stable Disease (SD) with 6 months or more progression free survival (PFS).

"Complete Response" means complete disappearance of all target lesions.

"Partial Response" means at least 30% decrease in the sum of the longest diameter (LD) of target lesions, taking as reference the baseline summed LD.

"Progressive Disease" (PD) means at least 20% increase in the sum of the LD of target lesions, taking as reference the smallest summed LD recorded since the treatment started, or the appearance of one or more new lesions.

"Stable Disease" means neither sufficient shrinkage of the target lesions to qualify for PR nor sufficient increase to qualify for progressive disease (PD), taking as reference the smallest summed LD since the treatment started.

"Progression Free Survival" (PFS) refers to the period from start date of treatment to the last date before entering PD status and correlation of gene mutation to PFS is analyzed by Logrank test and Cox proportional hazards model.

"Tumor shrinkage" (TS) means percent change of sum of diameters of target lesions, taking as reference the baseline sum diameters and correlation of gene mutation to TS is analyzed by Pearson product-moment correlation coefficient and Spearman's rank correlation coefficient test.

"Tumor response" (TR) compares subjects with "Partial Response" (PR) with subjects with either Stable Disease (SD) or Progressive Disease (PD). → not for mutation analysis, but for TG and blood biomarkers.

Example 6: Blood Biomarkers as Predictive and Response Biomarkers of E7080 Either Alone or in Combination with Everolimus in RCC Subjects Purpose:

The purpose of this analysis is to measure cytokine, chemokine and angiogenic factors (collectively referred to herein as "blood biomarkers") in blood samples obtained from patients in clinical trials at both pre- and post-treatment with E7080 and/or everolimus and to identify blood biomarkers which can be used to predict whether renal cell carcinoma patients will respond or fail to respond to treatment with E7080. For these analyses, four criteria of response are employed, namely: best overall response, tumor response, % of tumor shrinkage and progression free survival.

Materials and Methods:

Patients receive E7080 at a dose of 24 mg oral once daily in 28 day cycles either alone or in combination with everolimus. Serum samples are collected at Cycle 1 Day 1 (pre-treatment), Cycle 1 Day 15 and immediately before dosing on Day1 of each subsequent cycle and at the time when the patient is off-treatment. 7.5 mL of blood is drawn into serum stainless steel tube (SST) and let to clot at room temperature for at least 30 min. Within 60 minutes of sample collection, the tubes are centrifuged for 10 minutes at 20-25° C. at 1400×g. The supernatant is drawn without disturbing the pellet and the serum is mixed and divided into two sample tubes and stored frozen (−70° C.) at an upright position until further treatment for analysis. Serum samples from patients are used for blood biomarker analysis. Serum from Cycle 1 day 1 (baseline), cycle 1 day 15, pre-dose sample from Day1 of each subsequent cycle and serum sample when the patient comes off treatment are used in this analysis. The association of progression free survival with or without a covariate is analyzed. The covariates used are the following PK parameters: cycle 1 day 1 Cmax (E7080 concentration 2 hrs to 8 hrs after dosing on cycle 1 day 1: MAX1); cycle 2 day 1 Cmax (E7080 concentration 2 hrs to 8 hrs after dosing on cycle 2 day 1: MAX2); cycle 2 day 1 Ctrough (E7080 concentration before dosing on cycle 2 day 1: MIN2). Serum samples are tested in batch format where all timepoints from the same subject are assayed on the same day. On the day of assay, samples are removed from −80° C. and allowed to thaw and reach room temperature. The serum samples are tested using the following commercial assay kits as per the manufacturer's instructions: Human Soluble Tie-2 ELISA (R&D Systems Cat. No. DTE200), Human Angiopoietin-1 ELISA (R&D Systems Cat. No. DANG10), Human Angiopoietin-2 ELISA (R&D Systems Cat. No. DANG20), Human Soluble Receptor Multiplex (Millipore Cat. No. HSCR-32K; sVEGF R1, sVEGF R2 and sVEGF R3 only), Human Cytokine/Chemokine Panel I Multiplex (Millipore Cat. No. MPXHCYTO-60K; IL-1α, IL-1β, IL-1ra, IL-2, IL-4, IL-5, IL-6, IL-7, IL-8, IL-10, IL-12p40, IL-12p70, IL-13, IL-15, IL-17, sCD40L, EGF, Eotaxin, FGF-2, G-CSF, GM-CSF, IFN-γ, IP-10, MCP-1, MIP-1α, MIP-1β, PDGF-AA, RANTES, TGF-α, TNF-α and VEGF only) and Human Growth Factor Multiplex (Origene TruPLEX Cat. No. AM100096; PDGF-AB, PDGF-BB, FGF4, VEGFD, FGF2, EGF, HGF, FLT3LG, ANGPT2, PGF and VEGFA).

The ELISA plates are measured using a Molecular Devices UVmax kinetic microplate reader with SoftMax Pro 5.2 software. The multiplex assays are performed using the Bio-Rad Bio-Plex system with Bio-Plex Manager 4.1 software. Final protein concentrations (pg/mL) are calculated from the standard curve for each assay. Depending on the assay, serum samples may be diluted in assay buffer prior to testing. In these cases, protein concentrations are multiplied by the dilution factor.

The four criteria of response; best overall response, tumor response, tumor shrinkage, and progression free survival are defined below and analyzed by indicated methods.

"Best Overall Response" (BOR) refers to having one of the following statuses:—Complete Response (CR), Partial Response (PR), Stable Disease (SD) or Progressive Disease (PD) and association of BOR to gene mutation is analyzed by Fisher's exact test "Clinical benefit" (CB) refers to having one of the following statuses and association of CB to gene mutation is analyzed by student's t-test and Mann-Whitney U test.

—Complete Response (CR), Partial Response (PR); or Stable Disease (SD) with 6 months or more progression free survival (PFS)

"Complete Response" means complete disappearance of all target lesions.

"Partial Response" means at least 30% decrease in the sum of the longest diameter (LD) of target lesions, taking as reference the baseline summed LD.

"Progressive Disease" (PD) means at least 20% increase in the sum of the LD of target lesions, taking as reference the smallest summed LD recorded since the treatment started, or the appearance of one or more new lesions.

"Stable Disease" means neither sufficient shrinkage of the target lesions to qualify for PR nor sufficient increase to qualify for progressive disease (PD), taking as reference the smallest summed LD since the treatment started.

"Progression Free Survival" (PFS) refers to the period from start date of treatment to the last date before entering PD status and correlation of gene mutation to PFS is analyzed by Logrank test and cox proportional hazards model.

"Tumor shrinkage" (TS) means percent change of sum of diameters of target lesions, taking as reference the baseline sum diameters and correlation of gene mutation to TS is analyzed by Pearson product-moment correlation coefficient and * Spearman's rank correlation coefficient test.

"Tumor response" (TR) compares subjects with "Partial Response" (PR) with subjects with either Stable Disease (SD) or Progressive Disease (PD) and association of blood biomarkers is analyzed by student's t-test and Mann-Whitney U test.

Example 7: Multivariate Analysis to Develop Biomarkers Combining Two or More than 3 Factors for Prediction of Clinical Outcomes in RCC Patients Purpose:

The purpose of this analysis is to identify combinations of factors, such as mutations, and levels or expression ratios of cytokine, chemokine and angiogenic factors, that better associate with progression free survival (PFS) than a single factor and to predict clinical outcomes, such as PFS and TS, in RCC patients.

Materials and Methods:

All factors (i.e., mutations, cytokine, chemokine and angiogenic factors) are used as independent variables of interest, that is, as biomarker candidates. PFS is used as a dependent variable, that is, as a clinical outcome in this analysis. Firstly, all factors are screened according to p values calculated by Cox proportional hazards model with single factor. Secondly, all combinations of the screened factors are tested by Cox proportional hazards model to find significant factors in all combinations of the factors. Combinations in which all factors are significant are chosen for further analysis. Hazard functions of the combinations of factors defined by their coefficients are obtained from this analysis. Each patient has his/her own hazard value for each model, so that patients can be assigned into two groups when a threshold of hazard is given for a model. After grouping patients, log rank test of progression free survival is performed to test difference of survival curves between two groups (low hazard and high hazard). The best threshold of hazard for each model of combination of factors is identified by sweeping threshold to calculate log rank test p-values and finding a threshold that minimizes the smoothed curve constructed from the p-values, which is similar to the approach described in U. Abel, J. Berger and H. Wiebelt, "CRITLEVEL: An Exploratory Procedure for the Evaluation of Quantitative Prognostic Factors", Methods Inf. Medicine, 23(3):154-6(1984). The best thresholds of the models divides patients into high and low hazard groups. The criteria of patient prediction of longer PFS are defined as a hazard value calculated by hazard function that is lower than the threshold.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating thyroid cancer, comprising:
providing a biological sample obtained from a human subject having or suspected of having a thyroid cancer;
measuring in the biological sample a reduced concentration, as compared to a control, of ANGPT2 protein, wherein the control is the concentration of ANGPT2 protein in a sample or samples obtained from one or more subjects that have not responded to treatment with lenvatinib or a pharmaceutically acceptable salt thereof; and
administering lenvatinib or a pharmaceutically acceptable salt thereof to the human subject.

2. The method of claim 1, wherein the thyroid cancer is a differentiated thyroid cancer.

3. The method of claim 2, wherein the differentiated thyroid cancer is a follicular thyroid cancer.

4. The method of claim 2, wherein the differentiated thyroid cancer is a papillary thyroid cancer.

5. The method of claim 1, wherein the lenvatinib or pharmaceutically acceptable salt thereof is lenvatinib mesylate.

6. The method of claim 1, wherein the biological sample is a blood, serum, or plasma sample.

7. A method for treating thyroid cancer, comprising:
providing a biological sample obtained from a human subject having or suspected of having a thyroid cancer, wherein the biological sample is obtained from the human subject after administering a first lenvatinib or a pharmaceutically acceptable salt thereof treatment to the human subject;
measuring in the biological sample a reduced concentration, as compared to a control, of ANGPT2 protein, wherein the control is the concentration of ANGPT2 protein in a sample or samples obtained from one or more subjects that have not responded to treatment with lenvatinib or a pharmaceutically acceptable salt thereof; and
administering a second lenvatinib or a pharmaceutically acceptable salt thereof treatment to the human subject.

8. The method of claim 7, wherein the biological sample is obtained from the human subject between 5 days to 18 days after administering the first lenvatinib or a pharmaceutically acceptable salt thereof treatment to the human subject.

9. The method of claim 7, wherein the thyroid cancer is a differentiated thyroid cancer.

10. The method of claim 9, wherein the differentiated thyroid cancer is a follicular thyroid cancer.

11. The method of claim 9, wherein the differentiated thyroid cancer is a papillary thyroid cancer.

12. The method of claim 7, wherein the lenvatinib or pharmaceutically acceptable salt thereof is lenvatinib mesylate.

13. The method of claim 7, wherein the biological sample is a blood, serum, or plasma sample.

14. The method of claim 3, wherein the biological sample is a blood, serum, or plasma sample.

15. The method of claim 4, wherein the biological sample is a blood, serum, or plasma sample.

16. The method of claim 10, wherein the biological sample is a blood, serum, or plasma sample.

17. The method of claim 11, wherein the biological sample is a blood, serum, or plasma sample.

* * * * *